US011155585B2

(12) United States Patent
Guss et al.

(10) Patent No.: US 11,155,585 B2
(45) Date of Patent: Oct. 26, 2021

(54) **VACCINE AGAINST *S. SUIS* INFECTION**

(71) Applicant: INTERVACC AB, Hägersten (SE)

(72) Inventors: Bengt Guss, Uppsala (SE); Lars Frykberg, Storvreta (SE); Margareta Flock, Bromma (SE); Jan-Ingmar Flock, Bromma (SE); Karl Olov Zachrisson, Spånga (SE)

(73) Assignee: INTERVACC AB, Hägersten (SE)

( * ) Notice: Subject to any disclaimer, the term of this patent is extended or adjusted under 35 U.S.C. 154(b) by 271 days.

(21) Appl. No.: 15/735,548

(22) PCT Filed: Jul. 8, 2016

(86) PCT No.: PCT/EP2016/066311

§ 371 (c)(1),
(2) Date: Dec. 11, 2017

(87) PCT Pub. No.: WO2017/005913

PCT Pub. Date: Jan. 12, 2017

(65) Prior Publication Data

US 2018/0170974 A1 Jun. 21, 2018

(30) Foreign Application Priority Data

Jul. 9, 2015 (EP) .................................... 15176063

(51) Int. Cl.

| | |
|---|---|
| ***C07K 14/315*** | (2006.01) |
| ***A61P 31/04*** | (2006.01) |
| ***A61K 39/09*** | (2006.01) |
| *A61K 39/00* | (2006.01) |

(52) U.S. Cl.

CPC .......... *C07K 14/315* (2013.01); *A61K 39/092* (2013.01); *A61P 31/04* (2018.01); *A61K 2039/552* (2013.01); *A61K 2039/55505* (2013.01); *C07K 2319/00* (2013.01)

(58) Field of Classification Search

None

See application file for complete search history.

(56) References Cited

U.S. PATENT DOCUMENTS

| | | | | |
|---|---|---|---|---|
| 8,394,390 B2 * | 3/2013 | Galeotti | A61K 39/095 | 424/184.1 |
| 2006/0173162 A1 * | 8/2006 | Djurup | C07K 14/4723 | 530/324 |

FOREIGN PATENT DOCUMENTS

| | | | | |
|---|---|---|---|---|
| CH | 101906166 | | 3/2013 | |
| CN | 101613401 B | * | 4/2013 | |
| EP | 0626452 | | 11/1994 | |
| WO | WO-03012122 A2 | * | 2/2003 | C07K 14/78 |
| WO | WO-03040165 A2 | * | 5/2003 | A61K 39/385 |
| WO | WO 2015/181356 | | 12/2015 | |
| WO | WO-2015181356 A1 | * | 12/2015 | C07K 16/1275 |

OTHER PUBLICATIONS

PET-32a-c(+) Vectors product sheet. TB122 Dec. 1998.*

Mariela Segura (2015) Streptococcussuis vaccines: candidate antigens and progress, Expert Review of Vaccines, 14:12, 1587-1608.*

Uniprot Accession No. D5AHM7 Jun. 15, 2010.*

Uniprot Accession No. D5AEW5 Jun. 15, 2010.*

Uniprot Accession No. D5AGN6 Jun. 15, 2010.*

DATABASE UniProt [Online], "SubName: Full=Putative 5'-nucleotidase {ECG:0000313 | EMBL:ADE31342.1};", XP002751607, Jun. 15, 2010, retrieved from EBI accession No. UNIPRO:D5AHM7 Database accession No. D5AHM7 sequence.

DATABASE UniProt [Online], "SubName: Full=Putative cyclonucleotide phosphodiesterase {ECO:0000313 | EMBL: ABP91061.1};", XP002761028, May 29, 2007, retrieved from EBI accession No. UNIPRO:A4VY72 Database accession No. A4VY72 sequence.

DATABASE UniProt [Online], "SubName: Full=Putative 5' -nucleotidase {ECO:0000313 | EMBL:ABP90504.1}", XP002761029, May 29, 2007, retrieved from EBI accession No. UNIPRO:A4VWL5 Database accession No. A4VWL5 sequence.

DATABASE UniProt [Online], "SubName: Full=Methylaccepting chemotaxis protein {ECO:0000313 | EMBL ABP89511.1};", XP002761030, May 29, 2007, retrieved from EBI accession No. UNIPRO:A4VTS2 Database accession No. A4VTS2 sequence.

Li et al., "Induction of protective immune response against Streptococcus suis serotype 2 infection by the surface antigen HP0245", FEMS Microbiology Letters, 2011, 316(2): 115-122.

Chen et al., "A Glimpse of Streptococcal Toxic Shock Syndrome from Comparative Genomics of S. suis 2 Chinese Isolates", PLoS ONE, 2007, 3: e315.

* cited by examiner

*Primary Examiner* — Oluwatosin A Ogunbiyi

(74) *Attorney, Agent, or Firm* — James S. Keddie; Bozicevic, Field & Francis LLP

(57) ABSTRACT

The present disclosure relates to immunogenic polypeptides, immunogenic compositions and vaccine compositions and use thereof for immunization of mammals susceptible to *Streptococcus suis* infection. The disclosure also relates to methods for preparing, formulating and administrating such compositions.

25 Claims, 29 Drawing Sheets

Specification includes a Sequence Listing.

M = size marker
1 = M2N-H
2 = M2C-H
3 = SP2N-H
4 = SP2C-H
5 = SP4N-H
6 = SP4C-H
7 = SP7N-H
8 = SP7C-H 1 = M2N-S lysate 2 = M2N-S purified on silica 3 = SP2C-S lysate 4 = SP2C-S purified on silica 5 = SP4C-S lysate 6 = SP4C-S purified on silica 7 = SP7C-S lysate 8 = SP7C-S purified on silica M = size marker 1 = M2N-LSL lysate 2 = M2N-LSL silica purified 3 = SP2C-LSL lysate 4 = SP2C-LSL silica purified 5 = IdeE-S lysate 6 = IdeE-S silica purified 7 = SP2C-H lysate 8 = SP2C-H silica purified M = size marker

Figure 13A

| Name | Sequence | SEQ ID NO: |
|---|---|---|
| M2 | MNIQERFSLRKSAVGLVSVSLLCAIYTSTVAADTVVTGVNEIIEESQVKDEVSIESEKNESLDGSNIEIVEEIADNIPSPVIAEGEVAV<br>EMKVDRGTENVVSRNDTEVTTSEQNQIEVTETKEILNQTSYQTESGEQRQIIWAHGITPPAMEQSGGFVKEKYGDYLNYTAPFEAGKGY<br>YDTNKSLNASFIDLNLCFAAVSSNMVHWWLEQNSSYVERYLKEKKGTVNVEENYAITDLRRYINSFQNQQNSRVFDMFKTYYGYRTNGF<br>VSDALVDLFINGYKPKAQGGVNLEDSQLVPDSRGGFFYDVFKEKKLTNRIFSGSYERFGEDVRTVLESKGLLGLTYRTLGYATHIVTVW<br>GAEYDNQGKIKAVYITDSDDQQEQIGLKRMGITRDASGNPRLNNHMKNNSAGALLDYVHTIRLGQDLWEEYFNPLAKAKETASQTLADT<br>KKALDLSIQGQSELPESMRLIYLEKLNNLYNQGILSIQKAESSEMLSGALENGLNSLKSLDFPISEVGNALAPDLPVGDRSTVSDVDSL<br>SSQETSSTNLEADTENAGIIADGTNQLHFPVEAQTTSSVEAEGDNVFEQEADTLPIIIENKDEFGSELSRNMQTSETDSLVVAVEEDVK<br>NDEVAQVEELLESEKVENQSSELLSDTLIVESANDKEEDRVEAVVSEQPDSIPHQNVEISLVEPTNVETETVVTPINDAATPHGSPTYI<br>DNSVTESVATPLEKDSIQAGETEIAEPTSSESTNVETETVVTPVNDVATPHGSPTYIDNSVTESVATPLEKDSIQAGETEIAEPTSSES<br>TNVETETVVTPVNDVATPHGSPTYIDNSVTESVATPLEKDSIQAGETEIAEPTSSESTSVEAELVDNSEIHAATSSVTPCGSSAYADGS<br>TTESVATPLEKDSIQTGNTEIAEPTSSKSTNVEAASVDNSEIHADASLTAVSSVNLDNPVIEPVAISLIGSKRDTNAEVEVSSLSKREV<br>RKTNTDGLISVQSKVIKKELLESSLAEAGSPLLEATIAQSSNSNSTEIGMSYQNTVLLESNNTERQVSKAEIVMEHKETELVETVSSAS<br>EPVVLVENISQTSNNTIESGKNMGVQSQAGAKQILGVEQSSKVSTPTSRQIMGVGLLTLVLGSALGLLKKRRK | 1 |
| SP2 | MPKKGLFMKKKKILLPVMSTLLLAPFVLAQQVQAAETTTAATTTNQPATTDATATVPATTDATATVPATSVENVATEETVVPAAEETVE<br>AVIIHTNDVHGRILEEKNVIGDAKAAAVIEEERAKVENTIVVDAGDAFQGLPISNSTKGEDRANIMNQVGYDAMAVGNHEFDFGMDQAI<br>KYKETLNFPLLSANTYVNGARVFEASTIVDKTPTVVGDEFVVIGVTTPETATKTHPKNVEGVTFTDPVTEVNKVIDEVEARALADNRVY<br>KNYIILAHLGVDSTTPVEWRGSTLAEALSKNSKLAGKRVIVIDGHSHTVEATTYGDNVTYNQTGSYLNNIGKVTLKSDKLLGEASLISA<br>ADTKNVTPNAKIAALVDEIKAKYEAENAQVVIENNPVELNGDRSNVRVRETNLGNAVTDAIYAYGQTGFSNKTSLAVTNGGGLRATIAK<br>DQPVTKGDIIAVLPFGNIVSQITVTGQQIYDMFTKSLSSTLQVNPETGEMLLDENGMPLFEASGGFLHISGANVFYDPTLPVEERVLLI<br>GILNPETGEYDALDLEKTYYLATNDFLAAGGDGYTMLGGAREEGPSMDSVFAEYLKTADLSAYEVVNPYSRIIPVNSSIDTDEDGYPDF<br>IEILLDTDPENPASNPETVPAENTDSPSNQVQNTSATDKKAPVDSPKVGDKKTEVASPAKTTKAGVLPNTGDQMNLTLSLFGLGLAGLA<br>VAVGRRKEN | 2 |
| SP4 | MNFRFSKCAVALTLALLAASNPKLAQAEEILNTTPASSTEASQAVPVESDTTEEADNTESPVPATTEAENPSSSETAETSDPTSETTDT<br>TTSEARTVTPAATETSQPVEGQTVDVRILATTDLHTNLVNYDYYQDKPVETLGLAKTAVLIEEAKKENPNVVLVDNGDTIQGTPLGNYK<br>SIVDPIEEGEQHPMYAALETLGFDVGTLGNHEFNYGLAYLEKVIRTANMPLVNANVLDPTTKDFLYTPYTIVKKTFTDTEGKKVTLNVG<br>VTGIVPPQILNWDKAYLEGKVIVRDAVEAVRDIIPTMRENGADIVLVLSHSGIGDDQYEVGEENVGYQIASLSGVDAVITGHSHAEFPG<br>TAEKPSFYAKYSGVDDTNGKINGTPVTMAGKYGDHLGVIDLNLVFKDGKWTTTSSKAAIRKIDTKSSVADGRIIDLAKEAHNETIKYVR<br>QQVGETTAPINSFFALVQDDPSVQIVNNAQIWYAKQQLAGTSEANLPILSAAAPFKAGTRGDASAYTDIPAGPIAIKNVADLYLYDNVV<br>AILKVNGAQLKEWLEMSAGQFNQVDLSSTEPQNLVNTDFRTYNFDVIDGVTYQYDITQPNKYDRDGKIVNETASRVRNLQYNGQDVTAD<br>QEFIVVTNNYRANGTFPGVREASINRLLNLENRQAIINYIIAEKVINPTADNNWTFTDSIKGLDLRFLTADRAKSLVTDQECIVYLQAS<br>TASEGFGEFKFVYTESKVVTPDEQQSDQGNTGQDIVLESGQRITLPAVNPPAPAPQHKLASPHSQASTKTLPATGEATSMLSLLGLTLI<br>GFVGAWTKKKEH | 3 |
| SP7 | MKKNIRLKSSILALVAGFSVIATQAVLADELAVQIMGVNDFHGALDMTGTARLEGETVRNAGTAALLDAYMDDSQAEFEETAAETETPA | 4 |

Figure 13B

| | | |
|---|---|---|
| | ESIRVQAGDMVGASPSNSGLLQDEPTVKVFNKMDVEYGTLGNHEFDEGLDEYNRIMTGEAPKKGQFNEIVDNYTREAAKQEIVIANVID<br>KETGEIPYGWKPYAIKTIPVNDKEAKIGFIGVVTTEIPNLVLKKNYEQYTFLNEAETIAKYARELAEKGVNAIVVLAHVPATSKDGVAA<br>GEAADMIAKLNEIYPEHSVDLVFAGHNHVYTNGTTGKTLIVQATSQGKAYADVRAVYDTDIADFKAVPTAKIIAVAPGQKTPSPEIQAI<br>VDEANTIVKKVTEQKIATASQATDISREVNEFKESAVGNLVTSAQLAIAKKSGYDVDFAMTNDGGIRADLKVQEDGTVTWGAAQAVQPF<br>GNILQVVQMTGEQIYTALNQQYDEGEKYFLQMSGIKYIYTKADNPTEENPYKVVKAFKEDGTEIVPTETYTLVINDFLFGGGDGFSIFK<br>EAKLIGAINPDTEVFVEYLTDLEKAGQTISATIPGRKAFVEKYVEEPKAEEKEDNAGTTTDVKTPEKANDGGDSVTNQKATEQPAPSGS<br>MAPISNKKTEKASGNQTLPNTGQEALGSLLISLGGLVSLGMAVSVRRKEGE | |
| M2N | DTVVTGVNEIIEESQVKDEVSIESEKNESLDGSNIEIVEEIADNIPSPVIAEGEVAVEMKVDRGTENVVSRNDTEVTTSEQNQIEVTET<br>KEILNQTSYQTESGEQRQIIWAHGITPPAMEQSGGFVKEKYGDYLNYTAPFEAGKGYYDTNKSLNASFIDLNLCFAAVSSNMVHWWLEQ<br>NSSYVERYLKEKKGTVNVEENYAITDLRRYINSFQNQQNSRVFDMFKTYYGYRTNGFVSDALVDLFINGYKPKAQGGVNLEDSQLVPDS<br>RGGFFYDVFKEKKLTNRIFSGSYERFGEDVRTVLESKGLLGLTYRTLGYATHIVTVWGAEYDNQGKIKAVYITDSDDQQEQIGLKRMGI<br>TRDASGNPRLNNHMKNNSAGALLDYVHTIRLGQDLWEEYFN | 5 |
| M2C | SEQPDSIPHQNVEISLVEPTNVETETVVTPINDAATPHGSPTYIDNSVTESVATPLEKDSIQAGETEIAEPTSSESTNVETETVVTPVN<br>DVATPHGSPTYIDNSVTESVATPLEKDSIQAGETEIAEPTSSESTNVETETVVTPVNDVATPHGSPTYIDNSVTESVATPLEKDSIQAG<br>ETEIAEPTSSESTSVEAELVDNSEIHAATSSVTPCGSSAYADGSTTESVATPLEKDSIQTGNTEIAEPTSSKSTNVEAASVDNSEIHAD<br>ASLTAVSS | 6 |
| SP2N | AETTTAATTTNQPATTDATATVPATTDATATVPATSVENVATEETVVPAAEETVEAVIIHTNDVHGRILEEKNVIGDAKAAAVIEEERA<br>KVENTIVVDAGDAFQGLPISNSTKGEDRANIMNQVGYDAMAVGNHEFDFGMDQAIKYKETLNFPLLSANTYVNGARVFEASTIVDKTPT<br>VVGDEFVVIGVTTPETATKTHPKNVEGVTFTDPVTEVNKVIDEVEARALADNRVYKNYIILAHLGVDSTTPVEWRGSTLAEALSKNSKL<br>AGKRVIVIDGHSHTVEATTYGDNVTYNQTGSYLNNIGKVTLKSDKLLGEASLISAADTKNVTPNAKIAALVD | 7 |
| SP2C | DEIKAKYEAENAQVVIENNPVELNGDRSNVRVRETNLGNAVTDAIYAYGQTGFSNKTSLAVTNGGGLRATIAKDQPVTKGDIIAVLPFG<br>NIVSQITVTGQQIYDMFTKSLSSTLQVNPETGEMLLDENGMPLFEASGGFLHISGANVFYDPTLPVEERVLLIGILNPETGEYDALDLE<br>KTYYLATNDFLAAGGDGYTMLGGAREEGPSMDSVFAEYLKTADLSAYEVVNPYSRIIPVNSSIDTDEDGYPDFIEILLDTDPENPASNP<br>ETVPAENTDSPSNQVQNTSATDKKAPVDSPKVGDKKTEVASPAKTTKAG | 8 |
| SP4N | EEILNTTPASSTEASQAVPVESDTTEEADNTESPVPATTEAENPSSSETAETSDPTSETTDTTTSEARTVTPAATETSQPVEGQTVDVR<br>ILATTDLHTNLVNYDYYQDKPVETLGLAKTAVLIEEAKKENPNVVLVDNGDTIQGTPLGNYKSIVDPIEEGEQHPMYAALETLGFDVGT<br>LGNHEFNYGLAYLEKVIRTANMPLVNANVLDPTTKDFLYTPYTIVKKTFTDTEGKKVTLNVGVTGIVPPQILNWDKAYLEGKVIVRDAV<br>EAVRDIIPTMRENGADIVLVLSHSGIGDDQYEVGEENVGYQIASLSGVDAVITGHSHAEFPGTAEKPSFYAKYSGVDDTNGKINGTPVT<br>MAGKYGDHLGVIDLNLVFKDGKWTTTSSKAAIRKIDTKSSVADGRIIDLAKEAHNETIKYVRQQVGETT | 9 |
| SP4C | GETTAPINSFFALVQDDPSVQIVNNAQIWYAKQQLAGTSEANLPILSAAAPFKAGTRGDASAYTDIPAGPIAIKNVADLYLYDNVVAIL<br>KVNGAQLKEWLEMSAGQFNQVDLSSTEPQNLVNTDFRTYNFDVIDGVTYQYDITQPNKYDRDGKIVNETASRVRNLQYNGQDVTADQEF<br>IVVTNNYRANGTFPGVREASINRLLNLENRQAIINYIIAEKVINPTADNNWTFTDSIKGLDLRFLTADRAKSLVTDQECIVYLQASTAS<br>EGFGEFKFVYTESKVVTPDEQQSDQGNTGQDIVLESGQRITLPAVNPPAPAPQHKLASPHSQASTKT | 10 |
| SP7N | DELAVQIMGVNDFHGALDMTGTARLEGETVRNAGTAALLDAYMDDSQAEFEETAAETETPAESIRVQAGDMVGASPSNSGLLQDEPTVK<br>VFNKMDVEYGTLGNHEFDEGLDEYNRIMTGEAPKKGQFNEIVDNYTREAAKQEIVIANVIDKETGEIPYGWKPYAIKTIPVNDKEAKIG<br>FIGVVTTEIPNLVLKKNYEQYTFLNEAETIAKYARELAEKGVNAIVVLAHVPATSKDGVAAGEAADMIAKLNEIYPEHSVDLVFAGHNH | 11 |

Figure 13C

| | | |
|---|---|---|
| | VYTNGTTGKTLIVQATSQGKAYADVRAVYDTDIADFKAVPTAKIIAVAPGQKTPSPEIQAIVDEANTIVKK | |
| SP7C | EIQAIVDEANTIVKKVTEQKIATASQATDISREVNEFKESAVGNLVTSAQLAIAKKSGYDVDFAMTNDGGIRADLKVQEDGTVTWGAAQ<br>AVQPFGNILQVVQMTGEQIYTALNQQYDEGEKYFLQMSGIKYIYTKADNPTEENPYKVVKAFKEDGTEIVPTETYTLVINDFLFGGGDG<br>FSIFKEAKLIGAINPDTEVFVEYLTDLEKAGQTISATIPGRKAFVEKYVEEPKAEEKEDNAGTTTDVKTPEKANDGGDSVTNQKATEQP<br>APSGSMAPISNKKTEKASGNQT | 12 |
| M2N-H | **MTGS**DTVVTGVNEIIEESQVKDEVSIESEKNESLDGSNIEIVEEIADNIPSPVIAEGEVAVEMKVDRGTENVVSRNDTEVTTSEQNQIE<br>VTETKEILNQTSYQTESGEQRQIIWAHGITPPAMEQSGGFVKEKYGDYLNYTAPFEAGKGYYDTNKSLNASFIDLNLCFAAVSSNMVHW<br>WLEQNSSYVERYLKEKKGTVNVEENYAITDLRRYINSFQNQQNSRVFDMFKTYYGYRTNGFVSDALVDLFINGYKPKAQGGVNLEDSQL<br>VPDSRGGFFYDVFKEKKLTNRIFSGSYERFGEDVRTVLESKGLLGLTYRTLGYATHIVTVWGAEYDNQGKIKAVYITDSDDQQEQIGLK<br>RMGITRDASGNPRLNNHMKNNSAGALLDYVHTIRLGQDLWEEYFN**LE***HHHHHHHH* | 13 |
| M2C-H | **MTGS**SEQPDSIPHQNVEISLVEPTNVETETVVTPINDAATPHGSPTYIDNSVTESVATPLEKDSIQAGETEIAEPTSSESTNVETETVV<br>TPVNDVATPHGSPTYIDNSVTESVATPLEKDSIQAGETEIAEPTSSESTNVETETVVTPVNDVATPHGSPTYIDNSVTESVATPLEKDS<br>IQAGETEIAEPTSSESTSVEAELVDNSEIHAATSSVTPCGSSAYADGSTTESVATPLEKDSIQTGNTEIAEPTSSKSTNVEAASVDNSE<br>IHADASLTAVSS**LE***HHHHHHHH* | 14 |
| SP2N-H | **MTGS**AETTTAATTTNQPATTDATATVPATTDATATVPATSVENVATEETVVPAAEETVEAVIIHTNDVHGRILEEKNVIGDAKAAAVIE<br>EERAKVENTIVVDAGDAFQGLPISNSTKGEDRANIMNQVGYDAMAVGNHEFDFGMDQAIKYKETLNFPLLSANTYVNGARVFEASTIVD<br>KTPTVVGDEFVVIGVTTPETATKTHPKNVEGVTFTDPVTEVNKVIDEVEARALADNRVYKNYIILAHLGVDSTTPVEWRGSTLAEALSK<br>NSKLAGKRVIVIDGHSHTVEATTYGDNVTYNQTGSYLNNIGKVTLKSDKLLGEASLISAADTKNVTPNAKIAALVD*HHHHHH* | 15 |
| SP2C-H | **MTGS***HHHHHH*VDEIKAKYEAENAQVVIENNPVELNGDRSNVRVRETNLGNAVTDAIYAYGQTGFSNKTSLAVTNGGGLRATIAKDQPVT<br>KGDIIAVLPFGNIVSQITVTGQQIYDMFTKSLSSTLQVNPETGEMLLDENGMPLFEASGGFLHISGANVFYDPTLPVEERVLLIGILNP<br>ETGEYDALDLEKTYYLATNDFLAAGGDGYTMLGGAREEGPSMDSVFAEYLKTADLSAYEVVNPYSRIIPVNSSIDTDEDGYPDFIEILL<br>DTDPENPASNPETVPAENTDSPSNQVQNTSATDKKAPVDSPKVGDKKTEVASPAKTTKAGV | 16 |
| SP4N-H | **MTGS**EEILNTTPASSTEASQAVPVESDTTEEADNTESPVPATTEAENPSSSETAETSDPTSETTDTTTSEARTVTPAATETSQPVEGQT<br>VDVRILATTDLHTNLVNYDYYQDKPVETLGLAKTAVLIEEAKKENPNVVLVDNGDTIQGTPLGNYKSIVDPIEEGEQHPMYAALETLGF<br>DVGTLGNHEFNYGLAYLEKVIRTANMPLVNANVLDPTTKDFLYTPYTIVKKTFTDTEGKKVTLNVGVTGIVPPQILNWDKAYLEGKVIV<br>RDAVEAVRDIIPTMRENGADIVLVLSHSGIGDDQYEVGEENVGYQIASLSGVDAVITGHSHAEFPGTAEKPSFYAKYSGVDDTNGKING<br>TPVTMAGKYGDHLGVIDLNLVFKDGKWTTTSSKAAIRKIDTKSSVADGRIIDLAKEAHNETIKYVRQQVGETT*HHHHHH***LE** | 17 |
| SP4C-H | **MT***HHHHHH***GS**GETTAPINSFFALVQDDPSVQIVNNAQIWYAKQQLAGTSEANLPILSAAAPFKAGTRGDASAYTDIPAGPIAIKNVADL<br>YLYDNVVAILKVNGAQLKEWLEMSAGQFNQVDLSSTEPQNLVNTDFRTYNFDVIDGVTYQYDITQPNKYDRDGKIVNETASRVRNLQYN<br>GQDVTADQEFIVVTNNYRANGTFPGVREASINRLLNLENRQAIINYIIAEKVINPTADNNWTFTDSIKGLDLRFLTADRAKSLVTDQEC<br>IVYLQASTASEGFGEFKFVYTESKVVTPDEQQSDQGNTGQDIVLESGQRITLPAVNPPAPAPQHKLASPHSQASTKT**LE** | 18 |
| SP7N-H | **MTGS**DELAVQIMGVNDFHGALDMTGTARLEGETVRNAGTAALLDAYMDDSQAEFEETAAETETPAESIRVQAGDMVGASPSNSGLLQDE<br>PTVKVFNKMDVEYGTLGNHEFDEGLDEYNRIMTGEAPKKGQFNEIVDNYTREAAKQEIVIANVIDKETGEIPYGWKPYAIKTIPVNDKE<br>AKIGFIGVVTTEIPNLVLKKNYEQYTFLNEAETIAKYARELAEKGVNAIVVLAHVPATSKDGVAAGEAADMIAKLNEIYPEHSVDLVFA<br>GHNHVYTNGTTGKTLIVQATSQGKAYADVRAVYDTDIADFKAVPTAKIIAVAPGQKTPSPEIQAIVDEANTIVKK**LE***HHHHHHHH* | 19 |

Figure 13D

| | | |
|---|---|---|
| SP7C-H | **MT***HHHHHH***GS**EIQAIVDEANTIVKKVTEQKIATASQATDISREVNEFKESAVGNLVTSAQLAIAKKSGYDVDFAMTNDGGIRADLKVQE<br>DGTVTWGAAQAVQPFGNILQVVQMTGEQIYTALNQQYDEGEKYFLQMSGIKYIYTKADNPTEENPYKVVKAFKEDGTEIVPTETYTLVI<br>NDFLFGGGDGFSIFKEAKLIGAINPDTEVFVEYLTDLEKAGQTISATIPGRKAFVEKYVEEPKAEEKEDNAGTTTDVKTPEKANDGGDS<br>VTNQKATEQPAPSGSMAPISNKKTEKASGNQT**LE** | 20 |
| M2N-S | **MTGS**DTVVTGVNEIIEESQVKDEVSIESEKNESLDGSNIEIVEEIADNIPSPVIAEGEVAVEMKVDRGTENVVSRNDTEVTTSEQNQIE<br>VTETKEILNQTSYQTESGEQRQIIWAHGITPPAMEQSGGFVKEKYGDYLNYTAPFEAGKGYYDTNKSLNASFIDLNLCFAAVSSNMVHW<br>WLEQNSSYVERYLKEKKGTVNVEENYAITDLRRYINSFQNQQNSRVFDMFKTYYGYRTNGFVSDALVDLFINGYKPKAQGGVNLEDSQL<br>VPDSRGGFFYDVFKEKKLTNRIFSGSYERFGEDVRTVLESKGLLGLTYRTLGYATHIVTVWGAEYDNQGKIKAVYITDSDDQQEQIGLK<br>RMGITRDASGNPRLNNHMKNNSAGALLDYVHTIRLGQDLWEEYFN**LE***GLKTRNKKAKSDKLIVRRRNQK* | 21 |
| M2C-S | **MTGS**SEQPDSIPHQNVEISLVEPTNVETETVVTPINDAATPHGSPTYIDNSVTESVATPLEKDSIQAGETEIAEPTSSESTNVETETVV<br>TPVNDVATPHGSPTYIDNSVTESVATPLEKDSIQAGETEIAEPTSSESTNVETETVVTPVNDVATPHGSPTYIDNSVTESVATPLEKDS<br>IQAGETEIAEPTSSESTSVEAELVDNSEIHAATSSVTPCGSSAYADGSTTESVATPLEKDSIQTGNTEIAEPTSSKSTNVEAASVDNSE<br>IHADASLTAVSS**LE***GLKTRNKKAKSDKLIVRRRNQK* | 22 |
| SP2N-S | **MTGS**AETTTAATTTNQPATTDATATVPATTDATATVPATSVENVATEETVVPAAEETVEAVIIHTNDVHGRILEEKNVIGDAKAAAVIE<br>EERAKVENTIVVDAGDAFQGLPISNSTKGEDRANIMNQVGYDAMAVGNHEFDFGMDQAIKYKETLNFPLLSANTYVNGARVFEASTIVD<br>KTPTVVGDEFVVIGVTTPETATKTHPKNVEGVTFTDPVTEVNKVIDEVEARALADNRVYKNYIILAHLGVDSTTPVEWRGSTLAEALSK<br>NSKLAGKRVIVIDGHSHTVEATTYGDNVTYNQTGSYLNNIGKVTLKSDKLLGEASLISAADTKNVTPNAKIAALVD**LE***GLKTRNKKAKS*<br>*DKLIVRRRNQK* | 23 |
| SP2C-S | **MTGS**DEIKAKYEAENAQVVIENNPVELNGDRSNVRVRETNLGNAVTDAIYAYGQTGFSNKTSLAVTNGGGLRATIAKDQPVTKGDIIAV<br>LPFGNIVSQITVTGQQIYDMFTKSLSSTLQVNPETGEMLLDENGMPLFEASGGFLHISGANVFYDPTLPVEERVLLIGILNPETGEYDA<br>LDLEKTYYLATNDFLAAGGDGYTMLGGAREEGPSMDSVFAEYLKTADLSAYEVVNPYSRIIPVNSSIDTDEDGYPDFIEILLDTDPENP<br>ASNPETVPAENTDSPSNQVQNTSATDKKAPVDSPKVGDKKTEVASPAKTTKAG**LE***GLKTRNKKAKSDKLIVRRRNQK* | 24 |
| SP4N-S | **MTGS**EEILNTTPASSTEASQAVPVESDTTEEADNTESPVPATTEAENPSSSETAETSDPTSETTDTTTSEARTVTPAATETSQPVEGQT<br>VDVRILATTDLHTNLVNYDYYQDKPVETLGLAKTAVLIEEAKKENPNVVLVDNGDTIQGTPLGNYKSIVDPIEEGEQHPMYAALETLGF<br>DVGTLGNHEFNYGLAYLEKVIRTANMPLVNANVLDPTTKDFLYTPYTIVKKTFTDTEGKKVTLNVGVTGIVPPQILNWDKAYLEGKVIV<br>RDAVEAVRDIIPTMRENGADIVLVLSHSGIGDDQYEVGEENVGYQIASLSGVDAVITGHSHAEFPGTAEKPSFYAKYSGVDDTNGKING<br>TPVTMAGKYGDHLGVIDLNLVFKDGKWTTTSSKAAIRKIDTKSSVADGRIIDLAKEAHNETIKYVRQQVGETT**LE***GLKTRNKKAKSDKL*<br>*IVRRRNQK* | 25 |
| SP4C-S | **MTGS**GETTAPINSFFALVQDDPSVQIVNNAQIWYAKQQLAGTSEANLPILSAAAPFKAGTRGDASAYTDIPAGPIAIKNVADLYLYDNV<br>VAILKVNGAQLKEWLEMSAGQFNQVDLSSTEPQNLVNTDFRTYNFDVIDGVTYQYDITQPNKYDRDGKIVNETASRVRNLQYNGQDVTA<br>DQEFIVVTNNYRANGTFPGVREASINRLLNLENRQAIINYIIAEKVINPTADNNWTFTDSIKGLDLRFLTADRAKSLVTDQECIVYLQA<br>STASEGFGEFKFVYTESKVVTPDEQQSDQGNTGQDIVLESGQRITLPAVNPPAPAPQHKLASPHSQASTKT**LE***GLKTRNKKAKSDKLIV*<br>*RRRNQK* | 26 |
| SP7N-S | **MTGS**DELAVQIMGVNDFHGALDMTGTARLEGETVRNAGTAALLDAYMDDSQAEFEETAAETETPAESIRVQAGDMVGASPSNSGLLQDE<br>PTVKVFNKMDVEYGTLGNHEFDEGLDEYNRIMTGEAPKKGQFNEIVDNYTREAAKQEIVIANVIDKETGEIPYGWKPYAIKTIPVNDKE<br>AKIGFIGVVTTEIPNLVLKKNYEQYTFLNEAETIAKYARELAEKGVNAIVVLAHVPATSKDGVAAGEAADMIAKLNEIYPEHSVDLVFA | 27 |

Figure 13E

| | | |
|---|---|---|
| | GHNHVYTNGTTGKTLIVQATSQGKAYADVRAVYDTDIADFKAVPTAKIIAVAPGQKTPSPEIQAIVDEANTIVKK**LE***GLKTRNKKAKSD*<br>*KLIVRRRNQK* | |
| SP7C-S | **MTGS**EIQAIVDEANTIVKKVTEQKIATASQATDISREVNEFKESAVGNLVTSAQLAIAKKSGYDVDFAMTNDGGIRADLKVQEDGTVTW<br>GAAQAVQPFGNILQVVQMTGEQIYTALNQQYDEGEKYFLQMSGIKYIYTKADNPTEENPYKVVKAFKEDGTEIVPTETYTLVINDFLFG<br>GGDGFSIFKEAKLIGAINPDTEVFVEYLTDLEKAGQTISATIPGRKAFVEKYVEEPKAEEKEDNAGTTTDVKTPEKANDGGDSVTNQKA<br>TEQPAPSGSMAPISNKKTEKASGNQT**LE***GLKTRNKKAKSDKLIVRRRNQK* | 28 |
| M2N-LSL | **MT***KPALGLKTRNKKAKSDKLIVRRRNQK***GS**DTVVTGVNEIIEESQVKDEVSIESEKNESLDGSNIEIVEEIADNIPSPVIAEGEVAVEM<br>KVDRGTENVVSRNDTEVTTSEQNQIEVTETKEILNQTSYQTESGEQRQIIWAHGITPPAMEQSGGFVKEKYGDYLNYTAPFEAGKGYYD<br>TNKSLNASFIDLNLCFAAVSSNMVHWWLEQNSSYVERYLKEKKGTVNVEENYAITDLRRYINSFQNQQNSRVFDMFKTYYGYRTNGFVS<br>DALVDLFINGYKPKAQGGVNLEDSQLVPDSRGGFFYDVFKEKKLTNRIFSGSYERFGEDVRTVLESKGLLGLTYRTLGYATHIVTVWGA<br>EYDNQGKIKAVYITDSDDQQEQIGLKRMGITRDASGNPRLNNHMKNNSAGALLDYVHTIRLGQDLWEEYFN**LE** | 29 |
| SP2C-LSL | **MT***KPALGLKTRNKKAKSDKLIVRRRNQK***GS**DEIKAKYEAENAQVVIENNPVELNGDRSNVRVRETNLGNAVTDAIYAYGQTGFSNKTSL<br>AVTNGGGLRATIAKDQPVTKGDIIAVLPFGNIVSQITVTGQQIYDMFTKSLSSTLQVNPETGEMLLDENGMPLFEASGGFLHISGANVF<br>YDPTLPVEERVLLIGILNPETGEYDALDLEKTYYLATNDFLAAGGDGYTMLGGAREEGPSMDSVFAEYLKTADLSAYEVVNPYSRIIPV<br>NSSIDTDEDGYPDFIEILLDTDPENPASNPETVPAENTDSPSNQVQNTSATDKKAPVDSPKVGDKKTEVASPAKTTKAG**LE** | 30 |
| IdeE-S | **MTGS**DDYQRNATEAYAKEVPHQITSVWTKGVTPLTPEQFRYNNEDVIHAPYLAHQGWYDITKAFDGKDNLLCGAATAGNMLHWWFDQNK<br>TEIEAYLSKHPEKQKIIFNNQELFDLKAAIDTKDSQTNSQLFNYFRDKAFPNLSARQLGVMPDLVLDMFINGYYLNVFKTQSTDVNRPY<br>QDKDKRGGIFDAVFTRGDQTTLLTARHDLKNKGLNDISTIIKQELTEGRALALSHTYANVSISHVINLWGADFNAEGNLEAIYVTDSDA<br>NASIGMKKYFVGINAHRHVAISAKKIEGENIGAQVLGLFTLSSGKDIWQKLS**LE***GLKTRNKKAKSDKLIVRRRNQK* | 31 |
| SL2-tag | *GLKTRNKKAKSDKLIVRRRNQK* | 32 |
| LSL-tag | *KPALGLKTRNKKAKSDKLIVRRRNQK* | 33 |
| SP2M2 | DEIKAKYEAENAQVVIENNPVELNGDRSNVRVRETNLGNAVTDAIYAYGQTGFSNKTSLAVTNGGGLRATIAKDQPVTKGDIIAVLPFG<br>NIVSQITVTGQQIYDMFTKSLSSTLQVNPETGEMLLDENGMPLFEASGGFLHISGANVFYDPTLPVEERVLLIGILNPETGEYDALDLE<br>KTYYLATNDFLAAGGDGYTMLGGAREEGPSMDSVFAEYLKTADLSAYEVVNPYSRIIPVNSSIDTDEDGYPDFIEILLDTDPENPASNP<br>ETVPAENTDSPSNQVQNTSATDKKAPVDSPKVGDKKTEVASPAKTTKAG**GT**DTVVTGVNEIIEESQVKDEVSIESEKNESLDGSNIEIV<br>EEIADNIPSPVIAEGEVAVEMKVDRGTENVVSRNDTEVTTSEQNQIEVTETKEILNQTSYQTESGEQRQIIWAHGITPPAMEQSGGFVK<br>EKYGDYLNYTAPFEAGKGYYDTNKSLNASFIDLNLCFAAVSSNMVHWWLEQNSSYVERYLKEKKGTVNVEENYAITDLRRYINSFQNQQ<br>NSRVFDMFKTYYGYRTNGFVSDALVDLFINGYKPKAQGGVNLEDSQLVPDSRGGFFYDVFKEKKLTNRIFSGSYERFGEDVRTVLESKG<br>LLGLTYRTLGYATHIVTVWGAEYDNQGKIKAVYITDSDDQQEQIGLKRMGITRDASGNPRLNNHMKNNSAGALLDYVHTIRLGQDLWEE<br>YFNPLAKAK | 34 |
| SP74C | EIQAIVDEANTIVKKVTEQKIATASQATDISREVNEFKESAVGNLVTSAQLAIAKKSGYDVDFAMTNDGGIRADLKVQEDGTVTWGAAQ<br>AVQPFGNILQVVQMTGEQIYTALNQQYDEGEKYFLQMSGIKYIYTKADNPTEENPYKVVKAFKEDGTEIVPTETYTLVINDFLFGGGDG<br>FSIFKEAKLIGAINPDTEVFVEYLTDLEKAGQTISATIPGRKAFVEKYVEEPKAEEKEDNAGTTTDVKTPEKANDGGDSVTNQKATEQP<br>APSGSMAPISNKKTEKASGNQT**GT**GETTAPINSFFALVQDDPSVQIVNNAQIWYAKQQLAGTSEANLPILSAAAPFKAGTRGDASAYTD<br>IPAGPIAIKNVADLYLYDNVVAILKVNGAQLKEWLEMSAGQFNQVDLSSTEPQNLVNTDFRTYNFDVIDGVTYQYDITQPNKYDRDGKI | 35 |

Figure 13F

| | | |
|---|---|---|
| | VNETASRVRNLQYNGQDVTADQEFIVVTNNYRANGTFPGVREASINRLLNLENRQAIINYIIAEKVINPTADNNWTFTDSIKGLDLRFLTADRAKSLVTDQECIVYLQASTASEGFGEFKFVYTESKVVTPDEQQSDQGNTGQDIVLESGQRITLPAVNPPAPAPQHKLASPHSQASTKT | |
| SP2M2-S | **MTGS**DEIKAKYEAENAQVVIENNPVELNGDRSNVRVRETNLGNAVTDAIYAYGQTGFSNKTSLAVTNGGGLRATIAKDQPVTKGDIIAVLPFGNIVSQITVTGQQIYDMFTKSLSSTLQVNPETGEMLLDENGMPLFEASGGFLHISGANVFYDPTLPVEERVLLIGILNPETGEYDALDLEKTYYLATNDFLAAGGDGYTMLGGAREEGPSMDSVFAEYLKTADLSAYEVVNPYSRIIPVNSSIDTDEDGYPDFIEILLDTDPENPASNPETVPAENTDSPSNQVQNTSATDKKAPVDSPKVGDKKTEVASPAKTTKAG**GT**DTVVTGVNEIIEESQVKDEVSIESEKNESLDGSNIEIVEEIADNIPSPVIAEGEVAVEMKVDRGTENVVSRNDTEVTTSEQNQIEVTETKEILNQTSYQTESGEQRQIIWAHGITPPAMEQSGGFVKEKYGDYLNYTAPFEAGKGYYDTNKSLNASFIDLNLCFAAVSSNMVHWWLEQNSSYVERYLKEKKGTVNVEENYAITDLRRYINSFQNQQNSRVFDMFKTYYGYRTNGFVSDALVDLFINGYKPKAQGGVNLEDSQLVPDSRGGFFYDVFKEKKLTNRIFSGSYERFGEDVRTVLESKGLLGLTYRTLGYATHIVTVWGAEYDNQGKIKAVYITDSDDQQEQIGLKRMGITRDASGNPRLNNHMKNNSAGALLDYVHTIRLGQDLWEEYFNPLAKAK**LE***GLKTRNKKAKSDKLIVRRRNQK* | 36 |
| SP74C-S | **MTGS**EIQAIVDEANTIVKKVTEQKIATASQATDISREVNEFKESAVGNLVTSAQLAIAKKSGYDVDFAMTNDGGIRADLKVQEDGTVTWGAAQAVQPFGNILQVVQMTGEQIYTALNQQYDEGEKYFLQMSGIKYIYTKADNPTEENPYKVVKAFKEDGTEIVPTETYTLVINDFLFGGGDGFSIFKEAKLIGAINPDTEVFVEYLTDLEKAGQTISATIPGRKAFVEKYVEEPKAEEKEDNAGTTTDVKTPEKANDGGDSVTNQKATEQPAPSGSMAPISNKKTEKASGNQT**GT**GETTAPINSFFALVQDDPSVQIVNNAQIWYAKQQLAGTSEANLPILSAAAPFKAGTRGDASAYTDIPAGPIAIKNVADLYLYDNVVAILKVNGAQLKEWLEMSAGQFNQVDLSSTEPQNLVNTDFRTYNFDVIDGVTYQYDITQPNKYDRDGKIVNETASRVRNLQYNGQDVTADQEFIVVTNNYRANGTFPGVREASINRLLNLENRQAIINYIIAEKVINPTADNNWTFTDSIKGLDLRFLTADRAKSLVTDQECIVYLQASTASEGFGEFKFVYTESKVVTPDEQQSDQGNTGQDIVLESGQRITLPAVNPPAPAPQHKLASPHSQASTKT**LE***GLKTRNKKAKSDKLIVRRRNQK* | 37 |
| M2N$_{long}$ | DTVVTGVNEIIEESQVKDEVSIESEKNESLDGSNIEIVEEIADNIPSPVIAEGEVAVEMKVDRGTENVVSRNDTEVTTSEQNQIEVTETKEILNQTSYQTESGEQRQIIWAHGITPPAMEQSGGFVKEKYGDYLNYTAPFEAGKGYYDTNKSLNASFIDLNLCFAAVSSNMVHWWLEQNSSYVERYLKEKKGTVNVEENYAITDLRRYINSFQNQQNSRVFDMFKTYYGYRTNGFVSDALVDLFINGYKPKAQGGVNLEDSQLVPDSRGGFFYDVFKEKKLTNRIFSGSYERFGEDVRTVLESKGLLGLTYRTLGYATHIVTVWGAEYDNQGKIKAVYITDSDDQQEQIGLKRMGITRDASGNPRLNNHMKNNSAGALLDYVHTIRLGQDLWEEYFNPLAKAK | 38 |
| SP274C | DEIKAKYEAENAQVVIENNPVELNGDRSNVRVRETNLGNAVTDAIYAYGQTGFSNKTSLAVTNGGGLRATIAKDQPVTKGDIIAVLPFGNIVSQITVTGQQIYDMFTKSLSSTLQVNPETGEMLLDENGMPLFEASGGFLHISGANVFYDPTLPVEERVLLIGILNPETGEYDALDLEKTYYLATNDFLAAGGDGYTMLGGAREEGPSMDSVFAEYLKTADLSAYEVVNPYSRIIPVNSSIDTDEDGYPDFIEILLDTDPENPASNPETVPAENTDSPSNQVQNTSATDKKAPVDSPKVGDKKTEVASPAKTTKAG**EF**EIQAIVDEANTIVKKVTEQKIATASQATDISREVNEFKESAVGNLVTSAQLAIAKKSGYDVDFAMTNDGGIRADLKVQEDGTVTWGAAQAVQPFGNILQVVQMTGEQIYTALNQQYDEGEKYFLQMSGIKYIYTKADNPTEENPYKVVKAFKEDGTEIVPTETYTLVINDFLFGGGDGFSIFKEAKLIGAINPDTEVFVEYLTDLEKAGQTISATIPGRKAFVEKYVEEPKAEEKEDNAGTTTDVKTPEKANDGGDSVTNQKATEQPAPSGSMAPISNKKTEKASGNQT**GT**GETTAPINSFFALVQDDPSVQIVNNAQIWYAKQQLAGTSEANLPILSAAAPFKAGTRGDASAYTDIPAGPIAIKNVADLYLYDNVVAILKVNGAQLKEWLEMSAGQFNQVDLSSTEPQNLVNTDFRTYNFDVIDGVTYQYDITQPNKYDRDGKIVNETASRVRNLQYNGQDVTADQEFIVVTNNYRANGTFPGVREASINRLLNLENRQAIINYIIAEKVINPTADNNWTFTDSIKGLDLRFLTADRAKSLVTDQECIVYLQASTASEGFGEFKFVYTESKVVTPDEQQSDQGNTGQDIVLESGQRITLPAVNPPAPAPQHKLASPHSQASTKT | 107 |

Figure 13G

| | | |
|---|---|---|
| SP742C | EIQAIVDEANTIVKKVTEQKIATASQATDISREVNEFKESAVGNLVTSAQLAIAKKSGYDVDFAMTNDGGIRADLKVQEDGTVTWGAAQ<br>AVQPFGNILQVVQMTGEQIYTALNQQYDEGEKYFLQMSGIKYIYTKADNPTEENPYKVVKAFKEDGTEIVPTETYTLVINDFLFGGGDG<br>FSIFKEAKLIGAINPDTEVFVEYLTDLEKAGQTISATIPGRKAFVEKYVEEPKAEEKEDNAGTTTDVKTPEKANDGGDSVTNQKATEQP<br>APSGSMAPISNKKTEKASGNQT**GT**GETTAPINSFFALVQDDPSVQIVNNAQIWYAKQQLAGTSEANLPILSAAAPFKAGTRGDASAYTD<br>IPAGPIAIKNVADLYLYDNVVAILKVNGAQLKEWLEMSAGQFNQVDLSSTEPQNLVNTDFRTYNFDVIDGVTYQYDITQPNKYDRDGKI<br>VNETASRVRNLQYNGQDVTADQEFIVVTNNYRANGTFPGVREASINRLLNLENRQAIINYIIAEKVINPTADNNWTFTDSIKGLDLRFL<br>TADRAKSLVTDQECIVYLQASTASEGFGEFKFVYTESKVVTPDEQQSDQGNTGQDIVLESGQRITLPAVNPPAPAPQHKLASPHSQAST<br>KT**EF**DEIKAKYEAENAQVVIENNPVELNGDRSNVRVRETNLGNAVTDAIYAYGQTGFSNKTSLAVTNGGGLRATIAKDQPVTKGDIIAV<br>LPFGNIVSQITVTGQQIYDMFTKSLSSTLQVNPETGEMLLDENGMPLFEASGGFLHISGANVFYDPTLPVEERVLLIGILNPETGEYDA<br>LDLEKTYYLATNDFLAAGGDGYTMLGGAREEGPSMDSVFAEYLKTADLSAYEVVNPYSRIIPVNSSIDTDEDGYPDFIEILLDTDPENP<br>ASNPETVPAENTDSPSNQVQNTSATDKKAPVDSPKVGDKKTEVASPAKTTKAG | 108 |
| SP274C-<br>S | **MTGS**DEIKAKYEAENAQVVIENNPVELNGDRSNVRVRETNLGNAVTDAIYAYGQTGFSNKTSLAVTNGGGLRATIAKDQPVTKGDIIAV<br>LPFGNIVSQITVTGQQIYDMFTKSLSSTLQVNPETGEMLLDENGMPLFEASGGFLHISGANVFYDPTLPVEERVLLIGILNPETGEYDA<br>LDLEKTYYLATNDFLAAGGDGYTMLGGAREEGPSMDSVFAEYLKTADLSAYEVVNPYSRIIPVNSSIDTDEDGYPDFIEILLDTDPENP<br>ASNPETVPAENTDSPSNQVQNTSATDKKAPVDSPKVGDKKTEVASPAKTTKAG**EF**EIQAIVDEANTIVKKVTEQKIATASQATDISREV<br>NEFKESAVGNLVTSAQLAIAKKSGYDVDFAMTNDGGIRADLKVQEDGTVTWGAAQAVQPFGNILQVVQMTGEQIYTALNQQYDEGEKYF<br>LQMSGIKYIYTKADNPTEENPYKVVKAFKEDGTEIVPTETYTLVINDFLFGGGDGFSIFKEAKLIGAINPDTEVFVEYLTDLEKAGQTI<br>SATIPGRKAFVEKYVEEPKAEEKEDNAGTTTDVKTPEKANDGGDSVTNQKATEQPAPSGSMAPISNKKTEKASGNQT**GT**GETTAPINSF<br>FALVQDDPSVQIVNNAQIWYAKQQLAGTSEANLPILSAAAPFKAGTRGDASAYTDIPAGPIAIKNVADLYLYDNVVAILKVNGAQLKEW<br>LEMSAGQFNQVDLSSTEPQNLVNTDFRTYNFDVIDGVTYQYDITQPNKYDRDGKIVNETASRVRNLQYNGQDVTADQEFIVVTNNYRAN<br>GTFPGVREASINRLLNLENRQAIINYIIAEKVINPTADNNWTFTDSIKGLDLRFLTADRAKSLVTDQECIVYLQASTASEGFGEFKFVY<br>TESKVVTPDEQQSDQGNTGQDIVLESGQRITLPAVNPPAPAPQHKLASPHSQASTKT**LE***GLKTRNKKAKSDKLIVRRRNQK* | 109 |
| SP742C-<br>s | **MTGS**EIQAIVDEANTIVKKVTEQKIATASQATDISREVNEFKESAVGNLVTSAQLAIAKKSGYDVDFAMTNDGGIRADLKVQEDGTVTW<br>GAAQAVQPFGNILQVVQMTGEQIYTALNQQYDEGEKYFLQMSGIKYIYTKADNPTEENPYKVVKAFKEDGTEIVPTETYTLVINDFLFG<br>GGDGFSIFKEAKLIGAINPDTEVFVEYLTDLEKAGQTISATIPGRKAFVEKYVEEPKAEEKEDNAGTTTDVKTPEKANDGGDSVTNQKA<br>TEQPAPSGSMAPISNKKTEKASGNQT**GT**GETTAPINSFFALVQDDPSVQIVNNAQIWYAKQQLAGTSEANLPILSAAAPFKAGTRGDAS<br>AYTDIPAGPIAIKNVADLYLYDNVVAILKVNGAQLKEWLEMSAGQFNQVDLSSTEPQNLVNTDFRTYNFDVIDGVTYQYDITQPNKYDR<br>DGKIVNETASRVRNLQYNGQDVTADQEFIVVTNNYRANGTFPGVREASINRLLNLENRQAIINYIIAEKVINPTADNNWTFTDSIKGLD<br>LRFLTADRAKSLVTDQECIVYLQASTASEGFGEFKFVYTESKVVTPDEQQSDQGNTGQDIVLESGQRITLPAVNPPAPAPQHKLASPHS<br>QASTKT**EF**DEIKAKYEAENAQVVIENNPVELNGDRSNVRVRETNLGNAVTDAIYAYGQTGFSNKTSLAVTNGGGLRATIAKDQPVTKGD<br>IIAVLPFGNIVSQITVTGQQIYDMFTKSLSSTLQVNPETGEMLLDENGMPLFEASGGFLHISGANVFYDPTLPVEERVLLIGILNPETG<br>EYDALDLEKTYYLATNDFLAAGGDGYTMLGGAREEGPSMDSVFAEYLKTADLSAYEVVNPYSRIIPVNSSIDTDEDGYPDFIEILLDTD<br>PENPASNPETVPAENTDSPSNQVQNTSATDKKAPVDSPKVGDKKTEVASPAKTTKAG**LE***GLKTRNKKAKSDKLIVRRRNQK* | 110 |

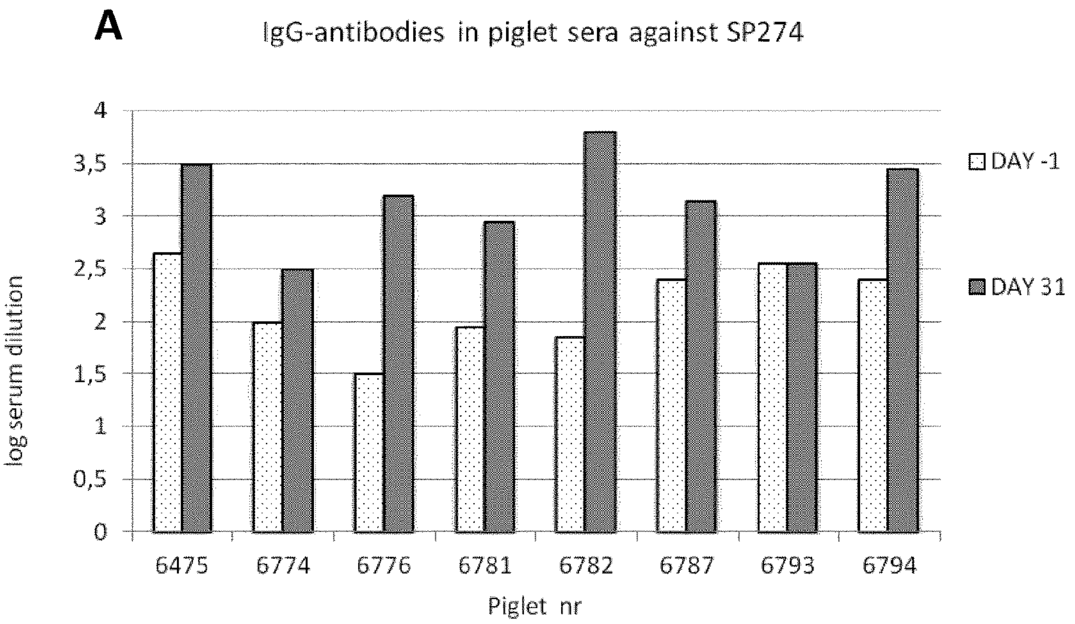
Figure 17
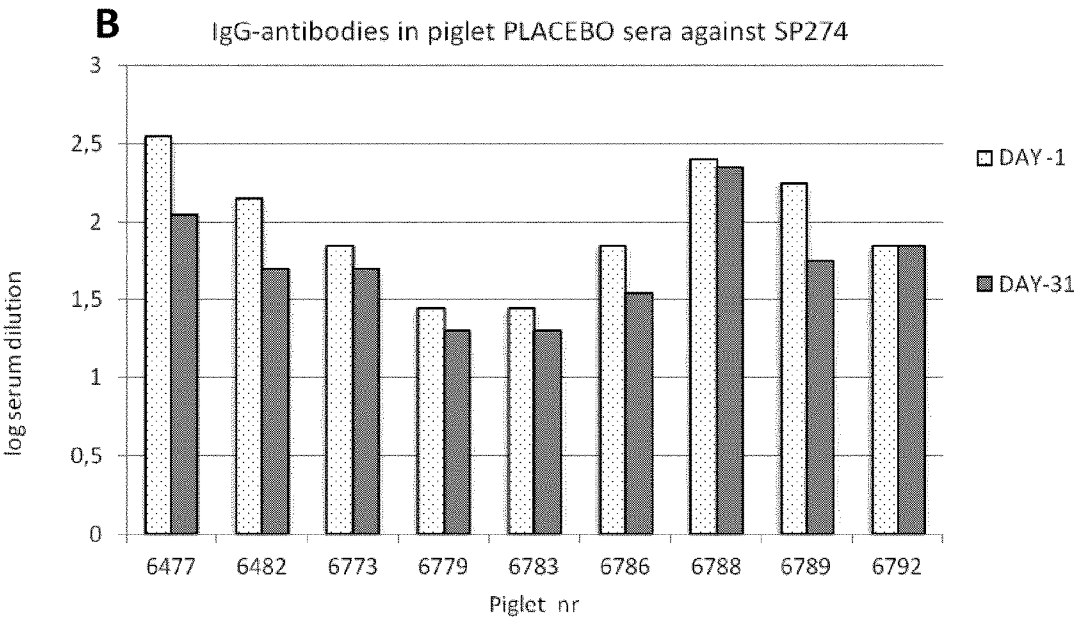

SEQUENCE LISTING

```
<160> NUMBER OF SEQ ID NOS: 129

<210> SEQ ID NO 1
<211> LENGTH: 1141
<212> TYPE: PRT
<213> ORGANISM: STREPTOCOCCUS SUIS

<400> SEQUENCE: 1
```

-continued

```
Met Asn Ile Gln Glu Arg Phe Ser Leu Arg Lys Ser Ala Val Gly Leu
1               5                   10                  15

Val Ser Val Ser Leu Leu Cys Ala Ile Tyr Thr Ser Thr Val Ala Ala
            20                  25                  30

Asp Thr Val Val Thr Gly Val Asn Glu Ile Ile Glu Glu Ser Gln Val
        35                  40                  45

Lys Asp Glu Val Ser Ile Glu Ser Glu Lys Asn Glu Ser Leu Asp Gly
    50                  55                  60

Ser Asn Ile Glu Ile Val Glu Glu Ile Ala Asp Asn Ile Pro Ser Pro
65                  70                  75                  80

Val Ile Ala Glu Gly Glu Val Ala Val Glu Met Lys Val Asp Arg Gly
                85                  90                  95

Thr Glu Asn Val Val Ser Arg Asn Asp Thr Glu Val Thr Thr Ser Glu
            100                 105                 110

Gln Asn Gln Ile Glu Val Thr Glu Thr Lys Glu Ile Leu Asn Gln Thr
        115                 120                 125

Ser Tyr Gln Thr Glu Ser Gly Glu Gln Arg Gln Ile Ile Trp Ala His
    130                 135                 140

Gly Ile Thr Pro Pro Ala Met Glu Gln Ser Gly Gly Phe Val Lys Glu
145                 150                 155                 160

Lys Tyr Gly Asp Tyr Leu Asn Tyr Thr Ala Pro Phe Glu Ala Gly Lys
                165                 170                 175

Gly Tyr Tyr Asp Thr Asn Lys Ser Leu Asn Ala Ser Phe Ile Asp Leu
            180                 185                 190

Asn Leu Cys Phe Ala Ala Val Ser Ser Asn Met Val His Trp Trp Leu
        195                 200                 205

Glu Gln Asn Ser Ser Tyr Val Glu Arg Tyr Leu Lys Glu Lys Lys Gly
    210                 215                 220

Thr Val Asn Val Glu Glu Asn Tyr Ala Ile Thr Asp Leu Arg Arg Tyr
225                 230                 235                 240

Ile Asn Ser Phe Gln Asn Gln Gln Asn Ser Arg Val Phe Asp Met Phe
                245                 250                 255

Lys Thr Tyr Tyr Gly Tyr Arg Thr Asn Gly Phe Val Ser Asp Ala Leu
            260                 265                 270

Val Asp Leu Phe Ile Asn Gly Tyr Lys Pro Lys Ala Gln Gly Gly Val
        275                 280                 285

Asn Leu Glu Asp Ser Gln Leu Val Pro Asp Ser Arg Gly Gly Phe Phe
    290                 295                 300

Tyr Asp Val Phe Lys Glu Lys Lys Leu Thr Asn Arg Ile Phe Ser Gly
305                 310                 315                 320

Ser Tyr Glu Arg Phe Gly Glu Asp Val Arg Thr Val Leu Glu Ser Lys
                325                 330                 335

Gly Leu Leu Gly Leu Thr Tyr Arg Thr Leu Gly Tyr Ala Thr His Ile
            340                 345                 350

Val Thr Val Trp Gly Ala Glu Tyr Asp Asn Gln Gly Lys Ile Lys Ala
        355                 360                 365

Val Tyr Ile Thr Asp Ser Asp Asp Gln Gln Glu Gln Ile Gly Leu Lys
    370                 375                 380

Arg Met Gly Ile Thr Arg Asp Ala Ser Gly Asn Pro Arg Leu Asn Asn
385                 390                 395                 400

His Met Lys Asn Asn Ser Ala Gly Ala Leu Leu Asp Tyr Val His Thr
                405                 410                 415

Ile Arg Leu Gly Gln Asp Leu Trp Glu Glu Tyr Phe Asn Pro Leu Ala
```

-continued

```
            420                 425                 430

Lys Ala Lys Glu Thr Ala Ser Gln Thr Leu Ala Asp Thr Lys Lys Ala
        435                 440                 445

Leu Asp Leu Ser Ile Gln Gly Gln Ser Glu Leu Pro Glu Ser Met Arg
    450                 455                 460

Leu Ile Tyr Leu Glu Lys Leu Asn Asn Leu Tyr Asn Gln Gly Ile Leu
465                 470                 475                 480

Ser Ile Gln Lys Ala Glu Ser Ser Glu Met Leu Ser Gly Ala Leu Glu
                485                 490                 495

Asn Gly Leu Asn Ser Leu Lys Ser Leu Asp Phe Pro Ile Ser Glu Val
            500                 505                 510

Gly Asn Ala Leu Ala Pro Asp Leu Pro Val Gly Asp Arg Ser Thr Val
        515                 520                 525

Ser Asp Val Asp Ser Leu Ser Ser Gln Glu Thr Ser Ser Thr Asn Leu
    530                 535                 540

Glu Ala Asp Thr Glu Asn Ala Gly Ile Ile Ala Asp Gly Thr Asn Gln
545                 550                 555                 560

Leu His Phe Pro Val Glu Ala Gln Thr Thr Ser Ser Val Glu Ala Glu
                565                 570                 575

Gly Asp Asn Val Phe Glu Gln Glu Ala Asp Thr Leu Pro Ile Ile Ile
            580                 585                 590

Glu Asn Lys Asp Glu Phe Gly Ser Glu Leu Ser Arg Asn Met Gln Thr
        595                 600                 605

Ser Glu Thr Asp Ser Leu Val Val Ala Val Glu Glu Asp Val Lys Asn
    610                 615                 620

Asp Glu Val Ala Gln Val Glu Glu Leu Leu Glu Ser Glu Lys Val Glu
625                 630                 635                 640

Asn Gln Ser Ser Glu Leu Leu Ser Asp Thr Leu Ile Val Glu Ser Ala
                645                 650                 655

Asn Asp Lys Glu Glu Asp Arg Val Glu Ala Val Val Ser Glu Gln Pro
            660                 665                 670

Asp Ser Ile Pro His Gln Asn Val Glu Ile Ser Leu Val Glu Pro Thr
        675                 680                 685

Asn Val Glu Thr Glu Thr Val Val Thr Pro Ile Asn Asp Ala Ala Thr
    690                 695                 700

Pro His Gly Ser Pro Thr Tyr Ile Asp Asn Ser Val Thr Glu Ser Val
705                 710                 715                 720

Ala Thr Pro Leu Glu Lys Asp Ser Ile Gln Ala Gly Glu Thr Glu Ile
                725                 730                 735

Ala Glu Pro Thr Ser Ser Glu Ser Thr Asn Val Glu Thr Glu Thr Val
            740                 745                 750

Val Thr Pro Val Asn Asp Val Ala Thr Pro His Gly Ser Pro Thr Tyr
        755                 760                 765

Ile Asp Asn Ser Val Thr Glu Ser Val Ala Thr Pro Leu Glu Lys Asp
    770                 775                 780

Ser Ile Gln Ala Gly Glu Thr Glu Ile Ala Glu Pro Thr Ser Ser Glu
785                 790                 795                 800

Ser Thr Asn Val Glu Thr Glu Thr Val Val Thr Pro Val Asn Asp Val
                805                 810                 815

Ala Thr Pro His Gly Ser Pro Thr Tyr Ile Asp Asn Ser Val Thr Glu
            820                 825                 830

Ser Val Ala Thr Pro Leu Glu Lys Asp Ser Ile Gln Ala Gly Glu Thr
        835                 840                 845
```

-continued

```
Glu Ile Ala Glu Pro Thr Ser Ser Glu Ser Thr Ser Val Glu Ala Glu
    850                 855                 860

Leu Val Asp Asn Ser Glu Ile His Ala Ala Thr Ser Ser Val Thr Pro
865                 870                 875                 880

Cys Gly Ser Ser Ala Tyr Ala Asp Gly Ser Thr Thr Glu Ser Val Ala
                885                 890                 895

Thr Pro Leu Glu Lys Asp Ser Ile Gln Thr Gly Asn Thr Glu Ile Ala
            900                 905                 910

Glu Pro Thr Ser Ser Lys Ser Thr Asn Val Glu Ala Ala Ser Val Asp
        915                 920                 925

Asn Ser Glu Ile His Ala Asp Ala Ser Leu Thr Ala Val Ser Ser Val
    930                 935                 940

Asn Leu Asp Asn Pro Val Ile Glu Pro Val Ala Ile Ser Leu Ile Gly
945                 950                 955                 960

Ser Lys Arg Asp Thr Asn Ala Glu Val Glu Val Ser Ser Leu Ser Lys
                965                 970                 975

Arg Glu Val Arg Lys Thr Asn Thr Asp Gly Leu Ile Ser Val Gln Ser
            980                 985                 990

Lys Val Ile Lys Lys Glu Leu Leu  Glu Ser Ser Leu Ala  Glu Ala Gly
        995                 1000                1005

Ser Pro  Leu Leu Glu Ala Thr  Ile Ala Gln Ser Ser  Asn Ser Asn
    1010                1015                1020

Ser Thr  Glu Ile Gly Met Ser  Tyr Gln Asn Thr Val  Leu Leu Glu
    1025                1030                1035

Ser Asn  Asn Thr Glu Arg Gln  Val Ser Lys Ala Glu  Ile Val Met
    1040                1045                1050

Glu His  Lys Glu Thr Glu Leu  Val Glu Thr Val Ser  Ser Ala Ser
    1055                1060                1065

Glu Pro  Val Val Leu Val Glu  Asn Ile Ser Gln Thr  Ser Asn Asn
    1070                1075                1080

Thr Ile  Glu Ser Gly Lys Asn  Met Gly Val Gln Ser  Gln Ala Gly
    1085                1090                1095

Ala Lys  Gln Ile Leu Gly Val  Glu Gln Ser Ser Lys  Val Ser Thr
    1100                1105                1110

Pro Thr  Ser Arg Gln Ile Met  Gly Val Gly Leu Leu  Thr Leu Val
    1115                1120                1125

Leu Gly  Ser Ala Leu Gly Leu  Leu Lys Lys Arg Arg  Lys
    1130                1135                1140


<210> SEQ ID NO 2
<211> LENGTH: 721
<212> TYPE: PRT
<213> ORGANISM: STREPTOCOCCUS SUIS

<400> SEQUENCE: 2

Met Pro Lys Lys Gly Leu Phe Met Lys Lys Lys Lys Ile Leu Leu Pro
1               5                   10                  15

Val Met Ser Thr Leu Leu Leu Ala Pro Phe Val Leu Ala Gln Gln Val
            20                  25                  30

Gln Ala Ala Glu Thr Thr Thr Ala Ala Thr Thr Thr Asn Gln Pro Ala
        35                  40                  45

Thr Thr Asp Ala Thr Ala Thr Val Pro Ala Thr Thr Asp Ala Thr Ala
    50                  55                  60

Thr Val Pro Ala Thr Ser Val Glu Asn Val Ala Thr Glu Glu Thr Val
```

-continued

```
65                  70                  75                  80

Val Pro Ala Ala Glu Glu Thr Val Glu Ala Val Ile Ile His Thr Asn
                85                  90                  95

Asp Val His Gly Arg Ile Leu Glu Glu Lys Asn Val Ile Gly Asp Ala
            100                 105                 110

Lys Ala Ala Ala Val Ile Glu Glu Glu Arg Ala Lys Val Glu Asn Thr
        115                 120                 125

Ile Val Val Asp Ala Gly Asp Ala Phe Gln Gly Leu Pro Ile Ser Asn
    130                 135                 140

Ser Thr Lys Gly Glu Asp Arg Ala Asn Ile Met Asn Gln Val Gly Tyr
145                 150                 155                 160

Asp Ala Met Ala Val Gly Asn His Glu Phe Asp Phe Gly Met Asp Gln
                165                 170                 175

Ala Ile Lys Tyr Lys Glu Thr Leu Asn Phe Pro Leu Leu Ser Ala Asn
            180                 185                 190

Thr Tyr Val Asn Gly Ala Arg Val Phe Glu Ala Ser Thr Ile Val Asp
        195                 200                 205

Lys Thr Pro Thr Val Val Gly Asp Glu Phe Val Val Ile Gly Val Thr
    210                 215                 220

Thr Pro Glu Thr Ala Thr Lys Thr His Pro Lys Asn Val Glu Gly Val
225                 230                 235                 240

Thr Phe Thr Asp Pro Val Thr Glu Val Asn Lys Val Ile Asp Glu Val
                245                 250                 255

Glu Ala Arg Ala Leu Ala Asp Asn Arg Val Tyr Lys Asn Tyr Ile Ile
            260                 265                 270

Leu Ala His Leu Gly Val Asp Ser Thr Thr Pro Val Glu Trp Arg Gly
        275                 280                 285

Ser Thr Leu Ala Glu Ala Leu Ser Lys Asn Ser Lys Leu Ala Gly Lys
    290                 295                 300

Arg Val Ile Val Ile Asp Gly His Ser His Thr Val Glu Ala Thr Thr
305                 310                 315                 320

Tyr Gly Asp Asn Val Thr Tyr Asn Gln Thr Gly Ser Tyr Leu Asn Asn
                325                 330                 335

Ile Gly Lys Val Thr Leu Lys Ser Asp Lys Leu Leu Gly Glu Ala Ser
            340                 345                 350

Leu Ile Ser Ala Ala Asp Thr Lys Asn Val Thr Pro Asn Ala Lys Ile
        355                 360                 365

Ala Ala Leu Val Asp Glu Ile Lys Ala Lys Tyr Glu Ala Glu Asn Ala
    370                 375                 380

Gln Val Val Ile Glu Asn Asn Pro Val Glu Leu Asn Gly Asp Arg Ser
385                 390                 395                 400

Asn Val Arg Val Arg Glu Thr Asn Leu Gly Asn Ala Val Thr Asp Ala
                405                 410                 415

Ile Tyr Ala Tyr Gly Gln Thr Gly Phe Ser Asn Lys Thr Ser Leu Ala
            420                 425                 430

Val Thr Asn Gly Gly Gly Leu Arg Ala Thr Ile Ala Lys Asp Gln Pro
        435                 440                 445

Val Thr Lys Gly Asp Ile Ile Ala Val Leu Pro Phe Gly Asn Ile Val
    450                 455                 460

Ser Gln Ile Thr Val Thr Gly Gln Gln Ile Tyr Asp Met Phe Thr Lys
465                 470                 475                 480

Ser Leu Ser Ser Thr Leu Gln Val Asn Pro Glu Thr Gly Glu Met Leu
                485                 490                 495
```

-continued

```
Leu Asp Glu Asn Gly Met Pro Leu Phe Glu Ala Ser Gly Gly Phe Leu
            500                 505                 510

His Ile Ser Gly Ala Asn Val Phe Tyr Asp Pro Thr Leu Pro Val Glu
        515                 520                 525

Glu Arg Val Leu Leu Ile Gly Ile Leu Asn Pro Glu Thr Gly Glu Tyr
    530                 535                 540

Asp Ala Leu Asp Leu Glu Lys Thr Tyr Tyr Leu Ala Thr Asn Asp Phe
545                 550                 555                 560

Leu Ala Ala Gly Gly Asp Gly Tyr Thr Met Leu Gly Gly Ala Arg Glu
                565                 570                 575

Glu Gly Pro Ser Met Asp Ser Val Phe Ala Glu Tyr Leu Lys Thr Ala
            580                 585                 590

Asp Leu Ser Ala Tyr Glu Val Val Asn Pro Tyr Ser Arg Ile Ile Pro
        595                 600                 605

Val Asn Ser Ser Ile Asp Thr Asp Glu Asp Gly Tyr Pro Asp Phe Ile
    610                 615                 620

Glu Ile Leu Leu Asp Thr Asp Pro Glu Asn Pro Ala Ser Asn Pro Glu
625                 630                 635                 640

Thr Val Pro Ala Glu Asn Thr Asp Ser Pro Ser Asn Gln Val Gln Asn
                645                 650                 655

Thr Ser Ala Thr Asp Lys Lys Ala Pro Val Asp Ser Pro Lys Val Gly
            660                 665                 670

Asp Lys Lys Thr Glu Val Ala Ser Pro Ala Lys Thr Thr Lys Ala Gly
        675                 680                 685

Val Leu Pro Asn Thr Gly Asp Gln Met Asn Leu Thr Leu Ser Leu Phe
    690                 695                 700

Gly Leu Gly Leu Ala Gly Leu Ala Val Ala Val Gly Arg Arg Lys Glu
705                 710                 715                 720

Asn


<210> SEQ ID NO 3
<211> LENGTH: 813
<212> TYPE: PRT
<213> ORGANISM: STREPTOCOCCUS SUIS

<400> SEQUENCE: 3

Met Asn Phe Arg Phe Ser Lys Cys Ala Val Ala Leu Thr Leu Ala Leu
1               5                   10                  15

Leu Ala Ala Ser Asn Pro Lys Leu Ala Gln Ala Glu Glu Ile Leu Asn
            20                  25                  30

Thr Thr Pro Ala Ser Ser Thr Glu Ala Ser Gln Ala Val Pro Val Glu
        35                  40                  45

Ser Asp Thr Thr Glu Glu Ala Asp Asn Thr Glu Ser Pro Val Pro Ala
    50                  55                  60

Thr Thr Glu Ala Glu Asn Pro Ser Ser Ser Glu Thr Ala Glu Thr Ser
65                  70                  75                  80

Asp Pro Thr Ser Glu Thr Thr Asp Thr Thr Thr Ser Glu Ala Arg Thr
                85                  90                  95

Val Thr Pro Ala Ala Thr Glu Thr Ser Gln Pro Val Glu Gly Gln Thr
            100                 105                 110

Val Asp Val Arg Ile Leu Ala Thr Thr Asp Leu His Thr Asn Leu Val
        115                 120                 125

Asn Tyr Asp Tyr Tyr Gln Asp Lys Pro Val Glu Thr Leu Gly Leu Ala
    130                 135                 140
```

-continued

```
Lys Thr Ala Val Leu Ile Glu Glu Ala Lys Lys Glu Asn Pro Asn Val
145                 150                 155                 160

Val Leu Val Asp Asn Gly Asp Thr Ile Gln Gly Thr Pro Leu Gly Asn
                165                 170                 175

Tyr Lys Ser Ile Val Asp Pro Ile Glu Glu Gly Glu Gln His Pro Met
            180                 185                 190

Tyr Ala Ala Leu Glu Thr Leu Gly Phe Asp Val Gly Thr Leu Gly Asn
        195                 200                 205

His Glu Phe Asn Tyr Gly Leu Ala Tyr Leu Glu Lys Val Ile Arg Thr
    210                 215                 220

Ala Asn Met Pro Leu Val Asn Ala Asn Val Leu Asp Pro Thr Thr Lys
225                 230                 235                 240

Asp Phe Leu Tyr Thr Pro Tyr Thr Ile Val Lys Lys Thr Phe Thr Asp
                245                 250                 255

Thr Glu Gly Lys Lys Val Thr Leu Asn Val Gly Val Thr Gly Ile Val
            260                 265                 270

Pro Pro Gln Ile Leu Asn Trp Asp Lys Ala Tyr Leu Glu Gly Lys Val
        275                 280                 285

Ile Val Arg Asp Ala Val Glu Ala Val Arg Asp Ile Ile Pro Thr Met
    290                 295                 300

Arg Glu Asn Gly Ala Asp Ile Val Leu Val Leu Ser His Ser Gly Ile
305                 310                 315                 320

Gly Asp Asp Gln Tyr Glu Val Gly Glu Glu Asn Val Gly Tyr Gln Ile
                325                 330                 335

Ala Ser Leu Ser Gly Val Asp Ala Val Ile Thr Gly His Ser His Ala
            340                 345                 350

Glu Phe Pro Gly Thr Ala Glu Lys Pro Ser Phe Tyr Ala Lys Tyr Ser
        355                 360                 365

Gly Val Asp Asp Thr Asn Gly Lys Ile Asn Gly Thr Pro Val Thr Met
    370                 375                 380

Ala Gly Lys Tyr Gly Asp His Leu Gly Val Ile Asp Leu Asn Leu Val
385                 390                 395                 400

Phe Lys Asp Gly Lys Trp Thr Thr Thr Ser Ser Lys Ala Ala Ile Arg
                405                 410                 415

Lys Ile Asp Thr Lys Ser Ser Val Ala Asp Gly Arg Ile Ile Asp Leu
            420                 425                 430

Ala Lys Glu Ala His Asn Glu Thr Ile Lys Tyr Val Arg Gln Gln Val
        435                 440                 445

Gly Glu Thr Thr Ala Pro Ile Asn Ser Phe Phe Ala Leu Val Gln Asp
    450                 455                 460

Asp Pro Ser Val Gln Ile Val Asn Asn Ala Gln Ile Trp Tyr Ala Lys
465                 470                 475                 480

Gln Gln Leu Ala Gly Thr Ser Glu Ala Asn Leu Pro Ile Leu Ser Ala
                485                 490                 495

Ala Ala Pro Phe Lys Ala Gly Thr Arg Gly Asp Ala Ser Ala Tyr Thr
            500                 505                 510

Asp Ile Pro Ala Gly Pro Ile Ala Ile Lys Asn Val Ala Asp Leu Tyr
        515                 520                 525

Leu Tyr Asp Asn Val Val Ala Ile Leu Lys Val Asn Gly Ala Gln Leu
    530                 535                 540

Lys Glu Trp Leu Glu Met Ser Ala Gly Gln Phe Asn Gln Val Asp Leu
545                 550                 555                 560
```

-continued

```
Ser Ser Thr Glu Pro Gln Asn Leu Val Asn Thr Asp Phe Arg Thr Tyr
                565                 570                 575

Asn Phe Asp Val Ile Asp Gly Val Thr Tyr Gln Tyr Asp Ile Thr Gln
            580                 585                 590

Pro Asn Lys Tyr Asp Arg Asp Gly Lys Ile Val Asn Glu Thr Ala Ser
        595                 600                 605

Arg Val Arg Asn Leu Gln Tyr Asn Gly Gln Asp Val Thr Ala Asp Gln
    610                 615                 620

Glu Phe Ile Val Val Thr Asn Asn Tyr Arg Ala Asn Gly Thr Phe Pro
625                 630                 635                 640

Gly Val Arg Glu Ala Ser Ile Asn Arg Leu Leu Asn Leu Glu Asn Arg
                645                 650                 655

Gln Ala Ile Ile Asn Tyr Ile Ile Ala Glu Lys Val Ile Asn Pro Thr
            660                 665                 670

Ala Asp Asn Asn Trp Thr Phe Thr Asp Ser Ile Lys Gly Leu Asp Leu
        675                 680                 685

Arg Phe Leu Thr Ala Asp Arg Ala Lys Ser Leu Val Thr Asp Gln Glu
    690                 695                 700

Cys Ile Val Tyr Leu Gln Ala Ser Thr Ala Ser Glu Gly Phe Gly Glu
705                 710                 715                 720

Phe Lys Phe Val Tyr Thr Glu Ser Lys Val Val Thr Pro Asp Glu Gln
                725                 730                 735

Gln Ser Asp Gln Gly Asn Thr Gly Gln Asp Ile Val Leu Glu Ser Gly
            740                 745                 750

Gln Arg Ile Thr Leu Pro Ala Val Asn Pro Pro Ala Pro Ala Pro Gln
        755                 760                 765

His Lys Leu Ala Ser Pro His Ser Gln Ala Ser Thr Lys Thr Leu Pro
    770                 775                 780

Ala Thr Gly Glu Ala Thr Ser Met Leu Ser Leu Leu Gly Leu Thr Leu
785                 790                 795                 800

Ile Gly Phe Val Gly Ala Trp Thr Lys Lys Lys Glu His
                805                 810


<210> SEQ ID NO 4
<211> LENGTH: 674
<212> TYPE: PRT
<213> ORGANISM: STREPTOCOCCUS SUIS

<400> SEQUENCE: 4

Met Lys Lys Asn Ile Arg Leu Lys Ser Ser Ile Leu Ala Leu Val Ala
1               5                   10                  15

Gly Phe Ser Val Ile Ala Thr Gln Ala Val Leu Ala Asp Glu Leu Ala
            20                  25                  30

Val Gln Ile Met Gly Val Asn Asp Phe His Gly Ala Leu Asp Met Thr
        35                  40                  45

Gly Thr Ala Arg Leu Glu Gly Glu Thr Val Arg Asn Ala Gly Thr Ala
    50                  55                  60

Ala Leu Leu Asp Ala Tyr Met Asp Asp Ser Gln Ala Glu Phe Glu Glu
65                  70                  75                  80

Thr Ala Ala Glu Thr Glu Thr Pro Ala Glu Ser Ile Arg Val Gln Ala
                85                  90                  95

Gly Asp Met Val Gly Ala Ser Pro Ser Asn Ser Gly Leu Leu Gln Asp
            100                 105                 110

Glu Pro Thr Val Lys Val Phe Asn Lys Met Asp Val Glu Tyr Gly Thr
        115                 120                 125
```

-continued

```
Leu Gly Asn His Glu Phe Asp Glu Gly Leu Asp Glu Tyr Asn Arg Ile
    130                 135                 140

Met Thr Gly Glu Ala Pro Lys Lys Gly Gln Phe Asn Glu Ile Val Asp
145                 150                 155                 160

Asn Tyr Thr Arg Glu Ala Ala Lys Gln Glu Ile Val Ile Ala Asn Val
                165                 170                 175

Ile Asp Lys Glu Thr Gly Glu Ile Pro Tyr Gly Trp Lys Pro Tyr Ala
            180                 185                 190

Ile Lys Thr Ile Pro Val Asn Asp Lys Glu Ala Lys Ile Gly Phe Ile
        195                 200                 205

Gly Val Val Thr Thr Glu Ile Pro Asn Leu Val Leu Lys Lys Asn Tyr
    210                 215                 220

Glu Gln Tyr Thr Phe Leu Asn Glu Ala Glu Thr Ile Ala Lys Tyr Ala
225                 230                 235                 240

Arg Glu Leu Ala Glu Lys Gly Val Asn Ala Ile Val Val Leu Ala His
                245                 250                 255

Val Pro Ala Thr Ser Lys Asp Gly Val Ala Ala Gly Glu Ala Ala Asp
            260                 265                 270

Met Ile Ala Lys Leu Asn Glu Ile Tyr Pro Glu His Ser Val Asp Leu
        275                 280                 285

Val Phe Ala Gly His Asn His Val Tyr Thr Asn Gly Thr Thr Gly Lys
    290                 295                 300

Thr Leu Ile Val Gln Ala Thr Ser Gln Gly Lys Ala Tyr Ala Asp Val
305                 310                 315                 320

Arg Ala Val Tyr Asp Thr Asp Ile Ala Asp Phe Lys Ala Val Pro Thr
                325                 330                 335

Ala Lys Ile Ile Ala Val Ala Pro Gly Gln Lys Thr Pro Ser Pro Glu
            340                 345                 350

Ile Gln Ala Ile Val Asp Glu Ala Asn Thr Ile Val Lys Lys Val Thr
        355                 360                 365

Glu Gln Lys Ile Ala Thr Ala Ser Gln Ala Thr Asp Ile Ser Arg Glu
    370                 375                 380

Val Asn Glu Phe Lys Glu Ser Ala Val Gly Asn Leu Val Thr Ser Ala
385                 390                 395                 400

Gln Leu Ala Ile Ala Lys Lys Ser Gly Tyr Asp Val Asp Phe Ala Met
                405                 410                 415

Thr Asn Asp Gly Gly Ile Arg Ala Asp Leu Lys Val Gln Glu Asp Gly
            420                 425                 430

Thr Val Thr Trp Gly Ala Ala Gln Ala Val Gln Pro Phe Gly Asn Ile
        435                 440                 445

Leu Gln Val Val Gln Met Thr Gly Glu Gln Ile Tyr Thr Ala Leu Asn
    450                 455                 460

Gln Gln Tyr Asp Glu Gly Glu Lys Tyr Phe Leu Gln Met Ser Gly Ile
465                 470                 475                 480

Lys Tyr Ile Tyr Thr Lys Ala Asp Asn Pro Thr Glu Glu Asn Pro Tyr
                485                 490                 495

Lys Val Val Lys Ala Phe Lys Glu Asp Gly Thr Glu Ile Val Pro Thr
            500                 505                 510

Glu Thr Tyr Thr Leu Val Ile Asn Asp Phe Leu Phe Gly Gly Gly Asp
        515                 520                 525

Gly Phe Ser Ile Phe Lys Glu Ala Lys Leu Ile Gly Ala Ile Asn Pro
    530                 535                 540
```

```
Asp Thr Glu Val Phe Val Glu Tyr Leu Thr Asp Leu Glu Lys Ala Gly
545                 550                 555                 560

Gln Thr Ile Ser Ala Thr Ile Pro Gly Arg Lys Ala Phe Val Glu Lys
                565                 570                 575

Tyr Val Glu Glu Pro Lys Ala Glu Glu Lys Glu Asp Asn Ala Gly Thr
            580                 585                 590

Thr Thr Asp Val Lys Thr Pro Glu Lys Ala Asn Asp Gly Gly Asp Ser
        595                 600                 605

Val Thr Asn Gln Lys Ala Thr Glu Gln Pro Ala Pro Ser Gly Ser Met
    610                 615                 620

Ala Pro Ile Ser Asn Lys Lys Thr Glu Lys Ala Ser Gly Asn Gln Thr
625                 630                 635                 640

Leu Pro Asn Thr Gly Gln Glu Ala Leu Gly Ser Leu Leu Ile Ser Leu
                645                 650                 655

Gly Gly Leu Val Ser Leu Gly Met Ala Val Ser Val Arg Arg Lys Glu
            660                 665                 670

Gly Glu


<210> SEQ ID NO 5
<211> LENGTH: 397
<212> TYPE: PRT
<213> ORGANISM: STREPTOCOCCUS SUIS

<400> SEQUENCE: 5

Asp Thr Val Val Thr Gly Val Asn Glu Ile Ile Glu Glu Ser Gln Val
1               5                   10                  15

Lys Asp Glu Val Ser Ile Glu Ser Glu Lys Asn Glu Ser Leu Asp Gly
            20                  25                  30

Ser Asn Ile Glu Ile Val Glu Glu Ile Ala Asp Asn Ile Pro Ser Pro
        35                  40                  45

Val Ile Ala Glu Gly Glu Val Ala Val Glu Met Lys Val Asp Arg Gly
    50                  55                  60

Thr Glu Asn Val Val Ser Arg Asn Asp Thr Glu Val Thr Thr Ser Glu
65                  70                  75                  80

Gln Asn Gln Ile Glu Val Thr Glu Thr Lys Glu Ile Leu Asn Gln Thr
                85                  90                  95

Ser Tyr Gln Thr Glu Ser Gly Glu Gln Arg Gln Ile Ile Trp Ala His
            100                 105                 110

Gly Ile Thr Pro Pro Ala Met Glu Gln Ser Gly Gly Phe Val Lys Glu
        115                 120                 125

Lys Tyr Gly Asp Tyr Leu Asn Tyr Thr Ala Pro Phe Glu Ala Gly Lys
    130                 135                 140

Gly Tyr Tyr Asp Thr Asn Lys Ser Leu Asn Ala Ser Phe Ile Asp Leu
145                 150                 155                 160

Asn Leu Cys Phe Ala Ala Val Ser Ser Asn Met Val His Trp Trp Leu
                165                 170                 175

Glu Gln Asn Ser Ser Tyr Val Glu Arg Tyr Leu Lys Glu Lys Lys Gly
            180                 185                 190

Thr Val Asn Val Glu Glu Asn Tyr Ala Ile Thr Asp Leu Arg Arg Tyr
        195                 200                 205

Ile Asn Ser Phe Gln Asn Gln Gln Asn Ser Arg Val Phe Asp Met Phe
    210                 215                 220

Lys Thr Tyr Tyr Gly Tyr Arg Thr Asn Gly Phe Val Ser Asp Ala Leu
225                 230                 235                 240
```

-continued

```
Val Asp Leu Phe Ile Asn Gly Tyr Lys Pro Lys Ala Gln Gly Gly Val
                245                 250                 255

Asn Leu Glu Asp Ser Gln Leu Val Pro Asp Ser Arg Gly Gly Phe Phe
            260                 265                 270

Tyr Asp Val Phe Lys Glu Lys Lys Leu Thr Asn Arg Ile Phe Ser Gly
        275                 280                 285

Ser Tyr Glu Arg Phe Gly Glu Asp Val Arg Thr Val Leu Glu Ser Lys
    290                 295                 300

Gly Leu Leu Gly Leu Thr Tyr Arg Thr Leu Gly Tyr Ala Thr His Ile
305                 310                 315                 320

Val Thr Val Trp Gly Ala Glu Tyr Asp Asn Gln Gly Lys Ile Lys Ala
                325                 330                 335

Val Tyr Ile Thr Asp Ser Asp Asp Gln Gln Glu Gln Ile Gly Leu Lys
            340                 345                 350

Arg Met Gly Ile Thr Arg Asp Ala Ser Gly Asn Pro Arg Leu Asn Asn
        355                 360                 365

His Met Lys Asn Asn Ser Ala Gly Ala Leu Leu Asp Tyr Val His Thr
    370                 375                 380

Ile Arg Leu Gly Gln Asp Leu Trp Glu Glu Tyr Phe Asn
385                 390                 395


<210> SEQ ID NO 6
<211> LENGTH: 275
<212> TYPE: PRT
<213> ORGANISM: STREPTOCOCCUS SUIS

<400> SEQUENCE: 6

Ser Glu Gln Pro Asp Ser Ile Pro His Gln Asn Val Glu Ile Ser Leu
1               5                   10                  15

Val Glu Pro Thr Asn Val Glu Thr Glu Thr Val Val Thr Pro Ile Asn
            20                  25                  30

Asp Ala Ala Thr Pro His Gly Ser Pro Thr Tyr Ile Asp Asn Ser Val
        35                  40                  45

Thr Glu Ser Val Ala Thr Pro Leu Glu Lys Asp Ser Ile Gln Ala Gly
    50                  55                  60

Glu Thr Glu Ile Ala Glu Pro Thr Ser Ser Glu Ser Thr Asn Val Glu
65                  70                  75                  80

Thr Glu Thr Val Val Thr Pro Val Asn Asp Val Ala Thr Pro His Gly
                85                  90                  95

Ser Pro Thr Tyr Ile Asp Asn Ser Val Thr Glu Ser Val Ala Thr Pro
            100                 105                 110

Leu Glu Lys Asp Ser Ile Gln Ala Gly Glu Thr Glu Ile Ala Glu Pro
        115                 120                 125

Thr Ser Ser Glu Ser Thr Asn Val Glu Thr Glu Thr Val Val Thr Pro
    130                 135                 140

Val Asn Asp Val Ala Thr Pro His Gly Ser Pro Thr Tyr Ile Asp Asn
145                 150                 155                 160

Ser Val Thr Glu Ser Val Ala Thr Pro Leu Glu Lys Asp Ser Ile Gln
                165                 170                 175

Ala Gly Glu Thr Glu Ile Ala Glu Pro Thr Ser Ser Glu Ser Thr Ser
            180                 185                 190

Val Glu Ala Glu Leu Val Asp Asn Ser Glu Ile His Ala Ala Thr Ser
        195                 200                 205

Ser Val Thr Pro Cys Gly Ser Ser Ala Tyr Ala Asp Gly Ser Thr Thr
    210                 215                 220
```

```
Glu Ser Val Ala Thr Pro Leu Glu Lys Asp Ser Ile Gln Thr Gly Asn
225                 230                 235                 240

Thr Glu Ile Ala Glu Pro Thr Ser Ser Lys Ser Thr Asn Val Glu Ala
                245                 250                 255

Ala Ser Val Asp Asn Ser Glu Ile His Ala Asp Ala Ser Leu Thr Ala
            260                 265                 270

Val Ser Ser
        275


<210> SEQ ID NO 7
<211> LENGTH: 339
<212> TYPE: PRT
<213> ORGANISM: STREPTOCOCCUS SUIS

<400> SEQUENCE: 7

Ala Glu Thr Thr Thr Ala Ala Thr Thr Thr Asn Gln Pro Ala Thr Thr
1               5                   10                  15

Asp Ala Thr Ala Thr Val Pro Ala Thr Thr Asp Ala Thr Ala Thr Val
            20                  25                  30

Pro Ala Thr Ser Val Glu Asn Val Ala Thr Glu Glu Thr Val Val Pro
        35                  40                  45

Ala Ala Glu Glu Thr Val Glu Ala Val Ile Ile His Thr Asn Asp Val
    50                  55                  60

His Gly Arg Ile Leu Glu Glu Lys Asn Val Ile Gly Asp Ala Lys Ala
65                  70                  75                  80

Ala Ala Val Ile Glu Glu Glu Arg Ala Lys Val Glu Asn Thr Ile Val
                85                  90                  95

Val Asp Ala Gly Asp Ala Phe Gln Gly Leu Pro Ile Ser Asn Ser Thr
            100                 105                 110

Lys Gly Glu Asp Arg Ala Asn Ile Met Asn Gln Val Gly Tyr Asp Ala
        115                 120                 125

Met Ala Val Gly Asn His Glu Phe Asp Phe Gly Met Asp Gln Ala Ile
    130                 135                 140

Lys Tyr Lys Glu Thr Leu Asn Phe Pro Leu Leu Ser Ala Asn Thr Tyr
145                 150                 155                 160

Val Asn Gly Ala Arg Val Phe Glu Ala Ser Thr Ile Val Asp Lys Thr
                165                 170                 175

Pro Thr Val Val Gly Asp Glu Phe Val Val Ile Gly Val Thr Thr Pro
            180                 185                 190

Glu Thr Ala Thr Lys Thr His Pro Lys Asn Val Glu Gly Val Thr Phe
        195                 200                 205

Thr Asp Pro Val Thr Glu Val Asn Lys Val Ile Asp Glu Val Glu Ala
    210                 215                 220

Arg Ala Leu Ala Asp Asn Arg Val Tyr Lys Asn Tyr Ile Ile Leu Ala
225                 230                 235                 240

His Leu Gly Val Asp Ser Thr Thr Pro Val Glu Trp Arg Gly Ser Thr
                245                 250                 255

Leu Ala Glu Ala Leu Ser Lys Asn Ser Lys Leu Ala Gly Lys Arg Val
            260                 265                 270

Ile Val Ile Asp Gly His Ser His Thr Val Glu Ala Thr Thr Tyr Gly
        275                 280                 285

Asp Asn Val Thr Tyr Asn Gln Thr Gly Ser Tyr Leu Asn Asn Ile Gly
    290                 295                 300

Lys Val Thr Leu Lys Ser Asp Lys Leu Leu Gly Glu Ala Ser Leu Ile
```

305 310 315 320

Ser Ala Ala Asp Thr Lys Asn Val Thr Pro Asn Ala Lys Ile Ala Ala
325 330 335

Leu Val Asp

<210> SEQ ID NO 8
<211> LENGTH: 316
<212> TYPE: PRT
<213> ORGANISM: STREPTOCOCCUS SUIS

<400> SEQUENCE: 8

Asp Glu Ile Lys Ala Lys Tyr Glu Ala Glu Asn Ala Gln Val Val Ile
1 5 10 15

Glu Asn Asn Pro Val Glu Leu Asn Gly Asp Arg Ser Asn Val Arg Val
20 25 30

Arg Glu Thr Asn Leu Gly Asn Ala Val Thr Asp Ala Ile Tyr Ala Tyr
35 40 45

Gly Gln Thr Gly Phe Ser Asn Lys Thr Ser Leu Ala Val Thr Asn Gly
50 55 60

Gly Gly Leu Arg Ala Thr Ile Ala Lys Asp Gln Pro Val Thr Lys Gly
65 70 75 80

Asp Ile Ile Ala Val Leu Pro Phe Gly Asn Ile Val Ser Gln Ile Thr
85 90 95

Val Thr Gly Gln Gln Ile Tyr Asp Met Phe Thr Lys Ser Leu Ser Ser
100 105 110

Thr Leu Gln Val Asn Pro Glu Thr Gly Glu Met Leu Leu Asp Glu Asn
115 120 125

Gly Met Pro Leu Phe Glu Ala Ser Gly Gly Phe Leu His Ile Ser Gly
130 135 140

Ala Asn Val Phe Tyr Asp Pro Thr Leu Pro Val Glu Glu Arg Val Leu
145 150 155 160

Leu Ile Gly Ile Leu Asn Pro Glu Thr Gly Glu Tyr Asp Ala Leu Asp
165 170 175

Leu Glu Lys Thr Tyr Tyr Leu Ala Thr Asn Asp Phe Leu Ala Ala Gly
180 185 190

Gly Asp Gly Tyr Thr Met Leu Gly Gly Ala Arg Glu Glu Gly Pro Ser
195 200 205

Met Asp Ser Val Phe Ala Glu Tyr Leu Lys Thr Ala Asp Leu Ser Ala
210 215 220

Tyr Glu Val Val Asn Pro Tyr Ser Arg Ile Ile Pro Val Asn Ser Ser
225 230 235 240

Ile Asp Thr Asp Glu Asp Gly Tyr Pro Asp Phe Ile Glu Ile Leu Leu
245 250 255

Asp Thr Asp Pro Glu Asn Pro Ala Ser Asn Pro Glu Thr Val Pro Ala
260 265 270

Glu Asn Thr Asp Ser Pro Ser Asn Gln Val Gln Asn Thr Ser Ala Thr
275 280 285

Asp Lys Lys Ala Pro Val Asp Ser Pro Lys Val Gly Asp Lys Lys Thr
290 295 300

Glu Val Ala Ser Pro Ala Lys Thr Thr Lys Ala Gly
305 310 315

<210> SEQ ID NO 9
<211> LENGTH: 425
<212> TYPE: PRT

<213> ORGANISM: STREPTOCOCCUS SUIS

<400> SEQUENCE: 9

```
Glu Glu Ile Leu Asn Thr Thr Pro Ala Ser Ser Thr Glu Ala Ser Gln
1               5                   10                  15

Ala Val Pro Val Glu Ser Asp Thr Thr Glu Glu Ala Asp Asn Thr Glu
            20                  25                  30

Ser Pro Val Pro Ala Thr Thr Glu Ala Glu Asn Pro Ser Ser Ser Glu
        35                  40                  45

Thr Ala Glu Thr Ser Asp Pro Thr Ser Glu Thr Thr Asp Thr Thr Thr
    50                  55                  60

Ser Glu Ala Arg Thr Val Thr Pro Ala Ala Thr Glu Thr Ser Gln Pro
65                  70                  75                  80

Val Glu Gly Gln Thr Val Asp Val Arg Ile Leu Ala Thr Thr Asp Leu
                85                  90                  95

His Thr Asn Leu Val Asn Tyr Asp Tyr Tyr Gln Asp Lys Pro Val Glu
            100                 105                 110

Thr Leu Gly Leu Ala Lys Thr Ala Val Leu Ile Glu Glu Ala Lys Lys
        115                 120                 125

Glu Asn Pro Asn Val Val Leu Val Asp Asn Gly Asp Thr Ile Gln Gly
    130                 135                 140

Thr Pro Leu Gly Asn Tyr Lys Ser Ile Val Asp Pro Ile Glu Glu Gly
145                 150                 155                 160

Glu Gln His Pro Met Tyr Ala Ala Leu Glu Thr Leu Gly Phe Asp Val
                165                 170                 175

Gly Thr Leu Gly Asn His Glu Phe Asn Tyr Gly Leu Ala Tyr Leu Glu
            180                 185                 190

Lys Val Ile Arg Thr Ala Asn Met Pro Leu Val Asn Ala Asn Val Leu
        195                 200                 205

Asp Pro Thr Thr Lys Asp Phe Leu Tyr Thr Pro Tyr Thr Ile Val Lys
    210                 215                 220

Lys Thr Phe Thr Asp Thr Glu Gly Lys Lys Val Thr Leu Asn Val Gly
225                 230                 235                 240

Val Thr Gly Ile Val Pro Pro Gln Ile Leu Asn Trp Asp Lys Ala Tyr
                245                 250                 255

Leu Glu Gly Lys Val Ile Val Arg Asp Ala Val Glu Ala Val Arg Asp
            260                 265                 270

Ile Ile Pro Thr Met Arg Glu Asn Gly Ala Asp Ile Val Leu Val Leu
        275                 280                 285

Ser His Ser Gly Ile Gly Asp Asp Gln Tyr Glu Val Gly Glu Glu Asn
    290                 295                 300

Val Gly Tyr Gln Ile Ala Ser Leu Ser Gly Val Asp Ala Val Ile Thr
305                 310                 315                 320

Gly His Ser His Ala Glu Phe Pro Gly Thr Ala Glu Lys Pro Ser Phe
                325                 330                 335

Tyr Ala Lys Tyr Ser Gly Val Asp Asp Thr Asn Gly Lys Ile Asn Gly
            340                 345                 350

Thr Pro Val Thr Met Ala Gly Lys Tyr Gly Asp His Leu Gly Val Ile
        355                 360                 365

Asp Leu Asn Leu Val Phe Lys Asp Gly Lys Trp Thr Thr Thr Ser Ser
    370                 375                 380

Lys Ala Ala Ile Arg Lys Ile Asp Thr Lys Ser Ser Val Ala Asp Gly
385                 390                 395                 400
```

-continued

```
Arg Ile Ile Asp Leu Ala Lys Glu Ala His Asn Glu Thr Ile Lys Tyr
                405                 410                 415

Val Arg Gln Gln Val Gly Glu Thr Thr
            420                 425


<210> SEQ ID NO 10
<211> LENGTH: 334
<212> TYPE: PRT
<213> ORGANISM: STREPTOCOCCUS SUIS

<400> SEQUENCE: 10

Gly Glu Thr Thr Ala Pro Ile Asn Ser Phe Phe Ala Leu Val Gln Asp
1               5                   10                  15

Asp Pro Ser Val Gln Ile Val Asn Asn Ala Gln Ile Trp Tyr Ala Lys
            20                  25                  30

Gln Gln Leu Ala Gly Thr Ser Glu Ala Asn Leu Pro Ile Leu Ser Ala
        35                  40                  45

Ala Ala Pro Phe Lys Ala Gly Thr Arg Gly Asp Ala Ser Ala Tyr Thr
    50                  55                  60

Asp Ile Pro Ala Gly Pro Ile Ala Ile Lys Asn Val Ala Asp Leu Tyr
65                  70                  75                  80

Leu Tyr Asp Asn Val Val Ala Ile Leu Lys Val Asn Gly Ala Gln Leu
                85                  90                  95

Lys Glu Trp Leu Glu Met Ser Ala Gly Gln Phe Asn Gln Val Asp Leu
            100                 105                 110

Ser Ser Thr Glu Pro Gln Asn Leu Val Asn Thr Asp Phe Arg Thr Tyr
        115                 120                 125

Asn Phe Asp Val Ile Asp Gly Val Thr Tyr Gln Tyr Asp Ile Thr Gln
    130                 135                 140

Pro Asn Lys Tyr Asp Arg Asp Gly Lys Ile Val Asn Glu Thr Ala Ser
145                 150                 155                 160

Arg Val Arg Asn Leu Gln Tyr Asn Gly Gln Asp Val Thr Ala Asp Gln
                165                 170                 175

Glu Phe Ile Val Val Thr Asn Asn Tyr Arg Ala Asn Gly Thr Phe Pro
            180                 185                 190

Gly Val Arg Glu Ala Ser Ile Asn Arg Leu Leu Asn Leu Glu Asn Arg
        195                 200                 205

Gln Ala Ile Ile Asn Tyr Ile Ile Ala Glu Lys Val Ile Asn Pro Thr
    210                 215                 220

Ala Asp Asn Asn Trp Thr Phe Thr Asp Ser Ile Lys Gly Leu Asp Leu
225                 230                 235                 240

Arg Phe Leu Thr Ala Asp Arg Ala Lys Ser Leu Val Thr Asp Gln Glu
                245                 250                 255

Cys Ile Val Tyr Leu Gln Ala Ser Thr Ala Ser Glu Gly Phe Gly Glu
            260                 265                 270

Phe Lys Phe Val Tyr Thr Glu Ser Lys Val Val Thr Pro Asp Glu Gln
        275                 280                 285

Gln Ser Asp Gln Gly Asn Thr Gly Gln Asp Ile Val Leu Glu Ser Gly
    290                 295                 300

Gln Arg Ile Thr Leu Pro Ala Val Asn Pro Pro Ala Pro Ala Pro Gln
305                 310                 315                 320

His Lys Leu Ala Ser Pro His Ser Gln Ala Ser Thr Lys Thr
                325                 330


<210> SEQ ID NO 11
```

<211> LENGTH: 338
<212> TYPE: PRT
<213> ORGANISM: STREPTOCOCCUS SUIS

<400> SEQUENCE: 11

Asp Glu Leu Ala Val Gln Ile Met Gly Val Asn Asp Phe His Gly Ala
1 5 10 15

Leu Asp Met Thr Gly Thr Ala Arg Leu Glu Gly Glu Thr Val Arg Asn
20 25 30

Ala Gly Thr Ala Ala Leu Leu Asp Ala Tyr Met Asp Asp Ser Gln Ala
35 40 45

Glu Phe Glu Glu Thr Ala Ala Glu Thr Glu Thr Pro Ala Glu Ser Ile
50 55 60

Arg Val Gln Ala Gly Asp Met Val Gly Ala Ser Pro Ser Asn Ser Gly
65 70 75 80

Leu Leu Gln Asp Glu Pro Thr Val Lys Val Phe Asn Lys Met Asp Val
85 90 95

Glu Tyr Gly Thr Leu Gly Asn His Glu Phe Asp Glu Gly Leu Asp Glu
100 105 110

Tyr Asn Arg Ile Met Thr Gly Glu Ala Pro Lys Lys Gly Gln Phe Asn
115 120 125

Glu Ile Val Asp Asn Tyr Thr Arg Glu Ala Ala Lys Gln Glu Ile Val
130 135 140

Ile Ala Asn Val Ile Asp Lys Glu Thr Gly Glu Ile Pro Tyr Gly Trp
145 150 155 160

Lys Pro Tyr Ala Ile Lys Thr Ile Pro Val Asn Asp Lys Glu Ala Lys
165 170 175

Ile Gly Phe Ile Gly Val Val Thr Thr Glu Ile Pro Asn Leu Val Leu
180 185 190

Lys Lys Asn Tyr Glu Gln Tyr Thr Phe Leu Asn Glu Ala Glu Thr Ile
195 200 205

Ala Lys Tyr Ala Arg Glu Leu Ala Glu Lys Gly Val Asn Ala Ile Val
210 215 220

Val Leu Ala His Val Pro Ala Thr Ser Lys Asp Gly Val Ala Ala Gly
225 230 235 240

Glu Ala Ala Asp Met Ile Ala Lys Leu Asn Glu Ile Tyr Pro Glu His
245 250 255

Ser Val Asp Leu Val Phe Ala Gly His Asn His Val Tyr Thr Asn Gly
260 265 270

Thr Thr Gly Lys Thr Leu Ile Val Gln Ala Thr Ser Gln Gly Lys Ala
275 280 285

Tyr Ala Asp Val Arg Ala Val Tyr Asp Thr Asp Ile Ala Asp Phe Lys
290 295 300

Ala Val Pro Thr Ala Lys Ile Ile Ala Val Ala Pro Gly Gln Lys Thr
305 310 315 320

Pro Ser Pro Glu Ile Gln Ala Ile Val Asp Glu Ala Asn Thr Ile Val
325 330 335

Lys Lys

<210> SEQ ID NO 12
<211> LENGTH: 289
<212> TYPE: PRT
<213> ORGANISM: STREPTOCOCCUS SUIS

<400> SEQUENCE: 12

-continued

```
Glu Ile Gln Ala Ile Val Asp Glu Ala Asn Thr Ile Val Lys Lys Val
1               5                   10                  15

Thr Glu Gln Lys Ile Ala Thr Ala Ser Gln Ala Thr Asp Ile Ser Arg
            20                  25                  30

Glu Val Asn Glu Phe Lys Glu Ser Ala Val Gly Asn Leu Val Thr Ser
        35                  40                  45

Ala Gln Leu Ala Ile Ala Lys Lys Ser Gly Tyr Asp Val Asp Phe Ala
    50                  55                  60

Met Thr Asn Asp Gly Gly Ile Arg Ala Asp Leu Lys Val Gln Glu Asp
65                  70                  75                  80

Gly Thr Val Thr Trp Gly Ala Ala Gln Ala Val Gln Pro Phe Gly Asn
                85                  90                  95

Ile Leu Gln Val Val Gln Met Thr Gly Glu Gln Ile Tyr Thr Ala Leu
            100                 105                 110

Asn Gln Gln Tyr Asp Glu Gly Glu Lys Tyr Phe Leu Gln Met Ser Gly
        115                 120                 125

Ile Lys Tyr Ile Tyr Thr Lys Ala Asp Asn Pro Thr Glu Glu Asn Pro
    130                 135                 140

Tyr Lys Val Val Lys Ala Phe Lys Glu Asp Gly Thr Glu Ile Val Pro
145                 150                 155                 160

Thr Glu Thr Tyr Thr Leu Val Ile Asn Asp Phe Leu Phe Gly Gly Gly
                165                 170                 175

Asp Gly Phe Ser Ile Phe Lys Glu Ala Lys Leu Ile Gly Ala Ile Asn
            180                 185                 190

Pro Asp Thr Glu Val Phe Val Glu Tyr Leu Thr Asp Leu Glu Lys Ala
        195                 200                 205

Gly Gln Thr Ile Ser Ala Thr Ile Pro Gly Arg Lys Ala Phe Val Glu
    210                 215                 220

Lys Tyr Val Glu Glu Pro Lys Ala Glu Glu Lys Glu Asp Asn Ala Gly
225                 230                 235                 240

Thr Thr Thr Asp Val Lys Thr Pro Glu Lys Ala Asn Asp Gly Gly Asp
                245                 250                 255

Ser Val Thr Asn Gln Lys Ala Thr Glu Gln Pro Ala Pro Ser Gly Ser
            260                 265                 270

Met Ala Pro Ile Ser Asn Lys Lys Thr Glu Lys Ala Ser Gly Asn Gln
        275                 280                 285

Thr
```

<210> SEQ ID NO 13
<211> LENGTH: 410
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 13

```
Met Thr Gly Ser Asp Thr Val Val Thr Gly Val Asn Glu Ile Ile Glu
1               5                   10                  15

Glu Ser Gln Val Lys Asp Glu Val Ser Ile Glu Ser Glu Lys Asn Glu
            20                  25                  30

Ser Leu Asp Gly Ser Asn Ile Glu Ile Val Glu Glu Ile Ala Asp Asn
        35                  40                  45

Ile Pro Ser Pro Val Ile Ala Glu Gly Glu Val Ala Val Glu Met Lys
    50                  55                  60

Val Asp Arg Gly Thr Glu Asn Val Val Ser Arg Asn Asp Thr Glu Val
```

-continued

```
65                  70                  75                  80

Thr Thr Ser Glu Gln Asn Gln Ile Glu Val Thr Glu Thr Lys Glu Ile
                85                  90                  95

Leu Asn Gln Thr Ser Tyr Gln Thr Glu Ser Gly Glu Gln Arg Gln Ile
            100                 105                 110

Ile Trp Ala His Gly Ile Thr Pro Pro Ala Met Glu Gln Ser Gly Gly
        115                 120                 125

Phe Val Lys Glu Lys Tyr Gly Asp Tyr Leu Asn Tyr Thr Ala Pro Phe
    130                 135                 140

Glu Ala Gly Lys Gly Tyr Tyr Asp Thr Asn Lys Ser Leu Asn Ala Ser
145                 150                 155                 160

Phe Ile Asp Leu Asn Leu Cys Phe Ala Ala Val Ser Ser Asn Met Val
                165                 170                 175

His Trp Trp Leu Glu Gln Asn Ser Ser Tyr Val Glu Arg Tyr Leu Lys
            180                 185                 190

Glu Lys Lys Gly Thr Val Asn Val Glu Glu Asn Tyr Ala Ile Thr Asp
        195                 200                 205

Leu Arg Arg Tyr Ile Asn Ser Phe Gln Asn Gln Gln Asn Ser Arg Val
    210                 215                 220

Phe Asp Met Phe Lys Thr Tyr Tyr Gly Tyr Arg Thr Asn Gly Phe Val
225                 230                 235                 240

Ser Asp Ala Leu Val Asp Leu Phe Ile Asn Gly Tyr Lys Pro Lys Ala
                245                 250                 255

Gln Gly Gly Val Asn Leu Glu Asp Ser Gln Leu Val Pro Asp Ser Arg
            260                 265                 270

Gly Gly Phe Phe Tyr Asp Val Phe Lys Glu Lys Lys Leu Thr Asn Arg
        275                 280                 285

Ile Phe Ser Gly Ser Tyr Glu Arg Phe Gly Glu Asp Val Arg Thr Val
    290                 295                 300

Leu Glu Ser Lys Gly Leu Leu Gly Leu Thr Tyr Arg Thr Leu Gly Tyr
305                 310                 315                 320

Ala Thr His Ile Val Thr Val Trp Gly Ala Glu Tyr Asp Asn Gln Gly
                325                 330                 335

Lys Ile Lys Ala Val Tyr Ile Thr Asp Ser Asp Asp Gln Gln Glu Gln
            340                 345                 350

Ile Gly Leu Lys Arg Met Gly Ile Thr Arg Asp Ala Ser Gly Asn Pro
        355                 360                 365

Arg Leu Asn Asn His Met Lys Asn Asn Ser Ala Gly Ala Leu Leu Asp
    370                 375                 380

Tyr Val His Thr Ile Arg Leu Gly Gln Asp Leu Trp Glu Glu Tyr Phe
385                 390                 395                 400

Asn Leu Glu His His His His His His His
                405                 410
```

<210> SEQ ID NO 14
<211> LENGTH: 288
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 14

```
Met Thr Gly Ser Ser Glu Gln Pro Asp Ser Ile Pro His Gln Asn Val
1               5                   10                  15

Glu Ile Ser Leu Val Glu Pro Thr Asn Val Glu Thr Glu Thr Val Val
```

```
            20                  25                  30

Thr Pro Ile Asn Asp Ala Ala Thr Pro His Gly Ser Pro Thr Tyr Ile
        35                  40                  45

Asp Asn Ser Val Thr Glu Ser Val Ala Thr Pro Leu Glu Lys Asp Ser
    50                  55                  60

Ile Gln Ala Gly Glu Thr Glu Ile Ala Glu Pro Thr Ser Ser Glu Ser
65                  70                  75                  80

Thr Asn Val Glu Thr Glu Thr Val Val Thr Pro Val Asn Asp Val Ala
                85                  90                  95

Thr Pro His Gly Ser Pro Thr Tyr Ile Asp Asn Ser Val Thr Glu Ser
            100                 105                 110

Val Ala Thr Pro Leu Glu Lys Asp Ser Ile Gln Ala Gly Glu Thr Glu
        115                 120                 125

Ile Ala Glu Pro Thr Ser Ser Glu Ser Thr Asn Val Glu Thr Glu Thr
    130                 135                 140

Val Val Thr Pro Val Asn Asp Val Ala Thr Pro His Gly Ser Pro Thr
145                 150                 155                 160

Tyr Ile Asp Asn Ser Val Thr Glu Ser Val Ala Thr Pro Leu Glu Lys
                165                 170                 175

Asp Ser Ile Gln Ala Gly Glu Thr Glu Ile Ala Glu Pro Thr Ser Ser
            180                 185                 190

Glu Ser Thr Ser Val Glu Ala Glu Leu Val Asp Asn Ser Glu Ile His
        195                 200                 205

Ala Ala Thr Ser Ser Val Thr Pro Cys Gly Ser Ser Ala Tyr Ala Asp
    210                 215                 220

Gly Ser Thr Thr Glu Ser Val Ala Thr Pro Leu Glu Lys Asp Ser Ile
225                 230                 235                 240

Gln Thr Gly Asn Thr Glu Ile Ala Glu Pro Thr Ser Ser Lys Ser Thr
                245                 250                 255

Asn Val Glu Ala Ala Ser Val Asp Asn Ser Glu Ile His Ala Asp Ala
            260                 265                 270

Ser Leu Thr Ala Val Ser Ser Leu Glu His His His His His His
        275                 280                 285


<210> SEQ ID NO 15
<211> LENGTH: 349
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 15

Met Thr Gly Ser Ala Glu Thr Thr Thr Ala Ala Thr Thr Thr Asn Gln
1               5                   10                  15

Pro Ala Thr Thr Asp Ala Thr Ala Thr Val Pro Ala Thr Thr Asp Ala
            20                  25                  30

Thr Ala Thr Val Pro Ala Thr Ser Val Glu Asn Val Ala Thr Glu Glu
        35                  40                  45

Thr Val Val Pro Ala Ala Glu Glu Thr Val Glu Ala Val Ile Ile His
    50                  55                  60

Thr Asn Asp Val His Gly Arg Ile Leu Glu Glu Lys Asn Val Ile Gly
65                  70                  75                  80

Asp Ala Lys Ala Ala Ala Val Ile Glu Glu Glu Arg Ala Lys Val Glu
                85                  90                  95

Asn Thr Ile Val Val Asp Ala Gly Asp Ala Phe Gln Gly Leu Pro Ile
```

```
            100                 105                 110

Ser Asn Ser Thr Lys Gly Glu Asp Arg Ala Asn Ile Met Asn Gln Val
        115                 120                 125

Gly Tyr Asp Ala Met Ala Val Gly Asn His Glu Phe Asp Phe Gly Met
    130                 135                 140

Asp Gln Ala Ile Lys Tyr Lys Glu Thr Leu Asn Phe Pro Leu Leu Ser
145                 150                 155                 160

Ala Asn Thr Tyr Val Asn Gly Ala Arg Val Phe Glu Ala Ser Thr Ile
                165                 170                 175

Val Asp Lys Thr Pro Thr Val Val Gly Asp Glu Phe Val Val Ile Gly
            180                 185                 190

Val Thr Thr Pro Glu Thr Ala Thr Lys Thr His Pro Lys Asn Val Glu
        195                 200                 205

Gly Val Thr Phe Thr Asp Pro Val Thr Glu Val Asn Lys Val Ile Asp
    210                 215                 220

Glu Val Glu Ala Arg Ala Leu Ala Asp Asn Arg Val Tyr Lys Asn Tyr
225                 230                 235                 240

Ile Ile Leu Ala His Leu Gly Val Asp Ser Thr Thr Pro Val Glu Trp
                245                 250                 255

Arg Gly Ser Thr Leu Ala Glu Ala Leu Ser Lys Asn Ser Lys Leu Ala
            260                 265                 270

Gly Lys Arg Val Ile Val Ile Asp Gly His Ser His Thr Val Glu Ala
        275                 280                 285

Thr Thr Tyr Gly Asp Asn Val Thr Tyr Asn Gln Thr Gly Ser Tyr Leu
    290                 295                 300

Asn Asn Ile Gly Lys Val Thr Leu Lys Ser Asp Lys Leu Leu Gly Glu
305                 310                 315                 320

Ala Ser Leu Ile Ser Ala Ala Asp Thr Lys Asn Val Thr Pro Asn Ala
                325                 330                 335

Lys Ile Ala Ala Leu Val Asp His His His His His His
            340                 345
```

<210> SEQ ID NO 16
<211> LENGTH: 328
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 16

```
Met Thr Gly Ser His His His His His His Val Asp Glu Ile Lys Ala
1               5                   10                  15

Lys Tyr Glu Ala Glu Asn Ala Gln Val Val Ile Glu Asn Asn Pro Val
            20                  25                  30

Glu Leu Asn Gly Asp Arg Ser Asn Val Arg Val Arg Glu Thr Asn Leu
        35                  40                  45

Gly Asn Ala Val Thr Asp Ala Ile Tyr Ala Tyr Gly Gln Thr Gly Phe
    50                  55                  60

Ser Asn Lys Thr Ser Leu Ala Val Thr Asn Gly Gly Gly Leu Arg Ala
65                  70                  75                  80

Thr Ile Ala Lys Asp Gln Pro Val Thr Lys Gly Asp Ile Ile Ala Val
                85                  90                  95

Leu Pro Phe Gly Asn Ile Val Ser Gln Ile Thr Val Thr Gly Gln Gln
            100                 105                 110

Ile Tyr Asp Met Phe Thr Lys Ser Leu Ser Ser Thr Leu Gln Val Asn
```

```
        115                 120                 125

Pro Glu Thr Gly Glu Met Leu Leu Asp Glu Asn Gly Met Pro Leu Phe
    130                 135                 140

Glu Ala Ser Gly Gly Phe Leu His Ile Ser Gly Ala Asn Val Phe Tyr
145                 150                 155                 160

Asp Pro Thr Leu Pro Val Glu Glu Arg Val Leu Leu Ile Gly Ile Leu
                165                 170                 175

Asn Pro Glu Thr Gly Glu Tyr Asp Ala Leu Asp Leu Glu Lys Thr Tyr
            180                 185                 190

Tyr Leu Ala Thr Asn Asp Phe Leu Ala Ala Gly Gly Asp Gly Tyr Thr
        195                 200                 205

Met Leu Gly Gly Ala Arg Glu Glu Gly Pro Ser Met Asp Ser Val Phe
    210                 215                 220

Ala Glu Tyr Leu Lys Thr Ala Asp Leu Ser Ala Tyr Glu Val Val Asn
225                 230                 235                 240

Pro Tyr Ser Arg Ile Ile Pro Val Asn Ser Ser Ile Asp Thr Asp Glu
                245                 250                 255

Asp Gly Tyr Pro Asp Phe Ile Glu Ile Leu Leu Asp Thr Asp Pro Glu
            260                 265                 270

Asn Pro Ala Ser Asn Pro Glu Thr Val Pro Ala Glu Asn Thr Asp Ser
        275                 280                 285

Pro Ser Asn Gln Val Gln Asn Thr Ser Ala Thr Asp Lys Lys Ala Pro
    290                 295                 300

Val Asp Ser Pro Lys Val Gly Asp Lys Lys Thr Glu Val Ala Ser Pro
305                 310                 315                 320

Ala Lys Thr Thr Lys Ala Gly Val
                325


<210> SEQ ID NO 17
<211> LENGTH: 437
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 17

Met Thr Gly Ser Glu Glu Ile Leu Asn Thr Thr Pro Ala Ser Ser Thr
1               5                   10                  15

Glu Ala Ser Gln Ala Val Pro Val Glu Ser Asp Thr Thr Glu Glu Ala
            20                  25                  30

Asp Asn Thr Glu Ser Pro Val Pro Ala Thr Thr Glu Ala Glu Asn Pro
        35                  40                  45

Ser Ser Ser Glu Thr Ala Glu Thr Ser Asp Pro Thr Ser Glu Thr Thr
    50                  55                  60

Asp Thr Thr Thr Ser Glu Ala Arg Thr Val Thr Pro Ala Ala Thr Glu
65                  70                  75                  80

Thr Ser Gln Pro Val Glu Gly Gln Thr Val Asp Val Arg Ile Leu Ala
                85                  90                  95

Thr Thr Asp Leu His Thr Asn Leu Val Asn Tyr Asp Tyr Tyr Gln Asp
            100                 105                 110

Lys Pro Val Glu Thr Leu Gly Leu Ala Lys Thr Ala Val Leu Ile Glu
        115                 120                 125

Glu Ala Lys Lys Glu Asn Pro Asn Val Val Leu Val Asp Asn Gly Asp
    130                 135                 140

Thr Ile Gln Gly Thr Pro Leu Gly Asn Tyr Lys Ser Ile Val Asp Pro
```

-continued

```
145                 150                 155                 160

Ile Glu Glu Gly Glu Gln His Pro Met Tyr Ala Ala Leu Glu Thr Leu
                165                 170                 175

Gly Phe Asp Val Gly Thr Leu Gly Asn His Glu Phe Asn Tyr Gly Leu
            180                 185                 190

Ala Tyr Leu Glu Lys Val Ile Arg Thr Ala Asn Met Pro Leu Val Asn
        195                 200                 205

Ala Asn Val Leu Asp Pro Thr Thr Lys Asp Phe Leu Tyr Thr Pro Tyr
    210                 215                 220

Thr Ile Val Lys Lys Thr Phe Thr Asp Thr Glu Gly Lys Lys Val Thr
225                 230                 235                 240

Leu Asn Val Gly Val Thr Gly Ile Val Pro Pro Gln Ile Leu Asn Trp
                245                 250                 255

Asp Lys Ala Tyr Leu Glu Gly Lys Val Ile Val Arg Asp Ala Val Glu
            260                 265                 270

Ala Val Arg Asp Ile Ile Pro Thr Met Arg Glu Asn Gly Ala Asp Ile
        275                 280                 285

Val Leu Val Leu Ser His Ser Gly Ile Gly Asp Asp Gln Tyr Glu Val
    290                 295                 300

Gly Glu Glu Asn Val Gly Tyr Gln Ile Ala Ser Leu Ser Gly Val Asp
305                 310                 315                 320

Ala Val Ile Thr Gly His Ser His Ala Glu Phe Pro Gly Thr Ala Glu
                325                 330                 335

Lys Pro Ser Phe Tyr Ala Lys Tyr Ser Gly Val Asp Asp Thr Asn Gly
            340                 345                 350

Lys Ile Asn Gly Thr Pro Val Thr Met Ala Gly Lys Tyr Gly Asp His
        355                 360                 365

Leu Gly Val Ile Asp Leu Asn Leu Val Phe Lys Asp Gly Lys Trp Thr
    370                 375                 380

Thr Thr Ser Ser Lys Ala Ala Ile Arg Lys Ile Asp Thr Lys Ser Ser
385                 390                 395                 400

Val Ala Asp Gly Arg Ile Ile Asp Leu Ala Lys Glu Ala His Asn Glu
                405                 410                 415

Thr Ile Lys Tyr Val Arg Gln Gln Val Gly Glu Thr Thr His His His
            420                 425                 430

His His His Leu Glu
        435


<210> SEQ ID NO 18
<211> LENGTH: 346
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 18

Met Thr His His His His His His Gly Ser Gly Glu Thr Thr Ala Pro
1               5                   10                  15

Ile Asn Ser Phe Phe Ala Leu Val Gln Asp Asp Pro Ser Val Gln Ile
            20                  25                  30

Val Asn Asn Ala Gln Ile Trp Tyr Ala Lys Gln Gln Leu Ala Gly Thr
        35                  40                  45

Ser Glu Ala Asn Leu Pro Ile Leu Ser Ala Ala Ala Pro Phe Lys Ala
    50                  55                  60

Gly Thr Arg Gly Asp Ala Ser Ala Tyr Thr Asp Ile Pro Ala Gly Pro
```

-continued

```
65                  70                  75                  80

Ile Ala Ile Lys Asn Val Ala Asp Leu Tyr Leu Tyr Asp Asn Val Val
                85                  90                  95

Ala Ile Leu Lys Val Asn Gly Ala Gln Leu Lys Glu Trp Leu Glu Met
            100                 105                 110

Ser Ala Gly Gln Phe Asn Gln Val Asp Leu Ser Ser Thr Glu Pro Gln
        115                 120                 125

Asn Leu Val Asn Thr Asp Phe Arg Thr Tyr Asn Phe Asp Val Ile Asp
    130                 135                 140

Gly Val Thr Tyr Gln Tyr Asp Ile Thr Gln Pro Asn Lys Tyr Asp Arg
145                 150                 155                 160

Asp Gly Lys Ile Val Asn Glu Thr Ala Ser Arg Val Arg Asn Leu Gln
                165                 170                 175

Tyr Asn Gly Gln Asp Val Thr Ala Asp Gln Glu Phe Ile Val Val Thr
            180                 185                 190

Asn Asn Tyr Arg Ala Asn Gly Thr Phe Pro Gly Val Arg Glu Ala Ser
        195                 200                 205

Ile Asn Arg Leu Leu Asn Leu Glu Asn Arg Gln Ala Ile Ile Asn Tyr
    210                 215                 220

Ile Ile Ala Glu Lys Val Ile Asn Pro Thr Ala Asp Asn Asn Trp Thr
225                 230                 235                 240

Phe Thr Asp Ser Ile Lys Gly Leu Asp Leu Arg Phe Leu Thr Ala Asp
                245                 250                 255

Arg Ala Lys Ser Leu Val Thr Asp Gln Glu Cys Ile Val Tyr Leu Gln
            260                 265                 270

Ala Ser Thr Ala Ser Glu Gly Phe Gly Glu Phe Lys Phe Val Tyr Thr
        275                 280                 285

Glu Ser Lys Val Val Thr Pro Asp Glu Gln Gln Ser Asp Gln Gly Asn
    290                 295                 300

Thr Gly Gln Asp Ile Val Leu Glu Ser Gly Gln Arg Ile Thr Leu Pro
305                 310                 315                 320

Ala Val Asn Pro Pro Ala Pro Ala Pro Gln His Lys Leu Ala Ser Pro
                325                 330                 335

His Ser Gln Ala Ser Thr Lys Thr Leu Glu
            340                 345


<210> SEQ ID NO 19
<211> LENGTH: 351
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 19

Met Thr Gly Ser Asp Glu Leu Ala Val Gln Ile Met Gly Val Asn Asp
1               5                   10                  15

Phe His Gly Ala Leu Asp Met Thr Gly Thr Ala Arg Leu Glu Gly Glu
            20                  25                  30

Thr Val Arg Asn Ala Gly Thr Ala Ala Leu Leu Asp Ala Tyr Met Asp
        35                  40                  45

Asp Ser Gln Ala Glu Phe Glu Glu Thr Ala Ala Glu Thr Glu Thr Pro
    50                  55                  60

Ala Glu Ser Ile Arg Val Gln Ala Gly Asp Met Val Gly Ala Ser Pro
65                  70                  75                  80

Ser Asn Ser Gly Leu Leu Gln Asp Glu Pro Thr Val Lys Val Phe Asn
```

-continued

```
                85                  90                  95

Lys Met Asp Val Glu Tyr Gly Thr Leu Gly Asn His Glu Phe Asp Glu
            100                 105                 110

Gly Leu Asp Glu Tyr Asn Arg Ile Met Thr Gly Glu Ala Pro Lys Lys
        115                 120                 125

Gly Gln Phe Asn Glu Ile Val Asp Asn Tyr Thr Arg Glu Ala Ala Lys
    130                 135                 140

Gln Glu Ile Val Ile Ala Asn Val Ile Asp Lys Glu Thr Gly Glu Ile
145                 150                 155                 160

Pro Tyr Gly Trp Lys Pro Tyr Ala Ile Lys Thr Ile Pro Val Asn Asp
                165                 170                 175

Lys Glu Ala Lys Ile Gly Phe Ile Gly Val Val Thr Thr Glu Ile Pro
            180                 185                 190

Asn Leu Val Leu Lys Lys Asn Tyr Glu Gln Tyr Thr Phe Leu Asn Glu
        195                 200                 205

Ala Glu Thr Ile Ala Lys Tyr Ala Arg Glu Leu Ala Glu Lys Gly Val
    210                 215                 220

Asn Ala Ile Val Val Leu Ala His Val Pro Ala Thr Ser Lys Asp Gly
225                 230                 235                 240

Val Ala Ala Gly Glu Ala Ala Asp Met Ile Ala Lys Leu Asn Glu Ile
                245                 250                 255

Tyr Pro Glu His Ser Val Asp Leu Val Phe Ala Gly His Asn His Val
            260                 265                 270

Tyr Thr Asn Gly Thr Thr Gly Lys Thr Leu Ile Val Gln Ala Thr Ser
        275                 280                 285

Gln Gly Lys Ala Tyr Ala Asp Val Arg Ala Val Tyr Asp Thr Asp Ile
    290                 295                 300

Ala Asp Phe Lys Ala Val Pro Thr Ala Lys Ile Ile Ala Val Ala Pro
305                 310                 315                 320

Gly Gln Lys Thr Pro Ser Pro Glu Ile Gln Ala Ile Val Asp Glu Ala
                325                 330                 335

Asn Thr Ile Val Lys Lys Leu Glu His His His His His His His
            340                 345                 350


<210> SEQ ID NO 20
<211> LENGTH: 301
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 20

Met Thr His His His His His His Gly Ser Glu Ile Gln Ala Ile Val
1               5                   10                  15

Asp Glu Ala Asn Thr Ile Val Lys Lys Val Thr Glu Gln Lys Ile Ala
            20                  25                  30

Thr Ala Ser Gln Ala Thr Asp Ile Ser Arg Glu Val Asn Glu Phe Lys
        35                  40                  45

Glu Ser Ala Val Gly Asn Leu Val Thr Ser Ala Gln Leu Ala Ile Ala
    50                  55                  60

Lys Lys Ser Gly Tyr Asp Val Asp Phe Ala Met Thr Asn Asp Gly Gly
65                  70                  75                  80

Ile Arg Ala Asp Leu Lys Val Gln Glu Asp Gly Thr Val Thr Trp Gly
                85                  90                  95

Ala Ala Gln Ala Val Gln Pro Phe Gly Asn Ile Leu Gln Val Val Gln
```

```
            100                 105                 110

Met Thr Gly Glu Gln Ile Tyr Thr Ala Leu Asn Gln Gln Tyr Asp Glu
        115                 120                 125

Gly Glu Lys Tyr Phe Leu Gln Met Ser Gly Ile Lys Tyr Ile Tyr Thr
    130                 135                 140

Lys Ala Asp Asn Pro Thr Glu Glu Asn Pro Tyr Lys Val Val Lys Ala
145                 150                 155                 160

Phe Lys Glu Asp Gly Thr Glu Ile Val Pro Thr Glu Thr Tyr Thr Leu
                165                 170                 175

Val Ile Asn Asp Phe Leu Phe Gly Gly Gly Asp Gly Phe Ser Ile Phe
            180                 185                 190

Lys Glu Ala Lys Leu Ile Gly Ala Ile Asn Pro Asp Thr Glu Val Phe
        195                 200                 205

Val Glu Tyr Leu Thr Asp Leu Glu Lys Ala Gly Gln Thr Ile Ser Ala
    210                 215                 220

Thr Ile Pro Gly Arg Lys Ala Phe Val Glu Lys Tyr Val Glu Glu Pro
225                 230                 235                 240

Lys Ala Glu Glu Lys Glu Asp Asn Ala Gly Thr Thr Thr Asp Val Lys
                245                 250                 255

Thr Pro Glu Lys Ala Asn Asp Gly Gly Asp Ser Val Thr Asn Gln Lys
            260                 265                 270

Ala Thr Glu Gln Pro Ala Pro Ser Gly Ser Met Ala Pro Ile Ser Asn
        275                 280                 285

Lys Lys Thr Glu Lys Ala Ser Gly Asn Gln Thr Leu Glu
    290                 295                 300


<210> SEQ ID NO 21
<211> LENGTH: 425
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 21

Met Thr Gly Ser Asp Thr Val Val Thr Gly Val Asn Glu Ile Ile Glu
1               5                   10                  15

Glu Ser Gln Val Lys Asp Glu Val Ser Ile Glu Ser Glu Lys Asn Glu
            20                  25                  30

Ser Leu Asp Gly Ser Asn Ile Glu Ile Val Glu Glu Ile Ala Asp Asn
        35                  40                  45

Ile Pro Ser Pro Val Ile Ala Glu Gly Glu Val Ala Val Glu Met Lys
    50                  55                  60

Val Asp Arg Gly Thr Glu Asn Val Val Ser Arg Asn Asp Thr Glu Val
65                  70                  75                  80

Thr Thr Ser Glu Gln Asn Gln Ile Glu Val Thr Glu Thr Lys Glu Ile
                85                  90                  95

Leu Asn Gln Thr Ser Tyr Gln Thr Glu Ser Gly Glu Gln Arg Gln Ile
            100                 105                 110

Ile Trp Ala His Gly Ile Thr Pro Pro Ala Met Glu Gln Ser Gly Gly
        115                 120                 125

Phe Val Lys Glu Lys Tyr Gly Asp Tyr Leu Asn Tyr Thr Ala Pro Phe
    130                 135                 140

Glu Ala Gly Lys Gly Tyr Tyr Asp Thr Asn Lys Ser Leu Asn Ala Ser
145                 150                 155                 160

Phe Ile Asp Leu Asn Leu Cys Phe Ala Ala Val Ser Ser Asn Met Val
```

```
                165                 170                 175

His Trp Trp Leu Glu Gln Asn Ser Ser Tyr Val Glu Arg Tyr Leu Lys
            180                 185                 190

Glu Lys Lys Gly Thr Val Asn Val Glu Glu Asn Tyr Ala Ile Thr Asp
        195                 200                 205

Leu Arg Arg Tyr Ile Asn Ser Phe Gln Asn Gln Gln Asn Ser Arg Val
    210                 215                 220

Phe Asp Met Phe Lys Thr Tyr Tyr Gly Tyr Arg Thr Asn Gly Phe Val
225                 230                 235                 240

Ser Asp Ala Leu Val Asp Leu Phe Ile Asn Gly Tyr Lys Pro Lys Ala
                245                 250                 255

Gln Gly Gly Val Asn Leu Glu Asp Ser Gln Leu Val Pro Asp Ser Arg
            260                 265                 270

Gly Gly Phe Phe Tyr Asp Val Phe Lys Glu Lys Lys Leu Thr Asn Arg
        275                 280                 285

Ile Phe Ser Gly Ser Tyr Glu Arg Phe Gly Glu Asp Val Arg Thr Val
    290                 295                 300

Leu Glu Ser Lys Gly Leu Leu Gly Leu Thr Tyr Arg Thr Leu Gly Tyr
305                 310                 315                 320

Ala Thr His Ile Val Thr Val Trp Gly Ala Glu Tyr Asp Asn Gln Gly
                325                 330                 335

Lys Ile Lys Ala Val Tyr Ile Thr Asp Ser Asp Asp Gln Gln Glu Gln
            340                 345                 350

Ile Gly Leu Lys Arg Met Gly Ile Thr Arg Asp Ala Ser Gly Asn Pro
        355                 360                 365

Arg Leu Asn Asn His Met Lys Asn Asn Ser Ala Gly Ala Leu Leu Asp
    370                 375                 380

Tyr Val His Thr Ile Arg Leu Gly Gln Asp Leu Trp Glu Glu Tyr Phe
385                 390                 395                 400

Asn Leu Glu Gly Leu Lys Thr Arg Asn Lys Lys Ala Lys Ser Asp Lys
                405                 410                 415

Leu Ile Val Arg Arg Arg Asn Gln Lys
            420                 425


<210> SEQ ID NO 22
<211> LENGTH: 303
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 22

Met Thr Gly Ser Ser Glu Gln Pro Asp Ser Ile Pro His Gln Asn Val
1               5                   10                  15

Glu Ile Ser Leu Val Glu Pro Thr Asn Val Glu Thr Glu Thr Val Val
            20                  25                  30

Thr Pro Ile Asn Asp Ala Ala Thr Pro His Gly Ser Pro Thr Tyr Ile
        35                  40                  45

Asp Asn Ser Val Thr Glu Ser Val Ala Thr Pro Leu Glu Lys Asp Ser
    50                  55                  60

Ile Gln Ala Gly Glu Thr Glu Ile Ala Glu Pro Thr Ser Ser Glu Ser
65                  70                  75                  80

Thr Asn Val Glu Thr Glu Thr Val Val Thr Pro Val Asn Asp Val Ala
                85                  90                  95

Thr Pro His Gly Ser Pro Thr Tyr Ile Asp Asn Ser Val Thr Glu Ser
```

```
            100                 105                 110

Val Ala Thr Pro Leu Glu Lys Asp Ser Ile Gln Ala Gly Glu Thr Glu
        115                 120                 125

Ile Ala Glu Pro Thr Ser Ser Glu Ser Thr Asn Val Glu Thr Glu Thr
    130                 135                 140

Val Val Thr Pro Val Asn Asp Val Ala Thr Pro His Gly Ser Pro Thr
145                 150                 155                 160

Tyr Ile Asp Asn Ser Val Thr Glu Ser Val Ala Thr Pro Leu Glu Lys
                165                 170                 175

Asp Ser Ile Gln Ala Gly Glu Thr Glu Ile Ala Glu Pro Thr Ser Ser
            180                 185                 190

Glu Ser Thr Ser Val Glu Ala Glu Leu Val Asp Asn Ser Glu Ile His
        195                 200                 205

Ala Ala Thr Ser Ser Val Thr Pro Cys Gly Ser Ser Ala Tyr Ala Asp
    210                 215                 220

Gly Ser Thr Thr Glu Ser Val Ala Thr Pro Leu Glu Lys Asp Ser Ile
225                 230                 235                 240

Gln Thr Gly Asn Thr Glu Ile Ala Glu Pro Thr Ser Ser Lys Ser Thr
                245                 250                 255

Asn Val Glu Ala Ala Ser Val Asp Asn Ser Glu Ile His Ala Asp Ala
            260                 265                 270

Ser Leu Thr Ala Val Ser Ser Leu Glu Gly Leu Lys Thr Arg Asn Lys
        275                 280                 285

Lys Ala Lys Ser Asp Lys Leu Ile Val Arg Arg Arg Asn Gln Lys
    290                 295                 300


<210> SEQ ID NO 23
<211> LENGTH: 367
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 23

Met Thr Gly Ser Ala Glu Thr Thr Thr Ala Ala Thr Thr Thr Asn Gln
1               5                   10                  15

Pro Ala Thr Thr Asp Ala Thr Ala Thr Val Pro Ala Thr Thr Asp Ala
            20                  25                  30

Thr Ala Thr Val Pro Ala Thr Ser Val Glu Asn Val Ala Thr Glu Glu
        35                  40                  45

Thr Val Val Pro Ala Ala Glu Glu Thr Val Glu Ala Val Ile Ile His
    50                  55                  60

Thr Asn Asp Val His Gly Arg Ile Leu Glu Glu Lys Asn Val Ile Gly
65                  70                  75                  80

Asp Ala Lys Ala Ala Ala Val Ile Glu Glu Glu Arg Ala Lys Val Glu
                85                  90                  95

Asn Thr Ile Val Val Asp Ala Gly Asp Ala Phe Gln Gly Leu Pro Ile
            100                 105                 110

Ser Asn Ser Thr Lys Gly Glu Asp Arg Ala Asn Ile Met Asn Gln Val
        115                 120                 125

Gly Tyr Asp Ala Met Ala Val Gly Asn His Glu Phe Asp Phe Gly Met
    130                 135                 140

Asp Gln Ala Ile Lys Tyr Lys Glu Thr Leu Asn Phe Pro Leu Leu Ser
145                 150                 155                 160

Ala Asn Thr Tyr Val Asn Gly Ala Arg Val Phe Glu Ala Ser Thr Ile
```

-continued

```
                165                 170                 175

Val Asp Lys Thr Pro Thr Val Val Gly Asp Glu Phe Val Val Ile Gly
            180                 185                 190

Val Thr Thr Pro Glu Thr Ala Thr Lys Thr His Pro Lys Asn Val Glu
        195                 200                 205

Gly Val Thr Phe Thr Asp Pro Val Thr Glu Val Asn Lys Val Ile Asp
    210                 215                 220

Glu Val Glu Ala Arg Ala Leu Ala Asp Asn Arg Val Tyr Lys Asn Tyr
225                 230                 235                 240

Ile Ile Leu Ala His Leu Gly Val Asp Ser Thr Thr Pro Val Glu Trp
                245                 250                 255

Arg Gly Ser Thr Leu Ala Glu Ala Leu Ser Lys Asn Ser Lys Leu Ala
            260                 265                 270

Gly Lys Arg Val Ile Val Ile Asp Gly His Ser His Thr Val Glu Ala
        275                 280                 285

Thr Thr Tyr Gly Asp Asn Val Thr Tyr Asn Gln Thr Gly Ser Tyr Leu
    290                 295                 300

Asn Asn Ile Gly Lys Val Thr Leu Lys Ser Asp Lys Leu Leu Gly Glu
305                 310                 315                 320

Ala Ser Leu Ile Ser Ala Ala Asp Thr Lys Asn Val Thr Pro Asn Ala
                325                 330                 335

Lys Ile Ala Ala Leu Val Asp Leu Glu Gly Leu Lys Thr Arg Asn Lys
            340                 345                 350

Lys Ala Lys Ser Asp Lys Leu Ile Val Arg Arg Arg Asn Gln Lys
        355                 360                 365


<210> SEQ ID NO 24
<211> LENGTH: 344
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 24

Met Thr Gly Ser Asp Glu Ile Lys Ala Lys Tyr Glu Ala Glu Asn Ala
1               5                   10                  15

Gln Val Val Ile Glu Asn Asn Pro Val Glu Leu Asn Gly Asp Arg Ser
            20                  25                  30

Asn Val Arg Val Arg Glu Thr Asn Leu Gly Asn Ala Val Thr Asp Ala
        35                  40                  45

Ile Tyr Ala Tyr Gly Gln Thr Gly Phe Ser Asn Lys Thr Ser Leu Ala
    50                  55                  60

Val Thr Asn Gly Gly Gly Leu Arg Ala Thr Ile Ala Lys Asp Gln Pro
65                  70                  75                  80

Val Thr Lys Gly Asp Ile Ile Ala Val Leu Pro Phe Gly Asn Ile Val
                85                  90                  95

Ser Gln Ile Thr Val Thr Gly Gln Gln Ile Tyr Asp Met Phe Thr Lys
            100                 105                 110

Ser Leu Ser Ser Thr Leu Gln Val Asn Pro Glu Thr Gly Glu Met Leu
        115                 120                 125

Leu Asp Glu Asn Gly Met Pro Leu Phe Glu Ala Ser Gly Gly Phe Leu
    130                 135                 140

His Ile Ser Gly Ala Asn Val Phe Tyr Asp Pro Thr Leu Pro Val Glu
145                 150                 155                 160

Glu Arg Val Leu Leu Ile Gly Ile Leu Asn Pro Glu Thr Gly Glu Tyr
```

```
                165                 170                 175

Asp Ala Leu Asp Leu Glu Lys Thr Tyr Tyr Leu Ala Thr Asn Asp Phe
            180                 185                 190

Leu Ala Ala Gly Gly Asp Gly Tyr Thr Met Leu Gly Gly Ala Arg Glu
        195                 200                 205

Glu Gly Pro Ser Met Asp Ser Val Phe Ala Glu Tyr Leu Lys Thr Ala
    210                 215                 220

Asp Leu Ser Ala Tyr Glu Val Val Asn Pro Tyr Ser Arg Ile Ile Pro
225                 230                 235                 240

Val Asn Ser Ser Ile Asp Thr Asp Glu Asp Gly Tyr Pro Asp Phe Ile
                245                 250                 255

Glu Ile Leu Leu Asp Thr Asp Pro Glu Asn Pro Ala Ser Asn Pro Glu
            260                 265                 270

Thr Val Pro Ala Glu Asn Thr Asp Ser Pro Ser Asn Gln Val Gln Asn
        275                 280                 285

Thr Ser Ala Thr Asp Lys Lys Ala Pro Val Asp Ser Pro Lys Val Gly
    290                 295                 300

Asp Lys Lys Thr Glu Val Ala Ser Pro Ala Lys Thr Thr Lys Ala Gly
305                 310                 315                 320

Leu Glu Gly Leu Lys Thr Arg Asn Lys Lys Ala Lys Ser Asp Lys Leu
                325                 330                 335

Ile Val Arg Arg Arg Asn Gln Lys
            340
```

<210> SEQ ID NO 25
<211> LENGTH: 453
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 25

```
Met Thr Gly Ser Glu Glu Ile Leu Asn Thr Thr Pro Ala Ser Ser Thr
1               5                   10                  15

Glu Ala Ser Gln Ala Val Pro Val Glu Ser Asp Thr Thr Glu Glu Ala
            20                  25                  30

Asp Asn Thr Glu Ser Pro Val Pro Ala Thr Thr Glu Ala Glu Asn Pro
        35                  40                  45

Ser Ser Ser Glu Thr Ala Glu Thr Ser Asp Pro Thr Ser Glu Thr Thr
    50                  55                  60

Asp Thr Thr Thr Ser Glu Ala Arg Thr Val Thr Pro Ala Ala Thr Glu
65                  70                  75                  80

Thr Ser Gln Pro Val Glu Gly Gln Thr Val Asp Val Arg Ile Leu Ala
                85                  90                  95

Thr Thr Asp Leu His Thr Asn Leu Val Asn Tyr Asp Tyr Tyr Gln Asp
            100                 105                 110

Lys Pro Val Glu Thr Leu Gly Leu Ala Lys Thr Ala Val Leu Ile Glu
        115                 120                 125

Glu Ala Lys Lys Glu Asn Pro Asn Val Val Leu Val Asp Asn Gly Asp
    130                 135                 140

Thr Ile Gln Gly Thr Pro Leu Gly Asn Tyr Lys Ser Ile Val Asp Pro
145                 150                 155                 160

Ile Glu Glu Gly Glu Gln His Pro Met Tyr Ala Ala Leu Glu Thr Leu
                165                 170                 175

Gly Phe Asp Val Gly Thr Leu Gly Asn His Glu Phe Asn Tyr Gly Leu
```

```
            180                 185                 190

Ala Tyr Leu Glu Lys Val Ile Arg Thr Ala Asn Met Pro Leu Val Asn
        195                 200                 205

Ala Asn Val Leu Asp Pro Thr Thr Lys Asp Phe Leu Tyr Thr Pro Tyr
    210                 215                 220

Thr Ile Val Lys Lys Thr Phe Thr Asp Thr Glu Gly Lys Lys Val Thr
225                 230                 235                 240

Leu Asn Val Gly Val Thr Gly Ile Val Pro Pro Gln Ile Leu Asn Trp
                245                 250                 255

Asp Lys Ala Tyr Leu Glu Gly Lys Val Ile Val Arg Asp Ala Val Glu
            260                 265                 270

Ala Val Arg Asp Ile Ile Pro Thr Met Arg Glu Asn Gly Ala Asp Ile
        275                 280                 285

Val Leu Val Leu Ser His Ser Gly Ile Gly Asp Asp Gln Tyr Glu Val
    290                 295                 300

Gly Glu Glu Asn Val Gly Tyr Gln Ile Ala Ser Leu Ser Gly Val Asp
305                 310                 315                 320

Ala Val Ile Thr Gly His Ser His Ala Glu Phe Pro Gly Thr Ala Glu
                325                 330                 335

Lys Pro Ser Phe Tyr Ala Lys Tyr Ser Gly Val Asp Asp Thr Asn Gly
            340                 345                 350

Lys Ile Asn Gly Thr Pro Val Thr Met Ala Gly Lys Tyr Gly Asp His
        355                 360                 365

Leu Gly Val Ile Asp Leu Asn Leu Val Phe Lys Asp Gly Lys Trp Thr
    370                 375                 380

Thr Thr Ser Ser Lys Ala Ala Ile Arg Lys Ile Asp Thr Lys Ser Ser
385                 390                 395                 400

Val Ala Asp Gly Arg Ile Ile Asp Leu Ala Lys Glu Ala His Asn Glu
                405                 410                 415

Thr Ile Lys Tyr Val Arg Gln Gln Val Gly Glu Thr Thr Leu Glu Gly
            420                 425                 430

Leu Lys Thr Arg Asn Lys Lys Ala Lys Ser Asp Lys Leu Ile Val Arg
        435                 440                 445

Arg Arg Asn Gln Lys
    450


<210> SEQ ID NO 26
<211> LENGTH: 362
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 26

Met Thr Gly Ser Gly Glu Thr Thr Ala Pro Ile Asn Ser Phe Phe Ala
1               5                   10                  15

Leu Val Gln Asp Asp Pro Ser Val Gln Ile Val Asn Asn Ala Gln Ile
            20                  25                  30

Trp Tyr Ala Lys Gln Gln Leu Ala Gly Thr Ser Glu Ala Asn Leu Pro
        35                  40                  45

Ile Leu Ser Ala Ala Ala Pro Phe Lys Ala Gly Thr Arg Gly Asp Ala
    50                  55                  60

Ser Ala Tyr Thr Asp Ile Pro Ala Gly Pro Ile Ala Ile Lys Asn Val
65                  70                  75                  80

Ala Asp Leu Tyr Leu Tyr Asp Asn Val Val Ala Ile Leu Lys Val Asn
```

-continued

```
                85                  90                  95

Gly Ala Gln Leu Lys Glu Trp Leu Glu Met Ser Ala Gly Gln Phe Asn
            100                 105                 110

Gln Val Asp Leu Ser Ser Thr Glu Pro Gln Asn Leu Val Asn Thr Asp
        115                 120                 125

Phe Arg Thr Tyr Asn Phe Asp Val Ile Asp Gly Val Thr Tyr Gln Tyr
    130                 135                 140

Asp Ile Thr Gln Pro Asn Lys Tyr Asp Arg Asp Gly Lys Ile Val Asn
145                 150                 155                 160

Glu Thr Ala Ser Arg Val Arg Asn Leu Gln Tyr Asn Gly Gln Asp Val
                165                 170                 175

Thr Ala Asp Gln Glu Phe Ile Val Val Thr Asn Asn Tyr Arg Ala Asn
            180                 185                 190

Gly Thr Phe Pro Gly Val Arg Glu Ala Ser Ile Asn Arg Leu Leu Asn
        195                 200                 205

Leu Glu Asn Arg Gln Ala Ile Ile Asn Tyr Ile Ile Ala Glu Lys Val
    210                 215                 220

Ile Asn Pro Thr Ala Asp Asn Asn Trp Thr Phe Thr Asp Ser Ile Lys
225                 230                 235                 240

Gly Leu Asp Leu Arg Phe Leu Thr Ala Asp Arg Ala Lys Ser Leu Val
                245                 250                 255

Thr Asp Gln Glu Cys Ile Val Tyr Leu Gln Ala Ser Thr Ala Ser Glu
            260                 265                 270

Gly Phe Gly Glu Phe Lys Phe Val Tyr Thr Glu Ser Lys Val Val Thr
        275                 280                 285

Pro Asp Glu Gln Gln Ser Asp Gln Gly Asn Thr Gly Gln Asp Ile Val
    290                 295                 300

Leu Glu Ser Gly Gln Arg Ile Thr Leu Pro Ala Val Asn Pro Pro Ala
305                 310                 315                 320

Pro Ala Pro Gln His Lys Leu Ala Ser Pro His Ser Gln Ala Ser Thr
                325                 330                 335

Lys Thr Leu Glu Gly Leu Lys Thr Arg Asn Lys Lys Ala Lys Ser Asp
            340                 345                 350

Lys Leu Ile Val Arg Arg Arg Asn Gln Lys
        355                 360


<210> SEQ ID NO 27
<211> LENGTH: 366
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 27

Met Thr Gly Ser Asp Glu Leu Ala Val Gln Ile Met Gly Val Asn Asp
1               5                   10                  15

Phe His Gly Ala Leu Asp Met Thr Gly Thr Ala Arg Leu Glu Gly Glu
            20                  25                  30

Thr Val Arg Asn Ala Gly Thr Ala Ala Leu Leu Asp Ala Tyr Met Asp
        35                  40                  45

Asp Ser Gln Ala Glu Phe Glu Glu Thr Ala Ala Glu Thr Glu Thr Pro
    50                  55                  60

Ala Glu Ser Ile Arg Val Gln Ala Gly Asp Met Val Gly Ala Ser Pro
65                  70                  75                  80

Ser Asn Ser Gly Leu Leu Gln Asp Glu Pro Thr Val Lys Val Phe Asn
```

-continued

```
                85                  90                  95

Lys Met Asp Val Glu Tyr Gly Thr Leu Gly Asn His Glu Phe Asp Glu
            100                 105                 110

Gly Leu Asp Glu Tyr Asn Arg Ile Met Thr Gly Glu Ala Pro Lys Lys
        115                 120                 125

Gly Gln Phe Asn Glu Ile Val Asp Asn Tyr Thr Arg Glu Ala Ala Lys
    130                 135                 140

Gln Glu Ile Val Ile Ala Asn Val Ile Asp Lys Glu Thr Gly Glu Ile
145                 150                 155                 160

Pro Tyr Gly Trp Lys Pro Tyr Ala Ile Lys Thr Ile Pro Val Asn Asp
                165                 170                 175

Lys Glu Ala Lys Ile Gly Phe Ile Gly Val Val Thr Thr Glu Ile Pro
            180                 185                 190

Asn Leu Val Leu Lys Lys Asn Tyr Glu Gln Tyr Thr Phe Leu Asn Glu
        195                 200                 205

Ala Glu Thr Ile Ala Lys Tyr Ala Arg Glu Leu Ala Glu Lys Gly Val
    210                 215                 220

Asn Ala Ile Val Val Leu Ala His Val Pro Ala Thr Ser Lys Asp Gly
225                 230                 235                 240

Val Ala Ala Gly Glu Ala Ala Asp Met Ile Ala Lys Leu Asn Glu Ile
                245                 250                 255

Tyr Pro Glu His Ser Val Asp Leu Val Phe Ala Gly His Asn His Val
            260                 265                 270

Tyr Thr Asn Gly Thr Thr Gly Lys Thr Leu Ile Val Gln Ala Thr Ser
        275                 280                 285

Gln Gly Lys Ala Tyr Ala Asp Val Arg Ala Val Tyr Asp Thr Asp Ile
    290                 295                 300

Ala Asp Phe Lys Ala Val Pro Thr Ala Lys Ile Ile Ala Val Ala Pro
305                 310                 315                 320

Gly Gln Lys Thr Pro Ser Pro Glu Ile Gln Ala Ile Val Asp Glu Ala
                325                 330                 335

Asn Thr Ile Val Lys Lys Leu Glu Gly Leu Lys Thr Arg Asn Lys Lys
            340                 345                 350

Ala Lys Ser Asp Lys Leu Ile Val Arg Arg Arg Asn Gln Lys
        355                 360                 365


<210> SEQ ID NO 28
<211> LENGTH: 317
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 28

Met Thr Gly Ser Glu Ile Gln Ala Ile Val Asp Glu Ala Asn Thr Ile
1               5                   10                  15

Val Lys Lys Val Thr Glu Gln Lys Ile Ala Thr Ala Ser Gln Ala Thr
            20                  25                  30

Asp Ile Ser Arg Glu Val Asn Glu Phe Lys Glu Ser Ala Val Gly Asn
        35                  40                  45

Leu Val Thr Ser Ala Gln Leu Ala Ile Ala Lys Lys Ser Gly Tyr Asp
    50                  55                  60

Val Asp Phe Ala Met Thr Asn Asp Gly Gly Ile Arg Ala Asp Leu Lys
65                  70                  75                  80

Val Gln Glu Asp Gly Thr Val Thr Trp Gly Ala Ala Gln Ala Val Gln
```

```
                85                  90                  95

Pro Phe Gly Asn Ile Leu Gln Val Val Gln Met Thr Gly Glu Gln Ile
            100                 105                 110

Tyr Thr Ala Leu Asn Gln Gln Tyr Asp Glu Gly Glu Lys Tyr Phe Leu
        115                 120                 125

Gln Met Ser Gly Ile Lys Tyr Ile Tyr Thr Lys Ala Asp Asn Pro Thr
    130                 135                 140

Glu Glu Asn Pro Tyr Lys Val Val Lys Ala Phe Lys Glu Asp Gly Thr
145                 150                 155                 160

Glu Ile Val Pro Thr Glu Thr Tyr Thr Leu Val Ile Asn Asp Phe Leu
                165                 170                 175

Phe Gly Gly Gly Asp Gly Phe Ser Ile Phe Lys Glu Ala Lys Leu Ile
            180                 185                 190

Gly Ala Ile Asn Pro Asp Thr Glu Val Phe Val Glu Tyr Leu Thr Asp
        195                 200                 205

Leu Glu Lys Ala Gly Gln Thr Ile Ser Ala Thr Ile Pro Gly Arg Lys
    210                 215                 220

Ala Phe Val Glu Lys Tyr Val Glu Glu Pro Lys Ala Glu Glu Lys Glu
225                 230                 235                 240

Asp Asn Ala Gly Thr Thr Thr Asp Val Lys Thr Pro Glu Lys Ala Asn
                245                 250                 255

Asp Gly Gly Asp Ser Val Thr Asn Gln Lys Ala Thr Glu Gln Pro Ala
            260                 265                 270

Pro Ser Gly Ser Met Ala Pro Ile Ser Asn Lys Lys Thr Glu Lys Ala
        275                 280                 285

Ser Gly Asn Gln Thr Leu Glu Gly Leu Lys Thr Arg Asn Lys Lys Ala
    290                 295                 300

Lys Ser Asp Lys Leu Ile Val Arg Arg Arg Asn Gln Lys
305                 310                 315


<210> SEQ ID NO 29
<211> LENGTH: 429
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 29

Met Thr Lys Pro Ala Leu Gly Leu Lys Thr Arg Asn Lys Lys Ala Lys
1               5                   10                  15

Ser Asp Lys Leu Ile Val Arg Arg Arg Asn Gln Lys Gly Ser Asp Thr
            20                  25                  30

Val Val Thr Gly Val Asn Glu Ile Ile Glu Glu Ser Gln Val Lys Asp
        35                  40                  45

Glu Val Ser Ile Glu Ser Glu Lys Asn Glu Ser Leu Asp Gly Ser Asn
    50                  55                  60

Ile Glu Ile Val Glu Glu Ile Ala Asp Asn Ile Pro Ser Pro Val Ile
65                  70                  75                  80

Ala Glu Gly Glu Val Ala Val Glu Met Lys Val Asp Arg Gly Thr Glu
                85                  90                  95

Asn Val Val Ser Arg Asn Asp Thr Glu Val Thr Thr Ser Glu Gln Asn
            100                 105                 110

Gln Ile Glu Val Thr Glu Thr Lys Glu Ile Leu Asn Gln Thr Ser Tyr
        115                 120                 125

Gln Thr Glu Ser Gly Glu Gln Arg Gln Ile Ile Trp Ala His Gly Ile
```

```
    130                 135                 140

Thr Pro Pro Ala Met Glu Gln Ser Gly Gly Phe Val Lys Glu Lys Tyr
145                 150                 155                 160

Gly Asp Tyr Leu Asn Tyr Thr Ala Pro Phe Glu Ala Gly Lys Gly Tyr
                165                 170                 175

Tyr Asp Thr Asn Lys Ser Leu Asn Ala Ser Phe Ile Asp Leu Asn Leu
            180                 185                 190

Cys Phe Ala Ala Val Ser Ser Asn Met Val His Trp Trp Leu Glu Gln
        195                 200                 205

Asn Ser Ser Tyr Val Glu Arg Tyr Leu Lys Glu Lys Lys Gly Thr Val
    210                 215                 220

Asn Val Glu Glu Asn Tyr Ala Ile Thr Asp Leu Arg Arg Tyr Ile Asn
225                 230                 235                 240

Ser Phe Gln Asn Gln Gln Asn Ser Arg Val Phe Asp Met Phe Lys Thr
                245                 250                 255

Tyr Tyr Gly Tyr Arg Thr Asn Gly Phe Val Ser Asp Ala Leu Val Asp
            260                 265                 270

Leu Phe Ile Asn Gly Tyr Lys Pro Lys Ala Gln Gly Gly Val Asn Leu
        275                 280                 285

Glu Asp Ser Gln Leu Val Pro Asp Ser Arg Gly Gly Phe Phe Tyr Asp
    290                 295                 300

Val Phe Lys Glu Lys Lys Leu Thr Asn Arg Ile Phe Ser Gly Ser Tyr
305                 310                 315                 320

Glu Arg Phe Gly Glu Asp Val Arg Thr Val Leu Glu Ser Lys Gly Leu
                325                 330                 335

Leu Gly Leu Thr Tyr Arg Thr Leu Gly Tyr Ala Thr His Ile Val Thr
            340                 345                 350

Val Trp Gly Ala Glu Tyr Asp Asn Gln Gly Lys Ile Lys Ala Val Tyr
        355                 360                 365

Ile Thr Asp Ser Asp Asp Gln Gln Glu Gln Ile Gly Leu Lys Arg Met
    370                 375                 380

Gly Ile Thr Arg Asp Ala Ser Gly Asn Pro Arg Leu Asn Asn His Met
385                 390                 395                 400

Lys Asn Asn Ser Ala Gly Ala Leu Leu Asp Tyr Val His Thr Ile Arg
                405                 410                 415

Leu Gly Gln Asp Leu Trp Glu Glu Tyr Phe Asn Leu Glu
            420                 425
```

<210> SEQ ID NO 30
<211> LENGTH: 348
<212> TYPE: PRT
<213> ORGANISM: ARTIFICIAL SEQUENCE
<220> FEATURE:
<223> OTHER INFORMATION: Fragment of S. suis protein with affinity-tag.

<400> SEQUENCE: 30

```
Met Thr Lys Pro Ala Leu Gly Leu Lys Thr Arg Asn Lys Lys Ala Lys
1               5                   10                  15

Ser Asp Lys Leu Ile Val Arg Arg Arg Asn Gln Lys Gly Ser Asp Glu
            20                  25                  30

Ile Lys Ala Lys Tyr Glu Ala Glu Asn Ala Gln Val Val Ile Glu Asn
        35                  40                  45

Asn Pro Val Glu Leu Asn Gly Asp Arg Ser Asn Val Arg Val Arg Glu
    50                  55                  60

Thr Asn Leu Gly Asn Ala Val Thr Asp Ala Ile Tyr Ala Tyr Gly Gln
```

```
65                  70                  75                  80

Thr Gly Phe Ser Asn Lys Thr Ser Leu Ala Val Thr Asn Gly Gly Gly
                85                  90                  95

Leu Arg Ala Thr Ile Ala Lys Asp Gln Pro Val Thr Lys Gly Asp Ile
            100                 105                 110

Ile Ala Val Leu Pro Phe Gly Asn Ile Val Ser Gln Ile Thr Val Thr
        115                 120                 125

Gly Gln Gln Ile Tyr Asp Met Phe Thr Lys Ser Leu Ser Ser Thr Leu
    130                 135                 140

Gln Val Asn Pro Glu Thr Gly Glu Met Leu Leu Asp Glu Asn Gly Met
145                 150                 155                 160

Pro Leu Phe Glu Ala Ser Gly Gly Phe Leu His Ile Ser Gly Ala Asn
                165                 170                 175

Val Phe Tyr Asp Pro Thr Leu Pro Val Glu Glu Arg Val Leu Leu Ile
            180                 185                 190

Gly Ile Leu Asn Pro Glu Thr Gly Glu Tyr Asp Ala Leu Asp Leu Glu
        195                 200                 205

Lys Thr Tyr Tyr Leu Ala Thr Asn Asp Phe Leu Ala Ala Gly Gly Asp
    210                 215                 220

Gly Tyr Thr Met Leu Gly Gly Ala Arg Glu Glu Gly Pro Ser Met Asp
225                 230                 235                 240

Ser Val Phe Ala Glu Tyr Leu Lys Thr Ala Asp Leu Ser Ala Tyr Glu
                245                 250                 255

Val Val Asn Pro Tyr Ser Arg Ile Ile Pro Val Asn Ser Ser Ile Asp
            260                 265                 270

Thr Asp Glu Asp Gly Tyr Pro Asp Phe Ile Glu Ile Leu Leu Asp Thr
        275                 280                 285

Asp Pro Glu Asn Pro Ala Ser Asn Pro Glu Thr Val Pro Ala Glu Asn
    290                 295                 300

Thr Asp Ser Pro Ser Asn Gln Val Gln Asn Thr Ser Ala Thr Asp Lys
305                 310                 315                 320

Lys Ala Pro Val Asp Ser Pro Lys Val Gly Asp Lys Lys Thr Glu Val
                325                 330                 335

Ala Ser Pro Ala Lys Thr Thr Lys Ala Gly Leu Glu
            340                 345
```

<210> SEQ ID NO 31
<211> LENGTH: 343
<212> TYPE: PRT
<213> ORGANISM: ARTIFICIAL SEQUENCE
<220> FEATURE:
<223> OTHER INFORMATION: S. equi protein with affinity-tag.

<400> SEQUENCE: 31

```
Met Thr Gly Ser Asp Asp Tyr Gln Arg Asn Ala Thr Glu Ala Tyr Ala
1               5                   10                  15

Lys Glu Val Pro His Gln Ile Thr Ser Val Trp Thr Lys Gly Val Thr
            20                  25                  30

Pro Leu Thr Pro Glu Gln Phe Arg Tyr Asn Asn Glu Asp Val Ile His
        35                  40                  45

Ala Pro Tyr Leu Ala His Gln Gly Trp Tyr Asp Ile Thr Lys Ala Phe
    50                  55                  60

Asp Gly Lys Asp Asn Leu Leu Cys Gly Ala Ala Thr Ala Gly Asn Met
65                  70                  75                  80

Leu His Trp Trp Phe Asp Gln Asn Lys Thr Glu Ile Glu Ala Tyr Leu
```

-continued

```
                85                  90                  95

Ser Lys His Pro Glu Lys Gln Lys Ile Ile Phe Asn Asn Gln Glu Leu
            100                 105                 110

Phe Asp Leu Lys Ala Ala Ile Asp Thr Lys Asp Ser Gln Thr Asn Ser
        115                 120                 125

Gln Leu Phe Asn Tyr Phe Arg Asp Lys Ala Phe Pro Asn Leu Ser Ala
    130                 135                 140

Arg Gln Leu Gly Val Met Pro Asp Leu Val Leu Asp Met Phe Ile Asn
145                 150                 155                 160

Gly Tyr Tyr Leu Asn Val Phe Lys Thr Gln Ser Thr Asp Val Asn Arg
                165                 170                 175

Pro Tyr Gln Asp Lys Asp Lys Arg Gly Gly Ile Phe Asp Ala Val Phe
            180                 185                 190

Thr Arg Gly Asp Gln Thr Thr Leu Leu Thr Ala Arg His Asp Leu Lys
        195                 200                 205

Asn Lys Gly Leu Asn Asp Ile Ser Thr Ile Ile Lys Gln Glu Leu Thr
    210                 215                 220

Glu Gly Arg Ala Leu Ala Leu Ser His Thr Tyr Ala Asn Val Ser Ile
225                 230                 235                 240

Ser His Val Ile Asn Leu Trp Gly Ala Asp Phe Asn Ala Glu Gly Asn
                245                 250                 255

Leu Glu Ala Ile Tyr Val Thr Asp Ser Asp Ala Asn Ala Ser Ile Gly
            260                 265                 270

Met Lys Lys Tyr Phe Val Gly Ile Asn Ala His Arg His Val Ala Ile
        275                 280                 285

Ser Ala Lys Lys Ile Glu Gly Glu Asn Ile Gly Ala Gln Val Leu Gly
    290                 295                 300

Leu Phe Thr Leu Ser Ser Gly Lys Asp Ile Trp Gln Lys Leu Ser Leu
305                 310                 315                 320

Glu Gly Leu Lys Thr Arg Asn Lys Lys Ala Lys Ser Asp Lys Leu Ile
                325                 330                 335

Val Arg Arg Arg Asn Gln Lys
            340


<210> SEQ ID NO 32
<211> LENGTH: 22
<212> TYPE: PRT
<213> ORGANISM: ARTIFICIAL SEQUENCE
<220> FEATURE:
<223> OTHER INFORMATION: Affinity tag.

<400> SEQUENCE: 32

Gly Leu Lys Thr Arg Asn Lys Lys Ala Lys Ser Asp Lys Leu Ile Val
1               5                   10                  15

Arg Arg Arg Asn Gln Lys
            20


<210> SEQ ID NO 33
<211> LENGTH: 26
<212> TYPE: PRT
<213> ORGANISM: ARTIFICIAL SEQUENCE
<220> FEATURE:
<223> OTHER INFORMATION: Affinty tag.

<400> SEQUENCE: 33

Lys Pro Ala Leu Gly Leu Lys Thr Arg Asn Lys Lys Ala Lys Ser Asp
1               5                   10                  15
```

Lys Leu Ile Val Arg Arg Arg Asn Gln Lys
20 25

<210> SEQ ID NO 34
<211> LENGTH: 721
<212> TYPE: PRT
<213> ORGANISM: ARTIFICIAL SEQUENCE
<220> FEATURE:
<223> OTHER INFORMATION: Fusion polypeptide of fragments of S. suis proteins.

<400> SEQUENCE: 34

Asp Glu Ile Lys Ala Lys Tyr Glu Ala Glu Asn Ala Gln Val Val Ile
1 5 10 15

Glu Asn Asn Pro Val Glu Leu Asn Gly Asp Arg Ser Asn Val Arg Val
20 25 30

Arg Glu Thr Asn Leu Gly Asn Ala Val Thr Asp Ala Ile Tyr Ala Tyr
35 40 45

Gly Gln Thr Gly Phe Ser Asn Lys Thr Ser Leu Ala Val Thr Asn Gly
50 55 60

Gly Gly Leu Arg Ala Thr Ile Ala Lys Asp Gln Pro Val Thr Lys Gly
65 70 75 80

Asp Ile Ile Ala Val Leu Pro Phe Gly Asn Ile Val Ser Gln Ile Thr
85 90 95

Val Thr Gly Gln Gln Ile Tyr Asp Met Phe Thr Lys Ser Leu Ser Ser
100 105 110

Thr Leu Gln Val Asn Pro Glu Thr Gly Glu Met Leu Leu Asp Glu Asn
115 120 125

Gly Met Pro Leu Phe Glu Ala Ser Gly Gly Phe Leu His Ile Ser Gly
130 135 140

Ala Asn Val Phe Tyr Asp Pro Thr Leu Pro Val Glu Glu Arg Val Leu
145 150 155 160

Leu Ile Gly Ile Leu Asn Pro Glu Thr Gly Glu Tyr Asp Ala Leu Asp
165 170 175

Leu Glu Lys Thr Tyr Tyr Leu Ala Thr Asn Asp Phe Leu Ala Ala Gly
180 185 190

Gly Asp Gly Tyr Thr Met Leu Gly Gly Ala Arg Glu Glu Gly Pro Ser
195 200 205

Met Asp Ser Val Phe Ala Glu Tyr Leu Lys Thr Ala Asp Leu Ser Ala
210 215 220

Tyr Glu Val Val Asn Pro Tyr Ser Arg Ile Ile Pro Val Asn Ser Ser
225 230 235 240

Ile Asp Thr Asp Glu Asp Gly Tyr Pro Asp Phe Ile Glu Ile Leu Leu
245 250 255

Asp Thr Asp Pro Glu Asn Pro Ala Ser Asn Pro Glu Thr Val Pro Ala
260 265 270

Glu Asn Thr Asp Ser Pro Ser Asn Gln Val Gln Asn Thr Ser Ala Thr
275 280 285

Asp Lys Lys Ala Pro Val Asp Ser Pro Lys Val Gly Asp Lys Lys Thr
290 295 300

Glu Val Ala Ser Pro Ala Lys Thr Thr Lys Ala Gly Gly Thr Asp Thr
305 310 315 320

Val Val Thr Gly Val Asn Glu Ile Ile Glu Glu Ser Gln Val Lys Asp
325 330 335

Glu Val Ser Ile Glu Ser Glu Lys Asn Glu Ser Leu Asp Gly Ser Asn
340 345 350

Ile Glu Ile Val Glu Glu Ile Ala Asp Asn Ile Pro Ser Pro Val Ile
355 360 365

Ala Glu Gly Glu Val Ala Val Glu Met Lys Val Asp Arg Gly Thr Glu
370 375 380

Asn Val Val Ser Arg Asn Asp Thr Glu Val Thr Thr Ser Glu Gln Asn
385 390 395 400

Gln Ile Glu Val Thr Glu Thr Lys Glu Ile Leu Asn Gln Thr Ser Tyr
405 410 415

Gln Thr Glu Ser Gly Glu Gln Arg Gln Ile Ile Trp Ala His Gly Ile
420 425 430

Thr Pro Pro Ala Met Glu Gln Ser Gly Gly Phe Val Lys Glu Lys Tyr
435 440 445

Gly Asp Tyr Leu Asn Tyr Thr Ala Pro Phe Glu Ala Gly Lys Gly Tyr
450 455 460

Tyr Asp Thr Asn Lys Ser Leu Asn Ala Ser Phe Ile Asp Leu Asn Leu
465 470 475 480

Cys Phe Ala Ala Val Ser Ser Asn Met Val His Trp Trp Leu Glu Gln
485 490 495

Asn Ser Ser Tyr Val Glu Arg Tyr Leu Lys Glu Lys Lys Gly Thr Val
500 505 510

Asn Val Glu Glu Asn Tyr Ala Ile Thr Asp Leu Arg Arg Tyr Ile Asn
515 520 525

Ser Phe Gln Asn Gln Gln Asn Ser Arg Val Phe Asp Met Phe Lys Thr
530 535 540

Tyr Tyr Gly Tyr Arg Thr Asn Gly Phe Val Ser Asp Ala Leu Val Asp
545 550 555 560

Leu Phe Ile Asn Gly Tyr Lys Pro Lys Ala Gln Gly Gly Val Asn Leu
565 570 575

Glu Asp Ser Gln Leu Val Pro Asp Ser Arg Gly Gly Phe Phe Tyr Asp
580 585 590

Val Phe Lys Glu Lys Lys Leu Thr Asn Arg Ile Phe Ser Gly Ser Tyr
595 600 605

Glu Arg Phe Gly Glu Asp Val Arg Thr Val Leu Glu Ser Lys Gly Leu
610 615 620

Leu Gly Leu Thr Tyr Arg Thr Leu Gly Tyr Ala Thr His Ile Val Thr
625 630 635 640

Val Trp Gly Ala Glu Tyr Asp Asn Gln Gly Lys Ile Lys Ala Val Tyr
645 650 655

Ile Thr Asp Ser Asp Asp Gln Gln Glu Gln Ile Gly Leu Lys Arg Met
660 665 670

Gly Ile Thr Arg Asp Ala Ser Gly Asn Pro Arg Leu Asn Asn His Met
675 680 685

Lys Asn Asn Ser Ala Gly Ala Leu Leu Asp Tyr Val His Thr Ile Arg
690 695 700

Leu Gly Gln Asp Leu Trp Glu Glu Tyr Phe Asn Pro Leu Ala Lys Ala
705 710 715 720

Lys

<210> SEQ ID NO 35
<211> LENGTH: 625
<212> TYPE: PRT
<213> ORGANISM: ARTIFICIAL SEQUENCE
<220> FEATURE:
<223> OTHER INFORMATION: Fusion polypeptide of fragments of S. suis proteins.

<400> SEQUENCE: 35

```
Glu Ile Gln Ala Ile Val Asp Glu Ala Asn Thr Ile Val Lys Lys Val
1               5                   10                  15

Thr Glu Gln Lys Ile Ala Thr Ala Ser Gln Ala Thr Asp Ile Ser Arg
            20                  25                  30

Glu Val Asn Glu Phe Lys Glu Ser Ala Val Gly Asn Leu Val Thr Ser
        35                  40                  45

Ala Gln Leu Ala Ile Ala Lys Lys Ser Gly Tyr Asp Val Asp Phe Ala
    50                  55                  60

Met Thr Asn Asp Gly Gly Ile Arg Ala Asp Leu Lys Val Gln Glu Asp
65                  70                  75                  80

Gly Thr Val Thr Trp Gly Ala Ala Gln Ala Val Gln Pro Phe Gly Asn
                85                  90                  95

Ile Leu Gln Val Val Gln Met Thr Gly Glu Gln Ile Tyr Thr Ala Leu
            100                 105                 110

Asn Gln Gln Tyr Asp Glu Gly Glu Lys Tyr Phe Leu Gln Met Ser Gly
        115                 120                 125

Ile Lys Tyr Ile Tyr Thr Lys Ala Asp Asn Pro Thr Glu Glu Asn Pro
    130                 135                 140

Tyr Lys Val Val Lys Ala Phe Lys Glu Asp Gly Thr Glu Ile Val Pro
145                 150                 155                 160

Thr Glu Thr Tyr Thr Leu Val Ile Asn Asp Phe Leu Phe Gly Gly Gly
                165                 170                 175

Asp Gly Phe Ser Ile Phe Lys Glu Ala Lys Leu Ile Gly Ala Ile Asn
            180                 185                 190

Pro Asp Thr Glu Val Phe Val Glu Tyr Leu Thr Asp Leu Glu Lys Ala
        195                 200                 205

Gly Gln Thr Ile Ser Ala Thr Ile Pro Gly Arg Lys Ala Phe Val Glu
    210                 215                 220

Lys Tyr Val Glu Glu Pro Lys Ala Glu Glu Lys Glu Asp Asn Ala Gly
225                 230                 235                 240

Thr Thr Thr Asp Val Lys Thr Pro Glu Lys Ala Asn Asp Gly Gly Asp
                245                 250                 255

Ser Val Thr Asn Gln Lys Ala Thr Glu Gln Pro Ala Pro Ser Gly Ser
            260                 265                 270

Met Ala Pro Ile Ser Asn Lys Lys Thr Glu Lys Ala Ser Gly Asn Gln
        275                 280                 285

Thr Gly Thr Gly Glu Thr Thr Ala Pro Ile Asn Ser Phe Phe Ala Leu
    290                 295                 300

Val Gln Asp Asp Pro Ser Val Gln Ile Val Asn Asn Ala Gln Ile Trp
305                 310                 315                 320

Tyr Ala Lys Gln Gln Leu Ala Gly Thr Ser Glu Ala Asn Leu Pro Ile
                325                 330                 335

Leu Ser Ala Ala Ala Pro Phe Lys Ala Gly Thr Arg Gly Asp Ala Ser
            340                 345                 350

Ala Tyr Thr Asp Ile Pro Ala Gly Pro Ile Ala Ile Lys Asn Val Ala
        355                 360                 365

Asp Leu Tyr Leu Tyr Asp Asn Val Val Ala Ile Leu Lys Val Asn Gly
    370                 375                 380

Ala Gln Leu Lys Glu Trp Leu Glu Met Ser Ala Gly Gln Phe Asn Gln
385                 390                 395                 400
```

```
Val Asp Leu Ser Ser Thr Glu Pro Gln Asn Leu Val Asn Thr Asp Phe
                405                 410                 415

Arg Thr Tyr Asn Phe Asp Val Ile Asp Gly Val Thr Tyr Gln Tyr Asp
            420                 425                 430

Ile Thr Gln Pro Asn Lys Tyr Asp Arg Asp Gly Lys Ile Val Asn Glu
        435                 440                 445

Thr Ala Ser Arg Val Arg Asn Leu Gln Tyr Asn Gly Gln Asp Val Thr
    450                 455                 460

Ala Asp Gln Glu Phe Ile Val Val Thr Asn Asn Tyr Arg Ala Asn Gly
465                 470                 475                 480

Thr Phe Pro Gly Val Arg Glu Ala Ser Ile Asn Arg Leu Leu Asn Leu
                485                 490                 495

Glu Asn Arg Gln Ala Ile Ile Asn Tyr Ile Ile Ala Glu Lys Val Ile
            500                 505                 510

Asn Pro Thr Ala Asp Asn Asn Trp Thr Phe Thr Asp Ser Ile Lys Gly
        515                 520                 525

Leu Asp Leu Arg Phe Leu Thr Ala Asp Arg Ala Lys Ser Leu Val Thr
    530                 535                 540

Asp Gln Glu Cys Ile Val Tyr Leu Gln Ala Ser Thr Ala Ser Glu Gly
545                 550                 555                 560

Phe Gly Glu Phe Lys Phe Val Tyr Thr Glu Ser Lys Val Val Thr Pro
                565                 570                 575

Asp Glu Gln Gln Ser Asp Gln Gly Asn Thr Gly Gln Asp Ile Val Leu
            580                 585                 590

Glu Ser Gly Gln Arg Ile Thr Leu Pro Ala Val Asn Pro Pro Ala Pro
        595                 600                 605

Ala Pro Gln His Lys Leu Ala Ser Pro His Ser Gln Ala Ser Thr Lys
    610                 615                 620

Thr
625


<210> SEQ ID NO 36
<211> LENGTH: 749
<212> TYPE: PRT
<213> ORGANISM: ARTIFICIAL SEQUENCE
<220> FEATURE:
<223> OTHER INFORMATION: Fusion polypeptide of fragments of S. suis
      proteins with affinity-tag.

<400> SEQUENCE: 36

Met Thr Gly Ser Asp Glu Ile Lys Ala Lys Tyr Glu Ala Glu Asn Ala
1               5                   10                  15

Gln Val Val Ile Glu Asn Asn Pro Val Glu Leu Asn Gly Asp Arg Ser
            20                  25                  30

Asn Val Arg Val Arg Glu Thr Asn Leu Gly Asn Ala Val Thr Asp Ala
        35                  40                  45

Ile Tyr Ala Tyr Gly Gln Thr Gly Phe Ser Asn Lys Thr Ser Leu Ala
    50                  55                  60

Val Thr Asn Gly Gly Gly Leu Arg Ala Thr Ile Ala Lys Asp Gln Pro
65                  70                  75                  80

Val Thr Lys Gly Asp Ile Ile Ala Val Leu Pro Phe Gly Asn Ile Val
                85                  90                  95

Ser Gln Ile Thr Val Thr Gly Gln Gln Ile Tyr Asp Met Phe Thr Lys
            100                 105                 110

Ser Leu Ser Ser Thr Leu Gln Val Asn Pro Glu Thr Gly Glu Met Leu
        115                 120                 125
```

```
Leu Asp Glu Asn Gly Met Pro Leu Phe Glu Ala Ser Gly Gly Phe Leu
    130                 135                 140

His Ile Ser Gly Ala Asn Val Phe Tyr Asp Pro Thr Leu Pro Val Glu
145                 150                 155                 160

Glu Arg Val Leu Leu Ile Gly Ile Leu Asn Pro Glu Thr Gly Glu Tyr
                165                 170                 175

Asp Ala Leu Asp Leu Glu Lys Thr Tyr Tyr Leu Ala Thr Asn Asp Phe
            180                 185                 190

Leu Ala Ala Gly Gly Asp Gly Tyr Thr Met Leu Gly Gly Ala Arg Glu
        195                 200                 205

Glu Gly Pro Ser Met Asp Ser Val Phe Ala Glu Tyr Leu Lys Thr Ala
    210                 215                 220

Asp Leu Ser Ala Tyr Glu Val Val Asn Pro Tyr Ser Arg Ile Ile Pro
225                 230                 235                 240

Val Asn Ser Ser Ile Asp Thr Asp Glu Asp Gly Tyr Pro Asp Phe Ile
                245                 250                 255

Glu Ile Leu Leu Asp Thr Asp Pro Glu Asn Pro Ala Ser Asn Pro Glu
            260                 265                 270

Thr Val Pro Ala Glu Asn Thr Asp Ser Pro Ser Asn Gln Val Gln Asn
        275                 280                 285

Thr Ser Ala Thr Asp Lys Lys Ala Pro Val Asp Ser Pro Lys Val Gly
    290                 295                 300

Asp Lys Lys Thr Glu Val Ala Ser Pro Ala Lys Thr Thr Lys Ala Gly
305                 310                 315                 320

Gly Thr Asp Thr Val Val Thr Gly Val Asn Glu Ile Ile Glu Glu Ser
                325                 330                 335

Gln Val Lys Asp Glu Val Ser Ile Glu Ser Glu Lys Asn Glu Ser Leu
            340                 345                 350

Asp Gly Ser Asn Ile Glu Ile Val Glu Glu Ile Ala Asp Asn Ile Pro
        355                 360                 365

Ser Pro Val Ile Ala Glu Gly Glu Val Ala Val Glu Met Lys Val Asp
    370                 375                 380

Arg Gly Thr Glu Asn Val Val Ser Arg Asn Asp Thr Glu Val Thr Thr
385                 390                 395                 400

Ser Glu Gln Asn Gln Ile Glu Val Thr Glu Thr Lys Glu Ile Leu Asn
                405                 410                 415

Gln Thr Ser Tyr Gln Thr Glu Ser Gly Glu Gln Arg Gln Ile Ile Trp
            420                 425                 430

Ala His Gly Ile Thr Pro Pro Ala Met Glu Gln Ser Gly Gly Phe Val
        435                 440                 445

Lys Glu Lys Tyr Gly Asp Tyr Leu Asn Tyr Thr Ala Pro Phe Glu Ala
    450                 455                 460

Gly Lys Gly Tyr Tyr Asp Thr Asn Lys Ser Leu Asn Ala Ser Phe Ile
465                 470                 475                 480

Asp Leu Asn Leu Cys Phe Ala Ala Val Ser Ser Asn Met Val His Trp
                485                 490                 495

Trp Leu Glu Gln Asn Ser Ser Tyr Val Glu Arg Tyr Leu Lys Glu Lys
            500                 505                 510

Lys Gly Thr Val Asn Val Glu Glu Asn Tyr Ala Ile Thr Asp Leu Arg
        515                 520                 525

Arg Tyr Ile Asn Ser Phe Gln Asn Gln Gln Asn Ser Arg Val Phe Asp
    530                 535                 540
```

```
Met Phe Lys Thr Tyr Tyr Gly Tyr Arg Thr Asn Gly Phe Val Ser Asp
545                 550                 555                 560

Ala Leu Val Asp Leu Phe Ile Asn Gly Tyr Lys Pro Lys Ala Gln Gly
                565                 570                 575

Gly Val Asn Leu Glu Asp Ser Gln Leu Val Pro Asp Ser Arg Gly Gly
            580                 585                 590

Phe Phe Tyr Asp Val Phe Lys Glu Lys Lys Leu Thr Asn Arg Ile Phe
        595                 600                 605

Ser Gly Ser Tyr Glu Arg Phe Gly Glu Asp Val Arg Thr Val Leu Glu
    610                 615                 620

Ser Lys Gly Leu Leu Gly Leu Thr Tyr Arg Thr Leu Gly Tyr Ala Thr
625                 630                 635                 640

His Ile Val Thr Val Trp Gly Ala Glu Tyr Asp Asn Gln Gly Lys Ile
                645                 650                 655

Lys Ala Val Tyr Ile Thr Asp Ser Asp Asp Gln Gln Glu Gln Ile Gly
            660                 665                 670

Leu Lys Arg Met Gly Ile Thr Arg Asp Ala Ser Gly Asn Pro Arg Leu
        675                 680                 685

Asn Asn His Met Lys Asn Asn Ser Ala Gly Ala Leu Leu Asp Tyr Val
    690                 695                 700

His Thr Ile Arg Leu Gly Gln Asp Leu Trp Glu Glu Tyr Phe Asn Pro
705                 710                 715                 720

Leu Ala Lys Ala Lys Leu Glu Gly Leu Lys Thr Arg Asn Lys Lys Ala
                725                 730                 735

Lys Ser Asp Lys Leu Ile Val Arg Arg Arg Asn Gln Lys
            740                 745


<210> SEQ ID NO 37
<211> LENGTH: 653
<212> TYPE: PRT
<213> ORGANISM: ARTIFICIAL SEQUENCE
<220> FEATURE:
<223> OTHER INFORMATION: Fusion polypeptide of fragments of S. suis
      proteins with affinity-tag.

<400> SEQUENCE: 37

Met Thr Gly Ser Glu Ile Gln Ala Ile Val Asp Glu Ala Asn Thr Ile
1               5                   10                  15

Val Lys Lys Val Thr Glu Gln Lys Ile Ala Thr Ala Ser Gln Ala Thr
            20                  25                  30

Asp Ile Ser Arg Glu Val Asn Glu Phe Lys Glu Ser Ala Val Gly Asn
        35                  40                  45

Leu Val Thr Ser Ala Gln Leu Ala Ile Ala Lys Lys Ser Gly Tyr Asp
    50                  55                  60

Val Asp Phe Ala Met Thr Asn Asp Gly Gly Ile Arg Ala Asp Leu Lys
65                  70                  75                  80

Val Gln Glu Asp Gly Thr Val Thr Trp Gly Ala Ala Gln Ala Val Gln
                85                  90                  95

Pro Phe Gly Asn Ile Leu Gln Val Val Gln Met Thr Gly Glu Gln Ile
            100                 105                 110

Tyr Thr Ala Leu Asn Gln Gln Tyr Asp Glu Gly Glu Lys Tyr Phe Leu
        115                 120                 125

Gln Met Ser Gly Ile Lys Tyr Ile Tyr Thr Lys Ala Asp Asn Pro Thr
    130                 135                 140

Glu Glu Asn Pro Tyr Lys Val Val Lys Ala Phe Lys Glu Asp Gly Thr
145                 150                 155                 160
```

-continued

```
Glu Ile Val Pro Thr Glu Thr Tyr Thr Leu Val Ile Asn Asp Phe Leu
                165                 170                 175

Phe Gly Gly Gly Asp Gly Phe Ser Ile Phe Lys Glu Ala Lys Leu Ile
            180                 185                 190

Gly Ala Ile Asn Pro Asp Thr Glu Val Phe Val Glu Tyr Leu Thr Asp
        195                 200                 205

Leu Glu Lys Ala Gly Gln Thr Ile Ser Ala Thr Ile Pro Gly Arg Lys
    210                 215                 220

Ala Phe Val Glu Lys Tyr Val Glu Glu Pro Lys Ala Glu Glu Lys Glu
225                 230                 235                 240

Asp Asn Ala Gly Thr Thr Thr Asp Val Lys Thr Pro Glu Lys Ala Asn
                245                 250                 255

Asp Gly Gly Asp Ser Val Thr Asn Gln Lys Ala Thr Glu Gln Pro Ala
            260                 265                 270

Pro Ser Gly Ser Met Ala Pro Ile Ser Asn Lys Lys Thr Glu Lys Ala
        275                 280                 285

Ser Gly Asn Gln Thr Gly Thr Gly Glu Thr Thr Ala Pro Ile Asn Ser
    290                 295                 300

Phe Phe Ala Leu Val Gln Asp Asp Pro Ser Val Gln Ile Val Asn Asn
305                 310                 315                 320

Ala Gln Ile Trp Tyr Ala Lys Gln Gln Leu Ala Gly Thr Ser Glu Ala
                325                 330                 335

Asn Leu Pro Ile Leu Ser Ala Ala Ala Pro Phe Lys Ala Gly Thr Arg
            340                 345                 350

Gly Asp Ala Ser Ala Tyr Thr Asp Ile Pro Ala Gly Pro Ile Ala Ile
        355                 360                 365

Lys Asn Val Ala Asp Leu Tyr Leu Tyr Asp Asn Val Val Ala Ile Leu
    370                 375                 380

Lys Val Asn Gly Ala Gln Leu Lys Glu Trp Leu Glu Met Ser Ala Gly
385                 390                 395                 400

Gln Phe Asn Gln Val Asp Leu Ser Ser Thr Glu Pro Gln Asn Leu Val
                405                 410                 415

Asn Thr Asp Phe Arg Thr Tyr Asn Phe Asp Val Ile Asp Gly Val Thr
            420                 425                 430

Tyr Gln Tyr Asp Ile Thr Gln Pro Asn Lys Tyr Asp Arg Asp Gly Lys
        435                 440                 445

Ile Val Asn Glu Thr Ala Ser Arg Val Arg Asn Leu Gln Tyr Asn Gly
    450                 455                 460

Gln Asp Val Thr Ala Asp Gln Glu Phe Ile Val Val Thr Asn Asn Tyr
465                 470                 475                 480

Arg Ala Asn Gly Thr Phe Pro Gly Val Arg Glu Ala Ser Ile Asn Arg
                485                 490                 495

Leu Leu Asn Leu Glu Asn Arg Gln Ala Ile Ile Asn Tyr Ile Ile Ala
            500                 505                 510

Glu Lys Val Ile Asn Pro Thr Ala Asp Asn Asn Trp Thr Phe Thr Asp
        515                 520                 525

Ser Ile Lys Gly Leu Asp Leu Arg Phe Leu Thr Ala Asp Arg Ala Lys
    530                 535                 540

Ser Leu Val Thr Asp Gln Glu Cys Ile Val Tyr Leu Gln Ala Ser Thr
545                 550                 555                 560

Ala Ser Glu Gly Phe Gly Glu Phe Lys Phe Val Tyr Thr Glu Ser Lys
                565                 570                 575
```

-continued

```
Val Val Thr Pro Asp Glu Gln Gln Ser Asp Gln Gly Asn Thr Gly Gln
            580                 585                 590

Asp Ile Val Leu Glu Ser Gly Gln Arg Ile Thr Leu Pro Ala Val Asn
        595                 600                 605

Pro Pro Ala Pro Ala Pro Gln His Lys Leu Ala Ser Pro His Ser Gln
    610                 615                 620

Ala Ser Thr Lys Thr Leu Glu Gly Leu Lys Thr Arg Asn Lys Lys Ala
625                 630                 635                 640

Lys Ser Asp Lys Leu Ile Val Arg Arg Arg Asn Gln Lys
                645                 650


<210> SEQ ID NO 38
<211> LENGTH: 403
<212> TYPE: PRT
<213> ORGANISM: STREPTOCOCCUS SUIS

<400> SEQUENCE: 38

Asp Thr Val Val Thr Gly Val Asn Glu Ile Ile Glu Glu Ser Gln Val
1               5                   10                  15

Lys Asp Glu Val Ser Ile Glu Ser Glu Lys Asn Glu Ser Leu Asp Gly
            20                  25                  30

Ser Asn Ile Glu Ile Val Glu Glu Ile Ala Asp Asn Ile Pro Ser Pro
        35                  40                  45

Val Ile Ala Glu Gly Glu Val Ala Val Glu Met Lys Val Asp Arg Gly
    50                  55                  60

Thr Glu Asn Val Val Ser Arg Asn Asp Thr Glu Val Thr Thr Ser Glu
65                  70                  75                  80

Gln Asn Gln Ile Glu Val Thr Glu Thr Lys Glu Ile Leu Asn Gln Thr
                85                  90                  95

Ser Tyr Gln Thr Glu Ser Gly Glu Gln Arg Gln Ile Ile Trp Ala His
            100                 105                 110

Gly Ile Thr Pro Pro Ala Met Glu Gln Ser Gly Gly Phe Val Lys Glu
        115                 120                 125

Lys Tyr Gly Asp Tyr Leu Asn Tyr Thr Ala Pro Phe Glu Ala Gly Lys
    130                 135                 140

Gly Tyr Tyr Asp Thr Asn Lys Ser Leu Asn Ala Ser Phe Ile Asp Leu
145                 150                 155                 160

Asn Leu Cys Phe Ala Ala Val Ser Ser Asn Met Val His Trp Trp Leu
                165                 170                 175

Glu Gln Asn Ser Ser Tyr Val Glu Arg Tyr Leu Lys Glu Lys Lys Gly
            180                 185                 190

Thr Val Asn Val Glu Glu Asn Tyr Ala Ile Thr Asp Leu Arg Arg Tyr
        195                 200                 205

Ile Asn Ser Phe Gln Asn Gln Gln Asn Ser Arg Val Phe Asp Met Phe
    210                 215                 220

Lys Thr Tyr Tyr Gly Tyr Arg Thr Asn Gly Phe Val Ser Asp Ala Leu
225                 230                 235                 240

Val Asp Leu Phe Ile Asn Gly Tyr Lys Pro Lys Ala Gln Gly Gly Val
                245                 250                 255

Asn Leu Glu Asp Ser Gln Leu Val Pro Asp Ser Arg Gly Gly Phe Phe
            260                 265                 270

Tyr Asp Val Phe Lys Glu Lys Lys Leu Thr Asn Arg Ile Phe Ser Gly
        275                 280                 285

Ser Tyr Glu Arg Phe Gly Glu Asp Val Arg Thr Val Leu Glu Ser Lys
    290                 295                 300
```

```
Gly Leu Leu Gly Leu Thr Tyr Arg Thr Leu Gly Tyr Ala Thr His Ile
305                 310                 315                 320

Val Thr Val Trp Gly Ala Glu Tyr Asp Asn Gln Gly Lys Ile Lys Ala
                325                 330                 335

Val Tyr Ile Thr Asp Ser Asp Asp Gln Gln Glu Gln Ile Gly Leu Lys
            340                 345                 350

Arg Met Gly Ile Thr Arg Asp Ala Ser Gly Asn Pro Arg Leu Asn Asn
        355                 360                 365

His Met Lys Asn Asn Ser Ala Gly Ala Leu Leu Asp Tyr Val His Thr
    370                 375                 380

Ile Arg Leu Gly Gln Asp Leu Trp Glu Glu Tyr Phe Asn Pro Leu Ala
385                 390                 395                 400

Lys Ala Lys
```

<210> SEQ ID NO 39
<211> LENGTH: 1242
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 39

```
catatgacag gatccgatac ggtagtaacg ggtgtaaatg aaatcattga agaatcgcag     60

gttaaagatg aggtgagcat cgagtccgag aagaacgaat ctctggatgg cagcaacatc    120

gaaattgttg aagaaattgc ggacaatatc ccgtcgccgg tgattgcaga gggtgaagtc    180

gccgtggaga tgaaagtgga ccgcggcacc gagaatgttg tctcgcgtaa tgatacggaa    240

gtcaccacga gcgaacaaaa tcaaatcgaa gtcaccgaga ctaaagaaat tctgaatcag    300

acgagctatc aaacggagag cggtgaacag cgtcagatca tttgggcgca cggtattacc    360

ccgcctgcga tggaacaatc cggtggtttc gttaaagaaa agtatggtga ttacctgaac    420

tacactgccc cgttcgaggc tggcaaaggt tactatgaca ccaataagag cctgaatgca    480

agctttattg atctgaatct gtgttttgca gcggtcagca gcaatatggt ccactggtgg    540

ctggagcaga atagcagcta tgtcgagcgt tacttgaaag aaaagaaggg caccgttaac    600

gtggaagaga attacgccat tactgacctg cgccgttaca ttaacagctt ccagaatcaa    660

cagaatagcc gtgtttttga tatgtttaag acgtactatg gctaccgtac gaacggcttc    720

gttagcgacg cactggtcga cctgtttatc aatggttaca agccgaaggc gcagggcggt    780

gttaacttgg aagattcgca actggttcca gatagccgtg gtggtttctt ctatgacgtt    840

ttcaaagaga agaagctgac gaaccgtatt ttcagcggta gctatgaacg tttcggtgaa    900

gatgttcgca ccgttctgga gagcaagggt ctgttgggtc tgacgtaccg taccctgggt    960

tacgccaccc acatcgtgac cgtttggggt gcggagtatg ataatcaagg caagatcaag   1020

gcagtgtaca tcaccgactc cgacgaccaa caggaacaga tcggtctgaa acgcatgggt   1080

atcacgcgcg acgccagcgg caatccgcgt ctgaacaacc acatgaaaaa caatagcgcc   1140

ggtgcactgc tggactacgt gcacacgatt cgcttgggtc aggatctgtg ggaagagtat   1200

ttcaatctcg agcatcacca tcaccatcac cattaaacta gt                      1242
```

<210> SEQ ID NO 40
<211> LENGTH: 1293
<212> TYPE: DNA
<213> ORGANISM: ARTIFICIAL SEQUENCE

<220> FEATURE:
<223> OTHER INFORMATION: Codon optimized DNA sequence of fragment of S. suis protein with affinity-tag.

<400> SEQUENCE: 40

```
catatgacag gatccgatac ggtagtaacg ggtgtaaatg aaatcattga agaatcgcag      60

gttaaagatg aggtgagcat cgagtccgag aagaacgaat ctctggatgg cagcaacatc     120

gaaattgttg aagaaattgc ggacaatatc ccgtcgccgg tgattgcaga gggtgaagtc     180

gccgtggaga tgaaagtgga ccgcggcacc gagaatgttg tctcgcgtaa tgatacggaa     240

gtcaccacga gcgaacaaaa tcaaatcgaa gtcaccgaga ctaaagaaat tctgaatcag     300

acgagctatc aaacggagag cggtgaacag cgtcagatca tttgggcgca cggtattacc     360

ccgcctgcga tggaacaatc cggtggtttc gttaaagaaa agtatggtga ttacctgaac     420

tacactgccc cgttcgaggc tggcaaaggt tactatgaca ccaataagag cctgaatgca     480

agctttattg atctgaatct gtgttttgca gcggtcagca gcaatatggt ccactggtgg     540

ctggagcaga atagcagcta tgtcgagcgt tacttgaaag aaaagaaggg caccgttaac     600

gtggaagaga attacgccat tactgacctg cgccgttaca ttaacagctt ccagaatcaa     660

cagaatagcc gtgtttttga tatgtttaag acgtactatg gctaccgtac gaacggcttc     720

gttagcgacg cactggtcga cctgtttatc aatggttaca agccgaaggc gcagggcggt     780

gttaacttgg aagattcgca actggttcca gatagccgtg gtggtttctt ctatgacgtt     840

ttcaaagaga agaagctgac gaaccgtatt ttcagcggta gctatgaacg tttcggtgaa     900

gatgttcgca ccgttctgga gagcaagggt ctgttgggtc tgacgtaccg taccctgggt     960

tacgccaccc acatcgtgac cgtttggggt gcggagtatg ataatcaagg caagatcaag    1020

gcagtgtaca tcaccgactc cgacgaccaa caggaacaga tcggtctgaa acgcatgggt    1080

atcacgcgcg acgccagcgg caatccgcgt ctgaacaacc acatgaaaaa caatagcgcc    1140

ggtgcactgc tggactacgt gcacacgatt cgcttgggtc aggatctgtg ggaagagtat    1200

ttcaatctcg agggactgaa gacccgcaat aagaaagcca aaagcgacaa acttattgtt    1260

cgccgtcgca atcagaagta atgattaact agt                                 1293
```

<210> SEQ ID NO 41
<211> LENGTH: 876
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 41

```
catatgacag gatccagcga gcagccggac agcattccgc accagaacgt ggagatttcc      60

ctggttgagc cgacgaatgt ggaaaccgaa accgtggtta ccccgattaa tgacgcggcg     120

acccctcatg gtagccctac gtatattgac aattccgtta ccgagtccgt tgcgacgccg     180

ctggagaagg atagcatcca ggcgggtgaa accgaaatcg cagagccgac cagctcggag     240

tccacgaatg tagaaacgga aaccgtcgtt accccggtta acgacgttgc aaccccacat     300

ggcagcccta cctacattga caactctgtg accgagagcg tcgctacccc gctggaaaaa     360

gattccatcc aagctggtga aacggagatc gcagaaccga ccagcagcga gagcaccaac     420

gttgaaaccg agactgtggt caccccggtg aacgatgtcg ccactccgca cggtagcccg     480

acttatatcg acaactccgt cacggaatcc gtggcgaccc cactggaaaa ggattctatt     540
```

```
caagcgggtg aaactgagat cgcggagccg acgtctagcg agagcactag cgttgaggca    600

gaactggtgg acaattctga gatccacgca gccacgagca gcgtcacccc gtgcggcagc    660

agcgcctatg cagacggtag cacgaccgag tctgtagcga ccccgttgga gaaggactct    720

attcaaaccg gtaacaccga aattgccgaa ccgacgagca gcaaaagcac caatgttgag    780

gcggcaagcg ttgacaatag cgagatccat gcggacgcat cgctgaccgc ggtgagcagc    840

ctcgagcatc accatcacca tcaccattaa actagt                              876
```

<210> SEQ ID NO 42
<211> LENGTH: 927
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 42

```
catatgacag gatccagcga gcagccggac agcattccgc accagaacgt ggagatttcc     60

ctggttgagc cgacgaatgt ggaaaccgaa accgtggtta ccccgattaa tgacgcggcg    120

acccctcatg gtagccctac gtatattgac aattccgtta ccgagtccgt tgcgacgccg    180

ctggagaagg atagcatcca ggcgggtgaa accgaaatcg cagagccgac cagctcggag    240

tccacgaatg tagaaacgga aaccgtcgtt accccggtta acgacgttgc aaccccacat    300

ggcagcccta cctacattga caactctgtg accgagagcg tcgctacccc gctggaaaaa    360

gattccatcc aagctggtga aacggagatc gcagaaccga ccagcagcga gagcaccaac    420

gttgaaaccg agactgtggt caccccggtg aacgatgtcg ccactccgca cggtagcccg    480

acttatatcg acaactccgt cacggaatcc gtggcgaccc cactggaaaa ggattctatt    540

caagcgggtg aaactgagat cgcggagccg acgtctagcg agagcactag cgttgaggca    600

gaactggtgg acaattctga gatccacgca gccacgagca gcgtcacccc gtgcggcagc    660

agcgcctatg cagacggtag cacgaccgag tctgtagcga ccccgttgga gaaggactct    720

attcaaaccg gtaacaccga aattgccgaa ccgacgagca gcaaaagcac caatgttgag    780

gcggcaagcg ttgacaatag cgagatccat gcggacgcat cgctgaccgc ggtgagcagc    840

ctcgagggac tgaagacccg caataagaaa gccaaaagcg acaaacttat tgttcgccgt    900

cgcaatcaga agtaatgatt aactagt                                        927
```

<210> SEQ ID NO 43
<211> LENGTH: 996
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 43

```
catatgacag gatcccatca tcatcatcat catgtcgacg aaatcaaagc aaaatacgaa     60

gccgaaaacg cccaggttgt catcgaaaat aatccggtgg aactgaatgg tgaccgcagc    120

aatgtgcgtg tccgcgaaac caacctgggt aatgcggtga cggatgcaat ttatgcttac    180

ggtcagaccg gctttagtaa caaaacctcc ctggccgtta cgaatggcgg tggcctgcgt    240

gcgaccatcg ccaaagacca gccggtgacg aagggtgata ttatcgcggt tctgccgttt    300

ggcaatattg tttctcaaat caccgtcacg ggtcagcaaa tttatgacat gttcaccaaa    360

agcctgagct ctacgctgca ggttaacccg gaaaccggtg aaatgctgct ggatgaaaat    420
```

```
ggcatgccgc tgtttgaagc gtcaggtggc ttcctgcata tctcgggcgc caacgtgttc    480

tatgatccga ccctgccggt cgaagaacgc gtgctgctga ttggtatcct gaatccggaa    540

acgggcgaat acgacgcact ggatctggaa aaaacctatt acctggctac gaacgacttt    600

ctggcggccg gtggcgatgg ttataccatg ctgggtggcg cccgtgaaga aggcccgagc    660

atggactctg ttttcgcaga atacctgaag accgcagatc tgagcgctta tgaagtggtt    720

aacccgtact ctcgcattat cccggtcaat agttccattg ataccgacga agatggctat    780

ccggatttta ttgaaatcct gctggacacc gatccggaaa acccggcaag taatccggaa    840

accgttccgg ctgaaaacac ggattcaccg tcgaaccagg tccaaaatac cagtgcgacg    900

gacaaaaagg ccccggtgga ttccccgaaa gtgggcgata agaaaaccga agtggcatcc    960

ccggcaaaaa cgaccaaagc aggtgtctaa ctcgag                               996
```

<210> SEQ ID NO 44
<211> LENGTH: 1050
<212> TYPE: DNA
<213> ORGANISM: ARTIFICIAL SEQUENCE
<220> FEATURE:
<223> OTHER INFORMATION: Codon optimized DNA sequence of fragment of *S. suis* protein with affinity-tag.

<400> SEQUENCE: 44

```
catatgacag gatccgacga aatcaaagca aaatacgaag ccgaaaacgc ccaggttgtc     60

atcgaaaata atccggtgga actgaatggt gaccgcagca atgtgcgtgt ccgcgaaacc    120

aacctgggta atgcggtgac ggatgcaatt tatgcttacg gtcagaccgg ctttagtaac    180

aaaacctccc tggccgttac gaatggcggt ggcctgcgtg cgaccatcgc caaagaccag    240

ccggtgacga agggtgatat tatcgcggtt ctgccgtttg gcaatattgt ttctcaaatc    300

accgtcacgg gtcagcaaat ttatgacatg ttcaccaaaa gcctgagctc tacgctgcag    360

gttaacccgg aaaccggtga aatgctgctg gatgaaaatg gcatgccgct gtttgaagcg    420

tcaggtggct tcctgcatat ctcgggcgcc aacgtgttct atgatccgac cctgccggtc    480

gaagaacgcg tgctgctgat tggtatcctg aatccggaaa cgggcgaata cgacgcactg    540

gatctggaaa aaacctatta cctggctacg aacgactttc tggcggccgg tggcgatggt    600

tataccatgc tgggtggcgc ccgtgaagaa ggcccgagca tggactctgt tttcgcagaa    660

tacctgaaga ccgcagatct gagcgcttat gaagtggtta acccgtactc tcgcattatc    720

ccggtcaata gttccattga taccgacgaa gatggctatc cggattttat tgaaatcctg    780

ctggacaccg atccggaaaa cccggcaagt aatccggaaa ccgttccggc tgaaaacacg    840

gattcaccgt cgaaccaggt ccaaaatacc agtgcgacgg acaaaaaggc cccggtggat    900

tccccgaaag tgggcgataa gaaaaccgaa gtggcatccc cggcaaaaac gaccaaagca    960

ggtctcgagg gactgaagac ccgcaataag aaagccaaaa gcgacaaact tattgttcgc   1020

cgtcgcaatc agaagtaatg attaactagt                                    1050
```

<210> SEQ ID NO 45
<211> LENGTH: 1059
<212> TYPE: DNA
<213> ORGANISM: ARTIFICIAL SEQUENCE
<220> FEATURE:
<223> OTHER INFORMATION: Codon optimized DNA sequence of fragment of *S. suis* protein with affinity-tag.

<400> SEQUENCE: 45

-continued

```
catatgacag gatccgcaga aaccaccacc gctgctacga cgacgaatca accggctacc     60

accgatgcta cggcaaccgt tccggcgacg accgatgcga ccgcaacggt tccggctacc    120

agcgttgaaa acgtcgcaac ggaagaaacc gtggttccgg cggccgaaga aacggtggaa    180

gctgttatta tccataccaa cgatgtccac ggtcgtattc tggaagaaaa gaacgtgatc    240

ggcgacgcaa aggcagctgc ggttattgaa gaagaacgcg ctaaagtcga aaacacgatc    300

gtcgtggatg cgggcgacgc ctttcagggt ctgccgatta gcaattctac caaaggtgaa    360

gatcgtgcga acatcatgaa tcaagtcggc tacgacgcca tggcagtggg taaccatgaa    420

tttgatttcg gcatggacca ggcgattaaa tacaaggaaa cgctgaattt tccgctgctg    480

agtgccaaca cctatgttaa tggtgcgcgc gtcttcgaag cctcaaccat tgttgataaa    540

accccgacgg ttgtcggtga cgaatttgtg gttatcggcg tgaccacgcc ggaaaccgca    600

acgaaaaccc atccgaagaa cgtcgaaggc gtgacgttca ccgatccggt taccgaagtc    660

aataaagtga tcgatgaagt tgaagctcgt gcgctggccg acaaccgcgt gtataagaat    720

tacattatcc tggcccacct gggtgtggat tcaaccacgc cggttgaatg gcgtggctcg    780

accctggcag aagctctgag taaaaattcc aagctggcgg gtaaacgcgt cattgtgatc    840

gatggccatt cccacaccgt ggaagccacc acgtatggtg acaacgttac gtacaatcaa    900

accggtagct atctgaacaa tattggcaaa gtgaccctga aatctgataa gctgctgggc    960

gaagcgtcgc tgatctccgc cgcagacacc aagaacgtca cgccgaacgc taaaatcgcc   1020

gcactggtcg accatcatca tcatcatcat taactcgag                          1059
```

<210> SEQ ID NO 46
<211> LENGTH: 1119
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 46

```
catatgacag gatccgcaga aaccaccacc gctgctacga cgacgaatca accggctacc     60

accgatgcta cggcaaccgt tccggcgacg accgatgcga ccgcaacggt tccggctacc    120

agcgttgaaa acgtcgcaac ggaagaaacc gtggttccgg cggccgaaga aacggtggaa    180

gctgttatta tccataccaa cgatgtccac ggtcgtattc tggaagaaaa gaacgtgatc    240

ggcgacgcaa aggcagctgc ggttattgaa gaagaacgcg ctaaagtcga aaacacgatc    300

gtcgtggatg cgggcgacgc ctttcagggt ctgccgatta gcaattctac caaaggtgaa    360

gatcgtgcga acatcatgaa tcaagtcggc tacgacgcca tggcagtggg taaccatgaa    420

tttgatttcg gcatggacca ggcgattaaa tacaaggaaa cgctgaattt tccgctgctg    480

agtgccaaca cctatgttaa tggtgcgcgc gtcttcgaag cctcaaccat tgttgataaa    540

accccgacgg ttgtcggtga cgaatttgtg gttatcggcg tgaccacgcc ggaaaccgca    600

acgaaaaccc atccgaagaa cgtcgaaggc gtgacgttca ccgatccggt taccgaagtc    660

aataaagtga tcgatgaagt tgaagctcgt gcgctggccg acaaccgcgt gtataagaat    720

tacattatcc tggcccacct gggtgtggat tcaaccacgc cggttgaatg gcgtggctcg    780

accctggcag aagctctgag taaaaattcc aagctggcgg gtaaacgcgt cattgtgatc    840

gatggccatt cccacaccgt ggaagccacc acgtatggtg acaacgttac gtacaatcaa    900

accggtagct atctgaacaa tattggcaaa gtgaccctga aatctgataa gctgctgggc    960
```

-continued

```
gaagcgtcgc tgatctccgc cgcagacacc aagaacgtca cgccgaacgc taaaatcgcc   1020

gcactggtcg acctcgaggg actgaagacc cgcaataaga aagccaaaag cgacaaactt   1080

attgttcgcc gtcgcaatca gaagtaatga ttaactagt                           1119
```

<210> SEQ ID NO 47
<211> LENGTH: 1056
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 47

```
catatgacac atcaccatca ccatcacgga tccggcgaaa cgacggcccc gattaacagc     60

ttctttgccc tggttcagga cgacccgagt gtccagattg tcaataacgc tcagatttgg    120

tatgctaaac agcaactggc aggcaccagc gaagcaaacc tgccgattct gtcggcagca    180

gcaccgttta aagcaggcac ccgtggtgat gctagcgcat acacggacat cccggcaggt    240

ccgattgcaa tcaaaaatgt tgcagatctg tatctgtacg acaacgtggt tgcaattctg    300

aaagtcaatg gcgctcagct gaaagaatgg ctggaaatgt ctgcgggcca gttcaaccaa    360

gtggatctga gctctaccga accgcagaac ctggttaata ccgattttcg tacgtataat    420

ttcgatgtga ttgacggcgt tacctatcag tacgatatca cgcaaccgaa caaatacgat    480

cgcgacggta aaatcgtcaa tgaaaccgca tcacgtgtgc gcaacctgca gtataatggc    540

caagatgtga cggcggacca ggaatttatt gtcgtgacca acaattaccg tgcaaacggc    600

acgtttccgg gcgtgcgtga agcttcgatc aatcgcctgc tgaacctgga aaatcgccag    660

gcgattatca actacatcat cgccgaaaaa gtgatcaacc cgaccgcgga taacaattgg    720

acctttacgg atagtatcaa aggtctggac ctgcgtttcc tgaccgccga tcgcgcaaaa    780

tccctggtta cggaccagga atgcattgtc tatctgcaag ctagtaccgc gtccgaaggc    840

tttggtgaat ttaaattcgt ttacaccgaa agcaaagttg tcacgccgga tgaacagcaa    900

tctgaccagg gcaacaccgg tcaagatatt gtcctggaaa gcggtcagcg tatcacgctg    960

ccggcagtga atccgccggc accggctccg cagcacaaac tggcgtcccc gcattcgcag   1020

gcatccacca aaaccctcga gtaatgatta actagt                             1056
```

<210> SEQ ID NO 48
<211> LENGTH: 1104
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 48

```
catatgacag gatccggcga aacgacggcc ccgattaaca gcttctttgc cctggttcag     60

gacgacccga gtgtccagat tgtcaataac gctcagattt ggtatgctaa acagcaactg    120

gcaggcacca gcgaagcaaa cctgccgatt ctgtcggcag cagcaccgtt taaagcaggc    180

acccgtggtg atgctagcgc atacacggac atcccggcag gtccgattgc aatcaaaaat    240

gttgcagatc tgtatctgta cgacaacgtg gttgcaattc tgaaagtcaa tggcgctcag    300

ctgaaagaat ggctggaaat gtctgcgggc cagttcaacc aagtggatct gagctctacc    360

gaaccgcaga acctggttaa taccgatttt cgtacgtata atttcgatgt gattgacggc    420

gttacctatc agtacgatat cacgcaaccg aacaaatacg atcgcgacgg taaaatcgtc    480
```

```
aatgaaaccg catcacgtgt gcgcaacctg cagtataatg gccaagatgt gacggcggac    540

caggaattta ttgtcgtgac caacaattac cgtgcaaacg gcacgtttcc gggcgtgcgt    600

gaagcttcga tcaatcgcct gctgaacctg gaaaatcgcc aggcgattat caactacatc    660

atcgccgaaa aagtgatcaa cccgaccgcg gataacaatt ggacctttac ggatagtatc    720

aaaggtctgg acctgcgttt cctgaccgcc gatcgcgcaa aatccctggt tacggaccag    780

gaatgcattg tctatctgca agctagtacc gcgtccgaag gctttggtga atttaaattc    840

gtttacaccg aaagcaaagt tgtcacgccg gatgaacagc aatctgacca gggcaacacc    900

ggtcaagata ttgtcctgga aagcggtcag cgtatcacgc tgccggcagt gaatccgccg    960

gcaccggctc cgcagcacaa actggcgtcc ccgcattcgc aggcatccac caaaaccctc   1020

gagggactga agacccgcaa taagaaagcc aaaagcgaca aacttattgt tcgccgtcgc   1080

aatcagaagt aatgattaac tagt                                          1104
```

<210> SEQ ID NO 49
<211> LENGTH: 1314
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 49

```
catatgacag gatccgaaga aatcctgaat accaccccgg cgagcagcac ggaagcctca     60

caagcagtcc cggttgaaag cgataccacg gaagaagcag ataacaccga aagcccggtg    120

ccggcaacca cggaagctga aaatccgagc tctagtgaaa cggcagaaac cagcgatccg    180

accagcgaaa ccacggacac cacgaccagc gaagctcgta ccgttacgcc ggcagcaacc    240

gaaacgtctc agccggtcga aggccaaacc gtcgatgtgc gtattctggc gacgaccgac    300

ctgcatacca acctggtcaa ttatgattat taccaggaca aaccggtgga aacgctgggc    360

ctggcaaaaa ccgctgttct gattgaagaa gccaaaaaag aaaacccgaa tgtggttctg    420

gttgataacg gtgacacgat ccagggcacc ccgctgggta actacaaaag tatcgttgat    480

ccgatcgaag aaggcgaaca acatccgatg tacgcagctc tggaaacgct gggttttgat    540

gttggcaccc tgggtaacca cgaattcaat tatggcctgg catacctgga aaaagtgatt    600

cgcaccgcaa acatgccgct ggtcaacgct aatgtgctgg acccgacgac caaagacttt    660

ctgtatacgc cgtacaccat cgtgaagaaa accttcacgg ataccgaagg taaaaaagtc    720

acgctgaacg ttggcgtcac cggtattgtg ccgccgcaga tcctgaattg ggataaagca    780

tatctggaag gcaaagtgat tgttcgtgat gcggttgaag ccgtccgcga cattatcccg    840

accatgcgtg aaaacggtgc tgatattgtc ctggtgctgt ctcatagtgg catcggtgat    900

gaccagtatg aagttggcga agaaaatgtc ggttaccaaa ttgcgtccct gtcaggcgtg    960

gatgccgtta tcacgggtca tagccacgcg gaatttccgg gcaccgccga aaaaccgtct   1020

ttctatgcga aatacagtgg tgttgatgac accaacggca aaattaatgg tacgccggtg   1080

accatggccg gcaaatacgg tgatcacctg ggcgtgatcg acctgaatct ggtttttaaa   1140

gatggtaaat ggacgaccac gtcctcaaaa gcggccattc gcaaaatcga caccaaatcg   1200

agcgtggccg atggtcgtat tatcgacctg gccaaagaag cacacaacga aaccatcaaa   1260

tacgtccgcc agcaagtcgg tgaaaccacg catcatcatc atcatcatct cgag         1314
```

<210> SEQ ID NO 50
<211> LENGTH: 1377
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 50
catatgacag gatccgaaga aatcctgaat accaccccgg cgagcagcac ggaagcctca 60
caagcagtcc cggttgaaag cgataccacg gaagaagcag ataacaccga aagcccggtg 120
ccggcaacca cggaagctga aaatccgagc tctagtgaaa cggcagaaac cagcgatccg 180
accagcgaaa ccacggacac cacgaccagc gaagctcgta ccgttacgcc ggcagcaacc 240
gaaacgtctc agccggtcga aggccaaacc gtcgatgtgc gtattctggc gacgaccgac 300
ctgcatacca acctggtcaa ttatgattat taccaggaca aaccggtgga aacgctgggc 360
ctggcaaaaa ccgctgttct gattgaagaa gccaaaaaag aaaacccgaa tgtggttctg 420
gttgataacg gtgacacgat ccagggcacc ccgctgggta actacaaaag tatcgttgat 480
ccgatcgaag aaggcgaaca acatccgatg tacgcagctc tggaaacgct gggttttgat 540
gttggcaccc tgggtaacca cgaattcaat tatggcctgg catacctgga aaaagtgatt 600
cgcaccgcaa acatgccgct ggtcaacgct aatgtgctgg acccgacgac caaagacttt 660
ctgtatacgc cgtacaccat cgtgaagaaa accttcacgg ataccgaagg taaaaaagtc 720
acgctgaacg ttggcgtcac cggtattgtg ccgccgcaga tcctgaattg ggataaagca 780
tatctggaag gcaaagtgat tgttcgtgat gcggttgaag ccgtccgcga cattatcccg 840
accatgcgtg aaaacggtgc tgatattgtc ctggtgctgt ctcatagtgg catcggtgat 900
gaccagtatg aagttggcga agaaaatgtc ggttaccaaa ttgcgtccct gtcaggcgtg 960
gatgccgtta tcacgggtca tagccacgcg gaatttccgg gcaccgccga aaaaccgtct 1020
ttctatgcga aatacagtgg tgttgatgac accaacggca aaattaatgg tacgccggtg 1080
accatggccg gcaaatacgg tgatcacctg ggcgtgatcg acctgaatct ggtttttaaa 1140
gatggtaaat ggacgaccac gtcctcaaaa gcggccattc gcaaaatcga caccaaatcg 1200
agcgtggccg atggtcgtat tatcgacctg gccaaagaag cacacaacga aaccatcaaa 1260
tacgtccgcc agcaagtcgg tgaaaccacg ctcgagggac tgaagacccg caataagaaa 1320
gccaaaagcg acaaacttat tgttcgccgt cgcaatcaga agtaatgatt aactagt 1377

<210> SEQ ID NO 51
<211> LENGTH: 921
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 51
catatgacac atcaccatca ccatcacgga tccgaaattc aagccattgt ggacgaagca 60
aataccatcg tcaaaaaagt cacggaacag aaaatcgcaa cggcaagcca agcaacggac 120
attagtcgtg aagtgaacga atttaaagaa agcgcggtgg gtaatctggt tacctctgcc 180
cagctggcaa ttgctaaaaa atccggctat gatgttgact tcgcaatgac caacgatggc 240
ggtatccgcg ctgacctgaa agttcaggaa gatggtacgg tcacctgggg tgcagcacag 300
gcagtgcaac cgtttggtaa cattctgcag gtggttcaaa tgaccggcga acagatctac 360

```
acggctctga atcagcaata tgatgaaggt gaaaaatact ttctgcaaat gagcggcatt    420

aaatatatct acaccaaagc ggataacccg acggaagaaa atccgtataa agtcgtgaaa    480

gccttcaaag aagatggcac cgaaattgtg ccgacggaaa cctacacgct ggttatcaac    540

gactttctgt tcggcggtgg cgatggtttt tcaatcttca aagaagcgaa actgattggc    600

gccatcaatc cggacaccga agtttttgtc gaatatctga cggatctgga aaaagcgggt    660

cagaccattt cggccacgat tccgggccgt aaagcattcg tcgaaaaata cgtggaagaa    720

ccgaaagcag aagaaaaaga agacaatgct ggcaccacga ccgatgtcaa aaccccggaa    780

aaagccaacg atggtggcga cagtgttacc aatcagaaag caacggaaca accggctccg    840

agtggctcaa tggccccgat tagcaataag aagacggaaa aagcaagtgg caaccaaacc    900

ctcgagtaat gattaactag t                                              921
```

<210> SEQ ID NO 52
<211> LENGTH: 969
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 52

```
catatgacag gatccgaaat tcaagccatt gtggacgaag caaataccat cgtcaaaaaa     60

gtcacggaac agaaaatcgc aacggcaagc caagcaacgg acattagtcg tgaagtgaac    120

gaatttaaag aaagcgcggt gggtaatctg gttacctctg cccagctggc aattgctaaa    180

aaatccggct atgatgttga cttcgcaatg accaacgatg gcggtatccg cgctgacctg    240

aaagttcagg aagatggtac ggtcacctgg ggtgcagcac aggcagtgca accgtttggt    300

aacattctgc aggtggttca aatgaccggc gaacagatct acacggctct gaatcagcaa    360

tatgatgaag gtgaaaaata ctttctgcaa atgagcggca ttaaatatat ctacaccaaa    420

gcggataacc cgacggaaga aaatccgtat aaagtcgtga aagccttcaa agaagatggc    480

accgaaattg tgccgacgga aacctacacg ctggttatca acgactttct gttcggcggt    540

ggcgatggtt tttcaatctt caaagaagcg aaactgattg gcgccatcaa tccggacacc    600

gaagtttttg tcgaatatct gacggatctg gaaaaagcgg gtcagaccat ttcggccacg    660

attccgggcc gtaaagcatt cgtcgaaaaa tacgtggaag aaccgaaagc agaagaaaaa    720

gaagacaatg ctggcaccac gaccgatgtc aaaaccccgg aaaaagccaa cgatggtggc    780

gacagtgtta ccaatcagaa agcaacggaa caaccggctc cgagtggctc aatggccccg    840

attagcaata agaagacgga aaaagcaagt ggcaaccaaa ccctcgaggg actgaagacc    900

cgcaataaga aagccaaaag cgacaaactt attgttcgcc gtcgcaatca gaagtaatga    960

ttaactagt                                                            969
```

<210> SEQ ID NO 53
<211> LENGTH: 1065
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 53

```
catatgacag gatccgacga actggctgtt caaattatgg gcgttaatga ctttcacggc     60

gcactggaca tgaccggcac ggcacgtctg gaaggcgaaa ccgtgcgtaa tgcaggcacc    120
```

```
gcagcactgc tggatgcata tatggatgac tcccaggcag aatttgaaga aaccgcagct    180

gaaaccgaaa cgccggcgga atcaattcgc gtgcaggccg gcgatatggt tggtgcaagc    240

ccgtctaaca gtggcctgct gcaagatgaa ccgaccgtta aagtctttaa caaaatggac    300

gtggaatatg gcacgctggg taatcatgaa ttcgatgaag gtctggacga atacaaccgt    360

attatgaccg gcgaagcccc gaaaaaaggc cagttcaacg aaatcgttga taattatacg    420

cgcgaagcgg ccaaacaaga aattgttatc gcgaatgtca ttgacaaaga aaccggcgaa    480

atcccgtatg gttggaaacc gtacgctatt aaaacgatcc cggtcaacga taaagaagcg    540

aaaattggct ttatcggtgt ggttaccacg gaaattccga acctggttct gaagaaaaac    600

tatgaacagt acaccttcct gaatgaagcg gaaacgattg caaaatacgc tcgtgaactg    660

gctgaaaaag gcgtgaacgc aatcgtcgtg ctggcacatg tcccggcaac ctcgaaagat    720

ggcgtggcag ctggtgaagc ggccgacatg attgctaaac tgaatgaaat ctatccggaa    780

cacagcgtgg atctggtttt tgcaggccat aaccacgtgt acaccaatgg caccacgggt    840

aaaaccctga ttgttcaggc cacgagtcag ggtaaagcgt atgcggatgt ccgcgcagtg    900

tacgataccg acatcgcaga cttcaaagct gttccgacgg cgaaaattat cgcggtcgcg    960

ccgggtcaaa aaaccccgag cccggaaatt caggcgattg tggatgaagc aaacaccatt   1020

gtgaaaaaac tcgagcatca ccatcaccat caccattaaa ctagt                   1065
```

```
<210> SEQ ID NO 54
<211> LENGTH: 1116
<212> TYPE: DNA
<213> ORGANISM: ARTIFICIAL SEQUENCE
<220> FEATURE:
<223> OTHER INFORMATION: Codon optimized DNA sequence of fragment of S.
      suis protein with affinity-tag.

<400> SEQUENCE: 54

catatgacag gatccgacga actggctgtt caaattatgg gcgttaatga ctttcacggc     60

gcactggaca tgaccggcac ggcacgtctg gaaggcgaaa ccgtgcgtaa tgcaggcacc    120

gcagcactgc tggatgcata tatggatgac tcccaggcag aatttgaaga aaccgcagct    180

gaaaccgaaa cgccggcgga atcaattcgc gtgcaggccg gcgatatggt tggtgcaagc    240

ccgtctaaca gtggcctgct gcaagatgaa ccgaccgtta aagtctttaa caaaatggac    300

gtggaatatg gcacgctggg taatcatgaa ttcgatgaag gtctggacga atacaaccgt    360

attatgaccg gcgaagcccc gaaaaaaggc cagttcaacg aaatcgttga taattatacg    420

cgcgaagcgg ccaaacaaga aattgttatc gcgaatgtca ttgacaaaga aaccggcgaa    480

atcccgtatg gttggaaacc gtacgctatt aaaacgatcc cggtcaacga taaagaagcg    540

aaaattggct ttatcggtgt ggttaccacg gaaattccga acctggttct gaagaaaaac    600

tatgaacagt acaccttcct gaatgaagcg gaaacgattg caaaatacgc tcgtgaactg    660

gctgaaaaag gcgtgaacgc aatcgtcgtg ctggcacatg tcccggcaac ctcgaaagat    720

ggcgtggcag ctggtgaagc ggccgacatg attgctaaac tgaatgaaat ctatccggaa    780

cacagcgtgg atctggtttt tgcaggccat aaccacgtgt acaccaatgg caccacgggt    840

aaaaccctga ttgttcaggc cacgagtcag ggtaaagcgt atgcggatgt ccgcgcagtg    900

tacgataccg acatcgcaga cttcaaagct gttccgacgg cgaaaattat cgcggtcgcg    960

ccgggtcaaa aaaccccgag cccggaaatt caggcgattg tggatgaagc aaacaccatt   1020

gtgaaaaaac tcgagggact gaagacccgc aataagaaag ccaaaagcga caaacttatt   1080
```

gttcgccgtc gcaatcagaa gtaatgatta actagt 1116

<210> SEQ ID NO 55
<211> LENGTH: 2265
<212> TYPE: DNA
<213> ORGANISM: ARTIFICIAL SEQUENCE
<220> FEATURE:
<223> OTHER INFORMATION: Codon optimized DNA sequence of fusion
polypeptide of fragments of S. suis proteins with affinity-tag.

<400> SEQUENCE: 55
catatgacag gatccgacga aatcaaagca aaatacgaag ccgaaaacgc ccaggttgtc 60
atcgaaaata atccggtgga actgaatggt gaccgcagca atgtgcgtgt ccgcgaaacc 120
aacctgggta atgcggtgac ggatgcaatt tatgcttacg gtcagaccgg ctttagtaac 180
aaaacctccc tggccgttac gaatggcggt ggcctgcgtg cgaccatcgc caaagaccag 240
ccggtgacga agggtgatat tatcgcggtt ctgccgtttg gcaatattgt ttctcaaatc 300
accgtcacgg gtcagcaaat ttatgacatg ttcaccaaaa gcctgagctc tacgctgcag 360
gttaacccgg aaaccggtga aatgctgctg gatgaaaatg gcatgccgct gtttgaagcg 420
tcaggtggct tcctgcatat ctcgggcgcc aacgtgttct atgatccgac cctgccggtc 480
gaagaacgcg tgctgctgat tggtatcctg aatccggaaa cgggcgaata cgacgcactg 540
gatctggaaa aaacctatta cctggctacg aacgactttc tggcggccgg tggcgatggt 600
tataccatgc tgggtggcgc ccgtgaagaa ggcccgagca tggactctgt tttcgcagaa 660
tacctgaaga ccgcagatct gagcgcttat gaagtggtta acccgtactc tcgcattatc 720
ccggtcaata gttccattga taccgacgaa gatggctatc cggattttat tgaaatcctg 780
ctggacaccg atccggaaaa cccggcaagt aatccggaaa ccgttccggc tgaaaacacg 840
gattcaccgt cgaaccaggt ccaaaatacc agtgcgacgg acaaaaaggc cccggtggat 900
tccccgaaag tgggcgataa gaaaaccgaa gtggcatccc cggcaaaaac gaccaaagca 960
ggtggtaccg atacggtagt aacgggtgta aatgaaatca ttgaagaatc gcaggttaaa 1020
gatgaggtga gcatcgagtc cgagaagaac gaatctctgg atggcagcaa catcgaaatt 1080
gttgaagaaa ttgcggacaa tatcccgtcg ccggtgattg cagagggtga agtcgccgtg 1140
gagatgaaag tggaccgcgg caccgagaat gttgtctcgc gtaatgatac ggaagtcacc 1200
acgagcgaac aaaatcaaat cgaagtcacc gagactaaag aaattctgaa tcagacgagc 1260
tatcaaacgg agagcggtga acagcgtcag atcatttggg cgcacggtat taccccgcct 1320
gcgatggaac aatccggtgg tttcgttaaa gaaaagtatg gtgattacct gaactacact 1380
gccccgttcg aggctggcaa aggttactat gacaccaata agagcctgaa tgcaagcttt 1440
attgatctga atctgtgttt tgcagcggtc agcagcaata tggtccactg gtggctggag 1500
cagaatagca gctatgtcga gcgttacttg aaagaaaaga agggcaccgt taacgtggaa 1560
gagaattacg ccattactga cctgcgccgt tacattaaca gcttccagaa tcaacagaat 1620
agccgtgttt ttgatatgtt taagacgtac tatggctacc gtacgaacgg cttcgttagc 1680
gacgcactgg tcgacctgtt tatcaatggt tacaagccga aggcgcaggg cggtgttaac 1740
ttggaagatt cgcaactggt tccagatagc cgtggtggtt tcttctatga cgttttcaaa 1800
gagaagaagc tgacgaaccg tattttcagc ggtagctatg aacgtttcgg tgaagatgtt 1860
cgcaccgttc tggagagcaa gggtctgttg ggtctgacgt accgtaccct gggttacgcc 1920
acccacatcg tgaccgtttg ggtgcggag tatgataatc aaggcaagat caaggcagtg 1980

```
tacatcaccg actccgacga ccaacaggaa cagatcggtc tgaaacgcat gggtatcacg   2040

cgcgacgcca gcggcaatcc gcgtctgaac aaccacatga aaaacaatag cgccggtgca   2100

ctgctggact acgtgcacac gattcgcttg ggtcaggatc tgtgggaaga gtatttcaat   2160

ccgttggcaa aggcgaaact cgagggactg aagacccgca ataagaaagc caaaagcgac   2220

aaacttattg ttcgccgtcg caatcagaag taatgattaa ctagt                   2265
```

<210> SEQ ID NO 56
<211> LENGTH: 1977
<212> TYPE: DNA
<213> ORGANISM: ARTIFICIAL SEQUENCE
<220> FEATURE:
<223> OTHER INFORMATION: Codon optimized DNA sequence of fusion polypeptide of fragments of S. suis proteins with affinity-tag.

<400> SEQUENCE: 56

```
catatgacag gatccgaaat tcaagccatt gtggacgaag caaataccat cgtcaaaaaa     60

gtcacggaac agaaaatcgc aacggcaagc caagcaacgg acattagtcg tgaagtgaac    120

gaatttaaag aaagcgcggt gggtaatctg gttacctctg cccagctggc aattgctaaa    180

aaatccggct atgatgttga cttcgcaatg accaacgatg gcggtatccg cgctgacctg    240

aaagttcagg aagatggtac ggtcacctgg ggtgcagcac aggcagtgca accgtttggt    300

aacattctgc aggtggttca aatgaccggc gaacagatct acacggctct gaatcagcaa    360

tatgatgaag gtgaaaaata ctttctgcaa atgagcggca ttaaatatat ctacaccaaa    420

gcggataacc cgacggaaga aaatccgtat aaagtcgtga aagccttcaa agaagatggc    480

accgaaattg tgccgacgga aacctacacg ctggttatca acgactttct gttcggcggt    540

ggcgatggtt tttcaatctt caaagaagcg aaactgattg gcgccatcaa tccggacacc    600

gaagtttttg tcgaatatct gacggatctg gaaaaagcgg gtcagaccat ttcggccacg    660

attccgggcc gtaaagcatt cgtcgaaaaa tacgtggaag aaccgaaagc agaagaaaaa    720

gaagacaatg ctggcaccac gaccgatgtc aaaaccccgg aaaaagccaa cgatggtggc    780

gacagtgtta ccaatcagaa agcaacggaa caaccggctc cgagtggctc aatggccccg    840

attagcaata agaagacgga aaaagcaagt ggcaaccaaa ccggtaccgg cgaaacgacg    900

gccccgatta acagcttctt tgccctggtt caggacgacc cgagtgtcca gattgtcaat    960

aacgctcaga tttggtatgc taaacagcaa ctggcaggca ccagcgaagc aaacctgccg   1020

attctgtcgg cagcagcacc gtttaaagca ggcacccgtg gtgatgctag cgcatacacg   1080

gacatcccgg caggtccgat tgcaatcaaa aatgttgcag atctgtatct gtacgacaac   1140

gtggttgcaa ttctgaaagt caatggcgct cagctgaaag aatggctgga aatgtctgcg   1200

ggccagttca accaagtgga tctgagctct accgaaccgc agaacctggt taataccgat   1260

tttcgtacgt ataatttcga tgtgattgac ggcgttacct atcagtacga tatcacgcaa   1320

ccgaacaaat acgatcgcga cggtaaaatc gtcaatgaaa ccgcatcacg tgtgcgcaac   1380

ctgcagtata atggccaaga tgtgacggcg gaccaggaat ttattgtcgt gaccaacaat   1440

taccgtgcaa acggcacgtt tccgggcgtg cgtgaagctt cgatcaatcg cctgctgaac   1500

ctggaaaatc gccaggcgat tatcaactac atcatcgccg aaaaagtgat caacccgacc   1560

gcggataaca attggacctt tacggatagt atcaaaggtc tggacctgcg tttcctgacc   1620

gccgatcgcg caaaatccct ggttacggac caggaatgca ttgtctatct gcaagctagt   1680

accgcgtccg aaggctttgg tgaatttaaa ttcgtttaca ccgaaagcaa agttgtcacg   1740
```

```
ccggatgaac agcaatctga ccagggcaac accggtcaag atattgtcct ggaaagcggt   1800

cagcgtatca cgctgccggc agtgaatccg ccggcaccgg ctccgcagca caaactggcg   1860

tccccgcatt cgcaggcatc caccaaaacc ctcgagggac tgaagacccg caataagaaa   1920

gccaaaagcg acaaacttat tgttcgccgt cgcaatcaga agtaatgatt aactagt      1977
```

<210> SEQ ID NO 57
<211> LENGTH: 1290
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 57

```
catatgacaa aacctgcact gggactgaag acccgcaata agaaagccaa aagcgacaaa     60

cttattgttc gccgtcgcaa tcagaaggga tccgatacgg tagtaacggg tgtaaatgaa    120

atcattgaag aatcgcaggt taaagatgag gtgagcatcg agtccgagaa gaacgaatct    180

ctggatggca gcaacatcga aattgttgaa gaaattgcgg acaatatccc gtcgccggtg    240

attgcagagg gtgaagtcgc cgtggagatg aaagtggacc gcggcaccga gaatgttgtc    300

tcgcgtaatg atacggaagt caccacgagc gaacaaaatc aaatcgaagt caccgagact    360

aaagaaattc tgaatcagac gagctatcaa acggagagcg gtgaacagcg tcagatcatt    420

tgggcgcacg gtattacccc gcctgcgatg gaacaatccg gtggtttcgt taaagaaaag    480

tatggtgatt acctgaacta cactgccccg ttcgaggctg gcaaaggtta ctatgacacc    540

aataagagcc tgaatgcaag ctttattgat ctgaatctgt gttttgcagc ggtcagcagc    600

aatatggtcc actggtggct ggagcagaat agcagctatg tcgagcgtta cttgaaagaa    660

aagaagggca ccgttaacgt ggaagagaat tacgccatta ctgacctgcg ccgttacatt    720

aacagcttcc agaatcaaca gaatagccgt gtttttgata tgtttaagac gtactatggc    780

taccgtacga acggcttcgt tagcgacgca ctggtcgacc tgtttatcaa tggttacaag    840

ccgaaggcgc agggcggtgt taacttggaa gattcgcaac tggttccaga tagccgtggt    900

ggtttcttct atgacgtttt caaagagaag aagctgacga accgtatttt cagcggtagc    960

tatgaacgtt tcggtgaaga tgttcgcacc gttctggaga gcaagggtct gttgggtctg   1020

acgtaccgta ccctgggtta cgccacccac atcgtgaccg tttggggtgc ggagtatgat   1080

aatcaaggca agatcaaggc agtgtacatc accgactccg acgaccaaca ggaacagatc   1140

ggtctgaaac gcatgggtat cacgcgcgac gccagcggca atccgcgtct gaacaaccac   1200

atgaaaaaca atagcgccgg tgcactgctg gactacgtgc acacgattcg cttgggtcag   1260

gatctgtggg aagagtattt caatctcgag                                    1290
```

<210> SEQ ID NO 58
<211> LENGTH: 1062
<212> TYPE: DNA
<213> ORGANISM: ARTIFICIAL SEQUENCE
<220> FEATURE:
<223> OTHER INFORMATION: Codon optimized DNA sequence of fragment of S. suis protein with affinity-tag.

<400> SEQUENCE: 58

```
catatgacaa aacctgcact gggactgaag acccgcaata agaaagccaa aagcgacaaa     60

cttattgttc gccgtcgcaa tcagaaggga tccgacgaaa tcaaagcaaa atacgaagcc    120
```

```
gaaaacgccc aggttgtcat cgaaaataat ccggtggaac tgaatggtga ccgcagcaat    180

gtgcgtgtcc gcgaaaccaa cctgggtaat gcggtgacgg atgcaattta tgcttacggt    240

cagaccggct ttagtaacaa aacctccctg gccgttacga atggcggtgg cctgcgtgcg    300

accatcgcca aagaccagcc ggtgacgaag ggtgatatta tcgcggttct gccgtttggc    360

aatattgttt ctcaaatcac cgtcacgggt cagcaaattt atgacatgtt caccaaaagc    420

ctgagctcta cgctgcaggt taacccggaa accggtgaaa tgctgctgga tgaaaatggc    480

atgccgctgt ttgaagcgtc aggtggcttc ctgcatatct cgggcgccaa cgtgttctat    540

gatccgaccc tgccggtcga agaacgcgtg ctgctgattg gtatcctgaa tccggaaacg    600

ggcgaatacg acgcactgga tctggaaaaa acctattacc tggctacgaa cgactttctg    660

gcggccggtg gcgatggtta taccatgctg ggtggcgccc gtgaagaagg cccgagcatg    720

gactctgttt tcgcagaata cctgaagacc gcagatctga gcgcttatga agtggttaac    780

ccgtactctc gcattatccc ggtcaatagt tccattgata ccgacgaaga tggctatccg    840

gattttattg aaatcctgct ggacaccgat ccggaaaacc cggcaagtaa tccggaaacc    900

gttccggctg aaaacacgga ttcaccgtcg aaccaggtcc aaaataccag tgcgacggac    960

aaaaaggccc cggtggattc cccgaaagtg ggcgataaga aaaccgaagt ggcatccccg   1020

gcaaaaacga ccaaagcagg tctcgagtaa tgattaacta gt                      1062
```

<210> SEQ ID NO 59
<211> LENGTH: 3996
<212> TYPE: DNA
<213> ORGANISM: ARTIFICIAL SEQUENCE
<220> FEATURE:
<223> OTHER INFORMATION: Plasmid vector.

<400> SEQUENCE: 59

```
gacgtcaggt ggcacttttc ggggaaatgt gcgcggaacc cctatttgtt tatttttcta     60

aatacattca aatatgtatc cgctcatgag acaataaccc tgataaatgc ttcaataata    120

ttgaaaaagg aagagtatga gtattcaaca tttccgtgtc gcccttattc ccttttttgc    180

ggcattttgc cttcctgttt ttgctcaccc agaaacgctg gtgaaagtaa aagatgctga    240

agatcagttg ggtgcacgag tgggttacat cgaactggat ctcaacagcg gtaagatcct    300

tgagagtttt cgccccgaag aacgttttcc aatgatgagc acttttaaag ttctgctatg    360

tggcgcggta ttatcccgtg ttgacgccgg gcaagagcaa ctcggtcgcc gcatacacta    420

ttctcagaat gacttggttg agtactcacc agtcacagaa aagcatctta cggatggcat    480

gacagtaaga gaattatgca gtgctgccat aaccatgagt gataacactg cggccaactt    540

acttctgaca acgatcggag gaccgaagga gctaaccgct tttttgcaca acatggggga    600

tcatgtaact cgccttgatc gttgggaacc ggagctgaat gaagccatac caaacgacga    660

gcgtgacacc acgatgcctg cagcaatggc aacaacgttg cgcaaactat taactggcga    720

actacttact ctagcttccc ggcaacaatt aatagactgg atggaggcgg ataaagttgc    780

aggaccactt ctgcgctcgg cccttccggc tggctggttt attgctgata aatctggagc    840

cggtgagcgt gggtctcgcg gtatcattgc agcactgggg ccagatggta agccctcccg    900

tatcgtagtt atctacacga cggggagtca ggcaactatg gatgaacgaa atagacagat    960

cgctgagata ggtgcctcac tgattaagca ttggtaactg tcagaccaag tttactcata   1020

tatactttag attgatttaa aacttcattt ttaatttaaa aggatctagg tgaagatcct   1080

ttttgataat ctcatgacca aaatccctta acgtgagttt tcgttccact gagcgtcaga   1140
```

-continued

```
ccccgtagaa aagatcaaag gatcttcttg agatcctttt tttctgcgcg taatctgctg   1200
cttgcaaaca aaaaaaccac cgctaccagc ggtggtttgt ttgccggatc aagagctacc   1260
aactcttttt ccgaaggtaa ctggcttcag cagagcgcag ataccaaata ctgtccttct   1320
agtgtagccg tagttaggcc accacttcaa gaactctgta gcaccgccta catacctcgc   1380
tctgctaatc ctgttaccag tggctgctgc cagtggcgat aagtcgtgtc ttaccgggtt   1440
ggactcaaga cgatagttac cggataaggc gcagcggtcg ggctgaacgg ggggttcgtg   1500
cacacagccc agcttggagc gaacgaccta caccgaactg agatacctac agcgtgagct   1560
atgagaaagc gccacgcttc ccgaagggag aaaggcggac aggtatccgg taagcggcag   1620
ggtcggaaca ggagagcgca cgagggagct tccaggggga aacgcctggt atctttatag   1680
tcctgtcggg tttcgccacc tctgacttga gcgtcgattt ttgtgatgct cgtcaggggg   1740
gcggagccta tggaaaaacg ccagcaacgc ggccttttta cggttcctgg ccttttgctg   1800
gccttttgct cacatgttct ttcctgcgtt atcccctgat tctgtggata accgtattac   1860
cgcctttgag tgagctgata ccgctcgccg cagccgaacg accgagcgca gcgagtcagt   1920
gagcgaggaa gcggaagagc gcctgatgcg gtattttctc cttacgcatc tgtgcggtat   1980
ttcacaccgc ataaattccg acaccatcga atggcgcaaa acctttcgcg gtatggcatg   2040
atagcgcccg gaagagagtc aattcagggt ggtgaatgtg aaaccagtaa cgttatacga   2100
tgtcgcagag tatgccggtg tctcttatca gaccgtttcc cgcgtggtga accaggccag   2160
ccacgtttct gcgaaaacgc gggaaaaagt ggaagcggcg atggcggagc tgaattacat   2220
tcccaaccgc gtggcacaac aactggcggg caaacagtcg ttgctgattg gcgttgccac   2280
ctccagtctg gccctgcacg cgccgtcgca aattgtcgcg gcgattaaat ctcgcgccga   2340
tcaactgggt gccagcgtgg tggtgtcgat ggtagaacga agcggcgtcg aagcctgtaa   2400
agcggcggtg cacaatcttc tcgcgcaacg cgtcagtggg ctgatcatta actatccgct   2460
ggatgaccag gatgccattg ctgtggaagc tgcctgcact aatgttccgg cgttatttct   2520
tgatgtctct gaccagacac ccatcaacag tattattttc tcccatgaag acggtacgcg   2580
actgggcgtg gagcatctgg tcgcattggg tcaccagcaa atcgcgctgt tagcgggccc   2640
attaagttct gtctcggcgc gtctgcgtct ggctggctgg cataaatatc tcactcgcaa   2700
tcaaattcag ccgatagcgg aacgggaagg cgactggagt gccatgtccg gttttcaaca   2760
aaccatgcaa atgctgaatg agggcatcgt tcccactgcg atgctggttg ccaacgatca   2820
gatggcgctg ggcgcaatgc gcgccattac cgagtccggg ctgcgcgttg gtgcggatat   2880
ctcggtagtg ggatacgacg ataccgaaga cagctcatgt tatatcccgc cgttaaccac   2940
catcaaacag gattttcgcc tgctggggca aaccagcgtg gaccgcttgc tgcaactctc   3000
tcagggccag gcggtgaagg gcaatcagct gttgcccgtc tcactggtga aaagaaaaac   3060
cacgctagcg cccaatacgc aaaccgcctc tccccgcgcg ttggccgatt cattaatgca   3120
gctggcacga caggtttccc gactggaaag cgggcagtga gcgcaacgca attaatgtaa   3180
gttagctcac tcattaggca ccccaggctt tacactttat gcttccggct cgtatgttgt   3240
gtggaattgt gagcggataa caatttcaca caggaaacag ctatgaccat gattacggat   3300
tcactggccg tcgttttaca acgtcgtgac tgggaaaacc ctggcgttac ccaacttaat   3360
cgccttgcag cacatccccc tttcgccagc tggcgtaata gcgaagaggc ccgcaccgat   3420
cgcccttccc aacagttgcg cagcctgaat ggcgaatggc gctttgcctg gtttccggca   3480
```

```
ccagaagcgg tgccggaaag ctggctggag tgcgatcttc ctgaggccga tactgtcgtc   3540

gtcccctcaa actggcagat gcacggttac gatgcgccca tctacaccaa cgtgacctat   3600

cccattacgg tcaatccgcc gtttgttccc acggcgactg cacggtgcac caatgcttct   3660

ggcgtcaggc agccatcgga agctgtggta tggctgtgca ggtcgtaaat cactgcataa   3720

ttcgtgtcgc tcaaggcgca ctcccgttct ggataatgtt ttttgcgccg acatcataac   3780

ggttctggca aatattctga aatgagctgt tgacaattaa tcatcggctc gtataatgtg   3840

tggaattgtg agcggataac aatttcacaa tttctttaac aattaatcat ttggaggaac   3900

aaatgacagg atccgcagaa ttcgcctacg tagcgctcga gtaatgatta actagtgaaa   3960

gcccccggaa gatcatcttc cgggggcttt tttttt                             3996
```

<210> SEQ ID NO 60
<211> LENGTH: 4029
<212> TYPE: DNA
<213> ORGANISM: ARTIFICIAL SEQUENCE
<220> FEATURE:
<223> OTHER INFORMATION: Plasmid vector.

<400> SEQUENCE: 60

```
gacgtcaggt gggaccaccg cgctactgcc gccaggcaaa caaggggtgt tatgagccat     60

attcaggtat aaatgggctc gcgataatgt tcagaattgg ttaattggtt gtaacactga    120

cccctatttg tttatttttc taaatacatt caaatatgta tccgctcatg agacaataac    180

cctgataaat gcttcaataa tattgaaaaa ggaagaatat gagccatttt caacgggaaa    240

cgtcgaggcc gcgattaaat tccaacatgg atgctgattt atatgggtat aaatgggctc    300

gcgataatgt cgggcaatca ggtgcgacaa tctatcgctt gtatgggaag cccgatgcgc    360

cagagttgtt tctgaaacat ggcaaaggta gcgttgccaa tgatgttaca gatgagatgg    420

tcagactaaa ctggctgacg gaatttatgc cacttccgac catcaagcat tttatccgta    480

ctcctgatga tgcatggtta ctcaccactg cgatccccgg aaaaacagcg ttccaggtat    540

tagaagaata tcctgattca ggtgaaaata ttgttgatgc gctggcagtg ttcctgcgcc    600

ggttgcactc gattcctgtt tgtaattgtc cttttaacag cgatcgcgta tttcgcctcg    660

ctcaggcgca atcacgaatg aataacggtt tggttgatgc gagtgatttt gatgacgagc    720

gtaatggctg gcctgttgaa caagtctgga aagaaatgca taaacttttg ccattctcac    780

cggattcagt cgtcactcat ggtgatttct cacttgataa ccttattttt gacgagggga    840

aattaatagg ttgtattgat gttggacgag tcggaatcgc agaccgatac caggatcttg    900

ccatcctatg gaactgcctc ggtgagtttt ctccttcatt acagaaacgg ctttttcaaa    960

aatatggtat tgataatcct gatatgaata aattgcaatt tcatttgatg ctcgatgagt   1020

ttttctaagc ggcgcgccat cgaatggcgc aaaacctttc gcggtcgggt aatcgaccgc   1080

gttttttttt aaaaggatct aggtgaagat cctttttgat aatctcatga ccaaaatccc   1140

ttaacgtgag ttttcgttcc actgagcgtc agaccccgta gaaaagatca aaggatcttc   1200

ttgagatcct ttttttctgc gcgtaatctg ctgcttgcaa acaaaaaaac caccgctacc   1260

agcggtggtt tgtttgccgg atcaagagct accaactctt tttccgaagg taactggctt   1320

cagcagagcg cagataccaa atactgtcct tctagtgtag ccgtagttag gccaccactt   1380

caagaactct gtagcaccgc ctacatacct cgctctgcta atcctgttac cagtggctgc   1440

tgccagtggc gataagtcgt gtcttaccgg gttggactca agacgatagt taccggataa   1500

ggcgcagcgg tcgggctgaa cggggggttc gtgcacacag cccagcttgg agcgaacgac   1560
```

ctacaccgaa ctgagatacc tacagcgtga gctatgagaa agcgccacgc ttcccgaagg 1620
gagaaaggcg gacaggtatc cggtaagcgg cagggtcgga acaggagagc gcacgaggga 1680
gcttccaggg ggaaacgcct ggtatcttta tagtcctgtc gggtttcgcc acctctgact 1740
tgagcgtcga tttttgtgat gctcgtcagg ggggcggagc ctatggaaaa acgccagcaa 1800
cgcggccttt ttacggttcc tggccttttg ctggcctttt gctcacatgt tctttcctgc 1860
gttatcccct gattctgtgg ataaccgtat taccgccttt gagtgagctg ataccgctcg 1920
ccgcagccga acgaccgagc gcagcgagtc agtgagcgag gaagcggaag agcgcctgat 1980
gcggtatttt ctccttacgc atctgtgcgg tatttcacac cgcataaatt ccgacaccat 2040
cgaatggcgc aaaacctttc gcggtatggc atgatagcgc ccggaagaga gtcaattcag 2100
ggtggtgaat gtgaaaccag taacgttata cgatgtcgca gagtatgccg gtgtctctta 2160
tcagaccgtt tcccgcgtgg tgaaccaggc cagccacgtt tctgcgaaaa cgcgggaaaa 2220
agtggaagcg gcgatggcgg agctgaatta cattcccaac cgcgtggcac aacaactggc 2280
gggcaaacag tcgttgctga ttggcgttgc cacctccagt ctggccctgc acgcgccgtc 2340
gcaaattgtc gcggcgatta aatctcgcgc cgatcaactg ggtgccagcg tggtggtgtc 2400
gatggtagaa cgaagcggcg tcgaagcctg taaagcggcg gtgcacaatc ttctcgcgca 2460
acgcgtcagt gggctgatca ttaactatcc gctggatgac caggatgcca ttgctgtgga 2520
agctgcctgc actaatgttc cggcgttatt tcttgatgtc tctgaccaga cacccatcaa 2580
cagtattatt ttctcccatg aagacggtac gcgactgggc gtggagcatc tggtcgcatt 2640
gggtcaccag caaatcgcgc tgttagcggg cccattaagt tctgtctcgg cgcgtctgcg 2700
tctggctggc tggcataaat atctcactcg caatcaaatt cagccgatag cggaacggga 2760
aggcgactgg agtgccatgt ccggttttca acaaaccatg caaatgctga atgagggcat 2820
cgttcccact gcgatgctgg ttgccaacga tcagatggcg ctgggcgcaa tgcgcgccat 2880
taccgagtcc gggctgcgcg ttggtgcgga tatctcggta gtgggatacg acgataccga 2940
agacagctca tgttatatcc cgccgttaac caccatcaaa caggattttc gcctgctggg 3000
gcaaaccagc gtggaccgct tgctgcaact ctctcagggc caggcggtga agggcaatca 3060
gctgttgccc gtctcactgg tgaaaagaaa aaccaccgcta gcgcccaata cgcaaaccgc 3120
ctctccccgc gcgttggccg attcattaat gcagctggca cgacaggttt cccgactgga 3180
aagcgggcag tgagcgcaac gcaattaatg taagttagct cactcattag gcaccccagg 3240
ctttacactt tatgcttccg gctcgtatgt tgtgtggaat tgtgagcgga taacaatttc 3300
acacaggaaa cagctatgac catgattacg gattcactgg ccgtcgtttt acaacgtcgt 3360
gactgggaaa accctggcgt tacccaactt aatcgccttg cagcacatcc ccctttcgcc 3420
agctggcgta atagcgaaga ggcccgcacc gatcgccctt cccaacagtt gcgcagcctg 3480
aatggcgaat ggcgctttgc ctggtttccg gcaccagaag cggtgccgga aagctggctg 3540
gagtgcgatc ttcctgaggc cgatactgtc gtcgtcccct caaactggca gatgcacggt 3600
tacgatgcgc ccatctacac caacgtgacc tatcccatta cggtcaatcc gccgtttgtt 3660
cccacggcga ctgcacggtg caccaatgct tctggcgtca ggcagccatc ggaagctgtg 3720
gtatggctgt gcaggtcgta aatcactgca taattcgtgt cgctcaaggc gcactcccgt 3780
tctggataat gtttttttgcg ccgacatcat aacggttctg gcaaatattc tgaaatgagc 3840
tgttgacaat taatcatcgg ctcgtataat gtgtggaatt gtgagcggat aacaatttca 3900

```
caatttcttt aacaattaat catttggagg aacaaatgac aggatccgca gaattcgcct   3960

acgtagcgct cgagtaatga ttaactagtg aaagcccccg gaagatcatc ttccgggggc   4020

tttttttt                                                            4029
```

<210> SEQ ID NO 61
<211> LENGTH: 3574
<212> TYPE: DNA
<213> ORGANISM: ARTIFICIAL SEQUENCE
<220> FEATURE:
<223> OTHER INFORMATION: Plasmid vector.

<400> SEQUENCE: 61

```
gacgtcaggt gggaccaccg cgctactgcc gccaggcaaa caaggggtgt tatgagccat     60

attcaggtat aaatgggctc gcgataatgt tcagaattgg ttaattggtt gtaacactga    120

cccctatttg tttatttttc taaatacatt caaatatgta tccgctcatg agacaataac    180

cctgataaat gcttcaataa tattgaaaaa ggaagaatat gagccatttt caacgggaaa    240

cgtcgaggcc gcgattaaat tccaacatgg atgctgattt atatgggtat aaatgggctc    300

gcgataatgt cgggcaatca ggtgcgacaa tctatcgctt gtatgggaag cccgatgcgc    360

cagagttgtt tctgaaacat ggcaaaggta gcgttgccaa tgatgttaca gatgagatgg    420

tcagactaaa ctggctgacg gaatttatgc cacttccgac catcaagcat tttatccgta    480

ctcctgatga tgcatggtta ctcaccactg cgatccccgg aaaaacagcg ttccaggtat    540

tagaagaata tcctgattca ggtgaaaata ttgttgatgc gctggcagtg ttcctgcgcc    600

ggttgcactc gattcctgtt tgtaattgtc cttttaacag cgatcgcgta tttcgcctcg    660

ctcaggcgca atcacgaatg aataacggtt tggttgatgc gagtgatttt gatgacgagc    720

gtaatggctg gcctgttgaa caagtctgga aagaaatgca taaacttttg ccattctcac    780

cggattcagt cgtcactcat ggtgatttct cacttgataa ccttattttt gacgagggga    840

aattaatagg ttgtattgat gttggacgag tcggaatcgc agaccgatac caggatcttg    900

ccatcctatg gaactgcctc ggtgagtttt ctccttcatt acagaaacgg ctttttcaaa    960

aatatggtat tgataatcct gatatgaata aattgcaatt tcatttgatg ctcgatgagt   1020

ttttctaagc ggcgcgccat cgaatggcgc aaaacctttc gcggtcgggt aatcgaccgc   1080

gttttttttt aaaaggatct aggtgaagat cctttttgat aatctcatga ccaaaatccc   1140

ttaacgtgag ttttcgttcc actgagcgtc agaccccgta gaaaagatca aaggatcttc   1200

ttgagatcct ttttttctgc gcgtaatctg ctgcttgcaa acaaaaaaac caccgctacc   1260

agcggtggtt tgtttgccgg atcaagagct accaactctt tttccgaagg taactggctt   1320

cagcagagcg cagataccaa atactgtcct tctagtgtag ccgtagttag gccaccactt   1380

caagaactct gtagcaccgc ctacatacct cgctctgcta atcctgttac cagtggctgc   1440

tgccagtggc gataagtcgt gtcttaccgg gttggactca agacgatagt taccggataa   1500

ggcgcagcgg tcgggctgaa cggggggttc gtgcacacag cccagcttgg agcgaacgac   1560

ctacaccgaa ctgagatacc tacagcgtga gctatgagaa agcgccacgc ttcccgaagg   1620

gagaaaggcg gacaggtatc cggtaagcgg cagggtcgga acaggagagc gcacgaggga   1680

gcttccaggg ggaaacgcct ggtatcttta tagtcctgtc gggtttcgcc acctctgact   1740

tgagcgtcga tttttgtgat gctcgtcagg ggggcggagc ctatggaaaa acgccagcaa   1800

cgcggccttt ttacggttcc tggccttttg ctggcctttt gctcacatgt tctttcctgc   1860

gttatcccct gattctgtgg ataaccgtat taccgccttt gagtgagctg ataccgctcg   1920
```

ccgcagccga acgaccgagc gcagcgagtc agtgagcgag gaagcggaag agcgcctgat 1980
gcggtatttt ctccttacgc atctgtgcgg tatttcacac cgcataaatt ccgacaccat 2040
cgaatggcgc aaaacctttc gcggtatggc atgatagcgc ccggaagaga gtcaattcag 2100
ggtggtgaat gtgaaaccag taacgttata cgatgtcgca gagtatgccg gtgtctctta 2160
tcagaccgtt tcccgcgtgg tgaaccaggc cagccacgtt tctgcgaaaa cgcgggaaaa 2220
agtggaagcg gcgatggcgg agctgaatta cattcccaac cgcgtggcac aacaactggc 2280
gggcaaacag tcgttgctga ttggcgttgc cacctccagt ctggccctgc acgcgccgtc 2340
gcaaattgtc gcggcgatta aatctcgcgc cgatcaactg ggtgccagcg tggtggtgtc 2400
gatggtagaa cgaagcggcg tcgaagcctg taaagcggcg gtgcacaatc ttctcgcgca 2460
acgcgtcagt gggctgatca ttaactatcc gctggatgac caggatgcca ttgctgtgga 2520
agctgcctgc actaatgttc cggcgttatt tcttgatgtc tctgaccaga cacccatcaa 2580
cagtattatt ttctcccatg aagacggtac gcgactgggc gtggagcatc tggtcgcatt 2640
gggtcaccag caaatcgcgc tgttagcggg cccattaagt tctgtctcgg cgcgtctgcg 2700
tctggctggc tggcataaat atctcactcg caatcaaatt cagccgatag cggaacggga 2760
aggcgactgg agtgccatgt ccggttttca acaaaccatg caaatgctga atgagggcat 2820
cgttcccact gcgatgctgg ttgccaacga tcagatggcg ctgggcgcaa tgcgcgccat 2880
taccgagtcc gggctgcgcg ttggtgcgga tatctcggta gtgggatacg acgataccga 2940
agacagctca tgttatatcc cgccgttaac caccatcaaa caggattttc gcctgctggg 3000
gcaaaccagc gtggaccgct tgctgcaact ctctcagggc caggcggtga agggcaatca 3060
gctgttgccc gtctcactgg tgaaaagaaa aaccacgcta gcgcccaata cgcaaaccgc 3120
ctctccccgc gcgttggccg attcattaat gcagctggca cgacaggttt cccgactgga 3180
aagcgggcag tgagcgcaac gcaattaatg taagttagct cactcattag gcaccaagct 3240
taaatgtaat cacactggct caccttcggg tgggcctttc tgcgtttatc gtaaatcact 3300
gcataattcg tgtcgctcaa ggcgcactcc cgttctggat aatgtttttt gcgccgacat 3360
cataacggtt ctggcaaata ttctgaaatg agctgttgac aattaatcat cggctcgtat 3420
aatgtgtgga attgtgagcg gataacaatt tcacaatttc tttaacaatt aatcatttgg 3480
aggaaacata tgacaggatc cgcagaattc gccctcgagt aatgattaac tagtgaaagc 3540
ccccggaaga tcatcttccg gggctttttt tttt 3574

<210> SEQ ID NO 62
<211> LENGTH: 3640
<212> TYPE: DNA
<213> ORGANISM: ARTIFICIAL SEQUENCE
<220> FEATURE:
<223> OTHER INFORMATION: Plasmid vector.

<400> SEQUENCE: 62
gacgtcaggt gggaccaccg cgctactgcc gccaggcaaa caaggggtgt tatgagccat 60
attcaggtat aaatgggctc gcgataatgt tcagaattgg ttaattggtt gtaacactga 120
cccctatttg tttatttttc taaatacatt caaatatgta tccgctcatg agacaataac 180
cctgataaat gcttcaataa tattgaaaaa ggaagaatat gagccatttt caacgggaaa 240
cgtcgaggcc gcgattaaat tccaacatgg atgctgattt atatgggtat aaatgggctc 300
gcgataatgt cgggcaatca ggtgcgacaa tctatcgctt gtatgggaag cccgatgcgc 360

-continued

```
cagagttgtt tctgaaacat ggcaaaggta gcgttgccaa tgatgttaca gatgagatgg    420
tcagactaaa ctggctgacg gaatttatgc cacttccgac catcaagcat tttatccgta    480
ctcctgatga tgcatggtta ctcaccactg cgatccccgg aaaaacagcg ttccaggtat    540
tagaagaata tcctgattca ggtgaaaata ttgttgatgc gctggcagtg ttcctgcgcc    600
ggttgcactc gattcctgtt tgtaattgtc cttttaacag cgatcgcgta tttcgcctcg    660
ctcaggcgca atcacgaatg aataacggtt tggttgatgc gagtgatttt gatgacgagc    720
gtaatggctg gcctgttgaa caagtctgga aagaaatgca taaacttttg ccattctcac    780
cggattcagt cgtcactcat ggtgatttct cacttgataa ccttattttt gacgagggga    840
aattaatagg ttgtattgat gttggacgag tcggaatcgc agaccgatac caggatcttg    900
ccatcctatg gaactgcctc ggtgagtttt ctccttcatt acagaaacgg ctttttcaaa    960
aatatggtat tgataatcct gatatgaata aattgcaatt tcatttgatg ctcgatgagt   1020
ttttctaagc ggcgcgccat cgaatggcgc aaaacctttc gcggtcgggt aatcgaccgc   1080
gttttttttt aaaaggatct aggtgaagat cctttttgat aatctcatga ccaaaatccc   1140
ttaacgtgag ttttcgttcc actgagcgtc agaccccgta gaaaagatca aaggatcttc   1200
ttgagatcct ttttttctgc gcgtaatctg ctgcttgcaa acaaaaaaac caccgctacc   1260
agcggtggtt tgtttgccgg atcaagagct accaactctt tttccgaagg taactggctt   1320
cagcagagcg cagataccaa atactgtcct tctagtgtag ccgtagttag gccaccactt   1380
caagaactct gtagcaccgc ctacatacct cgctctgcta atcctgttac cagtggctgc   1440
tgccagtggc gataagtcgt gtcttaccgg gttggactca agacgatagt taccggataa   1500
ggcgcagcgg tcgggctgaa cggggggttc gtgcacacag cccagcttgg agcgaacgac   1560
ctacaccgaa ctgagatacc tacagcgtga gctatgagaa agcgccacgc ttcccgaagg   1620
gagaaaggcg gacaggtatc cggtaagcgg cagggtcgga acaggagagc gcacgaggga   1680
gcttccaggg ggaaacgcct ggtatcttta tagtcctgtc gggtttcgcc acctctgact   1740
tgagcgtcga tttttgtgat gctcgtcagg ggggcggagc ctatggaaaa acgccagcaa   1800
cgcggccttt ttacggttcc tggccttttg ctggcctttt gctcacatgt tctttcctgc   1860
gttatcccct gattctgtgg ataaccgtat taccgccttt gagtgagctg ataccgctcg   1920
ccgcagccga acgaccgagc gcagcgagtc agtgagcgag gaagcggaag agcgcctgat   1980
gcggtatttt ctccttacgc atctgtgcgg tatttcacac cgcataaatt ccgacaccat   2040
cgaatggcgc aaaacctttc gcggtatggc atgatagcgc ccggaagaga gtcaattcag   2100
ggtggtgaat gtgaaaccag taacgttata cgatgtcgca gagtatgccg gtgtctctta   2160
tcagaccgtt tcccgcgtgg tgaaccaggc cagccacgtt tctgcgaaaa cgcgggaaaa   2220
agtggaagcg gcgatggcgg agctgaatta cattcccaac cgcgtggcac aacaactggc   2280
gggcaaacag tcgttgctga ttggcgttgc cacctccagt ctggccctgc acgcgccgtc   2340
gcaaattgtc gcggcgatta aatctcgcgc cgatcaactg ggtgccagcg tggtggtgtc   2400
gatggtagaa cgaagcggcg tcgaagcctg taaagcggcg gtgcacaatc ttctcgcgca   2460
acgcgtcagt gggctgatca ttaactatcc gctggatgac caggatgcca ttgctgtgga   2520
agctgcctgc actaatgttc cggcgttatt tcttgatgtc tctgaccaga cacccatcaa   2580
cagtattatt ttctcccatg aagacggtac gcgactgggc gtggagcatc tggtcgcatt   2640
gggtcaccag caaatcgcgc tgttagcggg cccattaagt tctgtctcgg cgcgtctgcg   2700
tctggctggc tggcataaat atctcactcg caatcaaatt cagccgatag cggaacggga   2760
```

aggcgactgg agtgccatgt ccggttttca acaaaccatg caaatgctga atgagggcat 2820
cgttcccact gcgatgctgg ttgccaacga tcagatggcg ctgggcgcaa tgcgcgccat 2880
taccgagtcc gggctgcgcg ttggtgcgga tatctcggta gtgggatacg acgataccga 2940
agacagctca tgttatatcc cgccgttaac caccatcaaa caggattttc gcctgctggg 3000
gcaaaccagc gtggaccgct tgctgcaact ctctcagggc caggcggtga agggcaatca 3060
gctgttgccc gtctcactgg tgaaaagaaa aaccacgcta gcgcccaata cgcaaaccgc 3120
ctctccccgc gcgttggccg attcattaat gcagctggca cgacaggttt cccgactgga 3180
aagcgggcag tgagcgcaac gcaattaatg taagttagct cactcattag gcaccaagct 3240
taaatgtaat cacactggct caccttcggg tgggcctttc tgcgtttatc gtaaatcact 3300
gcataattcg tgtcgctcaa ggcgcactcc cgttctggat aatgtttttt gcgccgacat 3360
cataacggtt ctggcaaata ttctgaaatg agctgttgac aattaatcat cggctcgtat 3420
aatgtgtgga attgtgagcg gataacaatt tcacaatttc tttaacaatt aatcatttgg 3480
aggaaacata tgacaggatc cgcagaattc gccctcgagg gactgaagac ccgcaataag 3540
aaagccaaaa gcgacaaact tattgttcgc cgtcgcaatc agaagtaatg attaactagt 3600
gaaagccccc ggaagatcat cttccggggg cttttttttt 3640

<210> SEQ ID NO 63
<211> LENGTH: 3589
<212> TYPE: DNA
<213> ORGANISM: ARTIFICIAL SEQUENCE
<220> FEATURE:
<223> OTHER INFORMATION: Plasmid vector.

<400> SEQUENCE: 63
gacgtcaggt gggaccaccg cgctactgcc gccaggcaaa caaggggtgt tatgagccat 60
attcaggtat aaatgggctc gcgataatgt tcagaattgg ttaattggtt gtaacactga 120
cccctatttg tttatttttc taaatacatt caaatatgta tccgctcatg agacaataac 180
cctgataaat gcttcaataa tattgaaaaa ggaagaatat gagccatttt caacgggaaa 240
cgtcgaggcc gcgattaaat tccaacatgg atgctgattt atatgggtat aaatgggctc 300
gcgataatgt cgggcaatca ggtgcgacaa tctatcgctt gtatgggaag cccgatgcgc 360
cagagttgtt tctgaaacat ggcaaaggta gcgttgccaa tgatgttaca gatgagatgg 420
tcagactaaa ctggctgacg gaatttatgc cacttccgac catcaagcat tttatccgta 480
ctcctgatga tgcatggtta ctcaccactg cgatccccgg aaaaacagcg ttccaggtat 540
tagaagaata tcctgattca ggtgaaaata ttgttgatgc gctggcagtg ttcctgcgcc 600
ggttgcactc gattcctgtt tgtaattgtc cttttaacag cgatcgcgta tttcgcctcg 660
ctcaggcgca atcacgaatg aataacggtt tggttgatgc gagtgatttt gatgacgagc 720
gtaatggctg gcctgttgaa caagtctgga aagaaatgca taaacttttg ccattctcac 780
cggattcagt cgtcactcat ggtgatttct cacttgataa ccttattttt gacgagggga 840
aattaatagg ttgtattgat gttggacgag tcggaatcgc agaccgatac caggatcttg 900
ccatcctatg gaactgcctc ggtgagtttt ctccttcatt acagaaacgg ctttttcaaa 960
aatatggtat tgataatcct gatatgaata aattgcaatt tcatttgatg ctcgatgagt 1020
ttttctaagc ggcgcgccat cgaatggcgc aaaacctttc gcggtcgggt aatcgaccgc 1080
gttttttttt aaaaggatct aggtgaagat cctttttgat aatctcatga ccaaaatccc 1140

```
ttaacgtgag ttttcgttcc actgagcgtc agaccccgta gaaaagatca aaggatcttc   1200
ttgagatcct ttttttctgc gcgtaatctg ctgcttgcaa acaaaaaaac caccgctacc   1260
agcggtggtt tgtttgccgg atcaagagct accaactctt tttccgaagg taactggctt   1320
cagcagagcg cagataccaa atactgtcct tctagtgtag ccgtagttag gccaccactt   1380
caagaactct gtagcaccgc ctacatacct cgctctgcta atcctgttac cagtggctgc   1440
tgccagtggc gataagtcgt gtcttaccgg gttggactca agacgatagt taccggataa   1500
ggcgcagcgg tcgggctgaa cggggggttc gtgcacacag cccagcttgg agcgaacgac   1560
ctacaccgaa ctgagatacc tacagcgtga gctatgagaa agcgccacgc ttcccgaagg   1620
gagaaaggcg gacaggtatc cggtaagcgg cagggtcgga acaggagagc gcacgaggga   1680
gcttccaggg ggaaacgcct ggtatcttta tagtcctgtc gggtttcgcc acctctgact   1740
tgagcgtcga tttttgtgat gctcgtcagg ggggcggagc ctatggaaaa acgccagcaa   1800
cgcggccttt ttacggttcc tggccttttg ctggcctttt gctcacatgt tctttcctgc   1860
gttatcccct gattctgtgg ataaccgtat taccgccttt gagtgagctg ataccgctcg   1920
ccgcagccga acgaccgagc gcagcgagtc agtgagcgag gaagcggaag agcgcctgat   1980
gcggtatttt ctccttacgc atctgtgcgg tatttcacac cgcataaatt ccgacaccat   2040
cgaatggcgc aaaacctttc gcggtatggc atgatagcgc ccggaagaga gtcaattcag   2100
ggtggtgaat gtgaaaccag taacgttata cgatgtcgca gagtatgccg gtgtctctta   2160
tcagaccgtt tcccgcgtgg tgaaccaggc cagccacgtt tctgcgaaaa cgcgggaaaa   2220
agtggaagcg gcgatggcgg agctgaatta cattcccaac cgcgtggcac aacaactggc   2280
gggcaaacag tcgttgctga ttggcgttgc cacctccagt ctggccctgc acgcgccgtc   2340
gcaaattgtc gcggcgatta aatctcgcgc cgatcaactg ggtgccagcg tggtggtgtc   2400
gatggtagaa cgaagcggcg tcgaagcctg taaagcggcg gtgcacaatc ttctcgcgca   2460
acgcgtcagt gggctgatca ttaactatcc gctggatgac caggatgcca ttgctgtgga   2520
agctgcctgc actaatgttc cggcgttatt tcttgatgtc tctgaccaga cacccatcaa   2580
cagtattatt ttctcccatg aagacggtac gcgactgggc gtggagcatc tggtcgcatt   2640
gggtcaccag caaatcgcgc tgttagcggg cccattaagt tctgtctcgg cgcgtctgcg   2700
tctggctggc tggcataaat atctcactcg caatcaaatt cagccgatag cggaacggga   2760
aggcgactgg agtgccatgt ccggttttca acaaaccatg caaatgctga atgagggcat   2820
cgttcccact gcgatgctgg ttgccaacga tcagatggcg ctgggcgcaa tgcgcgccat   2880
taccgagtcc gggctgcgcg ttggtgcgga tatctcggta gtgggatacg acgataccga   2940
agacagctca tgttatatcc cgccgttaac caccatcaaa caggattttc gcctgctggg   3000
gcaaaccagc gtggaccgct tgctgcaact ctctcagggc caggcggtga agggcaatca   3060
gctgttgccc gtctcactgg tgaaaagaaa aaccacgcta gcgcccaata cgcaaaccgc   3120
ctctccccgc gcgttggccg attcattaat gcagctggca cgacaggttt cccgactgga   3180
aagcgggcag tgagcgcaac gcaattaatg taagttagct cactcattag gcaccaagct   3240
taaatgtaat cacactggct caccttcggg tgggcctttc tgcgtttatc gtaaatcact   3300
gcataattcg tgtcgctcaa ggcgcactcc cgttctggat aatgtttttt gcgccgacat   3360
cataacggtt ctggcaaata ttctgaaatg agctgttgac aattaatcat cggctcgtat   3420
aatgtgtgga attgtgagcg gataacaatt tcacaatttc tttaacaatt aatcatttgg   3480
aggaaacata tgacaggatc cgcagaattc gccctcgagc atcaccatca ccatcaccat   3540
```

taaactagtg aaagcccccg gaagatcatc ttccgggggc tttttttt 3589

<210> SEQ ID NO 64
<211> LENGTH: 3652
<212> TYPE: DNA
<213> ORGANISM: ARTIFICIAL SEQUENCE
<220> FEATURE:
<223> OTHER INFORMATION: Plasmid vector.

<400> SEQUENCE: 64
gacgtcaggt gggaccaccg cgctactgcc gccaggcaaa caaggggtgt tatgagccat 60
attcaggtat aaatgggctc gcgataatgt tcagaattgg ttaattggtt gtaacactga 120
cccctatttg tttatttttc taaatacatt caaatatgta tccgctcatg agacaataac 180
cctgataaat gcttcaataa tattgaaaaa ggaagaatat gagccatttt caacgggaaa 240
cgtcgaggcc gcgattaaat tccaacatgg atgctgattt atatgggtat aaatgggctc 300
gcgataatgt cgggcaatca ggtgcgacaa tctatcgctt gtatgggaag cccgatgcgc 360
cagagttgtt tctgaaacat ggcaaaggta gcgttgccaa tgatgttaca gatgagatgg 420
tcagactaaa ctggctgacg gaatttatgc cacttccgac catcaagcat tttatccgta 480
ctcctgatga tgcatggtta ctcaccactg cgatccccgg aaaaacagcg ttccaggtat 540
tagaagaata tcctgattca ggtgaaaata ttgttgatgc gctggcagtg ttcctgcgcc 600
ggttgcactc gattcctgtt tgtaattgtc cttttaacag cgatcgcgta tttcgcctcg 660
ctcaggcgca atcacgaatg aataacggtt tggttgatgc gagtgatttt gatgacgagc 720
gtaatggctg gcctgttgaa caagtctgga aagaaatgca taaacttttg ccattctcac 780
cggattcagt cgtcactcat ggtgatttct cacttgataa ccttattttt gacgagggga 840
aattaatagg ttgtattgat gttggacgag tcggaatcgc agaccgatac caggatcttg 900
ccatcctatg gaactgcctc ggtgagtttt ctccttcatt acagaaacgg ctttttcaaa 960
aatatggtat tgataatcct gatatgaata aattgcaatt tcatttgatg ctcgatgagt 1020
ttttctaagc ggcgcgccat cgaatggcgc aaaacctttc gcggtcgggt aatcgaccgc 1080
gttttttttt aaaaggatct aggtgaagat cctttttgat aatctcatga ccaaaatccc 1140
ttaacgtgag ttttcgttcc actgagcgtc agaccccgta gaaaagatca aaggatcttc 1200
ttgagatcct ttttttctgc gcgtaatctg ctgcttgcaa acaaaaaaac caccgctacc 1260
agcggtggtt tgtttgccgg atcaagagct accaactctt tttccgaagg taactggctt 1320
cagcagagcg cagataccaa atactgtcct tctagtgtag ccgtagttag gccaccactt 1380
caagaactct gtagcaccgc ctacatacct cgctctgcta atcctgttac cagtggctgc 1440
tgccagtggc gataagtcgt gtcttaccgg gttggactca agacgatagt taccggataa 1500
ggcgcagcgg tcgggctgaa cggggggttc gtgcacacag cccagcttgg agcgaacgac 1560
ctacaccgaa ctgagatacc tacagcgtga gctatgagaa agcgccacgc ttcccgaagg 1620
gagaaaggcg gacaggtatc cggtaagcgg cagggtcgga acaggagagc gcacgaggga 1680
gcttccaggg ggaaacgcct ggtatcttta tagtcctgtc gggtttcgcc acctctgact 1740
tgagcgtcga tttttgtgat gctcgtcagg ggggcggagc ctatggaaaa acgccagcaa 1800
cgcggccttt ttacggttcc tggccttttg ctggcctttt gctcacatgt tctttcctgc 1860
gttatcccct gattctgtgg ataaccgtat taccgccttt gagtgagctg ataccgctcg 1920
ccgcagccga acgaccgagc gcagcgagtc agtgagcgag gaagcggaag agcgcctgat 1980
gcggtatttt ctccttacgc atctgtgcgg tatttcacac cgcataaatt ccgacaccat 2040
cgaatggcgc aaaacctttc gcggtatggc atgatagcgc ccggaagaga gtcaattcag 2100
ggtggtgaat gtgaaaccag taacgttata cgatgtcgca gagtatgccg gtgtctctta 2160
tcagaccgtt tcccgcgtgg tgaaccaggc cagccacgtt tctgcgaaaa cgcgggaaaa 2220
agtggaagcg gcgatggcgg agctgaatta cattcccaac cgcgtggcac aacaactggc 2280
gggcaaacag tcgttgctga ttggcgttgc cacctccagt ctggccctgc acgcgccgtc 2340
gcaaattgtc gcggcgatta aatctcgcgc cgatcaactg ggtgccagcg tggtggtgtc 2400
gatggtagaa cgaagcggcg tcgaagcctg taaagcggcg gtgcacaatc ttctcgcgca 2460
acgcgtcagt gggctgatca ttaactatcc gctggatgac caggatgcca ttgctgtgga 2520
agctgcctgc actaatgttc cggcgttatt tcttgatgtc tctgaccaga cacccatcaa 2580
cagtattatt ttctcccatg aagacggtac gcgactgggc gtggagcatc tggtcgcatt 2640
gggtcaccag caaatcgcgc tgttagcggg cccattaagt tctgtctcgg cgcgtctgcg 2700
tctggctggc tggcataaat atctcactcg caatcaaatt cagccgatag cggaacggga 2760
aggcgactgg agtgccatgt ccggttttca acaaaccatg caaatgctga atgagggcat 2820
cgttcccact gcgatgctgg ttgccaacga tcagatggcg ctgggcgcaa tgcgcgccat 2880
taccgagtcc gggctgcgcg ttggtgcgga tatctcggta gtgggatacg acgataccga 2940
agacagctca tgttatatcc cgccgttaac caccatcaaa caggattttc gcctgctggg 3000
gcaaaccagc gtggaccgct tgctgcaact ctctcagggc caggcggtga agggcaatca 3060
gctgttgccc gtctcactgg tgaaaagaaa aaccacgcta gcgcccaata cgcaaaccgc 3120
ctctccccgc gcgttggccg attcattaat gcagctggca cgacaggttt cccgactgga 3180
aagcgggcag tgagcgcaac gcaattaatg taagttagct cactcattag gcaccaagct 3240
taaatgtaat cacactggct caccttcggg tgggcctttc tgcgtttatc gtaaatcact 3300
gcataattcg tgtcgctcaa ggcgcactcc cgttctggat aatgtttttt gcgccgacat 3360
cataacggtt ctggcaaata ttctgaaatg agctgttgac aattaatcat cggctcgtat 3420
aatgtgtgga attgtgagcg gataacaatt tcacaatttc tttaacaatt aatcatttgg 3480
aggaaacata tgacaaaacc tgcactggga ctgaagaccc gcaataagaa agccaaaagc 3540
gacaaactta ttgttcgccg tcgcaatcag aagggatccg cagaattcgc cctcgagtaa 3600
tgattaacta gtgaaagccc ccggaagatc atcttccggg ggcttttttt tt 3652

<210> SEQ ID NO 65
<211> LENGTH: 30
<212> TYPE: DNA
<213> ORGANISM: ARTIFICIAL SEQUENCE
<220> FEATURE:
<223> OTHER INFORMATION: PCR primer.

<400> SEQUENCE: 65
atatgacgtc aggtgggacc accgcgctac 30

<210> SEQ ID NO 66
<211> LENGTH: 57
<212> TYPE: DNA
<213> ORGANISM: ARTIFICIAL SEQUENCE
<220> FEATURE:
<223> OTHER INFORMATION: PCR primer.

<400> SEQUENCE: 66
gcgttttaaa aaaaaacgcg gtcgattacc cgaccgcgaa aggttttgcg ccattcg 57

<210> SEQ ID NO 67
<211> LENGTH: 22
<212> TYPE: DNA
<213> ORGANISM: ARTIFICIAL SEQUENCE
<220> FEATURE:
<223> OTHER INFORMATION: PCR primer.

<400> SEQUENCE: 67
atatgacgtc aggtgggacc ac 22

<210> SEQ ID NO 68
<211> LENGTH: 32
<212> TYPE: DNA
<213> ORGANISM: ARTIFICIAL SEQUENCE
<220> FEATURE:
<223> OTHER INFORMATION: PCR primer.

<400> SEQUENCE: 68
atataagctt ggtgcctaat gagtgagcta ac 32

<210> SEQ ID NO 69
<211> LENGTH: 30
<212> TYPE: DNA
<213> ORGANISM: ARTIFICIAL SEQUENCE
<220> FEATURE:
<223> OTHER INFORMATION: PCR primer.

<400> SEQUENCE: 69
tcgagcatca ccatcaccat caccattaaa 30

<210> SEQ ID NO 70
<211> LENGTH: 30
<212> TYPE: DNA
<213> ORGANISM: ARTIFICIAL SEQUENCE
<220> FEATURE:
<223> OTHER INFORMATION: PCR primer.

<400> SEQUENCE: 70
ctagtttaat ggtgatggtg atggtgatgc 30

<210> SEQ ID NO 71
<211> LENGTH: 40
<212> TYPE: DNA
<213> ORGANISM: ARTIFICIAL SEQUENCE
<220> FEATURE:
<223> OTHER INFORMATION: PCR primer.

<400> SEQUENCE: 71
atatcatatg acaaaacctg cactgggact gaagacccgc 40

<210> SEQ ID NO 72
<211> LENGTH: 28
<212> TYPE: DNA
<213> ORGANISM: ARTIFICIAL SEQUENCE
<220> FEATURE:
<223> OTHER INFORMATION: PCR primer.

<400> SEQUENCE: 72
tataggatcc cttctgattg cgacggcg 28

<210> SEQ ID NO 73
<211> LENGTH: 29
<212> TYPE: DNA
<213> ORGANISM: ARTIFICIAL SEQUENCE
<220> FEATURE:

<223> OTHER INFORMATION: PCR primer.

<400> SEQUENCE: 73
atatggatcc gatacggtag taacgggtg 29

<210> SEQ ID NO 74
<211> LENGTH: 31
<212> TYPE: DNA
<213> ORGANISM: ARTIFICIAL SEQUENCE
<220> FEATURE:
<223> OTHER INFORMATION: PCR primer.

<400> SEQUENCE: 74
tatactcgag attgaaatac tcttcccaca g 31

<210> SEQ ID NO 75
<211> LENGTH: 32
<212> TYPE: DNA
<213> ORGANISM: ARTIFICIAL SEQUENCE
<220> FEATURE:
<223> OTHER INFORMATION: PCR primer.

<400> SEQUENCE: 75
atatggatcc gacgaaatca aagcaaaata cg 32

<210> SEQ ID NO 76
<211> LENGTH: 31
<212> TYPE: DNA
<213> ORGANISM: ARTIFICIAL SEQUENCE
<220> FEATURE:
<223> OTHER INFORMATION: PCR primer.

<400> SEQUENCE: 76
tatactcgag acctgctttg gtcgtttttg c 31

<210> SEQ ID NO 77
<211> LENGTH: 22
<212> TYPE: DNA
<213> ORGANISM: ARTIFICIAL SEQUENCE
<220> FEATURE:
<223> OTHER INFORMATION: PCR primer.

<400> SEQUENCE: 77
gccgacatca taacggttct gg 22

<210> SEQ ID NO 78
<211> LENGTH: 31
<212> TYPE: DNA
<213> ORGANISM: ARTIFICIAL SEQUENCE
<220> FEATURE:
<223> OTHER INFORMATION: PCR primer.

<400> SEQUENCE: 78
tataggtacc acctgctttg gtcgtttttg c 31

<210> SEQ ID NO 79
<211> LENGTH: 29
<212> TYPE: DNA
<213> ORGANISM: ARTIFICIAL SEQUENCE
<220> FEATURE:
<223> OTHER INFORMATION: PCR primer.

<400> SEQUENCE: 79
atatggtacc gatacggtag taacgggtg 29

-continued

<210> SEQ ID NO 80
<211> LENGTH: 28
<212> TYPE: DNA
<213> ORGANISM: ARTIFICIAL SEQUENCE
<220> FEATURE:
<223> OTHER INFORMATION: PCR primer.

<400> SEQUENCE: 80
tataggtacc ggtttggttg ccacttgc 28

<210> SEQ ID NO 81
<211> LENGTH: 24
<212> TYPE: DNA
<213> ORGANISM: ARTIFICIAL SEQUENCE
<220> FEATURE:
<223> OTHER INFORMATION: PCR primer.

<400> SEQUENCE: 81
atatggtacc ggcgaaacga cggc 24

<210> SEQ ID NO 82
<211> LENGTH: 19
<212> TYPE: DNA
<213> ORGANISM: ARTIFICIAL SEQUENCE
<220> FEATURE:
<223> OTHER INFORMATION: PCR primer.

<400> SEQUENCE: 82
ggtggtccca cctgacgtc 19

<210> SEQ ID NO 83
<211> LENGTH: 27
<212> TYPE: DNA
<213> ORGANISM: ARTIFICIAL SEQUENCE
<220> FEATURE:
<223> OTHER INFORMATION: PCR primer.

<400> SEQUENCE: 83
atatggatcc agcgagcagc cggacag 27

<210> SEQ ID NO 84
<211> LENGTH: 26
<212> TYPE: DNA
<213> ORGANISM: ARTIFICIAL SEQUENCE
<220> FEATURE:
<223> OTHER INFORMATION: PCR primer.

<400> SEQUENCE: 84
tatactcgag gctgctcacc gcggtc 26

<210> SEQ ID NO 85
<211> LENGTH: 26
<212> TYPE: DNA
<213> ORGANISM: ARTIFICIAL SEQUENCE
<220> FEATURE:
<223> OTHER INFORMATION: PCR primer.

<400> SEQUENCE: 85
tatactcgag gtcgaccagt gcggcg 26

<210> SEQ ID NO 86
<211> LENGTH: 29
<212> TYPE: DNA
<213> ORGANISM: ARTIFICIAL SEQUENCE
<220> FEATURE:
<223> OTHER INFORMATION: PCR primer.

<400> SEQUENCE: 86
tatactcgag cgtggtttca ccgacttgc 29

<210> SEQ ID NO 87
<211> LENGTH: 374
<212> TYPE: DNA
<213> ORGANISM: ARTIFICIAL SEQUENCE
<220> FEATURE:
<223> OTHER INFORMATION: Synthetic DNA sequence.

<400> SEQUENCE: 87
ccacggcgac tgcacggtgc accaatgctt ctggcgtcag gcagccatcg gaagctgtgg 60
tatggctgtg caggtcgtaa atcactgcat aattcgtgtc gctcaaggcg cactcccgtt 120
ctggataatg ttttttgcgc cgacatcata acggttctgg caaatattct gaaatgagct 180
gttgacaatt aatcatcggc tcgtataatg tgtggaattg tgagcggata acaatttcac 240
aatttcttta acaattaatc atttggagga acaaatgaca ggatccgcag aattcgccta 300
cgtagcgctc gagtaatgat taactagtga aagcccccgg aagatcatct tccgggggct 360 tttttttga cgtc 374

<210> SEQ ID NO 88
<211> LENGTH: 345
<212> TYPE: DNA
<213> ORGANISM: ARTIFICIAL SEQUENCE
<220> FEATURE:
<223> OTHER INFORMATION: Synthetic DNA sequence.

<400> SEQUENCE: 88
aagcttaaat gtaatcacac tggctcacct tcgggtgggc ctttctgcgt ttatcgtaaa 60
tcactgcata attcgtgtcg ctcaaggcgc actcccgttc tggataatgt tttttgcgcc 120
gacatcataa cggttctggc aaatattctg aaatgagctg ttgacaatta atcatcggct 180
cgtataatgt gtggaattgt gagcggataa caatttcaca atttctttaa caattaatca 240
tttggaggaa acatatgaca ggatccgcag aattcgccct cgagtaatga ttaactagtg 300
aaagcccccg gaagatcatc ttccgggggc ttttttttg acgtc 345

<210> SEQ ID NO 89
<211> LENGTH: 87
<212> TYPE: DNA
<213> ORGANISM: ARTIFICIAL SEQUENCE
<220> FEATURE:
<223> OTHER INFORMATION: Codon optimized DNA sequence of affinity-tag.

<400> SEQUENCE: 89
ctcgagggac tgaagacccg caataagaaa gccaaaagcg acaaacttat tgttcgccgt 60
cgcaatcaga agtaatgatt aactagt 87

<210> SEQ ID NO 90
<211> LENGTH: 93
<212> TYPE: DNA
<213> ORGANISM: ARTIFICIAL SEQUENCE
<220> FEATURE:
<223> OTHER INFORMATION: Codon optimized DNA sequence of affinity-tag.

<400> SEQUENCE: 90
catatgacaa aacctgcact gggactgaag acccgcaata agaaagccaa aagcgacaaa 60
cttattgttc gccgtcgcaa tcagaaggga tcc 93

<210> SEQ ID NO 91
<211> LENGTH: 1047
<212> TYPE: DNA
<213> ORGANISM: ARTIFICIAL SEQUENCE
<220> FEATURE:
<223> OTHER INFORMATION: Codon optimized DNA sequence of S. equi protein with affinity-tag.

<400> SEQUENCE: 91
catatgacag gatccgacga ctatcagcgc aacgcgaccg aagcctacgc aaaagaggtg 60
ccgcatcaaa tcacgagcgt gtggaccaaa ggcgtcaccc cactgacccc agaacagttc 120
cgttacaaca acgaggacgt catccacgcg ccgtatctgg cacaccaggg ctggtatgac 180
atcacgaagg cgtttgacgg taaggataat ctgttgtgcg gcgcagccac cgcaggtaat 240
atgctgcact ggtggtttga tcagaacaaa accgagattg aggcctacct gagcaaacac 300
cctgagaagc agaagatcat tttcaacaac caagagttgt tcgatctgaa ggctgcaatt 360
gataccaaag attctcagac gaatagccag ctgtttaact attttcgcga taaggcattc 420
ccgaatctga gcgcacgtca gttgggcgtg atgccggacc tggtgctgga tatgttcatt 480
aatggctact atctgaatgt gtttaagacg caaagcacgg atgtcaaccg tccgtaccag 540
gacaaggaca aacgcggtgg tatcttcgac gctgtgttta cccgtggtga tcagaccacc 600
ctgttgaccg cgcgtcatga tctgaaaaac aagggcctga acgacattag cacgatcatc 660
aaacaggagt tgacggaggg tcgtgctctg gcgcttagcc acacgtacgc gaatgttagc 720
attagccacg tgattaatct gtggggtgcg gacttcaacg cagagggtaa tctcgaagct 780
atctatgtta cggacagcga cgcaaacgca agcatcggta tgaaaaagta tttcgtcggt 840
atcaatgcgc accgccatgt tgcaatcagc gcgaaaaaga tcgagggcga gaacattggt 900
gcccaggttc tgggtctgtt caccctgagc agcggcaagg acatttggca aaagttgagc 960
ctcgagggac tgaagacccg caataagaaa gccaaaagcg acaaacttat tgttcgccgt 1020
cgcaatcaga agtaatgatt aactagt 1047

<210> SEQ ID NO 92
<211> LENGTH: 652
<212> TYPE: PRT
<213> ORGANISM: ARTIFICIAL SEQUENCE
<220> FEATURE:
<223> OTHER INFORMATION: Fusion polypeptide of fragments of S. suis proteins.

<400> SEQUENCE: 92

Asp Glu Ile Lys Ala Lys Tyr Glu Ala Glu Asn Ala Gln Val Val Ile
1 5 10 15

Glu Asn Asn Pro Val Glu Leu Asn Gly Asp Arg Ser Asn Val Arg Val
20 25 30

Arg Glu Thr Asn Leu Gly Asn Ala Val Thr Asp Ala Ile Tyr Ala Tyr
35 40 45

Gly Gln Thr Gly Phe Ser Asn Lys Thr Ser Leu Ala Val Thr Asn Gly
50 55 60

Gly Gly Leu Arg Ala Thr Ile Ala Lys Asp Gln Pro Val Thr Lys Gly
65 70 75 80

Asp Ile Ile Ala Val Leu Pro Phe Gly Asn Ile Val Ser Gln Ile Thr
85 90 95

Val Thr Gly Gln Gln Ile Tyr Asp Met Phe Thr Lys Ser Leu Ser Ser
100 105 110

Thr Leu Gln Val Asn Pro Glu Thr Gly Glu Met Leu Leu Asp Glu Asn

-continued

```
        115                 120                 125

Gly Met Pro Leu Phe Glu Ala Ser Gly Gly Phe Leu His Ile Ser Gly
    130                 135                 140

Ala Asn Val Phe Tyr Asp Pro Thr Leu Pro Val Glu Glu Arg Val Leu
145                 150                 155                 160

Leu Ile Gly Ile Leu Asn Pro Glu Thr Gly Glu Tyr Asp Ala Leu Asp
                165                 170                 175

Leu Glu Lys Thr Tyr Tyr Leu Ala Thr Asn Asp Phe Leu Ala Ala Gly
            180                 185                 190

Gly Asp Gly Tyr Thr Met Leu Gly Gly Ala Arg Glu Glu Gly Pro Ser
        195                 200                 205

Met Asp Ser Val Phe Ala Glu Tyr Leu Lys Thr Ala Asp Leu Ser Ala
    210                 215                 220

Tyr Glu Val Val Asn Pro Tyr Ser Arg Ile Ile Pro Val Asn Ser Ser
225                 230                 235                 240

Ile Asp Thr Asp Glu Asp Gly Tyr Pro Asp Phe Ile Glu Ile Leu Leu
                245                 250                 255

Asp Thr Asp Pro Glu Asn Pro Ala Ser Asn Pro Glu Thr Val Pro Ala
            260                 265                 270

Glu Asn Thr Asp Ser Pro Ser Asn Gln Val Gln Asn Thr Ser Ala Thr
        275                 280                 285

Asp Lys Lys Ala Pro Val Asp Ser Pro Lys Val Gly Asp Lys Lys Thr
    290                 295                 300

Glu Val Ala Ser Pro Ala Lys Thr Thr Lys Ala Gly Gly Thr Gly Glu
305                 310                 315                 320

Thr Thr Ala Pro Ile Asn Ser Phe Phe Ala Leu Val Gln Asp Asp Pro
                325                 330                 335

Ser Val Gln Ile Val Asn Asn Ala Gln Ile Trp Tyr Ala Lys Gln Gln
            340                 345                 350

Leu Ala Gly Thr Ser Glu Ala Asn Leu Pro Ile Leu Ser Ala Ala Ala
        355                 360                 365

Pro Phe Lys Ala Gly Thr Arg Gly Asp Ala Ser Ala Tyr Thr Asp Ile
    370                 375                 380

Pro Ala Gly Pro Ile Ala Ile Lys Asn Val Ala Asp Leu Tyr Leu Tyr
385                 390                 395                 400

Asp Asn Val Val Ala Ile Leu Lys Val Asn Gly Ala Gln Leu Lys Glu
                405                 410                 415

Trp Leu Glu Met Ser Ala Gly Gln Phe Asn Gln Val Asp Leu Ser Ser
            420                 425                 430

Thr Glu Pro Gln Asn Leu Val Asn Thr Asp Phe Arg Thr Tyr Asn Phe
        435                 440                 445

Asp Val Ile Asp Gly Val Thr Tyr Gln Tyr Asp Ile Thr Gln Pro Asn
    450                 455                 460

Lys Tyr Asp Arg Asp Gly Lys Ile Val Asn Glu Thr Ala Ser Arg Val
465                 470                 475                 480

Arg Asn Leu Gln Tyr Asn Gly Gln Asp Val Thr Ala Asp Gln Glu Phe
                485                 490                 495

Ile Val Val Thr Asn Asn Tyr Arg Ala Asn Gly Thr Phe Pro Gly Val
            500                 505                 510

Arg Glu Ala Ser Ile Asn Arg Leu Leu Asn Leu Glu Asn Arg Gln Ala
        515                 520                 525

Ile Ile Asn Tyr Ile Ile Ala Glu Lys Val Ile Asn Pro Thr Ala Asp
    530                 535                 540
```

Asn Asn Trp Thr Phe Thr Asp Ser Ile Lys Gly Leu Asp Leu Arg Phe
545 550 555 560

Leu Thr Ala Asp Arg Ala Lys Ser Leu Val Thr Asp Gln Glu Cys Ile
565 570 575

Val Tyr Leu Gln Ala Ser Thr Ala Ser Glu Gly Phe Gly Glu Phe Lys
580 585 590

Phe Val Tyr Thr Glu Ser Lys Val Val Thr Pro Asp Glu Gln Gln Ser
595 600 605

Asp Gln Gly Asn Thr Gly Gln Asp Ile Val Leu Glu Ser Gly Gln Arg
610 615 620

Ile Thr Leu Pro Ala Val Asn Pro Pro Ala Pro Ala Pro Gln His Lys
625 630 635 640

Leu Ala Ser Pro His Ser Gln Ala Ser Thr Lys Thr
645 650

<210> SEQ ID NO 93
<211> LENGTH: 688
<212> TYPE: PRT
<213> ORGANISM: ARTIFICIAL SEQUENCE
<220> FEATURE:
<223> OTHER INFORMATION: Fusion polypeptide of fragments of S. suis proteins.

<400> SEQUENCE: 93

Asp Thr Val Val Thr Gly Val Asn Glu Ile Ile Glu Glu Ser Gln Val
1 5 10 15

Lys Asp Glu Val Ser Ile Glu Ser Glu Lys Asn Glu Ser Leu Asp Gly
20 25 30

Ser Asn Ile Glu Ile Val Glu Glu Ile Ala Asp Asn Ile Pro Ser Pro
35 40 45

Val Ile Ala Glu Gly Glu Val Ala Val Glu Met Lys Val Asp Arg Gly
50 55 60

Thr Glu Asn Val Val Ser Arg Asn Asp Thr Glu Val Thr Thr Ser Glu
65 70 75 80

Gln Asn Gln Ile Glu Val Thr Glu Thr Lys Glu Ile Leu Asn Gln Thr
85 90 95

Ser Tyr Gln Thr Glu Ser Gly Glu Gln Arg Gln Ile Ile Trp Ala His
100 105 110

Gly Ile Thr Pro Pro Ala Met Glu Gln Ser Gly Gly Phe Val Lys Glu
115 120 125

Lys Tyr Gly Asp Tyr Leu Asn Tyr Thr Ala Pro Phe Glu Ala Gly Lys
130 135 140

Gly Tyr Tyr Asp Thr Asn Lys Ser Leu Asn Ala Ser Phe Ile Asp Leu
145 150 155 160

Asn Leu Cys Phe Ala Ala Val Ser Ser Asn Met Val His Trp Trp Leu
165 170 175

Glu Gln Asn Ser Ser Tyr Val Glu Arg Tyr Leu Lys Glu Lys Lys Gly
180 185 190

Thr Val Asn Val Glu Glu Asn Tyr Ala Ile Thr Asp Leu Arg Arg Tyr
195 200 205

Ile Asn Ser Phe Gln Asn Gln Gln Asn Ser Arg Val Phe Asp Met Phe
210 215 220

Lys Thr Tyr Tyr Gly Tyr Arg Thr Asn Gly Phe Val Ser Asp Ala Leu
225 230 235 240

Val Asp Leu Phe Ile Asn Gly Tyr Lys Pro Lys Ala Gln Gly Gly Val

-continued

```
                245                 250                 255

Asn Leu Glu Asp Ser Gln Leu Val Pro Asp Ser Arg Gly Gly Phe Phe
            260                 265                 270

Tyr Asp Val Phe Lys Glu Lys Lys Leu Thr Asn Arg Ile Phe Ser Gly
        275                 280                 285

Ser Tyr Glu Arg Phe Gly Glu Asp Val Arg Thr Val Leu Glu Ser Lys
    290                 295                 300

Gly Leu Leu Gly Leu Thr Tyr Arg Thr Leu Gly Tyr Ala Thr His Ile
305                 310                 315                 320

Val Thr Val Trp Gly Ala Glu Tyr Asp Asn Gln Gly Lys Ile Lys Ala
                325                 330                 335

Val Tyr Ile Thr Asp Ser Asp Asp Gln Gln Glu Gln Ile Gly Leu Lys
            340                 345                 350

Arg Met Gly Ile Thr Arg Asp Ala Ser Gly Asn Pro Arg Leu Asn Asn
        355                 360                 365

His Met Lys Asn Asn Ser Ala Gly Ala Leu Leu Asp Tyr Val His Thr
    370                 375                 380

Ile Arg Leu Gly Gln Asp Leu Trp Glu Glu Tyr Phe Asn Gly Thr Glu
385                 390                 395                 400

Ile Gln Ala Ile Val Asp Glu Ala Asn Thr Ile Val Lys Lys Val Thr
                405                 410                 415

Glu Gln Lys Ile Ala Thr Ala Ser Gln Ala Thr Asp Ile Ser Arg Glu
            420                 425                 430

Val Asn Glu Phe Lys Glu Ser Ala Val Gly Asn Leu Val Thr Ser Ala
        435                 440                 445

Gln Leu Ala Ile Ala Lys Lys Ser Gly Tyr Asp Val Asp Phe Ala Met
    450                 455                 460

Thr Asn Asp Gly Gly Ile Arg Ala Asp Leu Lys Val Gln Glu Asp Gly
465                 470                 475                 480

Thr Val Thr Trp Gly Ala Ala Gln Ala Val Gln Pro Phe Gly Asn Ile
                485                 490                 495

Leu Gln Val Val Gln Met Thr Gly Glu Gln Ile Tyr Thr Ala Leu Asn
            500                 505                 510

Gln Gln Tyr Asp Glu Gly Glu Lys Tyr Phe Leu Gln Met Ser Gly Ile
        515                 520                 525

Lys Tyr Ile Tyr Thr Lys Ala Asp Asn Pro Thr Glu Glu Asn Pro Tyr
    530                 535                 540

Lys Val Val Lys Ala Phe Lys Glu Asp Gly Thr Glu Ile Val Pro Thr
545                 550                 555                 560

Glu Thr Tyr Thr Leu Val Ile Asn Asp Phe Leu Phe Gly Gly Gly Asp
                565                 570                 575

Gly Phe Ser Ile Phe Lys Glu Ala Lys Leu Ile Gly Ala Ile Asn Pro
            580                 585                 590

Asp Thr Glu Val Phe Val Glu Tyr Leu Thr Asp Leu Glu Lys Ala Gly
        595                 600                 605

Gln Thr Ile Ser Ala Thr Ile Pro Gly Arg Lys Ala Phe Val Glu Lys
    610                 615                 620

Tyr Val Glu Glu Pro Lys Ala Glu Glu Lys Glu Asp Asn Ala Gly Thr
625                 630                 635                 640

Thr Thr Asp Val Lys Thr Pro Glu Lys Ala Asn Asp Gly Gly Asp Ser
                645                 650                 655

Val Thr Asn Gln Lys Ala Thr Glu Gln Pro Ala Pro Ser Gly Ser Met
            660                 665                 670
```

Ala Pro Ile Ser Asn Lys Lys Thr Glu Lys Ala Ser Gly Asn Gln Thr
675 680 685

<210> SEQ ID NO 94
<211> LENGTH: 694
<212> TYPE: PRT
<213> ORGANISM: ARTIFICIAL SEQUENCE
<220> FEATURE:
<223> OTHER INFORMATION: Fusion polypeptide of fragments of S. suis proteins.

<400> SEQUENCE: 94

Glu Ile Gln Ala Ile Val Asp Glu Ala Asn Thr Ile Val Lys Lys Val
1 5 10 15

Thr Glu Gln Lys Ile Ala Thr Ala Ser Gln Ala Thr Asp Ile Ser Arg
20 25 30

Glu Val Asn Glu Phe Lys Glu Ser Ala Val Gly Asn Leu Val Thr Ser
35 40 45

Ala Gln Leu Ala Ile Ala Lys Lys Ser Gly Tyr Asp Val Asp Phe Ala
50 55 60

Met Thr Asn Asp Gly Gly Ile Arg Ala Asp Leu Lys Val Gln Glu Asp
65 70 75 80

Gly Thr Val Thr Trp Gly Ala Ala Gln Ala Val Gln Pro Phe Gly Asn
85 90 95

Ile Leu Gln Val Val Gln Met Thr Gly Glu Gln Ile Tyr Thr Ala Leu
100 105 110

Asn Gln Gln Tyr Asp Glu Gly Glu Lys Tyr Phe Leu Gln Met Ser Gly
115 120 125

Ile Lys Tyr Ile Tyr Thr Lys Ala Asp Asn Pro Thr Glu Glu Asn Pro
130 135 140

Tyr Lys Val Val Lys Ala Phe Lys Glu Asp Gly Thr Glu Ile Val Pro
145 150 155 160

Thr Glu Thr Tyr Thr Leu Val Ile Asn Asp Phe Leu Phe Gly Gly Gly
165 170 175

Asp Gly Phe Ser Ile Phe Lys Glu Ala Lys Leu Ile Gly Ala Ile Asn
180 185 190

Pro Asp Thr Glu Val Phe Val Glu Tyr Leu Thr Asp Leu Glu Lys Ala
195 200 205

Gly Gln Thr Ile Ser Ala Thr Ile Pro Gly Arg Lys Ala Phe Val Glu
210 215 220

Lys Tyr Val Glu Glu Pro Lys Ala Glu Glu Lys Glu Asp Asn Ala Gly
225 230 235 240

Thr Thr Thr Asp Val Lys Thr Pro Glu Lys Ala Asn Asp Gly Gly Asp
245 250 255

Ser Val Thr Asn Gln Lys Ala Thr Glu Gln Pro Ala Pro Ser Gly Ser
260 265 270

Met Ala Pro Ile Ser Asn Lys Lys Thr Glu Lys Ala Ser Gly Asn Gln
275 280 285

Thr Gly Thr Asp Thr Val Val Thr Gly Val Asn Glu Ile Ile Glu Glu
290 295 300

Ser Gln Val Lys Asp Glu Val Ser Ile Glu Ser Glu Lys Asn Glu Ser
305 310 315 320

Leu Asp Gly Ser Asn Ile Glu Ile Val Glu Glu Ile Ala Asp Asn Ile
325 330 335

Pro Ser Pro Val Ile Ala Glu Gly Glu Val Ala Val Glu Met Lys Val

```
            340                 345                 350

Asp Arg Gly Thr Glu Asn Val Val Ser Arg Asn Asp Thr Glu Val Thr
        355                 360                 365

Thr Ser Glu Gln Asn Gln Ile Glu Val Thr Glu Thr Lys Glu Ile Leu
    370                 375                 380

Asn Gln Thr Ser Tyr Gln Thr Glu Ser Gly Glu Gln Arg Gln Ile Ile
385                 390                 395                 400

Trp Ala His Gly Ile Thr Pro Pro Ala Met Glu Gln Ser Gly Gly Phe
                405                 410                 415

Val Lys Glu Lys Tyr Gly Asp Tyr Leu Asn Tyr Thr Ala Pro Phe Glu
            420                 425                 430

Ala Gly Lys Gly Tyr Tyr Asp Thr Asn Lys Ser Leu Asn Ala Ser Phe
        435                 440                 445

Ile Asp Leu Asn Leu Cys Phe Ala Ala Val Ser Ser Asn Met Val His
    450                 455                 460

Trp Trp Leu Glu Gln Asn Ser Ser Tyr Val Glu Arg Tyr Leu Lys Glu
465                 470                 475                 480

Lys Lys Gly Thr Val Asn Val Glu Glu Asn Tyr Ala Ile Thr Asp Leu
                485                 490                 495

Arg Arg Tyr Ile Asn Ser Phe Gln Asn Gln Gln Asn Ser Arg Val Phe
            500                 505                 510

Asp Met Phe Lys Thr Tyr Tyr Gly Tyr Arg Thr Asn Gly Phe Val Ser
        515                 520                 525

Asp Ala Leu Val Asp Leu Phe Ile Asn Gly Tyr Lys Pro Lys Ala Gln
    530                 535                 540

Gly Gly Val Asn Leu Glu Asp Ser Gln Leu Val Pro Asp Ser Arg Gly
545                 550                 555                 560

Gly Phe Phe Tyr Asp Val Phe Lys Glu Lys Lys Leu Thr Asn Arg Ile
                565                 570                 575

Phe Ser Gly Ser Tyr Glu Arg Phe Gly Glu Asp Val Arg Thr Val Leu
            580                 585                 590

Glu Ser Lys Gly Leu Leu Gly Leu Thr Tyr Arg Thr Leu Gly Tyr Ala
        595                 600                 605

Thr His Ile Val Thr Val Trp Gly Ala Glu Tyr Asp Asn Gln Gly Lys
    610                 615                 620

Ile Lys Ala Val Tyr Ile Thr Asp Ser Asp Gln Gln Glu Gln Ile
625                 630                 635                 640

Gly Leu Lys Arg Met Gly Ile Thr Arg Asp Ala Ser Gly Asn Pro Arg
                645                 650                 655

Leu Asn Asn His Met Lys Asn Asn Ser Ala Gly Ala Leu Leu Asp Tyr
            660                 665                 670

Val His Thr Ile Arg Leu Gly Gln Asp Leu Trp Glu Glu Tyr Phe Asn
        675                 680                 685

Pro Leu Ala Lys Ala Lys
    690
```

<210> SEQ ID NO 95
<211> LENGTH: 733
<212> TYPE: PRT
<213> ORGANISM: ARTIFICIAL SEQUENCE
<220> FEATURE:
<223> OTHER INFORMATION: Fusion polypeptide of fragments of S. suis proteins.

<400> SEQUENCE: 95

-continued

```
Asp Thr Val Val Thr Gly Val Asn Glu Ile Ile Glu Glu Ser Gln Val
1               5                   10                  15

Lys Asp Glu Val Ser Ile Glu Ser Glu Lys Asn Glu Ser Leu Asp Gly
            20                  25                  30

Ser Asn Ile Glu Ile Val Glu Glu Ile Ala Asp Asn Ile Pro Ser Pro
        35                  40                  45

Val Ile Ala Glu Gly Glu Val Ala Val Glu Met Lys Val Asp Arg Gly
    50                  55                  60

Thr Glu Asn Val Val Ser Arg Asn Asp Thr Glu Val Thr Thr Ser Glu
65                  70                  75                  80

Gln Asn Gln Ile Glu Val Thr Glu Thr Lys Glu Ile Leu Asn Gln Thr
                85                  90                  95

Ser Tyr Gln Thr Glu Ser Gly Glu Gln Arg Gln Ile Ile Trp Ala His
            100                 105                 110

Gly Ile Thr Pro Pro Ala Met Glu Gln Ser Gly Gly Phe Val Lys Glu
        115                 120                 125

Lys Tyr Gly Asp Tyr Leu Asn Tyr Thr Ala Pro Phe Glu Ala Gly Lys
    130                 135                 140

Gly Tyr Tyr Asp Thr Asn Lys Ser Leu Asn Ala Ser Phe Ile Asp Leu
145                 150                 155                 160

Asn Leu Cys Phe Ala Ala Val Ser Ser Asn Met Val His Trp Trp Leu
                165                 170                 175

Glu Gln Asn Ser Ser Tyr Val Glu Arg Tyr Leu Lys Glu Lys Lys Gly
            180                 185                 190

Thr Val Asn Val Glu Glu Asn Tyr Ala Ile Thr Asp Leu Arg Arg Tyr
        195                 200                 205

Ile Asn Ser Phe Gln Asn Gln Gln Asn Ser Arg Val Phe Asp Met Phe
    210                 215                 220

Lys Thr Tyr Tyr Gly Tyr Arg Thr Asn Gly Phe Val Ser Asp Ala Leu
225                 230                 235                 240

Val Asp Leu Phe Ile Asn Gly Tyr Lys Pro Lys Ala Gln Gly Gly Val
                245                 250                 255

Asn Leu Glu Asp Ser Gln Leu Val Pro Asp Ser Arg Gly Gly Phe Phe
            260                 265                 270

Tyr Asp Val Phe Lys Glu Lys Lys Leu Thr Asn Arg Ile Phe Ser Gly
        275                 280                 285

Ser Tyr Glu Arg Phe Gly Glu Asp Val Arg Thr Val Leu Glu Ser Lys
    290                 295                 300

Gly Leu Leu Gly Leu Thr Tyr Arg Thr Leu Gly Tyr Ala Thr His Ile
305                 310                 315                 320

Val Thr Val Trp Gly Ala Glu Tyr Asp Asn Gln Gly Lys Ile Lys Ala
                325                 330                 335

Val Tyr Ile Thr Asp Ser Asp Asp Gln Gln Glu Gln Ile Gly Leu Lys
            340                 345                 350

Arg Met Gly Ile Thr Arg Asp Ala Ser Gly Asn Pro Arg Leu Asn Asn
        355                 360                 365

His Met Lys Asn Asn Ser Ala Gly Ala Leu Leu Asp Tyr Val His Thr
    370                 375                 380

Ile Arg Leu Gly Gln Asp Leu Trp Glu Glu Tyr Phe Asn Gly Thr Gly
385                 390                 395                 400

Glu Thr Thr Ala Pro Ile Asn Ser Phe Phe Ala Leu Val Gln Asp Asp
                405                 410                 415

Pro Ser Val Gln Ile Val Asn Asn Ala Gln Ile Trp Tyr Ala Lys Gln
```

```
            420                 425                 430

Gln Leu Ala Gly Thr Ser Glu Ala Asn Leu Pro Ile Leu Ser Ala Ala
        435                 440                 445

Ala Pro Phe Lys Ala Gly Thr Arg Gly Asp Ala Ser Ala Tyr Thr Asp
    450                 455                 460

Ile Pro Ala Gly Pro Ile Ala Ile Lys Asn Val Ala Asp Leu Tyr Leu
465                 470                 475                 480

Tyr Asp Asn Val Val Ala Ile Leu Lys Val Asn Gly Ala Gln Leu Lys
                485                 490                 495

Glu Trp Leu Glu Met Ser Ala Gly Gln Phe Asn Gln Val Asp Leu Ser
            500                 505                 510

Ser Thr Glu Pro Gln Asn Leu Val Asn Thr Asp Phe Arg Thr Tyr Asn
        515                 520                 525

Phe Asp Val Ile Asp Gly Val Thr Tyr Gln Tyr Asp Ile Thr Gln Pro
    530                 535                 540

Asn Lys Tyr Asp Arg Asp Gly Lys Ile Val Asn Glu Thr Ala Ser Arg
545                 550                 555                 560

Val Arg Asn Leu Gln Tyr Asn Gly Gln Asp Val Thr Ala Asp Gln Glu
                565                 570                 575

Phe Ile Val Val Thr Asn Asn Tyr Arg Ala Asn Gly Thr Phe Pro Gly
            580                 585                 590

Val Arg Glu Ala Ser Ile Asn Arg Leu Leu Asn Leu Glu Asn Arg Gln
        595                 600                 605

Ala Ile Ile Asn Tyr Ile Ile Ala Glu Lys Val Ile Asn Pro Thr Ala
    610                 615                 620

Asp Asn Asn Trp Thr Phe Thr Asp Ser Ile Lys Gly Leu Asp Leu Arg
625                 630                 635                 640

Phe Leu Thr Ala Asp Arg Ala Lys Ser Leu Val Thr Asp Gln Glu Cys
                645                 650                 655

Ile Val Tyr Leu Gln Ala Ser Thr Ala Ser Glu Gly Phe Gly Glu Phe
            660                 665                 670

Lys Phe Val Tyr Thr Glu Ser Lys Val Val Thr Pro Asp Glu Gln Gln
        675                 680                 685

Ser Asp Gln Gly Asn Thr Gly Gln Asp Ile Val Leu Glu Ser Gly Gln
    690                 695                 700

Arg Ile Thr Leu Pro Ala Val Asn Pro Pro Ala Pro Ala Pro Gln His
705                 710                 715                 720

Lys Leu Ala Ser Pro His Ser Gln Ala Ser Thr Lys Thr
                725                 730
```

<210> SEQ ID NO 96
<211> LENGTH: 609
<212> TYPE: PRT
<213> ORGANISM: ARTIFICIAL SEQUENCE
<220> FEATURE:
<223> OTHER INFORMATION: Fusion polypeptide of fragments of S. suis proteins.

<400> SEQUENCE: 96

```
Gly Ser Asp Glu Ile Lys Ala Lys Tyr Glu Ala Glu Asn Ala Gln Val
1               5                   10                  15

Val Ile Glu Asn Asn Pro Val Glu Leu Asn Gly Asp Arg Ser Asn Val
            20                  25                  30

Arg Val Arg Glu Thr Asn Leu Gly Asn Ala Val Thr Asp Ala Ile Tyr
        35                  40                  45
```

```
Ala Tyr Gly Gln Thr Gly Phe Ser Asn Lys Thr Ser Leu Ala Val Thr
    50                  55                  60

Asn Gly Gly Gly Leu Arg Ala Thr Ile Ala Lys Asp Gln Pro Val Thr
65                  70                  75                  80

Lys Gly Asp Ile Ile Ala Val Leu Pro Phe Gly Asn Ile Val Ser Gln
                85                  90                  95

Ile Thr Val Thr Gly Gln Gln Ile Tyr Asp Met Phe Thr Lys Ser Leu
            100                 105                 110

Ser Ser Thr Leu Gln Val Asn Pro Glu Thr Gly Glu Met Leu Leu Asp
        115                 120                 125

Glu Asn Gly Met Pro Leu Phe Glu Ala Ser Gly Gly Phe Leu His Ile
    130                 135                 140

Ser Gly Ala Asn Val Phe Tyr Asp Pro Thr Leu Pro Val Glu Glu Arg
145                 150                 155                 160

Val Leu Leu Ile Gly Ile Leu Asn Pro Glu Thr Gly Glu Tyr Asp Ala
                165                 170                 175

Leu Asp Leu Glu Lys Thr Tyr Tyr Leu Ala Thr Asn Asp Phe Leu Ala
            180                 185                 190

Ala Gly Gly Asp Gly Tyr Thr Met Leu Gly Gly Ala Arg Glu Glu Gly
        195                 200                 205

Pro Ser Met Asp Ser Val Phe Ala Glu Tyr Leu Lys Thr Ala Asp Leu
    210                 215                 220

Ser Ala Tyr Glu Val Val Asn Pro Tyr Ser Arg Ile Ile Pro Val Asn
225                 230                 235                 240

Ser Ser Ile Asp Thr Asp Glu Asp Gly Tyr Pro Asp Phe Ile Glu Ile
                245                 250                 255

Leu Leu Asp Thr Asp Pro Glu Asn Pro Ala Ser Asn Pro Glu Thr Val
            260                 265                 270

Pro Ala Glu Asn Thr Asp Ser Pro Ser Asn Gln Val Gln Asn Thr Ser
        275                 280                 285

Ala Thr Asp Lys Lys Ala Pro Val Asp Ser Pro Lys Val Gly Asp Lys
    290                 295                 300

Lys Thr Glu Val Ala Ser Pro Ala Lys Thr Thr Lys Ala Gly Gly Thr
305                 310                 315                 320

Glu Ile Gln Ala Ile Val Asp Glu Ala Asn Thr Ile Val Lys Lys Val
                325                 330                 335

Thr Glu Gln Lys Ile Ala Thr Ala Ser Gln Ala Thr Asp Ile Ser Arg
            340                 345                 350

Glu Val Asn Glu Phe Lys Glu Ser Ala Val Gly Asn Leu Val Thr Ser
        355                 360                 365

Ala Gln Leu Ala Ile Ala Lys Lys Ser Gly Tyr Asp Val Asp Phe Ala
    370                 375                 380

Met Thr Asn Asp Gly Gly Ile Arg Ala Asp Leu Lys Val Gln Glu Asp
385                 390                 395                 400

Gly Thr Val Thr Trp Gly Ala Ala Gln Ala Val Gln Pro Phe Gly Asn
                405                 410                 415

Ile Leu Gln Val Val Gln Met Thr Gly Glu Gln Ile Tyr Thr Ala Leu
            420                 425                 430

Asn Gln Gln Tyr Asp Glu Gly Glu Lys Tyr Phe Leu Gln Met Ser Gly
        435                 440                 445

Ile Lys Tyr Ile Tyr Thr Lys Ala Asp Asn Pro Thr Glu Glu Asn Pro
    450                 455                 460

Tyr Lys Val Val Lys Ala Phe Lys Glu Asp Gly Thr Glu Ile Val Pro
```

465 470 475 480

Thr Glu Thr Tyr Thr Leu Val Ile Asn Asp Phe Leu Phe Gly Gly Gly
485 490 495

Asp Gly Phe Ser Ile Phe Lys Glu Ala Lys Leu Ile Gly Ala Ile Asn
500 505 510

Pro Asp Thr Glu Val Phe Val Glu Tyr Leu Thr Asp Leu Glu Lys Ala
515 520 525

Gly Gln Thr Ile Ser Ala Thr Ile Pro Gly Arg Lys Ala Phe Val Glu
530 535 540

Lys Tyr Val Glu Glu Pro Lys Ala Glu Glu Lys Glu Asp Asn Ala Gly
545 550 555 560

Thr Thr Thr Asp Val Lys Thr Pro Glu Lys Ala Asn Asp Gly Gly Asp
565 570 575

Ser Val Thr Asn Gln Lys Ala Thr Glu Gln Pro Ala Pro Ser Gly Ser
580 585 590

Met Ala Pro Ile Ser Asn Lys Lys Thr Glu Lys Ala Ser Gly Asn Gln
595 600 605

Thr

<210> SEQ ID NO 97
<211> LENGTH: 680
<212> TYPE: PRT
<213> ORGANISM: ARTIFICIAL SEQUENCE
<220> FEATURE:
<223> OTHER INFORMATION: Fusion polypeptide of fragments of S. suis proteins with affinity-tag.

<400> SEQUENCE: 97

Met Thr Gly Ser Asp Glu Ile Lys Ala Lys Tyr Glu Ala Glu Asn Ala
1 5 10 15

Gln Val Val Ile Glu Asn Asn Pro Val Glu Leu Asn Gly Asp Arg Ser
20 25 30

Asn Val Arg Val Arg Glu Thr Asn Leu Gly Asn Ala Val Thr Asp Ala
35 40 45

Ile Tyr Ala Tyr Gly Gln Thr Gly Phe Ser Asn Lys Thr Ser Leu Ala
50 55 60

Val Thr Asn Gly Gly Gly Leu Arg Ala Thr Ile Ala Lys Asp Gln Pro
65 70 75 80

Val Thr Lys Gly Asp Ile Ile Ala Val Leu Pro Phe Gly Asn Ile Val
85 90 95

Ser Gln Ile Thr Val Thr Gly Gln Gln Ile Tyr Asp Met Phe Thr Lys
100 105 110

Ser Leu Ser Ser Thr Leu Gln Val Asn Pro Glu Thr Gly Glu Met Leu
115 120 125

Leu Asp Glu Asn Gly Met Pro Leu Phe Glu Ala Ser Gly Gly Phe Leu
130 135 140

His Ile Ser Gly Ala Asn Val Phe Tyr Asp Pro Thr Leu Pro Val Glu
145 150 155 160

Glu Arg Val Leu Leu Ile Gly Ile Leu Asn Pro Glu Thr Gly Glu Tyr
165 170 175

Asp Ala Leu Asp Leu Glu Lys Thr Tyr Tyr Leu Ala Thr Asn Asp Phe
180 185 190

Leu Ala Ala Gly Gly Asp Gly Tyr Thr Met Leu Gly Gly Ala Arg Glu
195 200 205

Glu Gly Pro Ser Met Asp Ser Val Phe Ala Glu Tyr Leu Lys Thr Ala

-continued

```
    210                 215                 220

Asp Leu Ser Ala Tyr Glu Val Val Asn Pro Tyr Ser Arg Ile Ile Pro
225                 230                 235                 240

Val Asn Ser Ser Ile Asp Thr Asp Glu Asp Gly Tyr Pro Asp Phe Ile
                245                 250                 255

Glu Ile Leu Leu Asp Thr Asp Pro Glu Asn Pro Ala Ser Asn Pro Glu
            260                 265                 270

Thr Val Pro Ala Glu Asn Thr Asp Ser Pro Ser Asn Gln Val Gln Asn
        275                 280                 285

Thr Ser Ala Thr Asp Lys Lys Ala Pro Val Asp Ser Pro Lys Val Gly
    290                 295                 300

Asp Lys Lys Thr Glu Val Ala Ser Pro Ala Lys Thr Thr Lys Ala Gly
305                 310                 315                 320

Gly Thr Gly Glu Thr Thr Ala Pro Ile Asn Ser Phe Phe Ala Leu Val
                325                 330                 335

Gln Asp Asp Pro Ser Val Gln Ile Val Asn Asn Ala Gln Ile Trp Tyr
            340                 345                 350

Ala Lys Gln Gln Leu Ala Gly Thr Ser Glu Ala Asn Leu Pro Ile Leu
        355                 360                 365

Ser Ala Ala Ala Pro Phe Lys Ala Gly Thr Arg Gly Asp Ala Ser Ala
    370                 375                 380

Tyr Thr Asp Ile Pro Ala Gly Pro Ile Ala Ile Lys Asn Val Ala Asp
385                 390                 395                 400

Leu Tyr Leu Tyr Asp Asn Val Val Ala Ile Leu Lys Val Asn Gly Ala
                405                 410                 415

Gln Leu Lys Glu Trp Leu Glu Met Ser Ala Gly Gln Phe Asn Gln Val
            420                 425                 430

Asp Leu Ser Ser Thr Glu Pro Gln Asn Leu Val Asn Thr Asp Phe Arg
        435                 440                 445

Thr Tyr Asn Phe Asp Val Ile Asp Gly Val Thr Tyr Gln Tyr Asp Ile
    450                 455                 460

Thr Gln Pro Asn Lys Tyr Asp Arg Asp Gly Lys Ile Val Asn Glu Thr
465                 470                 475                 480

Ala Ser Arg Val Arg Asn Leu Gln Tyr Asn Gly Gln Asp Val Thr Ala
                485                 490                 495

Asp Gln Glu Phe Ile Val Val Thr Asn Asn Tyr Arg Ala Asn Gly Thr
            500                 505                 510

Phe Pro Gly Val Arg Glu Ala Ser Ile Asn Arg Leu Leu Asn Leu Glu
        515                 520                 525

Asn Arg Gln Ala Ile Ile Asn Tyr Ile Ile Ala Glu Lys Val Ile Asn
    530                 535                 540

Pro Thr Ala Asp Asn Asn Trp Thr Phe Thr Asp Ser Ile Lys Gly Leu
545                 550                 555                 560

Asp Leu Arg Phe Leu Thr Ala Asp Arg Ala Lys Ser Leu Val Thr Asp
                565                 570                 575

Gln Glu Cys Ile Val Tyr Leu Gln Ala Ser Thr Ala Ser Glu Gly Phe
            580                 585                 590

Gly Glu Phe Lys Phe Val Tyr Thr Glu Ser Lys Val Val Thr Pro Asp
        595                 600                 605

Glu Gln Gln Ser Asp Gln Gly Asn Thr Gly Gln Asp Ile Val Leu Glu
    610                 615                 620

Ser Gly Gln Arg Ile Thr Leu Pro Ala Val Asn Pro Pro Ala Pro Ala
625                 630                 635                 640
```

```
Pro Gln His Lys Leu Ala Ser Pro His Ser Gln Ala Ser Thr Lys Thr
                645                 650                 655

Leu Glu Gly Leu Lys Thr Arg Asn Lys Lys Ala Lys Ser Asp Lys Leu
            660                 665                 670

Ile Val Arg Arg Arg Asn Gln Lys
        675                 680
```

<210> SEQ ID NO 98
<211> LENGTH: 716
<212> TYPE: PRT
<213> ORGANISM: ARTIFICIAL SEQUENCE
<220> FEATURE:
<223> OTHER INFORMATION: Fusion polypeptide of fragments of *S. suis* proteins with affinity-tag.

<400> SEQUENCE: 98

```
Met Thr Gly Ser Asp Thr Val Val Thr Gly Val Asn Glu Ile Ile Glu
1               5                   10                  15

Glu Ser Gln Val Lys Asp Glu Val Ser Ile Glu Ser Glu Lys Asn Glu
            20                  25                  30

Ser Leu Asp Gly Ser Asn Ile Glu Ile Val Glu Glu Ile Ala Asp Asn
        35                  40                  45

Ile Pro Ser Pro Val Ile Ala Glu Gly Glu Val Ala Val Glu Met Lys
    50                  55                  60

Val Asp Arg Gly Thr Glu Asn Val Val Ser Arg Asn Asp Thr Glu Val
65                  70                  75                  80

Thr Thr Ser Glu Gln Asn Gln Ile Glu Val Thr Glu Thr Lys Glu Ile
                85                  90                  95

Leu Asn Gln Thr Ser Tyr Gln Thr Glu Ser Gly Glu Gln Arg Gln Ile
            100                 105                 110

Ile Trp Ala His Gly Ile Thr Pro Pro Ala Met Glu Gln Ser Gly Gly
        115                 120                 125

Phe Val Lys Glu Lys Tyr Gly Asp Tyr Leu Asn Tyr Thr Ala Pro Phe
    130                 135                 140

Glu Ala Gly Lys Gly Tyr Tyr Asp Thr Asn Lys Ser Leu Asn Ala Ser
145                 150                 155                 160

Phe Ile Asp Leu Asn Leu Cys Phe Ala Ala Val Ser Ser Asn Met Val
                165                 170                 175

His Trp Trp Leu Glu Gln Asn Ser Ser Tyr Val Glu Arg Tyr Leu Lys
            180                 185                 190

Glu Lys Lys Gly Thr Val Asn Val Glu Glu Asn Tyr Ala Ile Thr Asp
        195                 200                 205

Leu Arg Arg Tyr Ile Asn Ser Phe Gln Asn Gln Gln Asn Ser Arg Val
    210                 215                 220

Phe Asp Met Phe Lys Thr Tyr Tyr Gly Tyr Arg Thr Asn Gly Phe Val
225                 230                 235                 240

Ser Asp Ala Leu Val Asp Leu Phe Ile Asn Gly Tyr Lys Pro Lys Ala
                245                 250                 255

Gln Gly Gly Val Asn Leu Glu Asp Ser Gln Leu Val Pro Asp Ser Arg
            260                 265                 270

Gly Gly Phe Phe Tyr Asp Val Phe Lys Glu Lys Lys Leu Thr Asn Arg
        275                 280                 285

Ile Phe Ser Gly Ser Tyr Glu Arg Phe Gly Glu Asp Val Arg Thr Val
    290                 295                 300

Leu Glu Ser Lys Gly Leu Leu Gly Leu Thr Tyr Arg Thr Leu Gly Tyr
```

-continued

```
305                 310                 315                 320

Ala Thr His Ile Val Thr Val Trp Gly Ala Glu Tyr Asp Asn Gln Gly
                325                 330                 335

Lys Ile Lys Ala Val Tyr Ile Thr Asp Ser Asp Asp Gln Gln Glu Gln
            340                 345                 350

Ile Gly Leu Lys Arg Met Gly Ile Thr Arg Asp Ala Ser Gly Asn Pro
        355                 360                 365

Arg Leu Asn Asn His Met Lys Asn Asn Ser Ala Gly Ala Leu Leu Asp
    370                 375                 380

Tyr Val His Thr Ile Arg Leu Gly Gln Asp Leu Trp Glu Glu Tyr Phe
385                 390                 395                 400

Asn Gly Thr Glu Ile Gln Ala Ile Val Asp Glu Ala Asn Thr Ile Val
                405                 410                 415

Lys Lys Val Thr Glu Gln Lys Ile Ala Thr Ala Ser Gln Ala Thr Asp
            420                 425                 430

Ile Ser Arg Glu Val Asn Glu Phe Lys Glu Ser Ala Val Gly Asn Leu
        435                 440                 445

Val Thr Ser Ala Gln Leu Ala Ile Ala Lys Lys Ser Gly Tyr Asp Val
    450                 455                 460

Asp Phe Ala Met Thr Asn Asp Gly Gly Ile Arg Ala Asp Leu Lys Val
465                 470                 475                 480

Gln Glu Asp Gly Thr Val Thr Trp Gly Ala Ala Gln Ala Val Gln Pro
                485                 490                 495

Phe Gly Asn Ile Leu Gln Val Val Gln Met Thr Gly Glu Gln Ile Tyr
            500                 505                 510

Thr Ala Leu Asn Gln Gln Tyr Asp Glu Gly Glu Lys Tyr Phe Leu Gln
        515                 520                 525

Met Ser Gly Ile Lys Tyr Ile Tyr Thr Lys Ala Asp Asn Pro Thr Glu
    530                 535                 540

Glu Asn Pro Tyr Lys Val Val Lys Ala Phe Lys Glu Asp Gly Thr Glu
545                 550                 555                 560

Ile Val Pro Thr Glu Thr Tyr Thr Leu Val Ile Asn Asp Phe Leu Phe
                565                 570                 575

Gly Gly Gly Asp Gly Phe Ser Ile Phe Lys Glu Ala Lys Leu Ile Gly
            580                 585                 590

Ala Ile Asn Pro Asp Thr Glu Val Phe Val Glu Tyr Leu Thr Asp Leu
        595                 600                 605

Glu Lys Ala Gly Gln Thr Ile Ser Ala Thr Ile Pro Gly Arg Lys Ala
    610                 615                 620

Phe Val Glu Lys Tyr Val Glu Glu Pro Lys Ala Glu Glu Lys Glu Asp
625                 630                 635                 640

Asn Ala Gly Thr Thr Thr Asp Val Lys Thr Pro Glu Lys Ala Asn Asp
                645                 650                 655

Gly Gly Asp Ser Val Thr Asn Gln Lys Ala Thr Glu Gln Pro Ala Pro
            660                 665                 670

Ser Gly Ser Met Ala Pro Ile Ser Asn Lys Lys Thr Glu Lys Ala Ser
        675                 680                 685

Gly Asn Gln Thr Leu Glu Gly Leu Lys Thr Arg Asn Lys Lys Ala Lys
    690                 695                 700

Ser Asp Lys Leu Ile Val Arg Arg Arg Asn Gln Lys
705                 710                 715
```

<210> SEQ ID NO 99

<211> LENGTH: 722
<212> TYPE: PRT
<213> ORGANISM: ARTIFICIAL SEQUENCE
<220> FEATURE:
<223> OTHER INFORMATION: Fusion polypeptide of fragments of S. suis proteins with affinity-tag.

<400> SEQUENCE: 99

```
Met Thr Gly Ser Glu Ile Gln Ala Ile Val Asp Glu Ala Asn Thr Ile
1               5                   10                  15

Val Lys Lys Val Thr Glu Gln Lys Ile Ala Thr Ala Ser Gln Ala Thr
            20                  25                  30

Asp Ile Ser Arg Glu Val Asn Glu Phe Lys Glu Ser Ala Val Gly Asn
        35                  40                  45

Leu Val Thr Ser Ala Gln Leu Ala Ile Ala Lys Lys Ser Gly Tyr Asp
    50                  55                  60

Val Asp Phe Ala Met Thr Asn Asp Gly Gly Ile Arg Ala Asp Leu Lys
65                  70                  75                  80

Val Gln Glu Asp Gly Thr Val Thr Trp Gly Ala Ala Gln Ala Val Gln
                85                  90                  95

Pro Phe Gly Asn Ile Leu Gln Val Val Gln Met Thr Gly Glu Gln Ile
            100                 105                 110

Tyr Thr Ala Leu Asn Gln Gln Tyr Asp Glu Gly Glu Lys Tyr Phe Leu
        115                 120                 125

Gln Met Ser Gly Ile Lys Tyr Ile Tyr Thr Lys Ala Asp Asn Pro Thr
    130                 135                 140

Glu Glu Asn Pro Tyr Lys Val Val Lys Ala Phe Lys Glu Asp Gly Thr
145                 150                 155                 160

Glu Ile Val Pro Thr Glu Thr Tyr Thr Leu Val Ile Asn Asp Phe Leu
                165                 170                 175

Phe Gly Gly Gly Asp Gly Phe Ser Ile Phe Lys Glu Ala Lys Leu Ile
            180                 185                 190

Gly Ala Ile Asn Pro Asp Thr Glu Val Phe Val Glu Tyr Leu Thr Asp
        195                 200                 205

Leu Glu Lys Ala Gly Gln Thr Ile Ser Ala Thr Ile Pro Gly Arg Lys
    210                 215                 220

Ala Phe Val Glu Lys Tyr Val Glu Glu Pro Lys Ala Glu Glu Lys Glu
225                 230                 235                 240

Asp Asn Ala Gly Thr Thr Thr Asp Val Lys Thr Pro Glu Lys Ala Asn
                245                 250                 255

Asp Gly Gly Asp Ser Val Thr Asn Gln Lys Ala Thr Glu Gln Pro Ala
            260                 265                 270

Pro Ser Gly Ser Met Ala Pro Ile Ser Asn Lys Lys Thr Glu Lys Ala
        275                 280                 285

Ser Gly Asn Gln Thr Gly Thr Asp Thr Val Val Thr Gly Val Asn Glu
    290                 295                 300

Ile Ile Glu Glu Ser Gln Val Lys Asp Glu Val Ser Ile Glu Ser Glu
305                 310                 315                 320

Lys Asn Glu Ser Leu Asp Gly Ser Asn Ile Glu Ile Val Glu Glu Ile
                325                 330                 335

Ala Asp Asn Ile Pro Ser Pro Val Ile Ala Glu Gly Glu Val Ala Val
            340                 345                 350

Glu Met Lys Val Asp Arg Gly Thr Glu Asn Val Val Ser Arg Asn Asp
        355                 360                 365

Thr Glu Val Thr Thr Ser Glu Gln Asn Gln Ile Glu Val Thr Glu Thr
```

```
    370                 375                 380

Lys Glu Ile Leu Asn Gln Thr Ser Tyr Gln Thr Glu Ser Gly Glu Gln
385                 390                 395                 400

Arg Gln Ile Ile Trp Ala His Gly Ile Thr Pro Pro Ala Met Glu Gln
                405                 410                 415

Ser Gly Gly Phe Val Lys Glu Lys Tyr Gly Asp Tyr Leu Asn Tyr Thr
            420                 425                 430

Ala Pro Phe Glu Ala Gly Lys Gly Tyr Tyr Asp Thr Asn Lys Ser Leu
        435                 440                 445

Asn Ala Ser Phe Ile Asp Leu Asn Leu Cys Phe Ala Ala Val Ser Ser
    450                 455                 460

Asn Met Val His Trp Trp Leu Glu Gln Asn Ser Ser Tyr Val Glu Arg
465                 470                 475                 480

Tyr Leu Lys Glu Lys Lys Gly Thr Val Asn Val Glu Glu Asn Tyr Ala
                485                 490                 495

Ile Thr Asp Leu Arg Arg Tyr Ile Asn Ser Phe Gln Asn Gln Gln Asn
            500                 505                 510

Ser Arg Val Phe Asp Met Phe Lys Thr Tyr Tyr Gly Tyr Arg Thr Asn
        515                 520                 525

Gly Phe Val Ser Asp Ala Leu Val Asp Leu Phe Ile Asn Gly Tyr Lys
    530                 535                 540

Pro Lys Ala Gln Gly Gly Val Asn Leu Glu Asp Ser Gln Leu Val Pro
545                 550                 555                 560

Asp Ser Arg Gly Gly Phe Phe Tyr Asp Val Phe Lys Glu Lys Lys Leu
                565                 570                 575

Thr Asn Arg Ile Phe Ser Gly Ser Tyr Glu Arg Phe Gly Glu Asp Val
            580                 585                 590

Arg Thr Val Leu Glu Ser Lys Gly Leu Leu Gly Leu Thr Tyr Arg Thr
        595                 600                 605

Leu Gly Tyr Ala Thr His Ile Val Thr Val Trp Gly Ala Glu Tyr Asp
    610                 615                 620

Asn Gln Gly Lys Ile Lys Ala Val Tyr Ile Thr Asp Ser Asp Asp Gln
625                 630                 635                 640

Gln Glu Gln Ile Gly Leu Lys Arg Met Gly Ile Thr Arg Asp Ala Ser
                645                 650                 655

Gly Asn Pro Arg Leu Asn Asn His Met Lys Asn Asn Ser Ala Gly Ala
            660                 665                 670

Leu Leu Asp Tyr Val His Thr Ile Arg Leu Gly Gln Asp Leu Trp Glu
        675                 680                 685

Glu Tyr Phe Asn Pro Leu Ala Lys Ala Lys Leu Glu Gly Leu Lys Thr
    690                 695                 700

Arg Asn Lys Lys Ala Lys Ser Asp Lys Leu Ile Val Arg Arg Arg Asn
705                 710                 715                 720

Gln Lys
```

<210> SEQ ID NO 100
<211> LENGTH: 761
<212> TYPE: PRT
<213> ORGANISM: ARTIFICIAL SEQUENCE
<220> FEATURE:
<223> OTHER INFORMATION: Fusion polypeptide of fragments of S. suis proteins with affinity-tag.

<400> SEQUENCE: 100

```
Met Thr Gly Ser Asp Thr Val Val Thr Gly Val Asn Glu Ile Ile Glu
```

-continued 1 5 10 15

Glu Ser Gln Val Lys Asp Glu Val Ser Ile Glu Ser Glu Lys Asn Glu
20 25 30

Ser Leu Asp Gly Ser Asn Ile Glu Ile Val Glu Glu Ile Ala Asp Asn
35 40 45

Ile Pro Ser Pro Val Ile Ala Glu Gly Glu Val Ala Val Glu Met Lys
50 55 60

Val Asp Arg Gly Thr Glu Asn Val Val Ser Arg Asn Asp Thr Glu Val
65 70 75 80

Thr Thr Ser Glu Gln Asn Gln Ile Glu Val Thr Glu Thr Lys Glu Ile
85 90 95

Leu Asn Gln Thr Ser Tyr Gln Thr Glu Ser Gly Glu Gln Arg Gln Ile
100 105 110

Ile Trp Ala His Gly Ile Thr Pro Pro Ala Met Glu Gln Ser Gly Gly
115 120 125

Phe Val Lys Glu Lys Tyr Gly Asp Tyr Leu Asn Tyr Thr Ala Pro Phe
130 135 140

Glu Ala Gly Lys Gly Tyr Tyr Asp Thr Asn Lys Ser Leu Asn Ala Ser
145 150 155 160

Phe Ile Asp Leu Asn Leu Cys Phe Ala Ala Val Ser Ser Asn Met Val
165 170 175

His Trp Trp Leu Glu Gln Asn Ser Ser Tyr Val Glu Arg Tyr Leu Lys
180 185 190

Glu Lys Lys Gly Thr Val Asn Val Glu Glu Asn Tyr Ala Ile Thr Asp
195 200 205

Leu Arg Arg Tyr Ile Asn Ser Phe Gln Asn Gln Gln Asn Ser Arg Val
210 215 220

Phe Asp Met Phe Lys Thr Tyr Tyr Gly Tyr Arg Thr Asn Gly Phe Val
225 230 235 240

Ser Asp Ala Leu Val Asp Leu Phe Ile Asn Gly Tyr Lys Pro Lys Ala
245 250 255

Gln Gly Gly Val Asn Leu Glu Asp Ser Gln Leu Val Pro Asp Ser Arg
260 265 270

Gly Gly Phe Phe Tyr Asp Val Phe Lys Glu Lys Lys Leu Thr Asn Arg
275 280 285

Ile Phe Ser Gly Ser Tyr Glu Arg Phe Gly Glu Asp Val Arg Thr Val
290 295 300

Leu Glu Ser Lys Gly Leu Leu Gly Leu Thr Tyr Arg Thr Leu Gly Tyr
305 310 315 320

Ala Thr His Ile Val Thr Val Trp Gly Ala Glu Tyr Asp Asn Gln Gly
325 330 335

Lys Ile Lys Ala Val Tyr Ile Thr Asp Ser Asp Asp Gln Gln Glu Gln
340 345 350

Ile Gly Leu Lys Arg Met Gly Ile Thr Arg Asp Ala Ser Gly Asn Pro
355 360 365

Arg Leu Asn Asn His Met Lys Asn Asn Ser Ala Gly Ala Leu Leu Asp
370 375 380

Tyr Val His Thr Ile Arg Leu Gly Gln Asp Leu Trp Glu Glu Tyr Phe
385 390 395 400

Asn Gly Thr Gly Glu Thr Thr Ala Pro Ile Asn Ser Phe Phe Ala Leu
405 410 415

Val Gln Asp Asp Pro Ser Val Gln Ile Val Asn Asn Ala Gln Ile Trp
420 425 430

Tyr Ala Lys Gln Gln Leu Ala Gly Thr Ser Glu Ala Asn Leu Pro Ile
435 440 445

Leu Ser Ala Ala Ala Pro Phe Lys Ala Gly Thr Arg Gly Asp Ala Ser
450 455 460

Ala Tyr Thr Asp Ile Pro Ala Gly Pro Ile Ala Ile Lys Asn Val Ala
465 470 475 480

Asp Leu Tyr Leu Tyr Asp Asn Val Val Ala Ile Leu Lys Val Asn Gly
485 490 495

Ala Gln Leu Lys Glu Trp Leu Glu Met Ser Ala Gly Gln Phe Asn Gln
500 505 510

Val Asp Leu Ser Ser Thr Glu Pro Gln Asn Leu Val Asn Thr Asp Phe
515 520 525

Arg Thr Tyr Asn Phe Asp Val Ile Asp Gly Val Thr Tyr Gln Tyr Asp
530 535 540

Ile Thr Gln Pro Asn Lys Tyr Asp Arg Asp Gly Lys Ile Val Asn Glu
545 550 555 560

Thr Ala Ser Arg Val Arg Asn Leu Gln Tyr Asn Gly Gln Asp Val Thr
565 570 575

Ala Asp Gln Glu Phe Ile Val Val Thr Asn Asn Tyr Arg Ala Asn Gly
580 585 590

Thr Phe Pro Gly Val Arg Glu Ala Ser Ile Asn Arg Leu Leu Asn Leu
595 600 605

Glu Asn Arg Gln Ala Ile Ile Asn Tyr Ile Ile Ala Glu Lys Val Ile
610 615 620

Asn Pro Thr Ala Asp Asn Asn Trp Thr Phe Thr Asp Ser Ile Lys Gly
625 630 635 640

Leu Asp Leu Arg Phe Leu Thr Ala Asp Arg Ala Lys Ser Leu Val Thr
645 650 655

Asp Gln Glu Cys Ile Val Tyr Leu Gln Ala Ser Thr Ala Ser Glu Gly
660 665 670

Phe Gly Glu Phe Lys Phe Val Tyr Thr Glu Ser Lys Val Val Thr Pro
675 680 685

Asp Glu Gln Gln Ser Asp Gln Gly Asn Thr Gly Gln Asp Ile Val Leu
690 695 700

Glu Ser Gly Gln Arg Ile Thr Leu Pro Ala Val Asn Pro Pro Ala Pro
705 710 715 720

Ala Pro Gln His Lys Leu Ala Ser Pro His Ser Gln Ala Ser Thr Lys
725 730 735

Thr Leu Glu Gly Leu Lys Thr Arg Asn Lys Lys Ala Lys Ser Asp Lys
740 745 750

Leu Ile Val Arg Arg Arg Asn Gln Lys
755 760

<210> SEQ ID NO 101
<211> LENGTH: 637
<212> TYPE: PRT
<213> ORGANISM: ARTIFICIAL SEQUENCE
<220> FEATURE:
<223> OTHER INFORMATION: Fusion polypeptide of fragments of S. suis proteins with affinity-tag.

<400> SEQUENCE: 101

Met Thr Gly Ser Gly Ser Asp Glu Ile Lys Ala Lys Tyr Glu Ala Glu
1 5 10 15

Asn Ala Gln Val Val Ile Glu Asn Asn Pro Val Glu Leu Asn Gly Asp

```
            20                  25                  30

Arg Ser Asn Val Arg Val Arg Glu Thr Asn Leu Gly Asn Ala Val Thr
        35                  40                  45

Asp Ala Ile Tyr Ala Tyr Gly Gln Thr Gly Phe Ser Asn Lys Thr Ser
    50                  55                  60

Leu Ala Val Thr Asn Gly Gly Gly Leu Arg Ala Thr Ile Ala Lys Asp
65                  70                  75                  80

Gln Pro Val Thr Lys Gly Asp Ile Ile Ala Val Leu Pro Phe Gly Asn
                85                  90                  95

Ile Val Ser Gln Ile Thr Val Thr Gly Gln Gln Ile Tyr Asp Met Phe
            100                 105                 110

Thr Lys Ser Leu Ser Ser Thr Leu Gln Val Asn Pro Glu Thr Gly Glu
        115                 120                 125

Met Leu Leu Asp Glu Asn Gly Met Pro Leu Phe Glu Ala Ser Gly Gly
    130                 135                 140

Phe Leu His Ile Ser Gly Ala Asn Val Phe Tyr Asp Pro Thr Leu Pro
145                 150                 155                 160

Val Glu Glu Arg Val Leu Leu Ile Gly Ile Leu Asn Pro Glu Thr Gly
                165                 170                 175

Glu Tyr Asp Ala Leu Asp Leu Glu Lys Thr Tyr Tyr Leu Ala Thr Asn
            180                 185                 190

Asp Phe Leu Ala Ala Gly Gly Asp Gly Tyr Thr Met Leu Gly Gly Ala
        195                 200                 205

Arg Glu Glu Gly Pro Ser Met Asp Ser Val Phe Ala Glu Tyr Leu Lys
    210                 215                 220

Thr Ala Asp Leu Ser Ala Tyr Glu Val Val Asn Pro Tyr Ser Arg Ile
225                 230                 235                 240

Ile Pro Val Asn Ser Ser Ile Asp Thr Asp Glu Asp Gly Tyr Pro Asp
                245                 250                 255

Phe Ile Glu Ile Leu Leu Asp Thr Asp Pro Glu Asn Pro Ala Ser Asn
            260                 265                 270

Pro Glu Thr Val Pro Ala Glu Asn Thr Asp Ser Pro Ser Asn Gln Val
        275                 280                 285

Gln Asn Thr Ser Ala Thr Asp Lys Lys Ala Pro Val Asp Ser Pro Lys
    290                 295                 300

Val Gly Asp Lys Lys Thr Glu Val Ala Ser Pro Ala Lys Thr Thr Lys
305                 310                 315                 320

Ala Gly Gly Thr Glu Ile Gln Ala Ile Val Asp Glu Ala Asn Thr Ile
                325                 330                 335

Val Lys Lys Val Thr Glu Gln Lys Ile Ala Thr Ala Ser Gln Ala Thr
            340                 345                 350

Asp Ile Ser Arg Glu Val Asn Glu Phe Lys Glu Ser Ala Val Gly Asn
        355                 360                 365

Leu Val Thr Ser Ala Gln Leu Ala Ile Ala Lys Lys Ser Gly Tyr Asp
    370                 375                 380

Val Asp Phe Ala Met Thr Asn Asp Gly Gly Ile Arg Ala Asp Leu Lys
385                 390                 395                 400

Val Gln Glu Asp Gly Thr Val Thr Trp Gly Ala Ala Gln Ala Val Gln
                405                 410                 415

Pro Phe Gly Asn Ile Leu Gln Val Val Gln Met Thr Gly Glu Gln Ile
            420                 425                 430

Tyr Thr Ala Leu Asn Gln Gln Tyr Asp Glu Gly Glu Lys Tyr Phe Leu
        435                 440                 445
```

```
Gln Met Ser Gly Ile Lys Tyr Ile Tyr Thr Lys Ala Asp Asn Pro Thr
    450                 455                 460

Glu Glu Asn Pro Tyr Lys Val Val Lys Ala Phe Lys Glu Asp Gly Thr
465                 470                 475                 480

Glu Ile Val Pro Thr Glu Thr Tyr Thr Leu Val Ile Asn Asp Phe Leu
                485                 490                 495

Phe Gly Gly Gly Asp Gly Phe Ser Ile Phe Lys Glu Ala Lys Leu Ile
            500                 505                 510

Gly Ala Ile Asn Pro Asp Thr Glu Val Phe Val Glu Tyr Leu Thr Asp
        515                 520                 525

Leu Glu Lys Ala Gly Gln Thr Ile Ser Ala Thr Ile Pro Gly Arg Lys
    530                 535                 540

Ala Phe Val Glu Lys Tyr Val Glu Glu Pro Lys Ala Glu Glu Lys Glu
545                 550                 555                 560

Asp Asn Ala Gly Thr Thr Thr Asp Val Lys Thr Pro Glu Lys Ala Asn
                565                 570                 575

Asp Gly Gly Asp Ser Val Thr Asn Gln Lys Ala Thr Glu Gln Pro Ala
            580                 585                 590

Pro Ser Gly Ser Met Ala Pro Ile Ser Asn Lys Lys Thr Glu Lys Ala
        595                 600                 605

Ser Gly Asn Gln Thr Leu Glu Gly Leu Lys Thr Arg Asn Lys Lys Ala
    610                 615                 620

Lys Ser Asp Lys Leu Ile Val Arg Arg Arg Asn Gln Lys
625                 630                 635
```

<210> SEQ ID NO 102
<211> LENGTH: 2058
<212> TYPE: DNA
<213> ORGANISM: ARTIFICIAL SEQUENCE
<220> FEATURE:
<223> OTHER INFORMATION: Codon optimized DNA sequence of fusion polypeptide of fragments of S. suis proteins with affinity-tag.

<400> SEQUENCE: 102

```
catatgacag gatccgacga aatcaaagca aaatacgaag ccgaaaacgc ccaggttgtc     60

atcgaaaata atccggtgga actgaatggt gaccgcagca atgtgcgtgt ccgcgaaacc    120

aacctgggta atgcggtgac ggatgcaatt tatgcttacg gtcagaccgg ctttagtaac    180

aaaacctccc tggccgttac gaatggcggt ggcctgcgtg cgaccatcgc caaagaccag    240

ccggtgacga agggtgatat tatcgcggtt ctgccgtttg gcaatattgt ttctcaaatc    300

accgtcacgg gtcagcaaat ttatgacatg ttcaccaaaa gcctgagctc tacgctgcag    360

gttaacccgg aaaccggtga aatgctgctg gatgaaaatg gcatgccgct gtttgaagcg    420

tcaggtggct tcctgcatat ctcgggcgcc aacgtgttct atgatccgac cctgccggtc    480

gaagaacgcg tgctgctgat tggtatcctg aatccggaaa cgggcgaata cgacgcactg    540

gatctggaaa aaacctatta cctggctacg aacgactttc tggcggccgg tggcgatggt    600

tataccatgc tgggtggcgc ccgtgaagaa ggcccgagca tggactctgt tttcgcagaa    660

tacctgaaga ccgcagatct gagcgcttat gaagtggtta acccgtactc tcgcattatc    720

ccggtcaata gttccattga taccgacgaa gatggctatc cggattttat tgaaatcctg    780

ctggacaccg atccggaaaa cccggcaagt aatccggaaa ccgttccggc tgaaaacacg    840

gattcaccgt cgaaccaggt ccaaaatacc agtgcgacgg acaaaaaggc cccggtggat    900

tccccgaaag tgggcgataa gaaaaccgaa gtggcatccc cggcaaaaac gaccaaagca    960
```

ggtggtaccg gcgaaacgac ggccccgatt aacagcttct ttgccctggt tcaggacgac 1020
ccgagtgtcc agattgtcaa taacgctcag atttggtatg ctaaacagca actggcaggc 1080
accagcgaag caaacctgcc gattctgtcg gcagcagcac cgtttaaagc aggcacccgt 1140
ggtgatgcta gcgcatacac ggacatcccg gcaggtccga ttgcaatcaa aaatgttgca 1200
gatctgtatc tgtacgacaa cgtggttgca attctgaaag tcaatggcgc tcagctgaaa 1260
gaatggctgg aaatgtctgc gggccagttc aaccaagtgg atctgagctc taccgaaccg 1320
cagaacctgg ttaataccga ttttcgtacg tataatttcg atgtgattga cggcgttacc 1380
tatcagtacg atatcacgca accgaacaaa tacgatcgcg acggtaaaat cgtcaatgaa 1440
accgcatcac gtgtgcgcaa cctgcagtat aatggccaag atgtgacggc ggaccaggaa 1500
tttattgtcg tgaccaacaa ttaccgtgca aacggcacgt ttccgggcgt gcgtgaagct 1560
tcgatcaatc gcctgctgaa cctggaaaat cgccaggcga ttatcaacta catcatcgcc 1620
gaaaaagtga tcaacccgac cgcggataac aattggacct ttacggatag tatcaaaggt 1680
ctggacctgc gtttcctgac cgccgatcgc gcaaaatccc tggttacgga ccaggaatgc 1740
attgtctatc tgcaagctag taccgcgtcc gaaggctttg gtgaatttaa attcgtttac 1800
accgaaagca aagttgtcac gccggatgaa cagcaatctg accagggcaa caccggtcaa 1860
gatattgtcc tggaaagcgg tcagcgtatc acgctgccgg cagtgaatcc gccggcaccg 1920
gctccgcagc acaaactggc gtccccgcat tcgcaggcat ccaccaaaac cctcgaggga 1980
ctgaagaccc gcaataagaa agccaaaagc gacaaactta ttgttcgccg tcgcaatcag 2040
aagtaatgat taactagt 2058

<210> SEQ ID NO 103
<211> LENGTH: 2166
<212> TYPE: DNA
<213> ORGANISM: ARTIFICIAL SEQUENCE
<220> FEATURE:
<223> OTHER INFORMATION: Codon optimized DNA sequence of fusion polypeptide of fragments of S. suis proteins with affinity-tag.

<400> SEQUENCE: 103
catatgacag gatccgatac ggtagtaacg ggtgtaaatg aaatcattga agaatcgcag 60
gttaaagatg aggtgagcat cgagtccgag aagaacgaat ctctggatgg cagcaacatc 120
gaaattgttg aagaaattgc ggacaatatc ccgtcgccgg tgattgcaga gggtgaagtc 180
gccgtggaga tgaaagtgga ccgcggcacc gagaatgttg tctcgcgtaa tgatacggaa 240
gtcaccacga gcgaacaaaa tcaaatcgaa gtcaccgaga ctaaagaaat tctgaatcag 300
acgagctatc aaacggagag cggtgaacag cgtcagatca tttgggcgca cggtattacc 360
ccgcctgcga tggaacaatc cggtggtttc gttaaagaaa agtatggtga ttacctgaac 420
tacactgccc cgttcgaggc tggcaaaggt tactatgaca ccaataagag cctgaatgca 480
agctttattg atctgaatct gtgttttgca gcggtcagca gcaatatggt ccactggtgg 540
ctggagcaga atagcagcta tgtcgagcgt tacttgaaag aaaagaaggg caccgttaac 600
gtggaagaga attacgccat tactgacctg cgccgttaca ttaacagctt ccagaatcaa 660
cagaatagcc gtgtttttga tatgtttaag acgtactatg gctaccgtac gaacggcttc 720
gttagcgacg cactggtcga cctgtttatc aatggttaca agccgaaggc gcagggcggt 780
gttaacttgg aagattcgca actggttcca gatagccgtg gtggtttctt ctatgacgtt 840
ttcaaagaga agaagctgac gaaccgtatt ttcagcggta gctatgaacg tttcggtgaa 900
gatgttcgca ccgttctgga gagcaagggt ctgttgggtc tgacgtaccg taccctgggt 960
tacgccaccc acatcgtgac cgtttggggt gcggagtatg ataatcaagg caagatcaag 1020
gcagtgtaca tcaccgactc cgacgaccaa caggaacaga tcggtctgaa acgcatgggt 1080
atcacgcgcg acgccagcgg caatccgcgt ctgaacaacc acatgaaaaa caatagcgcc 1140
ggtgcactgc tggactacgt gcacacgatt cgcttgggtc aggatctgtg ggaagagtat 1200
ttcaatggta ccgaaattca agccattgtg gacgaagcaa ataccatcgt caaaaaagtc 1260
acggaacaga aaatcgcaac ggcaagccaa gcaacggaca ttagtcgtga agtgaacgaa 1320
tttaaagaaa gcgcggtggg taatctggtt acctctgccc agctggcaat tgctaaaaaa 1380
tccggctatg atgttgactt cgcaatgacc aacgatggcg gtatccgcgc tgacctgaaa 1440
gttcaggaag atggtacggt cacctggggt gcagcacagg cagtgcaacc gtttggtaac 1500
attctgcagg tggttcaaat gaccggcgaa cagatctaca cggctctgaa tcagcaatat 1560
gatgaaggtg aaaaatactt tctgcaaatg agcggcatta aatatatcta caccaaagcg 1620
gataacccga cggaagaaaa tccgtataaa gtcgtgaaag ccttcaaaga agatggcacc 1680
gaaattgtgc cgacggaaac ctacacgctg gttatcaacg actttctgtt cggcggtggc 1740
gatggttttt caatcttcaa agaagcgaaa ctgattggcg ccatcaatcc ggacaccgaa 1800
gtttttgtcg aatatctgac ggatctggaa aaagcgggtc agaccatttc ggccacgatt 1860
ccgggccgta aagcattcgt cgaaaaatac gtggaagaac cgaaagcaga agaaaaagaa 1920
gacaatgctg gcaccacgac cgatgtcaaa accccggaaa aagccaacga tggtggcgac 1980
agtgttacca atcagaaagc aacggaacaa ccggctccga gtggctcaat ggccccgatt 2040
agcaataaga agacggaaaa agcaagtggc aaccaaaccc tcgagggact gaagacccgc 2100
aataagaaag ccaaaagcga caaacttatt gttcgccgtc gcaatcagaa gtaatgatta 2160
actagt 2166

<210> SEQ ID NO 104
<211> LENGTH: 2184
<212> TYPE: DNA
<213> ORGANISM: ARTIFICIAL SEQUENCE
<220> FEATURE:
<223> OTHER INFORMATION: Codon optimized DNA sequence of fusion
polypeptide of fragments of S. suis proteins with affinity-tag.

<400> SEQUENCE: 104
catatgacag gatccgaaat tcaagccatt gtggacgaag caaataccat cgtcaaaaaa 60
gtcacggaac agaaaatcgc aacggcaagc caagcaacgg acattagtcg tgaagtgaac 120
gaatttaaag aaagcgcggt gggtaatctg gttacctctg cccagctggc aattgctaaa 180
aaatccggct atgatgttga cttcgcaatg accaacgatg gcggtatccg cgctgacctg 240
aaagttcagg aagatggtac ggtcacctgg ggtgcagcac aggcagtgca accgtttggt 300
aacattctgc aggtggttca aatgaccggc gaacagatct acacggctct gaatcagcaa 360
tatgatgaag gtgaaaaata ctttctgcaa atgagcggca ttaaatatat ctacaccaaa 420
gcggataacc cgacggaaga aaatccgtat aaagtcgtga aagccttcaa agaagatggc 480
accgaaattg tgccgacgga aacctacacg ctggttatca acgactttct gttcggcggt 540
ggcgatggtt tttcaatctt caaagaagcg aaactgattg gcgccatcaa tccggacacc 600
gaagtttttg tcgaatatct gacggatctg gaaaaagcgg gtcagaccat ttcggccacg 660
attccgggcc gtaaagcatt cgtcgaaaaa tacgtggaag aaccgaaagc agaagaaaaa 720
gaagacaatg ctggcaccac gaccgatgtc aaaaccccgg aaaaagccaa cgatggtggc 780
gacagtgtta ccaatcagaa agcaacggaa caaccggctc cgagtggctc aatggccccg 840
attagcaata agaagacgga aaaagcaagt ggcaaccaaa ccggtaccga tacggtagta 900
acgggtgtaa atgaaatcat tgaagaatcg caggttaaag atgaggtgag catcgagtcc 960
gagaagaacg aatctctgga tggcagcaac atcgaaattg ttgaagaaat tgcggacaat 1020
atcccgtcgc cggtgattgc agagggtgaa gtcgccgtgg agatgaaagt ggaccgcggc 1080
accgagaatg ttgtctcgcg taatgatacg gaagtcacca cgagcgaaca aaatcaaatc 1140
gaagtcaccg agactaaaga aattctgaat cagacgagct atcaaacgga gagcggtgaa 1200
cagcgtcaga tcatttgggc gcacggtatt accccgcctg cgatggaaca atccggtggt 1260
ttcgttaaag aaaagtatgg tgattacctg aactacactg ccccgttcga ggctggcaaa 1320
ggttactatg acaccaataa gagcctgaat gcaagcttta ttgatctgaa tctgtgtttt 1380
gcagcggtca gcagcaatat ggtccactgg tggctggagc agaatagcag ctatgtcgag 1440
cgttacttga aagaaaagaa gggcaccgtt aacgtggaag agaattacgc cattactgac 1500
ctgcgccgtt acattaacag cttccagaat caacagaata gccgtgtttt tgatatgttt 1560
aagacgtact atggctaccg tacgaacggc ttcgttagcg acgcactggt cgacctgttt 1620
atcaatggtt acaagccgaa ggcgcagggc ggtgttaact tggaagattc gcaactggtt 1680
ccagatagcc gtggtggttt cttctatgac gttttcaaag agaagaagct gacgaaccgt 1740
attttcagcg gtagctatga acgtttcggt gaagatgttc gcaccgttct ggagagcaag 1800
ggtctgttgg gtctgacgta ccgtaccctg ggttacgcca cccacatcgt gaccgtttgg 1860
ggtgcggagt atgataatca aggcaagatc aaggcagtgt acatcaccga ctccgacgac 1920
caacaggaac agatcggtct gaaacgcatg ggtatcacgc gcgacgccag cggcaatccg 1980
cgtctgaaca accacatgaa aaacaatagc gccggtgcac tgctggacta cgtgcacacg 2040
attcgcttgg gtcaggatct gtgggaagag tatttcaatc cgttggcaaa ggcgaaactc 2100
gagggactga agacccgcaa taagaaagcc aaaagcgaca aacttattgt tcgccgtcgc 2160
aatcagaagt aatgattaac tagt 2184

<210> SEQ ID NO 105
<211> LENGTH: 2301
<212> TYPE: DNA
<213> ORGANISM: ARTIFICIAL SEQUENCE
<220> FEATURE:
<223> OTHER INFORMATION: Codon optimized DNA sequence of fusion polypeptide of fragments of S. suis proteins with affinity-tag.

<400> SEQUENCE: 105
catatgacag gatccgatac ggtagtaacg ggtgtaaatg aaatcattga agaatcgcag 60
gttaaagatg aggtgagcat cgagtccgag aagaacgaat ctctggatgg cagcaacatc 120
gaaattgttg aagaaattgc ggacaatatc ccgtcgccgg tgattgcaga gggtgaagtc 180
gccgtggaga tgaaagtgga ccgcggcacc gagaatgttg tctcgcgtaa tgatacggaa 240
gtcaccacga gcgaacaaaa tcaaatcgaa gtcaccgaga ctaaagaaat tctgaatcag 300
acgagctatc aaacggagag cggtgaacag cgtcagatca tttgggcgca cggtattacc 360
ccgcctgcga tggaacaatc cggtggtttc gttaaagaaa agtatggtga ttacctgaac 420
tacactgccc cgttcgaggc tggcaaaggt tactatgaca ccaataagag cctgaatgca 480
agctttattg atctgaatct gtgttttgca gcggtcagca gcaatatggt ccactggtgg 540
ctggagcaga atagcagcta tgtcgagcgt tacttgaaag aaaagaaggg caccgttaac 600
gtggaagaga attacgccat tactgacctg cgccgttaca ttaacagctt ccagaatcaa 660
cagaatagcc gtgtttttga tatgtttaag acgtactatg gctaccgtac gaacggcttc 720
gttagcgacg cactggtcga cctgtttatc aatggttaca agccgaaggc gcagggcggt 780
gttaacttgg aagattcgca actggttcca gatagccgtg gtggtttctt ctatgacgtt 840
ttcaaagaga agaagctgac gaaccgtatt ttcagcggta gctatgaacg tttcggtgaa 900
gatgttcgca ccgttctgga gagcaagggt ctgttgggtc tgacgtaccg taccctgggt 960
tacgccaccc acatcgtgac cgtttggggt gcggagtatg ataatcaagg caagatcaag 1020
gcagtgtaca tcaccgactc cgacgaccaa caggaacaga tcggtctgaa acgcatgggt 1080
atcacgcgcg acgccagcgg caatccgcgt ctgaacaacc acatgaaaaa caatagcgcc 1140
ggtgcactgc tggactacgt gcacacgatt cgcttgggtc aggatctgtg ggaagagtat 1200
ttcaatggta ccggcgaaac gacggccccg attaacagct tctttgccct ggttcaggac 1260
gacccgagtg tccagattgt caataacgct cagatttggt atgctaaaca gcaactggca 1320
ggcaccagcg aagcaaacct gccgattctg tcggcagcag caccgtttaa agcaggcacc 1380
cgtggtgatg ctagcgcata cacggacatc ccggcaggtc cgattgcaat caaaaatgtt 1440
gcagatctgt atctgtacga caacgtggtt gcaattctga aagtcaatgg cgctcagctg 1500
aaagaatggc tggaaatgtc tgcgggccag ttcaaccaag tggatctgag ctctaccgaa 1560
ccgcagaacc tggttaatac cgattttcgt acgtataatt tcgatgtgat tgacggcgtt 1620
acctatcagt acgatatcac gcaaccgaac aaatacgatc gcgacggtaa aatcgtcaat 1680
gaaaccgcat cacgtgtgcg caacctgcag tataatggcc aagatgtgac ggcggaccag 1740
gaatttattg tcgtgaccaa caattaccgt gcaaacggca cgtttccggg cgtgcgtgaa 1800
gcttcgatca atcgcctgct gaacctggaa aatcgccagg cgattatcaa ctacatcatc 1860
gccgaaaaag tgatcaaccc gaccgcggat aacaattgga cctttacgga tagtatcaaa 1920
ggtctggacc tgcgtttcct gaccgccgat cgcgcaaaat ccctggttac ggaccaggaa 1980
tgcattgtct atctgcaagc tagtaccgcg tccgaaggct ttggtgaatt taaattcgtt 2040
tacaccgaaa gcaaagttgt cacgccggat gaacagcaat ctgaccaggg caacaccggt 2100
caagatattg tcctggaaag cggtcagcgt atcacgctgc cggcagtgaa tccgccggca 2160
ccggctccgc agcacaaact ggcgtccccg cattcgcagg catccaccaa aaccctcgag 2220
ggactgaaga cccgcaataa gaaagccaaa agcgacaaac ttattgttcg ccgtcgcaat 2280
cagaagtaat gattaactag t 2301

<210> SEQ ID NO 106
<211> LENGTH: 1929
<212> TYPE: DNA
<213> ORGANISM: ARTIFICIAL SEQUENCE
<220> FEATURE:
<223> OTHER INFORMATION: Codon optimized DNA sequence of fusion polypeptide of fragments of S. suis proteins with affinity-tag.

<400> SEQUENCE: 106
catatgacag gatccggatc cgacgaaatc aaagcaaaat acgaagccga aaacgcccag 60
gttgtcatcg aaaataatcc ggtggaactg aatggtgacc gcagcaatgt gcgtgtccgc 120
gaaaccaacc tgggtaatgc ggtgacggat gcaatttatg cttacggtca gaccggcttt 180
agtaacaaaa cctccctggc cgttacgaat ggcggtggcc tgcgtgcgac catcgccaaa 240

```
gaccagccgg tgacgaaggg tgatattatc gcggttctgc cgtttggcaa tattgtttct    300

caaatcaccg tcacgggtca gcaaatttat gacatgttca ccaaaagcct gagctctacg    360

ctgcaggtta acccggaaac cggtgaaatg ctgctggatg aaaatggcat gccgctgttt    420

gaagcgtcag gtggcttcct gcatatctcg ggcgccaacg tgttctatga tccgaccctg    480

ccggtcgaag aacgcgtgct gctgattggt atcctgaatc cggaaacggg cgaatacgac    540

gcactggatc tggaaaaaac ctattacctg gctacgaacg actttctggc ggccggtggc    600

gatggttata ccatgctggg tggcgcccgt gaagaaggcc cgagcatgga ctctgttttc    660

gcagaatacc tgaagaccgc agatctgagc gcttatgaag tggttaaccc gtactctcgc    720

attatcccgg tcaatagttc cattgatacc gacgaagatg gctatccgga ttttattgaa    780

atcctgctgg acaccgatcc ggaaaacccg gcaagtaatc cggaaaccgt tccggctgaa    840

aacacggatt caccgtcgaa ccaggtccaa aataccagtg cgacggacaa aaaggccccg    900

gtggattccc cgaaagtggg cgataagaaa accgaagtgg catccccggc aaaaacgacc    960

aaagcaggtg gtaccgaaat tcaagccatt gtggacgaag caaataccat cgtcaaaaaa   1020

gtcacggaac agaaaatcgc aacggcaagc caagcaacgg acattagtcg tgaagtgaac   1080

gaatttaaag aaagcgcggt gggtaatctg gttacctctg cccagctggc aattgctaaa   1140

aaatccggct atgatgttga cttcgcaatg accaacgatg gcggtatccg cgctgacctg   1200

aaagttcagg aagatggtac ggtcacctgg ggtgcagcac aggcagtgca accgtttggt   1260

aacattctgc aggtggttca aatgaccggc gaacagatct acacggctct gaatcagcaa   1320

tatgatgaag gtgaaaaata ctttctgcaa atgagcggca ttaaatatat ctacaccaaa   1380

gcggataacc cgacggaaga aaatccgtat aaagtcgtga aagccttcaa agaagatggc   1440

accgaaattg tgccgacgga aacctacacg ctggttatca acgactttct gttcggcggt   1500

ggcgatggtt tttcaatctt caaagaagcg aaactgattg gcgccatcaa tccggacacc   1560

gaagtttttg tcgaatatct gacggatctg gaaaaagcgg gtcagaccat ttcggccacg   1620

attccgggcc gtaaagcatt cgtcgaaaaa tacgtggaag aaccgaaagc agaagaaaaa   1680

gaagacaatg ctggcaccac gaccgatgtc aaaaccccgg aaaaagccaa cgatggtggc   1740

gacagtgtta ccaatcagaa agcaacggaa caaccggctc cgagtggctc aatggccccg   1800

attagcaata agaagacgga aaaagcaagt ggcaaccaaa ccctcgaggg actgaagacc   1860

cgcaataaga aagccaaaag cgacaaactt attgttcgcc gtcgcaatca gaagtaatga   1920

ttaactagt                                                           1929
```

<210> SEQ ID NO 107
<211> LENGTH: 943
<212> TYPE: PRT
<213> ORGANISM: ARTIFICIAL SEQUENCE
<220> FEATURE:
<223> OTHER INFORMATION: Fusion polypeptide of fragments of S. suis
proteins.

<400> SEQUENCE: 107

```
Asp Glu Ile Lys Ala Lys Tyr Glu Ala Glu Asn Ala Gln Val Val Ile
1               5                   10                  15

Glu Asn Asn Pro Val Glu Leu Asn Gly Asp Arg Ser Asn Val Arg Val
            20                  25                  30

Arg Glu Thr Asn Leu Gly Asn Ala Val Thr Asp Ala Ile Tyr Ala Tyr
        35                  40                  45
```

-continued

```
Gly Gln Thr Gly Phe Ser Asn Lys Thr Ser Leu Ala Val Thr Asn Gly
    50                  55                  60

Gly Gly Leu Arg Ala Thr Ile Ala Lys Asp Gln Pro Val Thr Lys Gly
65                  70                  75                  80

Asp Ile Ile Ala Val Leu Pro Phe Gly Asn Ile Val Ser Gln Ile Thr
                85                  90                  95

Val Thr Gly Gln Gln Ile Tyr Asp Met Phe Thr Lys Ser Leu Ser Ser
            100                 105                 110

Thr Leu Gln Val Asn Pro Glu Thr Gly Glu Met Leu Leu Asp Glu Asn
        115                 120                 125

Gly Met Pro Leu Phe Glu Ala Ser Gly Gly Phe Leu His Ile Ser Gly
    130                 135                 140

Ala Asn Val Phe Tyr Asp Pro Thr Leu Pro Val Glu Glu Arg Val Leu
145                 150                 155                 160

Leu Ile Gly Ile Leu Asn Pro Glu Thr Gly Glu Tyr Asp Ala Leu Asp
                165                 170                 175

Leu Glu Lys Thr Tyr Tyr Leu Ala Thr Asn Asp Phe Leu Ala Ala Gly
            180                 185                 190

Gly Asp Gly Tyr Thr Met Leu Gly Gly Ala Arg Glu Glu Gly Pro Ser
        195                 200                 205

Met Asp Ser Val Phe Ala Glu Tyr Leu Lys Thr Ala Asp Leu Ser Ala
    210                 215                 220

Tyr Glu Val Val Asn Pro Tyr Ser Arg Ile Ile Pro Val Asn Ser Ser
225                 230                 235                 240

Ile Asp Thr Asp Glu Asp Gly Tyr Pro Asp Phe Ile Glu Ile Leu Leu
                245                 250                 255

Asp Thr Asp Pro Glu Asn Pro Ala Ser Asn Pro Glu Thr Val Pro Ala
            260                 265                 270

Glu Asn Thr Asp Ser Pro Ser Asn Gln Val Gln Asn Thr Ser Ala Thr
        275                 280                 285

Asp Lys Lys Ala Pro Val Asp Ser Pro Lys Val Gly Asp Lys Lys Thr
    290                 295                 300

Glu Val Ala Ser Pro Ala Lys Thr Thr Lys Ala Gly Glu Phe Glu Ile
305                 310                 315                 320

Gln Ala Ile Val Asp Glu Ala Asn Thr Ile Val Lys Lys Val Thr Glu
                325                 330                 335

Gln Lys Ile Ala Thr Ala Ser Gln Ala Thr Asp Ile Ser Arg Glu Val
            340                 345                 350

Asn Glu Phe Lys Glu Ser Ala Val Gly Asn Leu Val Thr Ser Ala Gln
        355                 360                 365

Leu Ala Ile Ala Lys Lys Ser Gly Tyr Asp Val Asp Phe Ala Met Thr
    370                 375                 380

Asn Asp Gly Gly Ile Arg Ala Asp Leu Lys Val Gln Glu Asp Gly Thr
385                 390                 395                 400

Val Thr Trp Gly Ala Ala Gln Ala Val Gln Pro Phe Gly Asn Ile Leu
                405                 410                 415

Gln Val Val Gln Met Thr Gly Glu Gln Ile Tyr Thr Ala Leu Asn Gln
            420                 425                 430

Gln Tyr Asp Glu Gly Glu Lys Tyr Phe Leu Gln Met Ser Gly Ile Lys
        435                 440                 445

Tyr Ile Tyr Thr Lys Ala Asp Asn Pro Thr Glu Glu Asn Pro Tyr Lys
    450                 455                 460

Val Val Lys Ala Phe Lys Glu Asp Gly Thr Glu Ile Val Pro Thr Glu
```

-continued

```
465                 470                 475                 480

Thr Tyr Thr Leu Val Ile Asn Asp Phe Leu Phe Gly Gly Gly Asp Gly
                485                 490                 495

Phe Ser Ile Phe Lys Glu Ala Lys Leu Ile Gly Ala Ile Asn Pro Asp
            500                 505                 510

Thr Glu Val Phe Val Glu Tyr Leu Thr Asp Leu Glu Lys Ala Gly Gln
        515                 520                 525

Thr Ile Ser Ala Thr Ile Pro Gly Arg Lys Ala Phe Val Glu Lys Tyr
    530                 535                 540

Val Glu Glu Pro Lys Ala Glu Glu Lys Glu Asp Asn Ala Gly Thr Thr
545                 550                 555                 560

Thr Asp Val Lys Thr Pro Glu Lys Ala Asn Asp Gly Gly Asp Ser Val
                565                 570                 575

Thr Asn Gln Lys Ala Thr Glu Gln Pro Ala Pro Ser Gly Ser Met Ala
            580                 585                 590

Pro Ile Ser Asn Lys Lys Thr Glu Lys Ala Ser Gly Asn Gln Thr Gly
        595                 600                 605

Thr Gly Glu Thr Thr Ala Pro Ile Asn Ser Phe Phe Ala Leu Val Gln
    610                 615                 620

Asp Asp Pro Ser Val Gln Ile Val Asn Asn Ala Gln Ile Trp Tyr Ala
625                 630                 635                 640

Lys Gln Gln Leu Ala Gly Thr Ser Glu Ala Asn Leu Pro Ile Leu Ser
                645                 650                 655

Ala Ala Ala Pro Phe Lys Ala Gly Thr Arg Gly Asp Ala Ser Ala Tyr
            660                 665                 670

Thr Asp Ile Pro Ala Gly Pro Ile Ala Ile Lys Asn Val Ala Asp Leu
        675                 680                 685

Tyr Leu Tyr Asp Asn Val Val Ala Ile Leu Lys Val Asn Gly Ala Gln
    690                 695                 700

Leu Lys Glu Trp Leu Glu Met Ser Ala Gly Gln Phe Asn Gln Val Asp
705                 710                 715                 720

Leu Ser Ser Thr Glu Pro Gln Asn Leu Val Asn Thr Asp Phe Arg Thr
                725                 730                 735

Tyr Asn Phe Asp Val Ile Asp Gly Val Thr Tyr Gln Tyr Asp Ile Thr
            740                 745                 750

Gln Pro Asn Lys Tyr Asp Arg Asp Gly Lys Ile Val Asn Glu Thr Ala
        755                 760                 765

Ser Arg Val Arg Asn Leu Gln Tyr Asn Gly Gln Asp Val Thr Ala Asp
    770                 775                 780

Gln Glu Phe Ile Val Val Thr Asn Asn Tyr Arg Ala Asn Gly Thr Phe
785                 790                 795                 800

Pro Gly Val Arg Glu Ala Ser Ile Asn Arg Leu Leu Asn Leu Glu Asn
                805                 810                 815

Arg Gln Ala Ile Ile Asn Tyr Ile Ile Ala Glu Lys Val Ile Asn Pro
            820                 825                 830

Thr Ala Asp Asn Asn Trp Thr Phe Thr Asp Ser Ile Lys Gly Leu Asp
        835                 840                 845

Leu Arg Phe Leu Thr Ala Asp Arg Ala Lys Ser Leu Val Thr Asp Gln
    850                 855                 860

Glu Cys Ile Val Tyr Leu Gln Ala Ser Thr Ala Ser Glu Gly Phe Gly
865                 870                 875                 880

Glu Phe Lys Phe Val Tyr Thr Glu Ser Lys Val Val Thr Pro Asp Glu
                885                 890                 895
```

```
Gln Gln Ser Asp Gln Gly Asn Thr Gly Gln Asp Ile Val Leu Glu Ser
            900                 905                 910

Gly Gln Arg Ile Thr Leu Pro Ala Val Asn Pro Pro Ala Pro Ala Pro
        915                 920                 925

Gln His Lys Leu Ala Ser Pro His Ser Gln Ala Ser Thr Lys Thr
    930                 935                 940


<210> SEQ ID NO 108
<211> LENGTH: 943
<212> TYPE: PRT
<213> ORGANISM: ARTIFICIAL SEQUENCE
<220> FEATURE:
<223> OTHER INFORMATION: Fusion polypeptide of fragments of S. suis
      proteins.

<400> SEQUENCE: 108

Glu Ile Gln Ala Ile Val Asp Glu Ala Asn Thr Ile Val Lys Lys Val
1               5                   10                  15

Thr Glu Gln Lys Ile Ala Thr Ala Ser Gln Ala Thr Asp Ile Ser Arg
            20                  25                  30

Glu Val Asn Glu Phe Lys Glu Ser Ala Val Gly Asn Leu Val Thr Ser
        35                  40                  45

Ala Gln Leu Ala Ile Ala Lys Lys Ser Gly Tyr Asp Val Asp Phe Ala
    50                  55                  60

Met Thr Asn Asp Gly Gly Ile Arg Ala Asp Leu Lys Val Gln Glu Asp
65                  70                  75                  80

Gly Thr Val Thr Trp Gly Ala Ala Gln Ala Val Gln Pro Phe Gly Asn
                85                  90                  95

Ile Leu Gln Val Val Gln Met Thr Gly Glu Gln Ile Tyr Thr Ala Leu
            100                 105                 110

Asn Gln Gln Tyr Asp Glu Gly Glu Lys Tyr Phe Leu Gln Met Ser Gly
        115                 120                 125

Ile Lys Tyr Ile Tyr Thr Lys Ala Asp Asn Pro Thr Glu Glu Asn Pro
    130                 135                 140

Tyr Lys Val Val Lys Ala Phe Lys Glu Asp Gly Thr Glu Ile Val Pro
145                 150                 155                 160

Thr Glu Thr Tyr Thr Leu Val Ile Asn Asp Phe Leu Phe Gly Gly Gly
                165                 170                 175

Asp Gly Phe Ser Ile Phe Lys Glu Ala Lys Leu Ile Gly Ala Ile Asn
            180                 185                 190

Pro Asp Thr Glu Val Phe Val Glu Tyr Leu Thr Asp Leu Glu Lys Ala
        195                 200                 205

Gly Gln Thr Ile Ser Ala Thr Ile Pro Gly Arg Lys Ala Phe Val Glu
    210                 215                 220

Lys Tyr Val Glu Glu Pro Lys Ala Glu Glu Lys Glu Asp Asn Ala Gly
225                 230                 235                 240

Thr Thr Thr Asp Val Lys Thr Pro Glu Lys Ala Asn Asp Gly Gly Asp
                245                 250                 255

Ser Val Thr Asn Gln Lys Ala Thr Glu Gln Pro Ala Pro Ser Gly Ser
            260                 265                 270

Met Ala Pro Ile Ser Asn Lys Lys Thr Glu Lys Ala Ser Gly Asn Gln
        275                 280                 285

Thr Gly Thr Gly Glu Thr Thr Ala Pro Ile Asn Ser Phe Phe Ala Leu
    290                 295                 300

Val Gln Asp Asp Pro Ser Val Gln Ile Val Asn Asn Ala Gln Ile Trp
```

-continued

```
305                 310                 315                 320

Tyr Ala Lys Gln Gln Leu Ala Gly Thr Ser Glu Ala Asn Leu Pro Ile
                325                 330                 335

Leu Ser Ala Ala Ala Pro Phe Lys Ala Gly Thr Arg Gly Asp Ala Ser
            340                 345                 350

Ala Tyr Thr Asp Ile Pro Ala Gly Pro Ile Ala Ile Lys Asn Val Ala
        355                 360                 365

Asp Leu Tyr Leu Tyr Asp Asn Val Val Ala Ile Leu Lys Val Asn Gly
    370                 375                 380

Ala Gln Leu Lys Glu Trp Leu Glu Met Ser Ala Gly Gln Phe Asn Gln
385                 390                 395                 400

Val Asp Leu Ser Ser Thr Glu Pro Gln Asn Leu Val Asn Thr Asp Phe
                405                 410                 415

Arg Thr Tyr Asn Phe Asp Val Ile Asp Gly Val Thr Tyr Gln Tyr Asp
            420                 425                 430

Ile Thr Gln Pro Asn Lys Tyr Asp Arg Asp Gly Lys Ile Val Asn Glu
        435                 440                 445

Thr Ala Ser Arg Val Arg Asn Leu Gln Tyr Asn Gly Gln Asp Val Thr
    450                 455                 460

Ala Asp Gln Glu Phe Ile Val Val Thr Asn Asn Tyr Arg Ala Asn Gly
465                 470                 475                 480

Thr Phe Pro Gly Val Arg Glu Ala Ser Ile Asn Arg Leu Leu Asn Leu
                485                 490                 495

Glu Asn Arg Gln Ala Ile Ile Asn Tyr Ile Ile Ala Glu Lys Val Ile
            500                 505                 510

Asn Pro Thr Ala Asp Asn Asn Trp Thr Phe Thr Asp Ser Ile Lys Gly
        515                 520                 525

Leu Asp Leu Arg Phe Leu Thr Ala Asp Arg Ala Lys Ser Leu Val Thr
    530                 535                 540

Asp Gln Glu Cys Ile Val Tyr Leu Gln Ala Ser Thr Ala Ser Glu Gly
545                 550                 555                 560

Phe Gly Glu Phe Lys Phe Val Tyr Thr Glu Ser Lys Val Val Thr Pro
                565                 570                 575

Asp Glu Gln Gln Ser Asp Gln Gly Asn Thr Gly Gln Asp Ile Val Leu
            580                 585                 590

Glu Ser Gly Gln Arg Ile Thr Leu Pro Ala Val Asn Pro Pro Ala Pro
        595                 600                 605

Ala Pro Gln His Lys Leu Ala Ser Pro His Ser Gln Ala Ser Thr Lys
    610                 615                 620

Thr Glu Phe Asp Glu Ile Lys Ala Lys Tyr Glu Ala Glu Asn Ala Gln
625                 630                 635                 640

Val Val Ile Glu Asn Asn Pro Val Glu Leu Asn Gly Asp Arg Ser Asn
                645                 650                 655

Val Arg Val Arg Glu Thr Asn Leu Gly Asn Ala Val Thr Asp Ala Ile
            660                 665                 670

Tyr Ala Tyr Gly Gln Thr Gly Phe Ser Asn Lys Thr Ser Leu Ala Val
        675                 680                 685

Thr Asn Gly Gly Gly Leu Arg Ala Thr Ile Ala Lys Asp Gln Pro Val
    690                 695                 700

Thr Lys Gly Asp Ile Ile Ala Val Leu Pro Phe Gly Asn Ile Val Ser
705                 710                 715                 720

Gln Ile Thr Val Thr Gly Gln Gln Ile Tyr Asp Met Phe Thr Lys Ser
                725                 730                 735
```

```
Leu Ser Ser Thr Leu Gln Val Asn Pro Glu Thr Gly Glu Met Leu Leu
            740                 745                 750

Asp Glu Asn Gly Met Pro Leu Phe Glu Ala Ser Gly Gly Phe Leu His
        755                 760                 765

Ile Ser Gly Ala Asn Val Phe Tyr Asp Pro Thr Leu Pro Val Glu Glu
    770                 775                 780

Arg Val Leu Leu Ile Gly Ile Leu Asn Pro Glu Thr Gly Glu Tyr Asp
785                 790                 795                 800

Ala Leu Asp Leu Glu Lys Thr Tyr Tyr Leu Ala Thr Asn Asp Phe Leu
                805                 810                 815

Ala Ala Gly Gly Asp Gly Tyr Thr Met Leu Gly Gly Ala Arg Glu Glu
            820                 825                 830

Gly Pro Ser Met Asp Ser Val Phe Ala Glu Tyr Leu Lys Thr Ala Asp
        835                 840                 845

Leu Ser Ala Tyr Glu Val Val Asn Pro Tyr Ser Arg Ile Ile Pro Val
    850                 855                 860

Asn Ser Ser Ile Asp Thr Asp Glu Asp Gly Tyr Pro Asp Phe Ile Glu
865                 870                 875                 880

Ile Leu Leu Asp Thr Asp Pro Glu Asn Pro Ala Ser Asn Pro Glu Thr
                885                 890                 895

Val Pro Ala Glu Asn Thr Asp Ser Pro Ser Asn Gln Val Gln Asn Thr
            900                 905                 910

Ser Ala Thr Asp Lys Lys Ala Pro Val Asp Ser Pro Lys Val Gly Asp
        915                 920                 925

Lys Lys Thr Glu Val Ala Ser Pro Ala Lys Thr Thr Lys Ala Gly
    930                 935                 940
```

<210> SEQ ID NO 109
<211> LENGTH: 971
<212> TYPE: PRT
<213> ORGANISM: ARTIFICIAL SEQUENCE
<220> FEATURE:
<223> OTHER INFORMATION: Fusion polypeptide of fragments of S. suis proteins with affinity-tag.

<400> SEQUENCE: 109

```
Met Thr Gly Ser Asp Glu Ile Lys Ala Lys Tyr Glu Ala Glu Asn Ala
1               5                   10                  15

Gln Val Val Ile Glu Asn Asn Pro Val Glu Leu Asn Gly Asp Arg Ser
            20                  25                  30

Asn Val Arg Val Arg Glu Thr Asn Leu Gly Asn Ala Val Thr Asp Ala
        35                  40                  45

Ile Tyr Ala Tyr Gly Gln Thr Gly Phe Ser Asn Lys Thr Ser Leu Ala
    50                  55                  60

Val Thr Asn Gly Gly Gly Leu Arg Ala Thr Ile Ala Lys Asp Gln Pro
65                  70                  75                  80

Val Thr Lys Gly Asp Ile Ile Ala Val Leu Pro Phe Gly Asn Ile Val
                85                  90                  95

Ser Gln Ile Thr Val Thr Gly Gln Gln Ile Tyr Asp Met Phe Thr Lys
            100                 105                 110

Ser Leu Ser Ser Thr Leu Gln Val Asn Pro Glu Thr Gly Glu Met Leu
        115                 120                 125

Leu Asp Glu Asn Gly Met Pro Leu Phe Glu Ala Ser Gly Gly Phe Leu
    130                 135                 140

His Ile Ser Gly Ala Asn Val Phe Tyr Asp Pro Thr Leu Pro Val Glu
```

-continued

```
145                 150                 155                 160

Glu Arg Val Leu Leu Ile Gly Ile Leu Asn Pro Glu Thr Gly Glu Tyr
                165                 170                 175

Asp Ala Leu Asp Leu Glu Lys Thr Tyr Tyr Leu Ala Thr Asn Asp Phe
            180                 185                 190

Leu Ala Ala Gly Gly Asp Gly Tyr Thr Met Leu Gly Gly Ala Arg Glu
        195                 200                 205

Glu Gly Pro Ser Met Asp Ser Val Phe Ala Glu Tyr Leu Lys Thr Ala
    210                 215                 220

Asp Leu Ser Ala Tyr Glu Val Val Asn Pro Tyr Ser Arg Ile Ile Pro
225                 230                 235                 240

Val Asn Ser Ser Ile Asp Thr Asp Glu Asp Gly Tyr Pro Asp Phe Ile
                245                 250                 255

Glu Ile Leu Leu Asp Thr Asp Pro Glu Asn Pro Ala Ser Asn Pro Glu
            260                 265                 270

Thr Val Pro Ala Glu Asn Thr Asp Ser Pro Ser Asn Gln Val Gln Asn
        275                 280                 285

Thr Ser Ala Thr Asp Lys Lys Ala Pro Val Asp Ser Pro Lys Val Gly
    290                 295                 300

Asp Lys Lys Thr Glu Val Ala Ser Pro Ala Lys Thr Thr Lys Ala Gly
305                 310                 315                 320

Glu Phe Glu Ile Gln Ala Ile Val Asp Glu Ala Asn Thr Ile Val Lys
                325                 330                 335

Lys Val Thr Glu Gln Lys Ile Ala Thr Ala Ser Gln Ala Thr Asp Ile
            340                 345                 350

Ser Arg Glu Val Asn Glu Phe Lys Glu Ser Ala Val Gly Asn Leu Val
        355                 360                 365

Thr Ser Ala Gln Leu Ala Ile Ala Lys Lys Ser Gly Tyr Asp Val Asp
    370                 375                 380

Phe Ala Met Thr Asn Asp Gly Gly Ile Arg Ala Asp Leu Lys Val Gln
385                 390                 395                 400

Glu Asp Gly Thr Val Thr Trp Gly Ala Ala Gln Ala Val Gln Pro Phe
                405                 410                 415

Gly Asn Ile Leu Gln Val Val Gln Met Thr Gly Glu Gln Ile Tyr Thr
            420                 425                 430

Ala Leu Asn Gln Gln Tyr Asp Glu Gly Glu Lys Tyr Phe Leu Gln Met
        435                 440                 445

Ser Gly Ile Lys Tyr Ile Tyr Thr Lys Ala Asp Asn Pro Thr Glu Glu
    450                 455                 460

Asn Pro Tyr Lys Val Val Lys Ala Phe Lys Glu Asp Gly Thr Glu Ile
465                 470                 475                 480

Val Pro Thr Glu Thr Tyr Thr Leu Val Ile Asn Asp Phe Leu Phe Gly
                485                 490                 495

Gly Gly Asp Gly Phe Ser Ile Phe Lys Glu Ala Lys Leu Ile Gly Ala
            500                 505                 510

Ile Asn Pro Asp Thr Glu Val Phe Val Glu Tyr Leu Thr Asp Leu Glu
        515                 520                 525

Lys Ala Gly Gln Thr Ile Ser Ala Thr Ile Pro Gly Arg Lys Ala Phe
    530                 535                 540

Val Glu Lys Tyr Val Glu Glu Pro Lys Ala Glu Glu Lys Glu Asp Asn
545                 550                 555                 560

Ala Gly Thr Thr Thr Asp Val Lys Thr Pro Glu Lys Ala Asn Asp Gly
                565                 570                 575
```

```
Gly Asp Ser Val Thr Asn Gln Lys Ala Thr Glu Gln Pro Ala Pro Ser
            580                 585                 590

Gly Ser Met Ala Pro Ile Ser Asn Lys Lys Thr Glu Lys Ala Ser Gly
        595                 600                 605

Asn Gln Thr Gly Thr Gly Glu Thr Thr Ala Pro Ile Asn Ser Phe Phe
    610                 615                 620

Ala Leu Val Gln Asp Asp Pro Ser Val Gln Ile Val Asn Asn Ala Gln
625                 630                 635                 640

Ile Trp Tyr Ala Lys Gln Gln Leu Ala Gly Thr Ser Glu Ala Asn Leu
                645                 650                 655

Pro Ile Leu Ser Ala Ala Ala Pro Phe Lys Ala Gly Thr Arg Gly Asp
            660                 665                 670

Ala Ser Ala Tyr Thr Asp Ile Pro Ala Gly Pro Ile Ala Ile Lys Asn
        675                 680                 685

Val Ala Asp Leu Tyr Leu Tyr Asp Asn Val Val Ala Ile Leu Lys Val
    690                 695                 700

Asn Gly Ala Gln Leu Lys Glu Trp Leu Glu Met Ser Ala Gly Gln Phe
705                 710                 715                 720

Asn Gln Val Asp Leu Ser Ser Thr Glu Pro Gln Asn Leu Val Asn Thr
                725                 730                 735

Asp Phe Arg Thr Tyr Asn Phe Asp Val Ile Asp Gly Val Thr Tyr Gln
            740                 745                 750

Tyr Asp Ile Thr Gln Pro Asn Lys Tyr Asp Arg Asp Gly Lys Ile Val
        755                 760                 765

Asn Glu Thr Ala Ser Arg Val Arg Asn Leu Gln Tyr Asn Gly Gln Asp
    770                 775                 780

Val Thr Ala Asp Gln Glu Phe Ile Val Val Thr Asn Asn Tyr Arg Ala
785                 790                 795                 800

Asn Gly Thr Phe Pro Gly Val Arg Glu Ala Ser Ile Asn Arg Leu Leu
                805                 810                 815

Asn Leu Glu Asn Arg Gln Ala Ile Ile Asn Tyr Ile Ile Ala Glu Lys
            820                 825                 830

Val Ile Asn Pro Thr Ala Asp Asn Asn Trp Thr Phe Thr Asp Ser Ile
        835                 840                 845

Lys Gly Leu Asp Leu Arg Phe Leu Thr Ala Asp Arg Ala Lys Ser Leu
    850                 855                 860

Val Thr Asp Gln Glu Cys Ile Val Tyr Leu Gln Ala Ser Thr Ala Ser
865                 870                 875                 880

Glu Gly Phe Gly Glu Phe Lys Phe Val Tyr Thr Glu Ser Lys Val Val
                885                 890                 895

Thr Pro Asp Glu Gln Gln Ser Asp Gln Gly Asn Thr Gly Gln Asp Ile
            900                 905                 910

Val Leu Glu Ser Gly Gln Arg Ile Thr Leu Pro Ala Val Asn Pro Pro
        915                 920                 925

Ala Pro Ala Pro Gln His Lys Leu Ala Ser Pro His Ser Gln Ala Ser
    930                 935                 940

Thr Lys Thr Leu Glu Gly Leu Lys Thr Arg Asn Lys Lys Ala Lys Ser
945                 950                 955                 960

Asp Lys Leu Ile Val Arg Arg Arg Asn Gln Lys
                965                 970
```

<210> SEQ ID NO 110
<211> LENGTH: 971

<212> TYPE: PRT
<213> ORGANISM: ARTIFICIAL SEQUENCE
<220> FEATURE:
<223> OTHER INFORMATION: Fusion polypeptide of fragments of S. suis
proteins with affinity-tag.

<400> SEQUENCE: 110

```
Met Thr Gly Ser Glu Ile Gln Ala Ile Val Asp Glu Ala Asn Thr Ile
1               5                   10                  15

Val Lys Lys Val Thr Glu Gln Lys Ile Ala Thr Ala Ser Gln Ala Thr
            20                  25                  30

Asp Ile Ser Arg Glu Val Asn Glu Phe Lys Glu Ser Ala Val Gly Asn
        35                  40                  45

Leu Val Thr Ser Ala Gln Leu Ala Ile Ala Lys Lys Ser Gly Tyr Asp
    50                  55                  60

Val Asp Phe Ala Met Thr Asn Asp Gly Gly Ile Arg Ala Asp Leu Lys
65                  70                  75                  80

Val Gln Glu Asp Gly Thr Val Thr Trp Gly Ala Ala Gln Ala Val Gln
                85                  90                  95

Pro Phe Gly Asn Ile Leu Gln Val Val Gln Met Thr Gly Glu Gln Ile
            100                 105                 110

Tyr Thr Ala Leu Asn Gln Gln Tyr Asp Glu Gly Glu Lys Tyr Phe Leu
        115                 120                 125

Gln Met Ser Gly Ile Lys Tyr Ile Tyr Thr Lys Ala Asp Asn Pro Thr
    130                 135                 140

Glu Glu Asn Pro Tyr Lys Val Val Lys Ala Phe Lys Glu Asp Gly Thr
145                 150                 155                 160

Glu Ile Val Pro Thr Glu Thr Tyr Thr Leu Val Ile Asn Asp Phe Leu
                165                 170                 175

Phe Gly Gly Gly Asp Gly Phe Ser Ile Phe Lys Glu Ala Lys Leu Ile
            180                 185                 190

Gly Ala Ile Asn Pro Asp Thr Glu Val Phe Val Glu Tyr Leu Thr Asp
        195                 200                 205

Leu Glu Lys Ala Gly Gln Thr Ile Ser Ala Thr Ile Pro Gly Arg Lys
    210                 215                 220

Ala Phe Val Glu Lys Tyr Val Glu Glu Pro Lys Ala Glu Glu Lys Glu
225                 230                 235                 240

Asp Asn Ala Gly Thr Thr Thr Asp Val Lys Thr Pro Glu Lys Ala Asn
                245                 250                 255

Asp Gly Gly Asp Ser Val Thr Asn Gln Lys Ala Thr Glu Gln Pro Ala
            260                 265                 270

Pro Ser Gly Ser Met Ala Pro Ile Ser Asn Lys Lys Thr Glu Lys Ala
        275                 280                 285

Ser Gly Asn Gln Thr Gly Thr Gly Glu Thr Thr Ala Pro Ile Asn Ser
    290                 295                 300

Phe Phe Ala Leu Val Gln Asp Asp Pro Ser Val Gln Ile Val Asn Asn
305                 310                 315                 320

Ala Gln Ile Trp Tyr Ala Lys Gln Gln Leu Ala Gly Thr Ser Glu Ala
                325                 330                 335

Asn Leu Pro Ile Leu Ser Ala Ala Ala Pro Phe Lys Ala Gly Thr Arg
            340                 345                 350

Gly Asp Ala Ser Ala Tyr Thr Asp Ile Pro Ala Gly Pro Ile Ala Ile
        355                 360                 365

Lys Asn Val Ala Asp Leu Tyr Leu Tyr Asp Asn Val Val Ala Ile Leu
    370                 375                 380
```

```
Lys Val Asn Gly Ala Gln Leu Lys Glu Trp Leu Glu Met Ser Ala Gly
385                 390                 395                 400

Gln Phe Asn Gln Val Asp Leu Ser Ser Thr Glu Pro Gln Asn Leu Val
                405                 410                 415

Asn Thr Asp Phe Arg Thr Tyr Asn Phe Asp Val Ile Asp Gly Val Thr
            420                 425                 430

Tyr Gln Tyr Asp Ile Thr Gln Pro Asn Lys Tyr Asp Arg Asp Gly Lys
        435                 440                 445

Ile Val Asn Glu Thr Ala Ser Arg Val Arg Asn Leu Gln Tyr Asn Gly
    450                 455                 460

Gln Asp Val Thr Ala Asp Gln Glu Phe Ile Val Val Thr Asn Asn Tyr
465                 470                 475                 480

Arg Ala Asn Gly Thr Phe Pro Gly Val Arg Glu Ala Ser Ile Asn Arg
                485                 490                 495

Leu Leu Asn Leu Glu Asn Arg Gln Ala Ile Ile Asn Tyr Ile Ile Ala
            500                 505                 510

Glu Lys Val Ile Asn Pro Thr Ala Asp Asn Asn Trp Thr Phe Thr Asp
        515                 520                 525

Ser Ile Lys Gly Leu Asp Leu Arg Phe Leu Thr Ala Asp Arg Ala Lys
    530                 535                 540

Ser Leu Val Thr Asp Gln Glu Cys Ile Val Tyr Leu Gln Ala Ser Thr
545                 550                 555                 560

Ala Ser Glu Gly Phe Gly Glu Phe Lys Phe Val Tyr Thr Glu Ser Lys
                565                 570                 575

Val Val Thr Pro Asp Glu Gln Gln Ser Asp Gln Gly Asn Thr Gly Gln
            580                 585                 590

Asp Ile Val Leu Glu Ser Gly Gln Arg Ile Thr Leu Pro Ala Val Asn
        595                 600                 605

Pro Pro Ala Pro Ala Pro Gln His Lys Leu Ala Ser Pro His Ser Gln
    610                 615                 620

Ala Ser Thr Lys Thr Glu Phe Asp Glu Ile Lys Ala Lys Tyr Glu Ala
625                 630                 635                 640

Glu Asn Ala Gln Val Val Ile Glu Asn Asn Pro Val Glu Leu Asn Gly
                645                 650                 655

Asp Arg Ser Asn Val Arg Val Arg Glu Thr Asn Leu Gly Asn Ala Val
            660                 665                 670

Thr Asp Ala Ile Tyr Ala Tyr Gly Gln Thr Gly Phe Ser Asn Lys Thr
        675                 680                 685

Ser Leu Ala Val Thr Asn Gly Gly Gly Leu Arg Ala Thr Ile Ala Lys
    690                 695                 700

Asp Gln Pro Val Thr Lys Gly Asp Ile Ile Ala Val Leu Pro Phe Gly
705                 710                 715                 720

Asn Ile Val Ser Gln Ile Thr Val Thr Gly Gln Gln Ile Tyr Asp Met
                725                 730                 735

Phe Thr Lys Ser Leu Ser Ser Thr Leu Gln Val Asn Pro Glu Thr Gly
            740                 745                 750

Glu Met Leu Leu Asp Glu Asn Gly Met Pro Leu Phe Glu Ala Ser Gly
        755                 760                 765

Gly Phe Leu His Ile Ser Gly Ala Asn Val Phe Tyr Asp Pro Thr Leu
    770                 775                 780

Pro Val Glu Glu Arg Val Leu Leu Ile Gly Ile Leu Asn Pro Glu Thr
785                 790                 795                 800
```

```
Gly Glu Tyr Asp Ala Leu Asp Leu Glu Lys Thr Tyr Tyr Leu Ala Thr
                805                 810                 815

Asn Asp Phe Leu Ala Ala Gly Gly Asp Gly Tyr Thr Met Leu Gly Gly
            820                 825                 830

Ala Arg Glu Glu Gly Pro Ser Met Asp Ser Val Phe Ala Glu Tyr Leu
        835                 840                 845

Lys Thr Ala Asp Leu Ser Ala Tyr Glu Val Val Asn Pro Tyr Ser Arg
    850                 855                 860

Ile Ile Pro Val Asn Ser Ser Ile Asp Thr Asp Glu Asp Gly Tyr Pro
865                 870                 875                 880

Asp Phe Ile Glu Ile Leu Leu Asp Thr Asp Pro Glu Asn Pro Ala Ser
                885                 890                 895

Asn Pro Glu Thr Val Pro Ala Glu Asn Thr Asp Ser Pro Ser Asn Gln
            900                 905                 910

Val Gln Asn Thr Ser Ala Thr Asp Lys Lys Ala Pro Val Asp Ser Pro
        915                 920                 925

Lys Val Gly Asp Lys Lys Thr Glu Val Ala Ser Pro Ala Lys Thr Thr
    930                 935                 940

Lys Ala Gly Leu Glu Gly Leu Lys Thr Arg Asn Lys Lys Ala Lys Ser
945                 950                 955                 960

Asp Lys Leu Ile Val Arg Arg Arg Asn Gln Lys
                965                 970
```

<210> SEQ ID NO 111
<211> LENGTH: 2931
<212> TYPE: DNA
<213> ORGANISM: ARTIFICIAL SEQUENCE
<220> FEATURE:
<223> OTHER INFORMATION: Codon optimized DNA sequence of fusion polypeptide of fragments of S. suis proteins with affinity-tag.

<400> SEQUENCE: 111

```
catatgacag gatccgacga aatcaaagca aaatacgaag ccgaaaacgc ccaggttgtc     60

atcgaaaata atccggtgga actgaatggt gaccgcagca atgtgcgtgt ccgcgaaacc    120

aacctgggta atgcggtgac ggatgcaatt tatgcttacg gtcagaccgg ctttagtaac    180

aaaacctccc tggccgttac gaatggcggt ggcctgcgtg cgaccatcgc caaagaccag    240

ccggtgacga agggtgatat tatcgcggtt ctgccgtttg gcaatattgt ttctcaaatc    300

accgtcacgg gtcagcaaat ttatgacatg ttcaccaaaa gcctgagctc tacgctgcag    360

gttaacccgg aaaccggtga aatgctgctg gatgaaaatg gcatgccgct gtttgaagcg    420

tcaggtggct tcctgcatat ctcgggcgcc aacgtgttct atgatccgac cctgccggtc    480

gaagaacgcg tgctgctgat tggtatcctg aatccggaaa cgggcgaata cgacgcactg    540

gatctggaaa aaacctatta cctggctacg aacgactttc tggcggccgg tggcgatggt    600

tataccatgc tgggtggcgc ccgtgaagaa ggcccgagca tggactctgt tttcgcagaa    660

tacctgaaga ccgcagatct gagcgcttat gaagtggtta acccgtactc tcgcattatc    720

ccggtcaata gttccattga taccgacgaa gatggctatc cggattttat tgaaatcctg    780

ctggacaccg atccggaaaa cccggcaagt aatccggaaa ccgttccggc tgaaaacacg    840

gattcaccgt cgaaccaggt ccaaaatacc agtgcgacgg acaaaaaggc cccggtggat    900

tccccgaaag tgggcgataa gaaaaccgaa gtggcatccc cggcaaaaac gaccaaagca    960

ggtgaattcg aaattcaagc cattgtggac gaagcaaata ccatcgtcaa aaaagtcacg   1020

gaacagaaaa tcgcaacggc aagccaagca acggacatta gtcgtgaagt gaacgaattt   1080
```

```
aaagaaagcg cggtgggtaa tctggttacc tctgcccagc tggcaattgc taaaaaatcc   1140

ggctatgatg ttgacttcgc aatgaccaac gatggcggta tccgcgctga cctgaaagtt   1200

caggaagatg gtacggtcac ctggggtgca gcacaggcag tgcaaccgtt tggtaacatt   1260

ctgcaggtgg ttcaaatgac cggcgaacag atctacacgg ctctgaatca gcaatatgat   1320

gaaggtgaaa aatactttct gcaaatgagc ggcattaaat atatctacac caaagcggat   1380

aacccgacgg aagaaaatcc gtataaagtc gtgaaagcct tcaaagaaga tggcaccgaa   1440

attgtgccga cggaaaccta cacgctggtt atcaacgact ttctgttcgg cggtggcgat   1500

ggtttttcaa tcttcaaaga agcgaaactg attggcgcca tcaatccgga caccgaagtt   1560

tttgtcgaat atctgacgga tctggaaaaa gcgggtcaga ccatttcggc cacgattccg   1620

ggccgtaaag cattcgtcga aaaatacgtg gaagaaccga aagcagaaga aaaagaagac   1680

aatgctggca ccacgaccga tgtcaaaacc ccggaaaaag ccaacgatgg tggcgacagt   1740

gttaccaatc agaaagcaac ggaacaaccg gctccgagtg gctcaatggc cccgattagc   1800

aataagaaga cggaaaaagc aagtggcaac caaaccggta ccggcgaaac gacggccccg   1860

attaacagct tctttgccct ggttcaggac gacccgagtg tccagattgt caataacgct   1920

cagatttggt atgctaaaca gcaactggca ggcaccagcg aagcaaacct gccgattctg   1980

tcggcagcag caccgtttaa agcaggcacc cgtggtgatg ctagcgcata cacggacatc   2040

ccggcaggtc cgattgcaat caaaaatgtt gcagatctgt atctgtacga caacgtggtt   2100

gcaattctga aagtcaatgg cgctcagctg aaagaatggc tggaaatgtc tgcgggccag   2160

ttcaaccaag tggatctgag ctctaccgaa ccgcagaacc tggttaatac cgattttcgt   2220

acgtataatt tcgatgtgat tgacggcgtt acctatcagt acgatatcac gcaaccgaac   2280

aaatacgatc gcgacggtaa aatcgtcaat gaaaccgcat cacgtgtgcg caacctgcag   2340

tataatggcc aagatgtgac ggcggaccag gaatttattg tcgtgaccaa caattaccgt   2400

gcaaacggca cgtttccggg cgtgcgtgaa gcttcgatca atcgcctgct gaacctggaa   2460

aatcgccagg cgattatcaa ctacatcatc gccgaaaaag tgatcaaccc gaccgcggat   2520

aacaattgga cctttacgga tagtatcaaa ggtctggacc tgcgtttcct gaccgccgat   2580

cgcgcaaaat ccctggttac ggaccaggaa tgcattgtct atctgcaagc tagtaccgcg   2640

tccgaaggct ttggtgaatt taaattcgtt tacaccgaaa gcaaagttgt cacgccggat   2700

gaacagcaat ctgaccaggg caacaccggt caagatattg tcctggaaag cggtcagcgt   2760

atcacgctgc cggcagtgaa tccgccggca ccggctccgc agcacaaact ggcgtccccg   2820

cattcgcagg catccaccaa aaccctcgag ggactgaaga cccgcaataa gaaagccaaa   2880

agcgacaaac ttattgttcg ccgtcgcaat cagaagtaat gattaactag t             2931
```

<210> SEQ ID NO 112
<211> LENGTH: 2931
<212> TYPE: DNA
<213> ORGANISM: ARTIFICIAL SEQUENCE
<220> FEATURE:
<223> OTHER INFORMATION: Codon optimized DNA sequence of fusion polypeptide of fragments of S. suis proteins with affinity-tag.

<400> SEQUENCE: 112

```
catatgacag gatccgaaat tcaagccatt gtggacgaag caaataccat cgtcaaaaaa     60

gtcacggaac agaaaatcgc aacggcaagc caagcaacgg acattagtcg tgaagtgaac    120

gaatttaaag aaagcgcggt gggtaatctg gttacctctg cccagctggc aattgctaaa    180
```

```
aaatccggct atgatgttga cttcgcaatg accaacgatg gcggtatccg cgctgacctg    240
aaagttcagg aagatggtac ggtcacctgg ggtgcagcac aggcagtgca accgtttggt    300
aacattctgc aggtggttca aatgaccggc gaacagatct acacggctct gaatcagcaa    360
tatgatgaag gtgaaaaata ctttctgcaa atgagcggca ttaaatatat ctacaccaaa    420
gcggataacc cgacggaaga aaatccgtat aaagtcgtga aagccttcaa agaagatggc    480
accgaaattg tgccgacgga aacctacacg ctggttatca acgactttct gttcggcggt    540
ggcgatggtt tttcaatctt caaagaagcg aaactgattg gcgccatcaa tccggacacc    600
gaagtttttg tcgaatatct gacggatctg gaaaaagcgg gtcagaccat ttcggccacg    660
attccgggcc gtaaagcatt cgtcgaaaaa tacgtggaag aaccgaaagc agaagaaaaa    720
gaagacaatg ctggcaccac gaccgatgtc aaaaccccgg aaaaagccaa cgatggtggc    780
gacagtgtta ccaatcagaa agcaacggaa caaccggctc cgagtggctc aatggccccg    840
attagcaata agaagacgga aaaagcaagt ggcaaccaaa ccggtaccgg cgaaacgacg    900
gccccgatta acagcttctt tgccctggtt caggacgacc cgagtgtcca gattgtcaat    960
aacgctcaga tttggtatgc taaacagcaa ctggcaggca ccagcgaagc aaacctgccg   1020
attctgtcgg cagcagcacc gtttaaagca ggcacccgtg gtgatgctag cgcatacacg   1080
gacatcccgg caggtccgat tgcaatcaaa aatgttgcag atctgtatct gtacgacaac   1140
gtggttgcaa ttctgaaagt caatggcgct cagctgaaag aatggctgga aatgtctgcg   1200
ggccagttca accaagtgga tctgagctct accgaaccgc agaacctggt taataccgat   1260
tttcgtacgt ataatttcga tgtgattgac ggcgttacct atcagtacga tatcacgcaa   1320
ccgaacaaat acgatcgcga cggtaaaatc gtcaatgaaa ccgcatcacg tgtgcgcaac   1380
ctgcagtata atggccaaga tgtgacggcg gaccaggaat ttattgtcgt gaccaacaat   1440
taccgtgcaa acggcacgtt tccgggcgtg cgtgaagctt cgatcaatcg cctgctgaac   1500
ctggaaaatc gccaggcgat tatcaactac atcatcgccg aaaaagtgat caacccgacc   1560
gcggataaca attggacctt tacggatagt atcaaaggtc tggacctgcg tttcctgacc   1620
gccgatcgcg caaaatccct ggttacggac caggaatgca ttgtctatct gcaagctagt   1680
accgcgtccg aaggctttgg tgaatttaaa ttcgtttaca ccgaaagcaa agttgtcacg   1740
ccggatgaac agcaatctga ccagggcaac accggtcaag atattgtcct ggaaagcggt   1800
cagcgtatca cgctgccggc agtgaatccg ccggcaccgg ctccgcagca caaactggcg   1860
tccccgcatt cgcaggcatc caccaaaacc gaattcgacg aaatcaaagc aaaatacgaa   1920
gccgaaaacg cccaggttgt catcgaaaat aatccggtgg aactgaatgg tgaccgcagc   1980
aatgtgcgtg tccgcgaaac caacctgggt aatgcggtga cggatgcaat ttatgcttac   2040
ggtcagaccg gctttagtaa caaaacctcc ctggccgtta cgaatggcgg tggcctgcgt   2100
gcgaccatcg ccaaagacca gccggtgacg aagggtgata ttatcgcggt tctgccgttt   2160
ggcaatattg tttctcaaat caccgtcacg ggtcagcaaa tttatgacat gttcaccaaa   2220
agcctgagct ctacgctgca ggttaacccg gaaaccggtg aaatgctgct ggatgaaaat   2280
ggcatgccgc tgtttgaagc gtcaggtggc ttcctgcata tctcgggcgc caacgtgttc   2340
tatgatccga ccctgccggt cgaagaacgc gtgctgctga ttggtatcct gaatccggaa   2400
acgggcgaat acgacgcact ggatctggaa aaaacctatt acctggctac gaacgacttt   2460
ctggcggccg gtggcgatgg ttataccatg ctgggtggcg cccgtgaaga aggcccgagc   2520
```

```
atggactctg ttttcgcaga atacctgaag accgcagatc tgagcgctta tgaagtggtt   2580

aacccgtact ctcgcattat cccggtcaat agttccattg ataccgacga agatggctat   2640

ccggatttta ttgaaatcct gctggacacc gatccggaaa acccggcaag taatccggaa   2700

accgttccgg ctgaaaacac ggattcaccg tcgaaccagg tccaaaatac cagtgcgacg   2760

gacaaaaagg ccccggtgga ttccccgaaa gtgggcgata agaaaaccga agtggcatcc   2820

ccggcaaaaa cgaccaaagc aggtctcgag ggactgaaga cccgcaataa gaaagccaaa   2880

agcgacaaac ttattgttcg ccgtcgcaat cagaagtaat gattaactag t            2931
```

```
<210> SEQ ID NO 113
<211> LENGTH: 16
<212> TYPE: PRT
<213> ORGANISM: Artificial sequence
<220> FEATURE:
<223> OTHER INFORMATION: Linker

<400> SEQUENCE: 113

Gly Gly Gly Gly Ser Leu Val Pro Arg Gly Ser Gly Gly Gly Gly Ser
1               5                   10                  15


<210> SEQ ID NO 114
<211> LENGTH: 6
<212> TYPE: PRT
<213> ORGANISM: Artificial sequence
<220> FEATURE:
<223> OTHER INFORMATION: Linker

<400> SEQUENCE: 114

Gly Ser Gly Ser Gly Ser
1               5


<210> SEQ ID NO 115
<211> LENGTH: 8
<212> TYPE: PRT
<213> ORGANISM: Artificial sequence
<220> FEATURE:
<223> OTHER INFORMATION: Linker

<400> SEQUENCE: 115

Gly Ser Gly Ser Gly Ser Gly Ser
1               5


<210> SEQ ID NO 116
<211> LENGTH: 16
<212> TYPE: PRT
<213> ORGANISM: Artificial sequence
<220> FEATURE:
<223> OTHER INFORMATION: Linker

<400> SEQUENCE: 116

Gly Ser Gly Ser Gly Ser Gly Ser Gly Ser Gly Ser Gly Ser Gly Ser
1               5                   10                  15


<210> SEQ ID NO 117
<211> LENGTH: 11
<212> TYPE: PRT
<213> ORGANISM: Artificial sequence
<220> FEATURE:
<223> OTHER INFORMATION: Linker

<400> SEQUENCE: 117

Gly Gly Ser Gly Gly His Met Gly Ser Gly Gly
1               5                   10
```

<210> SEQ ID NO 118
<211> LENGTH: 11
<212> TYPE: PRT
<213> ORGANISM: Artificial sequence
<220> FEATURE:
<223> OTHER INFORMATION: Linker

<400> SEQUENCE: 118

Gly Gly Ser Gly Gly Ser Gly Gly Ser Gly Gly
1               5                   10

<210> SEQ ID NO 119
<211> LENGTH: 5
<212> TYPE: PRT
<213> ORGANISM: Artificial sequence
<220> FEATURE:
<223> OTHER INFORMATION: Linker

<400> SEQUENCE: 119

Gly Gly Ser Gly Gly
1               5

<210> SEQ ID NO 120
<211> LENGTH: 8
<212> TYPE: PRT
<213> ORGANISM: Artificial sequence
<220> FEATURE:
<223> OTHER INFORMATION: Linker

<400> SEQUENCE: 120

Gly Gly Ser Gly Gly Gly Gly Gly
1               5

<210> SEQ ID NO 121
<211> LENGTH: 18
<212> TYPE: PRT
<213> ORGANISM: Artificial sequence
<220> FEATURE:
<223> OTHER INFORMATION: Linker

<400> SEQUENCE: 121

Gly Gly Gly Ser Glu Gly Gly Gly Ser Glu Gly Gly Gly Ser Glu Gly
1               5                   10                  15

Gly Gly

<210> SEQ ID NO 122
<211> LENGTH: 8
<212> TYPE: PRT
<213> ORGANISM: Artificial sequence
<220> FEATURE:
<223> OTHER INFORMATION: Linker

<400> SEQUENCE: 122

Ala Ala Gly Ala Ala Thr Ala Ala
1               5

<210> SEQ ID NO 123
<211> LENGTH: 5
<212> TYPE: PRT
<213> ORGANISM: Artificial sequence
<220> FEATURE:
<223> OTHER INFORMATION: Linker

<400> SEQUENCE: 123

Gly Gly Gly Gly Gly
1               5

<210> SEQ ID NO 124
<211> LENGTH: 5
<212> TYPE: PRT
<213> ORGANISM: Artificial sequence
<220> FEATURE:
<223> OTHER INFORMATION: Linker

<400> SEQUENCE: 124

Gly Gly Ser Ser Gly
1               5

<210> SEQ ID NO 125
<211> LENGTH: 11
<212> TYPE: PRT
<213> ORGANISM: Artificial sequence
<220> FEATURE:
<223> OTHER INFORMATION: Linker

<400> SEQUENCE: 125

Gly Ser Gly Gly Gly Thr Gly Gly Gly Ser Gly
1               5                   10

<210> SEQ ID NO 126
<211> LENGTH: 11
<212> TYPE: PRT
<213> ORGANISM: Artificial sequence
<220> FEATURE:
<223> OTHER INFORMATION: Linker

<400> SEQUENCE: 126

Gly Ser Gly Gly Gly Thr Gly Gly Gly Ser Gly
1               5                   10

<210> SEQ ID NO 127
<211> LENGTH: 12
<212> TYPE: PRT
<213> ORGANISM: Artificial sequence
<220> FEATURE:
<223> OTHER INFORMATION: Linker

<400> SEQUENCE: 127

Gly Ser Gly Ser Gly Ser Gly Ser Gly Gly Ser Gly
1               5                   10

<210> SEQ ID NO 128
<211> LENGTH: 14
<212> TYPE: PRT
<213> ORGANISM: Artificial sequence
<220> FEATURE:
<223> OTHER INFORMATION: Linker

<400> SEQUENCE: 128

Gly Ser Gly Gly Ser Gly Gly Ser Gly Gly Ser Gly Gly Ser
1               5                   10

<210> SEQ ID NO 129
<211> LENGTH: 14
<212> TYPE: PRT
<213> ORGANISM: Artificial sequence
<220> FEATURE:
<223> OTHER INFORMATION: Linker

<400> SEQUENCE: 129

Gly Ser Gly Gly Ser Gly Ser Gly Gly Ser Gly Gly Ser Gly
1               5                   10

VACCINE AGAINST *S. SUIS* INFECTION

CROSS-REFERENCE TO RELATED APPLICATIONS

This application is a § 371 national phase of International Application No. PCT/EP2016/066311, filed on Jul. 8, 2016, which claims the benefit of European Patent Application No. 15176063.4, filed on Jul. 9, 2015, which applications are incorporated by reference herein.

FIELD OF THE INVENTION

The present disclosure relates to immunogenic polypeptides, immunogenic compositions and vaccine compositions and use thereof for immunization of mammals susceptible to *Streptococcus suis* infection. The disclosure also relates to methods for preparing, formulating and administrating such compositions.

BACKGROUND

*Streptococcus suis* is a major pathogen causing bacterial disease in pigs and is responsible for large economic losses in the swine industry. *S. suis* causes a variety of diseases in pigs, including meningitis, arthritis, pericarditis, polyserositis, septicaemia, pneumonia and sudden death. Additionally, it is also emerging as a zoonotic agent of meningitis and streptococcal toxic shock-like syndrome and there is a high prevalence of *S. suis* human disease in southeast and east Asia. However, human cases have also been reported in several European countries, Australia as well North and South America. In western countries, *S. suis* infections are most often restricted to people who work in the swine industry, while in southeast and east Asia *S. suis* infections are a significant public health concern (Fittipaldi et al (2012), Future Microbiol. 7 (2); 259-279).

*S. suis* is a gram-positive facultative anaerobic coccus, originally defined as Lancefield groups R, S, R/S or T. Later, a new typing system based on the type-specific capsular polysaccharide antigens located in the cell wall was proposed. This led to a system comprising 35 serotypes (Rasmussen and Andresen (1998), Int. J. Syst. Bacteriol. 48, 1063-1065) of which serotypes 2, 1, 9, 7 and 1/2 are the most prevalent. Especially, serotype 2 has been reported as a zoonotic agent.

Control of *S. suis* in pig herd is of a large interest in the pig industry. Pigs may acquire *S. suis* via both vertical and horizontal transmission and colonized animals typically harbor the bacteria in their tonsils. While the adult pigs usually serve as asymptomatic carries, some carrier piglets will develop bacteremia, septicemia and/or meningitis due to dissemination of the bacteria from the tonsils and/or other mucosal surfaces. This usually occurs when the maternal antibodies decline in the piglets. To cause disease, the bacterial must breach the epithelial barriers, reach and survive in the bloodstream, invade different organs and cause exaggerated inflammation. The actual early mechanisms used by *S. suis* to colonize the host are poorly known, however several virulence factors have been proposed. The various *S. suis* virulence factors include; capsule, fibronectin/fibrinogen binding protein, serum opacity-like factor and modifications of the cell wall lipoteichoic acids and peptidoglycan (Fittipaldi supra). Furthermore, the virulence factors shared among various strains of the same serotype show a wide variation (Berthelot-Herault et al (2005) Can J Vet Res. July; 69(3):236-40; Quessy et al (1995) Infect Immun. May; 63(5):1975-9; Vecht et al (1992) Infect Immun. February; 60(2):550-6).

The development of vaccines have been focused on the above mentioned virulence factors. For example, vaccines compositions comprising a surface expressed protein, such as Sao and hp0245, are described in TW201412982, CN104248754 and CN102443053 and Li et al (2011) FEMS Micro Letters 316: 115-122. The protective effect of another surface localized protein (HP0197) is described in Zhang et al Vaccine (2009) 27: 5209-5213. A secreted protein (Ss-PepO) with a protective effect was described in Li et al (2011) Vaccine 29: 6514-6519. As of today, there is no well performing vaccine available against *S. suis* infection. In a recent study, the pan-surfome of *S. suis* was described identifying 113 surface expressed proteins (Gómez-Gascóna et al (2012), Journal of Proteomics October 22; 75(18): 5654-66).

One commonly followed route to make a vaccine against a bacterial disease, is the production and testing of a whole cell vaccine preparation.

Known in the art is Porcilis® Strepsuis, an attenuated bacterial vaccine for immunization of healthy pigs against disease caused by *S. suis* serotype 2. Additionally, vaccines comprising *Streptococcus* mutants deficient in capsular expression and the htpsA-gene have been described in WO0005378 and CN103352015, respectively. It seems likely however (Kebede et al (1990), Vet. Microbiol. 22: 249-257), that protection obtained with whole cell preparations is serotype-specific. Additionally, there are other disadvantages of whole cell vaccines. For example, unwanted reactions at and around the site of injection are common and it is often required to administer a large amount of non-specific protein, compared to the amount of material actually responsible for the induction of protection. The limited availability of efficient vaccines is likely caused by the large number of existing serotypes, the variation in virulence among strains and the still scarce knowledge about the factors that contribute to virulence and protection. Recently, a protein encoded by IgM specific protease denoted $Ide_{Ssuis}$ has been shown to elicit protective activity when immunized in pigs (Seele et al (2015) Vaccine, 33, 2207-2212), however large amounts of said protein are required for protective immunity, which leads to large costs associated with a vaccine based on said protein.

Lack of an effective vaccine against *S. suis* infections is a major problem in modern swine production. Thus, the provision of an effective and safe vaccine against *S. suis* infection is of large interest in the field.

SUMMARY OF THE INVENTION

It is an object of the present disclosure to provide an effective *S. suis* vaccine, which vaccine overcomes the disadvantages of the prior art, for example in terms of elicited protection and cost efficiency.

It is an object of the present disclosure to provide an immunogenic polypeptide for the use as a medicament, such as in prophylactic treatment of *S. suis* infections.

Also provided are immunogenic polypeptide fragments and fusion polypeptides per se.

Another object of the present disclosure is to provide related immunogenic compositions and vaccine composition as well as related treatment methods.

Yet another object of the present invention is to provide an immunogenic mixture with adjuvant properties.

These and other objects which are evident to the skilled person from the present disclosure are met by different aspects of the invention as claimed in the appended claims and as generally disclosed herein.

Briefly, the pan-surfome of *S. suis* has been described (Gómez-Gascóna supra). Gómez-Gascóna and co-workers obtained 39 *S. suis* strains obtained from infected pigs, corresponding to 19 of the most prevalent serotypes. They identified a set of 113 proteins, corresponding to both common and unique surface proteins in these strains, and listed them as potential antigens for vaccine development. The present inventors identified four of these as particularly useful in the context of a vaccine against *S. suis* infection.

The protein encoded by SSU0496 is an 1141 amino acid residues long IgM specific protease denoted IdeE (*S. suis*) or $Ide_{Ssuis}$ (Seele et al (2013) Journal of Bacteriology, 195(5): 930-940) and is herein denoted M2. The other three proteins (SSU0860, SSU1879 and SSU1355 denoted herein SP2, SP4 and SP7, respectively) show homology to the nucleotidase family of proteins. The importance of nucleotidases for virulence of bacteria has been shown for *S. aureus* (Thammavongsa et al 2009), *S. sanguinis* (Fan et al (2012) PLoS ONE 7(6): e38059), *S. agalactiae* (Firon et al (2014) The Journal of Biological Chemistry, 289(9):5479-5489) and *S. suis* (Liu et al (2014) The Journal of Infectious Diseases, Vol 210, Issue 1, p. 35-45). The published nucleotidase in *S. suis* has been denoted Ssads and corresponds to SP2. The two remaining selected polypeptides are putative genes: SP4 is a 813 amino acid long putative surface-anchored 2',3'-cyclic-nucleotide 2'-phosphodiesterase; and SP7 is a 674 amino acid long putative surface-anchored 5'-nucleotidase.

Thus, present disclosure is based on the finding that the proteins M2, SP2, SP4 and SP7, which are expressed on the surface of *S. suis*, are useful in the context of prophylactic treatment of *S. suis* infection.

TABLE 1

Summary of selected antigens (immunogenic polypeptides) from *S. suis* P1/7.

| Denotation | Locus | Protein | SEQ ID NO: | GenBank Accession number |
|---|---|---|---|---|
| SP2 | SSU0860 | Ssads | 2 | CAR45827 |
| SP4 | SSU1879 | putative surface-anchored 2',3'-cyclic-nucleotide 2'-phosphodiesterase | 3 | CAR47573 |
| SP7 | SSU1355 | surface-anchored 5'-nucleotidase | 4 | CAR46815 |
| M2 | SSU0496 | IdeE (*S. suis*) | 1 | C5W022 |

Thus, in a first aspect of the present disclosure there is provided a an immunogenic polypeptide for use as a medicament, wherein said polypeptide comprises an amino acid sequence selected from the group consisting of SEQ ID NO:4 and fragments thereof; SEQ ID NO:3 and fragments thereof; SEQ ID NO:2 and fragments thereof; a fragment comprising SEQ ID NO:5, provided the fragment comprising SEQ ID NO:5 is less than 500 amino acids long; a fragment comprising SEQ ID NO:6, provided the fragment comprising SEQ ID NO:6 is less than 500 amino acids long; and amino acid sequences with at least 80%-identity to any one of said amino acid sequences, such as an amino acid sequence selected from the group consisting of SEQ ID NO:4 and fragments thereof; SEQ ID NO:3 and fragments thereof; SEQ ID NO:2 and fragments thereof; SEQ ID NO:5; SEQ ID NO:38, SEQ ID NO:6; and amino acid sequences with at least 80%-identity to any one of said amino acid sequences. The skilled person will appreciate that the immunogenic polypeptide may comprise the complete SP2, SP4, SP7 polypeptide or alternatively a fragment thereof, provided that said polypeptide comprises at least one immunogenic region. Also, the skilled person will appreciate that the immunogenic polypeptide may comprise M2N, $M2N_{long}$ or M2C, which are fragments of M2, provided that it said immunogenic polypeptide comprising M2N, $M2N_{long}$ or M2C does not encompass the full length M2 polypeptide. Thus in one embodiment, said fragment comprising SEQ ID NO:5 or SEQ ID NO:38 is less than 500 amino acids long, such as less than 450 amino acids long, such as less than 400 amino acids long. In one embodiment, said fragment comprising SEQ ID NO:6 is less than 500 amino acids long, such as less than 450 amino acids long, such as less than 400 amino acids long. In one embodiment, said fragment is at approximately 100-500 amino acids long, such as at approximately 200-500 amino acids long, such as at approximately 250-450 amino acids long.

As the skilled person will realize, the properties of a polypeptide, such as the immunogenicity of the polypeptides of the present disclosure, may be dependent on the tertiary structure of the polypeptide and the presence and accessibility of immunogenic regions within said polypeptide. It is therefore possible to make minor changes to the sequence of amino acids in a polypeptide without affecting the function thereof. Thus, the disclosure encompasses modified variants of the immunogenic polypeptide as described herein, which are such that the immunogenic characteristics are retained.

In this way, also encompassed by the present disclosure is an immunogenic polypeptide as defined herein comprising an amino acid sequence with at least 80%-identity to said SEQ ID NO:4 or fragment thereof; SEQ ID NO:3 or fragment thereof; SEQ ID NO:2 or fragment thereof; SEQ ID NO:5, SEQ ID NO:38 or SEQ ID NO:6. In some embodiments, the polypeptide may comprise a sequence which is at least 81%, such as at least 82% such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 93%, such as at least 95%, such as at least 96%, such as at least 97%, such as at least 98% or such as at least 99% identical to said SEQ ID NO:4, SEQ ID NO:3, SEQ ID NO:2, SEQ ID NO:5, SEQ ID NO:38 or SEQ ID NO:6. In some embodiments, said polypeptide may comprise a sequence which is at least 81%, such as at least 82% such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 93%, such as at least 95%, such as at least 96%, such as at least 97%, such as at least 98% or such as at least 99% identical to the corresponding fragment of SEQ ID NO:4, SEQ ID NO:3 or SEQ ID NO:2.

For example, it is possible that one or several amino acid residue belonging to a certain functional grouping of amino acid residues (e.g. hydrophobic, hydrophilic, polar etc.) could be exchanged for another amino acid residue from the same functional group. It is also possible, that one or several amino acid residues are exchanged for one or several amino acid residues that belong to a different functional group, provided that the resulting polypeptide retains its immunogenic properties.

The term "% identity", as used throughout the specification, may for example be calculated as follows. The query sequence is aligned to the target sequence using the CLUSTAL W algorithm (Thompson et al, Nucleic Acids Research, 22: 4673-4680 (1994)). A comparison is made over the window corresponding to the shortest of the aligned sequences. The shortest of the aligned sequences may in some instances be the target sequence. In other instances, the query sequence may constitute the shortest of the aligned sequences. The amino acid residues at each position are compared, and the percentage of positions in the query sequence that have identical correspondences in the target sequence is reported as % identity.

To clarify, the text above relating to %-identity is equally relevant to the second, third and fourth aspects of the present disclosure and will for the sake of brevity not be repeated.

In one embodiment, there is provided immunogenic polypeptide for use in the prophylactic treatment of a *S. suis* infection, wherein said immunogenic polypeptide comprises an amino acid sequence selected from the group consisting of SEQ ID NO:4 and fragments thereof; SEQ ID NO:3 and fragments thereof; SEQ ID NO:2 and fragments thereof; a fragment comprising SEQ ID NO:5, provided the fragment comprising SEQ ID NO:5 is less than 500 amino acids long; a fragment comprising SEQ ID NO:6, provided the fragment comprising SEQ ID NO:6 is less than 500 amino acids long; and amino acid sequences with at least 80%-identity to any one of said amino acid sequences, such as an amino acid sequence selected from the group consisting of SEQ ID NO:4 and fragments thereof; SEQ ID NO:3 and fragments thereof; SEQ ID NO:2 and fragments thereof; SEQ ID NO:5; SEQ ID NO:38, SEQ ID NO:6; and amino acid sequences with at least 80%-identity to any one of said amino acid sequences.

In one embodiment of the present disclosure, there is provided an amino acid sequence for use as defined herein, which amino acid sequence is selected from the group consisting of SEQ ID NO:4 and fragments thereof, SEQ ID NO:3 and fragments thereof, SEQ ID NO:2 and fragments thereof; a fragment comprising SEQ ID NO:5, provided the fragment comprising SEQ ID NO:5 is less than 500 amino acids long; and amino acid sequences with at least 80%-identity to any one of said amino acid sequences, such as the group consisting of SEQ ID NO:4 and fragments thereof; SEQ ID NO:3 and fragments thereof; SEQ ID NO:2 and fragments thereof; SEQ ID NO:5; SEQ ID NO:38 and amino acid sequences with at least 80%-identity to any one of said amino acid sequences, such as the group consisting of SEQ ID NO:4 and fragments thereof; SEQ ID NO:3 and fragments thereof; SEQ ID NO:2 and fragments thereof; and amino acid sequences with at least 80%-identity to any one of said amino acid sequences.

In one embodiment, the prophylactic treatment is of a *S. suis* infection selected from the group of infections caused by any one of the 35 identified serotypes of *S. suis*. In another embodiment, said infection is selected from the group of infections caused by any one of serotypes 1, 2, 7, 9 and 1/2, such as the group of infections caused by any one of serotypes 1, 2 and 7, such as the group of infections caused by serotype 2 and 7. In one embodiment, said infection is caused by *S. suis* serotype 2 and in another embodiment said infection is cause by *S. suis* serotype 7. In one embodiment, there is provided an immunogenic polypeptide as described herein, for use in the prophylactic treatment of a *S. suis* infection, which immunogenic polypeptide fragment or fusion polypeptide is effective in the prophylactic treatment of infection caused by any one of at least 2, such as at least 3, such as at least 5, such as at least 7, such as at least 10 of the 35 identified serotypes.

As used herein, the term "prophylactic treatment" is a general term including anything between prevention of contracting the infection/disease and reduction of the severity of infection. The degree of prophylactic treatment can be measured in various ways, concerning e.g. *S. suis* infections in pigs the effect of the vaccine can be reduced clinical symptoms and reduced clinical disease. For example, reduced increase in temperature and reduced dissemination of bacteria from infected animals may be observed. Methods and procedures how to measure the efficacy of an immunizing composition after challenge are known to the person skilled in the art.

As used herein, the term "immunogenic" is used to refer to the properties of an immunogen, which is an entity capable of eliciting humoral and/or cell-mediated immune response. An immunogen first initiates an innate immune response, which then causes the activation of the adaptive immune response.

In contrast, the term "antigen" as used herein refers to an entity which has the potential to be immunogenic, however it is well established that not all antigens elicit immune responses. Thus, all immunogen molecules are also antigens, however the reverse is not true.

The skilled person is aware of the meaning of the term immunogenic, immunogen as well as antigenic and antigen.

As used herein, the term "fragment" of a molecule such as an immunogenic polypeptide fragment is meant to refer to a portion of the amino acid sequence of the full-length native polypeptide.

As used herein, the term "native polypeptide" is meant to refer to the form of a polypeptide which occurs in the nature and is as such not manipulated by molecular biology techniques. In the context of the present disclosure, native polypeptides include, but are not limited to, SSU0860, SSU1879, SSU1355 and SSU0496, corresponding to SEQ ID NO:2, 3, 4 and 1, respectively.

Thus, in one embodiment, there is provided an immunogenic polypeptide for use as described herein, wherein said polypeptide is selected from the group consisting of fragments of SEQ ID NO:4; fragments of SEQ ID NO:3; fragments of SEQ ID NO:2; a fragment comprising SEQ ID NO:5, provided the fragment comprising SEQ ID NO:5 is less than 500 amino acids long; a fragment comprising SEQ ID NO:6, provided the fragment comprising SEQ ID NO:6 is less than 500 amino acids long; and amino acid sequences with at least 80%-identity to any one of said fragments, such as the group consisting of fragments of SEQ ID NO:4; fragments of SEQ ID NO:3; fragments of SEQ ID NO:2; a fragment comprising SEQ ID NO:5, provided the fragment comprising SEQ ID NO:5 is less than 500 amino acids long; and amino acid sequences with at least 80%-identity to any one of said fragments, such as the group consisting of fragments of SEQ ID NO:4; fragments of SEQ ID NO:3; fragments of SEQ ID NO:2; SEQ ID NO:5; SEQ ID NO:38; and amino acid sequences with at least 80%-identity to any one of said fragments, such as the group consisting of fragments of SEQ ID NO:4; fragments of SEQ ID NO:3; fragments of SEQ ID NO:2; and amino acid sequences with at least 80%-identity to said fragments.

The skilled person will appreciate that said fragments suitably contain at least one immunogenic region. In one particular embodiment, said fragment is at least 100 amino acids long, such at least 200 amino acids long, such as at least 250 amino acids long, such as at least 300 amino acids long. In one embodiment said fragment is less than 500 amino acids long, such as less than 450 amino acids long, such as less than 400 amino acids long. In one embodiment, said fragment is at approximately 100-500 amino acids long, such as at approximately 200-500 amino acids long, such as at approximately 250-450 amino acids long.

In one embodiment, the immunogenic polypeptide as described herein is an N-terminal fragment and in another embodiment, said immunogenic polypeptide is a C-terminal fragment. As used herein, the term "N-terminal fragment" refers to a fragment which comprises at least one amino acid located within 50 amino acid residues from the N-terminus of SEQ ID NO:1, SEQ ID NO:2, SEQ ID NO:3 and SEQ ID NO:4. As used herein, the term "C-terminal fragment" refers to a fragment which comprises at least one amino acid located within 250 amino acid residues from the C-terminus of SEQ ID NO:1. As used herein, the term "C-terminal fragment" refers to a fragment which comprises at least one amino acid located within 50 amino acid residues from the C-terminus of SEQ ID NO:2, SEQ ID NO:3 and SEQ ID NO:4. Thus, in one embodiment, said immunogenic polypeptide is an N-terminal fragment comprising at least one amino acid located within 50 amino acid residues from the N-terminus of SEQ ID NO:1. In one embodiment said immunogenic polypeptide is a C-terminal fragment comprising at least one amino acid located within 50 amino acid residues from the N-terminus of SEQ ID NO:2, SEQ ID NO:3 or SEQ ID NO:3. In one embodiment said immunogenic polypeptide is a C-terminal fragment comprising at least one amino acid located within 50 amino acid residues from the N-terminus of SEQ ID NO:2. In one embodiment said immunogenic polypeptide is a C-terminal fragment comprising at least one amino acid located within 50 amino acid residues from the N-terminus of SEQ ID NO:3 and in another embodiment, said immunogenic polypeptide is a C-terminal fragment comprising at least one amino acid located within 50 amino acid residues from the N-terminus of SEQ ID NO:4.

In one particular embodiment, there is provided an immunogenic polypeptide for use as described herein, wherein said polypeptide is a fragment selected from the group consisting of fragments comprising SEQ ID NO:7 or SEQ ID NO:8; fragments comprising SEQ ID NO:9 or SEQ ID NO:10; fragments comprising SEQ ID NO:11 or SEQ ID NO:12; a fragment comprising SEQ ID NO:5, provided the fragment comprising SEQ ID NO:5 is less than 500 amino acids long; a fragment comprising SEQ ID NO:6, provided the fragment comprising SEQ ID NO:6 is less than 500 amino acids long; and amino acid sequences with at least 80%-identity to any one of said fragments, such as a fragment selected from the group consisting of fragments comprising SEQ ID NO:7 or SEQ ID NO:8; fragments comprising SEQ ID NO:9 or SEQ ID NO:10; fragments comprising SEQ ID NO:11 or SEQ ID NO:12; SEQ ID NO:5, SEQ ID NO:38 or SEQ ID NO:6; and amino acid sequences with at least 80%-identity to any one of said fragments, such as a fragment selected from the group consisting of fragments comprising SEQ ID NO:7 or SEQ ID NO:8; fragments comprising SEQ ID NO:9 or SEQ ID NO:10; fragments comprising SEQ ID NO:11 or SEQ ID NO:12; SEQ ID NO:5 or SEQ ID NO:38 ($M2_{long}$); and amino acid sequences with at least 80%-identity to any one of said fragments, such as a fragment selected from the group consisting of fragments comprising SEQ ID NO:7 or SEQ ID NO:8; fragments comprising SEQ ID NO:10; fragments comprising SEQ ID NO:12; SEQ ID NO:5; and amino acid sequences with at least 80%-identity to any one of said fragments.

In one embodiment, said fragment is selected from the group consisting of fragments comprising SEQ ID NO:7 or SEQ ID NO:8; fragments comprising SEQ ID NO:9 or SEQ ID NO:10; fragments comprising SEQ ID NO:11 or SEQ ID NO:12; a fragment comprising SEQ ID NO:5, provided the fragment comprising SEQ ID NO:5 is less than 500 amino acids long; and amino acid sequences with at least 80%-identity to any one of said fragments.

In one embodiment, said fragment is selected from the group consisting of fragments comprising SEQ ID NO:7 or SEQ ID NO:8; fragments comprising SEQ ID NO:10; fragments comprising SEQ ID NO:12; a fragment comprising SEQ ID NO:5, provided the fragment comprising SEQ ID NO:5 is less than 500 amino acids long; and amino acid sequences with at least 80%-identity to any one of said fragments.

In one embodiment, said fragment is selected from the group consisting of fragments comprising SEQ ID NO:8; fragments comprising SEQ ID NO:10; fragments comprising SEQ ID NO:12; a fragment comprising SEQ ID NO:5, provided the fragment comprising SEQ ID NO:5 is less than 500 amino acids long; and amino acid sequences with at least 80%-identity to any one of said fragments.

In one particular embodiment, said fragment is selected from the group consisting of fragments comprising SEQ ID NO:8; fragments comprising SEQ ID NO:10; fragments comprising SEQ ID NO:12; SEQ ID NO:5 or SEQ ID NO:38; and amino acid sequences with at least 80%-identity to any one of said fragments, such as a fragment selected from the group consisting of fragments comprising SEQ ID NO:8; fragments comprising SEQ ID NO:10; fragments comprising SEQ ID NO:12; and SEQ ID NO:5; and amino acid sequences with at least 80%-identity to any one of said fragments, such as a fragment selected from the group consisting of fragments comprising SEQ ID NO:8; fragments comprising SEQ ID NO:10; fragments comprising SEQ ID NO:12; and amino acid sequences with at least 80%-identity to any one of said fragments.

In one particular embodiment, there is provided an immunogenic polypeptide for use as described herein, wherein said immunogenic polypeptide is a fragment selected from the group consisting of SEQ ID NO:7 or SEQ ID NO:8; SEQ ID NO:9 or SEQ ID NO:10; SEQ ID NO:11 or SEQ ID NO:12; and SEQ ID NO:5, SEQ ID NO:38 or SEQ ID NO:6; and amino acid sequences with at least 80%-identity to any one of said fragments, such as the group consisting of SEQ ID NO:7 or SEQ ID NO:8; SEQ ID NO:9 or SEQ ID NO:10; SEQ ID NO:11 or SEQ ID NO:12; SEQ ID NO:5 or SEQ ID NO:38; and amino acid sequences with at least 80%-identity to any one of said fragments, such as the group consisting SEQ ID NO:7 or SEQ ID NO:8; SEQ ID NO:10; SEQ ID NO:12; SEQ ID NO:5 or SEQ ID NO:38; and amino acid sequences with at least 80%-identity to any one of said fragments. In one embodiment, said fragment is selected from the group consisting of SEQ ID NO:8; SEQ ID NO:10; SEQ ID NO:12; SEQ ID NO:5; and amino acid sequences with at least 80%-identity to any one of said fragments. In another embodiment, said fragment is selected from the group consisting of SEQ ID NO:8; SEQ ID NO:10; SEQ ID NO:12; and amino acid sequences with at least 80%-identity to any one of said fragments.

In one embodiment, said fragment is SEQ ID NO:8 or a fragment with at least 80%-identity thereto. In another embodiment, said fragment is SEQ ID NO:10 or a fragment with at least 80%-identity thereto. In one embodiment, said fragment is SEQ ID NO:12 or a fragment with at least 80%-identity thereto. In one embodiment, said fragment is SEQ ID NO:5 or a fragment with at least 80%-identity thereto and in yet another embodiment said fragment is SEQ ID NO:38 or a fragment with at least 80%-identity thereto. In one embodiment, said fragment is SEQ ID NO:8; in another embodiment, said fragment is SEQ ID NO:10; in one embodiment, said fragment is SEQ ID NO:12; in one embodiment, said fragment is SEQ ID NO:5 and in yet another embodiment said fragment is SEQ ID NO:8.

It will be appreciated that polypeptides comprising minor changes as compared to the above amino acid sequences corresponding to SEQ ID NO:7, 8, 9, 10, 11, 12, 5, 38 and 6 without largely affecting immunogenicity are also within the scope of the present disclosure. Thus, in some embodiments, immunogenic polypeptide fragment as defined above may for example have a sequence which is at least 80% identical to the sequence of the corresponding fragment. In some embodiments, the polypeptide may comprise a sequence which is at least 81%, such as at least 82% such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 93%, such as at least 95%, such as at least 96%, such as at least 97%, such as at least 98% or such as at least 99 identical to said corresponding fragment.

The skilled person will understand that various modifications and/or additions can be made to an immunogenic polypeptide as defined herein, in order to tailor the polypeptide to a specific application without departing from the scope of the present disclosure. For example, an immunogenic polypeptide as defined herein may comprise additional amino acid residues for the purpose of improving production, purification and/or stabilization in vivo or in vitro of the polypeptide. Thus, an immunogenic polypeptide may comprise any suitable number of additional amino acid residues, for example at least one additional amino acid residue. Each additional amino acid residue may individually or collectively be added in order to, for example, improve production, purification, solubility and/or stabilization in vivo or in vitro. Such additional amino acid residues may also provide a "tag" for purification, such as a His-tag (also referred to herein as "—H" (such as for example a $His_6$-tag or a $His_7$-tag) or a "myc" (c-myc) tag or a "FLAG" tag for interaction with antibodies specific to the tag or immobilized metal affinity chromatography (IMAC) in the case of the His_-tag. The additional amino acid residues may also comprise a SL2-tag (SEQ ID NO:32) or LSL-tag (SEQ ID NO:33) as described herein.

Thus, in one embodiment, there is provided an immunogenic polypeptide for use as described herein, wherein said immunogenic polypeptide or fragment thereof further comprises additional amino acid residues at the N- and/or C-terminus of said fragment. Such an immunogenic polypeptide should be understood as a polypeptide having one or more additional amino acid residues at the very first and/or the very last position in the polypeptide chain, i.e. at the N- and/or C-terminus. For the sake of clarity, the presence of an additional amino acid residue at the N- and/or C-terminus of said immunogenic polypeptide does not preclude the presence of additional N- or C-terminal extensions, for example in the form a "tag" for purification as described above.

For example, in the case where the immunogenic polypeptide is selected from immunogenic polypeptides or fragments as defined herein, said additional amino acid residue at the N-terminus may be a methionine. Thus, in one embodiment, there is provided an immunogenic polypeptide as described herein, wherein said fragment comprises a methionine residue at the N-terminus. In one embodiment, said fragment comprises the amino acid residues MT, MTG or MTGS at the N-terminus. In one embodiment said fragment of comprises the amino acid residues LE at the C-terminus.

In one embodiment, there is provided an immunogenic polypeptide as described herein, wherein said additional amino acid residue(s) at the N-terminus and/or C-terminus or at the N-terminal and/or C-terminal improve production, purification and/or stabilization in vivo or in vitro of said immunogenic polypeptide.

In one embodiment, said additional amino acid residue(s) improve for purification of said immunogenic polypeptide. The additional amino acid residue(s) comprise a tag, such as a tag selected from the group consisting of a His_-tag, a "myc" (c-myc) tag, a SL2-tag (SEQ ID NO:32) or LSL-tag (SEQ ID NO:33) and a "FLAG" tag.

In one particular embodiment, said immunogenic polypeptide for use as described herein further comprises an amino acid sequence capable of binding to silica. In one embodiment, said amino acid sequence capable of binding to silica is selected from SEQ ID NO:32, SEQ ID NO:33 and amino acids sequences with at least 80%-identity to SEQ ID NO:32 or SEQ ID NO:33. In some embodiments, the amino acid sequence capable of binding to silica may exhibit at least 81%, such as at least 82% such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 93%, such as at least 95%, such as at least 96%, such as at least 97%, such as at least 98% or such as at least 99% sequence identity with SEQ ID NO:32 or SEQ ID NO:33.

In one embodiment, said amino acid sequence capable of binding to silica is SEQ ID NO:32. In another embodiment, said amino acid sequence capable of binding to silica is SEQ ID NO:33.

For the sake of clarity, the presence of additional amino acid residues at the N- and/or C-terminus of said immunogenic polypeptide does not preclude the presence of additional N- or C-terminal extensions, for example in the form a "tag" for purification as described above.

In one particular embodiment, said fragment may comprise the residues LE and the SL2-tag (SEQ ID NO:32) at the C-terminus and the amino acid residues MTGS at the N-terminus. In another embodiment, said fragment may comprise the amino acid residues MT, a His-tag and the amino acid residues GS at the N-terminus or the amino acid residues MTGS followed by the His-tag at the N-terminus.

In a second aspect of the present disclosure, there is provided a immunogenic polypeptide fragment, comprising an amino acid sequence selected from i) an amino acid sequence selected the group consisting of SEQ ID NO: 7, SEQ ID NO:8, SEQ ID NO:9, SEQ ID NO:10, SEQ ID NO:11 and SEQ ID NO:12, and,
ii) an amino acid sequence with at least 80%-identity to an amino acid sequence defined in i).

In a third aspect of the present disclosure, there is provided a immunogenic polypeptide fragment, comprising an amino acid sequence selected from iii) an amino acid sequence selected the group consisting of SEQ ID NO:5, SEQ ID NO:38, SEQ ID NO:6, SEQ ID NO:7, SEQ ID NO:8, SEQ ID NO:9, SEQ ID NO:10, SEQ ID NO:11 and SEQ ID NO:12, and, iv) an amino acid sequence with at least 80%-identity to an amino acid sequence defined in iii), for use in the prophylactic treatment of a *S. suis* infection.

In one embodiment, said fragment is at approximately 100-500 amino acids long, such as at approximately 200-500 amino acids long, such as at approximately 250-450 amino acids long.

The skilled person will appreciate that the following disclosure is equally relevant in the context of the second and third aspects described herein. Thus, the skilled person will appreciate that any of said fragments may be immunogenic, provided it comprises at least one immunogenic region. Again, polypeptides comprising minor changes as compared to the above amino acid sequences corresponding to SEQ ID NO:7, 8, 9, 10, 11, 12, 5, 38 and 6 without largely affecting immunogenicity are also within the scope of the present disclosure. Thus, in some embodiments, immunogenic polypeptide fragment as defined above may for example have a sequence which is at least 80% identical to the sequence defined by i) or iii). In some embodiments, the polypeptide may comprise a sequence which is at least 81%, such as at least 82% such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 93%, such as at least 95%, such as at least 96%, such as at least 97%, such as at least 98% or such as at least 99% identical to said to the sequence defined by i) or iii).

In one embodiment there is provided an immunogenic polypeptide fragment, wherein the sequence iii) is selected from the group consisting of SEQ ID NO:5, SEQ ID NO:38, SEQ ID NO:8, SEQ ID NO:10 and SEQ ID NO:12, such as the group consisting of SEQ ID NO:5, SEQ ID NO:8, SEQ ID NO:10 and SEQ ID NO:12. In one embodiment, there is provided an immunogenic polypeptide fragment, wherein the sequence i) or iii) is selected from the group consisting of SEQ ID NO:8, SEQ ID NO:10 and SEQ ID NO:12, such as the group consisting of SEQ ID NO:10 and SEQ ID NO:12, such as the group consisting of SEQ ID NO:8 and SEQ ID NO:12, such as the group consisting of SEQ ID NO:8 and SEQ ID NO:10. In one embodiment, there is provided an immunogenic polypeptide fragment, wherein the sequence i) or iii) is SEQ ID NO:8, SEQ ID NO:10 or SEQ ID NO:12. In one embodiment, there is provided an immunogenic polypeptide fragment, wherein the sequence iii) is SEQ ID NO:5.

The skilled person will appreciate that fragments of any one of SP2, SP4 and SP7 (for example SP2N, SP2C, SP4N, SP4C, SP7N or SP7C) or fragment comprising M2N or M2C (for example M2N, $M2N_{long}$ or M2C), provided said fragments are less than 500 amino acids long, may be arranged in the form of a fusion polypeptide and that such fusion polypeptides may exhibit equally good or better immunogenic properties compared to said fragments individually. For example, such fusion polypeptides may comprise two or more immunogenic regions. As used herein, the term "fusion polypeptide" refers to a polypeptide comprising a least two units which are derived from different native polypeptides or proteins.

Thus, in a first embodiment of the fourth aspect disclosed herein, there is provided a fusion polypeptide comprising a) a first immunogenic polypeptide unit, and b) a second immunogenic polypeptide unit, wherein at least one of said first and second immunogenic polypeptide units is selected from the group consisting of fragments of SEQ ID NO:4, fragments of SEQ ID NO:3, fragments of SEQ ID NO:2, a fragment comprising SEQ ID NO:5, provided the fragment comprising SEQ ID NO:5 is less than 500 amino acids long; a fragment comprising SEQ ID NO:6, provided the fragment comprising SEQ ID NO:6 is less than 500 amino acids long; and amino acid sequences with at least 80%-identity to any one of said fragments, such as the group consisting of fragments of SEQ ID NO:4, fragments of SEQ ID NO:3, fragments of SEQ ID NO:2, a fragment comprising SEQ ID NO:5, provided the fragment comprising SEQ ID NO:5 is less than 500 amino acids long, and amino acid sequences with at least 80%-identity to any one of said fragments. In one embodiment, said first and second immunogenic polypeptide units are selected from the group consisting of fragments comprising the group consisting of fragments of SEQ ID NO:4; fragments of SEQ ID NO:3; fragments of SEQ ID NO:2; SEQ ID NO:5; SEQ ID NO:38; SEQ ID NO:6, and amino acid sequences with at least 80%-identity to any one of said fragments, provided that said first and said second immunogenic polypeptide units are from different native proteins. In one embodiment, at least one of said first and second immunogenic polypeptide units is a immunogenic polypeptide fragment selected from the group consisting of fragments of SEQ ID NO:4; fragments of SEQ ID NO:3; fragments of SEQ ID NO:2; SEQ ID NO:5; and SEQ ID NO:38, and amino acid sequences with at least 80%-identity to any one of said fragments. In one embodiment, at least one of said first and second immunogenic polypeptide units is immunogenic polypeptide fragment selected from the group consisting of fragments of SEQ ID NO:4; fragments of SEQ ID NO:3 and fragments of SEQ ID NO:2; and amino acid sequences with at least 80%-identity to any one of said fragments.

In one embodiment of the this aspect, there is provided a fusion polypeptide comprising c) a first immunogenic polypeptide unit, and d) a second immunogenic polypeptide unit, wherein said first and second immunogenic polypeptide units are selected from the group consisting of fragments of SEQ ID NO:4, fragments of SEQ ID NO:3, fragments of SEQ ID NO:2, a fragment comprising SEQ ID NO:5, provided the fragment comprising SEQ ID NO:5 is less than 500 amino acids long; a fragment comprising SEQ ID NO:6, provided the fragment comprising SEQ ID NO:6 is less than 500 amino acids long; and amino acid sequences with at least 80%-identity to any one of said fragments, such as the group consisting of fragments of SEQ ID NO:4, fragments of SEQ ID NO:3, fragments of SEQ ID NO:2, a fragment comprising SEQ ID NO:5, provided the fragment comprising SEQ ID NO:5 is less than 500 amino acids long, and amino acid sequences with at least 80%-identity to any one of said fragments. In one embodiment, said first and second immunogenic polypeptide units are selected from the group consisting of fragments comprising the group consisting of fragments of SEQ ID NO:4; fragments of SEQ ID NO:3; fragments of SEQ ID NO:2; SEQ ID NO:5; SEQ ID NO:38; SEQ ID NO:6, and amino acid sequences with at least 80%-identity to any one of said fragments, provided that said first and said second immunogenic polypeptide units are from different native proteins. In one embodiment, said first and second immunogenic polypeptide units are immunogenic polypeptide fragments selected from the group consisting of fragments of SEQ ID NO:4; fragments of SEQ ID NO:3; fragments of SEQ ID NO:2; SEQ ID NO:5; and SEQ ID NO:38, and amino acid sequences with at least 80%- identity to any one of said fragments. In one embodiment, said first and second immunogenic polypeptide units are immunogenic polypeptide fragments selected from the group consisting of fragments of SEQ ID NO:4; fragments of SEQ ID NO:3 and fragments of SEQ ID NO:2; and amino acid sequences with at least 80%-identity to any one of said fragments.

In one particular embodiment, there is provided a fusion polypeptide as defined herein, further comprising a third immunogenic polypeptide unit, which unit is selected from the units defined above, provided that said third immunogenic polypeptide unit is from a different native proteins than said first and second immunogenic polypeptide units. To clarify, any two of said first, second and third polypeptide units may not be from the same native protein, or be derived from said native proteins. As used herein, the term "derived from a native protein" encompasses polypeptides exhibiting more than 80 identity with native proteins or a corresponding fragment thereof. Non-limiting examples of fusion polypeptides comprising three units are SEQ ID NO:107 and 108. Also SEQ ID NO:109 and 110 are examples of fusion polypeptides comprising three units.

For the sake of clarity, the designation of first, second and third immunogenic polypeptide unit as used throughout the present disclosure is made for clarity reasons to distinguish between them, and is not intended to refer to the actual order of the immunogenic polypeptide unit in the polypeptide chain of the fusion polypeptide. Thus, for example, said first immunogenic polypeptide unit may appear N-terminally or C-terminally in a polypeptide chain, with respect to said second and third immunogenic polypeptide units, respectively.

In one particular embodiment, said immunogenic polypeptide units are, independently of each other, at least 100 amino acids long, such as at least 200 amino acids long, such as at least 250 amino acids long, such as at least 300 amino acids long. In one embodiment said immunogenic peptide units are, independently of each other, less than 500 amino acids long, such as less than 450 amino acids long, such as less than 400 amino acids long. In one embodiment, each of the first, second immunogenic and optionally third polypeptide unit are, independently of each other, approximately 100-500 amino acids long, such as approximately 200-500 amino acids long, such as approximately 250-450 amino acids long.

In one embodiment, said first, second and optional third immunogenic polypeptide units are selected from the group consisting of fragments comprising SEQ ID NO:7 or SEQ ID NO:8; fragments comprising SEQ ID NO:9 or SEQ ID NO:10; fragments comprising SEQ ID NO:11 or SEQ ID NO:12; a fragment comprising SEQ ID NO:5, provided the fragment comprising SEQ ID NO:5 is less than 500 amino acids long and; a fragment comprising SEQ ID NO:6, provided the fragment comprising SEQ ID NO:6 is less than 500 amino acids long; and amino acid sequences with at least 80%-identity to any one of said fragments, such as the group consisting of fragments comprising SEQ ID NO:7 or SEQ ID NO:8; fragments comprising SEQ ID NO:9 or SEQ ID NO:10; fragments comprising SEQ ID NO:11 or SEQ ID NO:12; a fragment comprising SEQ ID NO:5, provided the fragment comprising SEQ ID NO:5 is less than 500 amino acids long; and amino acid sequences with at least 80%-identity to any one of said fragments, such as the group consisting of fragments comprising SEQ ID NO:7 or SEQ ID NO:8; fragments comprising SEQ ID NO:10; fragments comprising SEQ ID NO:12; a fragment comprising SEQ ID NO:5, provided the fragment comprising SEQ ID NO:5 is less than 500 amino acids long; and amino acid sequences with at least 80%-identity to any one of said fragments, such as the group consisting of fragments comprising SEQ ID NO:8; fragments comprising SEQ ID NO:10; fragments comprising SEQ ID NO:12; a fragment comprising SEQ ID NO:5, provided the fragment comprising SEQ ID NO:5 is less than 500 amino acids long; and amino acid sequences with at least 80%-identity to any one of said fragments, such as the group consisting of fragments comprising SEQ ID NO:8; fragments comprising SEQ ID NO:10; fragments comprising SEQ ID NO:12; and amino acid sequences with at least 80%-identity to any one of said fragments.

In one embodiment, said first, second and optional third immunogenic polypeptide units are selected from the group consisting of fragments SEQ ID NO:5, SEQ ID NO:38, SEQ ID NO:6, SEQ ID NO:7, SEQ ID NO:8, SEQ ID NO:9, SEQ ID NO:10, SEQ ID NO:11 and SEQ ID NO:12, and amino acid sequences with at least 80%-identity to any one of said fragments, such as the group consisting of fragments SEQ ID NO:5, SEQ ID NO:38, SEQ ID NO:7, SEQ ID NO:8, SEQ ID NO:9, SEQ ID NO:10, SEQ ID NO:11 and SEQ ID NO:12, and amino acid sequences with at least 80%-identity to any one of said fragments, such as the group consisting of fragments SEQ ID NO:5, SEQ ID NO:38, SEQ ID NO:7, SEQ ID NO:8, SEQ ID NO:10, and SEQ ID NO:12, and amino acid sequences with at least 80%-identity to any one of said fragments, such as the group consisting of fragments SEQ ID NO:5, SEQ ID NO:38, SEQ ID NO:8, SEQ ID NO:10, and SEQ ID NO:12, and amino acid sequences with at least 80%-identity to any one of said fragments, such as the group consisting of fragments SEQ ID NO:8, SEQ ID NO:10, and SEQ ID NO:12, and amino acid sequences with at least 80%-identity to any one of said fragments.

In one embodiment, there is provided a fusion polypeptide as described herein selected from the group consisting of fusion polypeptides comprising SEQ ID NO:9 and SEQ ID NO:7; fusion polypeptides comprising SEQ ID NO:10 and SEQ ID NO:7; fusion polypeptides comprising SEQ ID NO:11 and SEQ ID NO:7; fusion polypeptides comprising SEQ ID NO:12 and SEQ ID NO:7; fusion polypeptides comprising SEQ ID NO:5 and SEQ ID NO:7; fusion polypeptides comprising SEQ ID NO:38 and SEQ ID NO:7; fusion polypeptides comprising SEQ ID NO:6 and SEQ ID NO:7; fusion polypeptides comprising SEQ ID NO:9 and SEQ ID NO:8; fusion polypeptides comprising SEQ ID NO:10 and SEQ ID NO:8; fusion polypeptides comprising SEQ ID NO:11 and SEQ ID NO:8; fusion polypeptides comprising SEQ ID NO:12 and SEQ ID NO:8; fusion polypeptides comprising SEQ ID NO:5 and SEQ ID NO:8; SEQ ID NO:38 and SEQ ID NO:8; SEQ ID NO:6 and SEQ ID NO:8; fusion polypeptides comprising SEQ ID NO:11 and SEQ ID NO:9; fusion polypeptides comprising SEQ ID NO:12 and SEQ ID NO:9; fusion polypeptides comprising SEQ ID NO:5 and SEQ ID NO:9; fusion polypeptides comprising SEQ ID NO:38 and SEQ ID NO:9; fusion polypeptides comprising SEQ ID NO:6 and SEQ ID NO:9; fusion polypeptides comprising SEQ ID NO:11 and SEQ ID NO:10; fusion polypeptides comprising SEQ ID NO:12 and SEQ ID NO:10; fusion polypeptides comprising SEQ ID NO:5 and SEQ ID NO:10; fusion polypeptides comprising SEQ ID NO:38 and SEQ ID NO:10; fusion polypeptides comprising SEQ ID NO:6 and SEQ ID NO:10; fusion polypeptides comprising SEQ ID NO:5 and SEQ ID NO:11; fusion polypeptides comprising SEQ ID NO:38 and SEQ ID NO:11; fusion polypeptides comprising SEQ ID NO:6 and SEQ ID NO:11; fusion polypeptides comprising SEQ ID NO:5 and SEQ ID NO:12; SEQ ID NO:38 and SEQ ID NO:12; and fusion polypeptides comprising SEQ ID NO:6 and SEQ ID NO:12, such as the group consisting of fusion polypeptides comprising SEQ ID NO:9 and SEQ ID NO:7; fusion polypeptides comprising SEQ ID NO:10 and SEQ ID NO:7; fusion polypeptides comprising SEQ ID NO:11 and SEQ ID NO:7; fusion polypeptides comprising SEQ ID NO:12 and SEQ ID NO:7; fusion polypeptides comprising SEQ ID NO:5 and SEQ ID NO:7; fusion polypeptides comprising SEQ ID NO:6 and SEQ ID NO:7; fusion polypeptides comprising SEQ ID NO:9 and SEQ ID NO:8; fusion polypeptides comprising SEQ ID NO:10 and SEQ ID NO:8; fusion polypeptides comprising SEQ ID NO:11 and SEQ ID NO:8; fusion polypeptides comprising SEQ ID NO:12 and SEQ ID NO:8; fusion polypeptides comprising SEQ ID NO:5 and SEQ ID NO:8; fusion polypeptides comprising SEQ ID NO:6 and SEQ ID NO:8; fusion polypeptides comprising SEQ ID NO:11 and SEQ ID NO:9; fusion polypeptides comprising SEQ ID NO:12 and SEQ ID NO:9; fusion polypeptides comprising SEQ ID NO:5 and SEQ ID NO:9; fusion polypeptides comprising SEQ ID NO:6 and SEQ ID NO:9; fusion polypeptides comprising SEQ ID NO:11 and SEQ ID NO:10; fusion polypeptides comprising SEQ ID NO:12 and SEQ ID NO:10; fusion polypeptides comprising SEQ ID NO:5 and SEQ ID NO:10; fusion polypeptides comprising SEQ ID NO:6 and SEQ ID NO:10; fusion polypeptides comprising SEQ ID NO:5 and SEQ ID NO:11; fusion polypeptides comprising SEQ ID NO:6 and SEQ ID NO:11; fusion polypeptides comprising SEQ ID NO:5 and fusion polypeptides comprising SEQ ID NO:12; and SEQ ID NO:6 and SEQ ID NO:12, such as the group consisting of fusion polypeptides comprising SEQ ID NO:10 and SEQ ID NO:8; fusion polypeptides comprising SEQ ID NO:5 and SEQ ID NO:12; fusion polypeptides comprising SEQ ID NO:5 and SEQ ID NO:10; fusion polypeptides comprising SEQ ID NO:8 and SEQ ID NO:12; SEQ ID NO:8 and fusion polypeptides comprising SEQ ID NO:5 or SEQ ID NO:38; and fusion polypeptides comprising SEQ ID NO:12 and SEQ ID NO:10, such as the group consisting of fusion polypeptides comprising SEQ ID NO:10 and SEQ ID NO:8; fusion polypeptides comprising SEQ ID NO:8 and SEQ ID NO:5; fusion polypeptides comprising SEQ ID NO:8 and SEQ ID NO:38; and fusion polypeptides comprising SEQ ID NO:12 and SEQ ID NO:10, such as the group consisting of fusion polypeptides comprising SEQ ID NO:8 and SEQ ID NO:5; fusion polypeptides comprising SEQ ID NO:8 and SEQ ID NO:38; and fusion polypeptides comprising SEQ ID NO:12 and SEQ ID NO:10.

In one embodiment, said fusion polypeptide comprises SEQ ID NO:8 and SEQ ID NO:5. In one embodiment, said fusion polypeptide comprises SEQ ID NO:8 and SEQ ID NO:38. In another embodiment, said fusion polypeptide comprises SEQ ID NO:12 and SEQ ID NO:10.

In one particular embodiment of the fusion polypeptide disclosed herein, said fusion polypeptide comprises an amino acid sequence selected from the group consisting of SEQ ID NO:92, SEQ ID NO:93, SEQ ID NO:94, SEQ ID NO:95, SEQ ID NO:96, SEQ ID NO:34, SEQ ID NO:35 and any of said fusion polypeptides wherein at least one of said units exhibits at least 80%-identity to any one of SEQ ID NO:8, SEQ ID NO:10, SEQ ID NO:12 or SEQ ID NO:5. In one embodiment, said fusion polypeptide comprises a amino acid sequence selected from the group consisting of SEQ ID NO:34; SEQ ID NO:35; SEQ ID NO:92 and any of said fusion polypeptides wherein at least one of said units exhibits at least 80%-identity to any one of SEQ ID NO:8, SEQ ID NO:10, SEQ ID NO:12 and SEQ ID NO:5, such as the group consisting SEQ ID NO:34; SEQ ID NO:35, and any of said fusion polypeptides wherein at least one of said units exhibits at least 80%-identity to any one of SEQ ID NO:8, SEQ ID NO:10, SEQ ID NO:12 and SEQ ID NO:5.

As mentioned above, within the scope of the present disclosure there are fusion polypeptides comprising three or four immunogenic polypeptide fragments or units as described herein. Thus, in one embodiment said fusion polypeptide comprises three or four of the immunogenic polypeptide fragments as disclosed herein. In one particular embodiment, said fusion polypeptide comprises SEQ ID NO:5, SEQ ID NO:8 and SEQ ID NO:12 or an immunogenic polypeptide fragments which exhibits at least 80%-identity to any one of SEQ ID NO:5, SEQ ID NO:8 and SEQ ID NO:12. In one particular embodiment, said fusion polypeptide comprises SEQ ID NO:5, SEQ ID NO:8 and SEQ ID NO:12. In one embodiment, said fusion polypeptide comprises SEQ ID NO:5, SEQ ID NO:10 and SEQ ID NO:12 or an immunogenic polypeptide fragments which exhibits at least 80%-identity to any one of SEQ ID NO:5, SEQ ID NO:10 and SEQ ID NO:12. In one embodiment, said fusion polypeptide comprises SEQ ID NO:5, SEQ ID NO:10 and SEQ ID NO:12. In one embodiment, said fusion polypeptide comprises SEQ ID NO:8, SEQ ID NO:10 and SEQ ID NO:12 or an immunogenic polypeptide fragments which exhibits at least 80%-identity to any one of SEQ ID NO:8, SEQ ID NO:10 and SEQ ID NO:12. In one embodiment, said fusion polypeptide comprises SEQ ID NO:8, SEQ ID NO:10 and SEQ ID NO:12. To clarify, the present disclosure encompasses fusion polypeptides, wherein one, two, three or four units exhibit at least 80%-identity to the aforementioned units. Thus, in one embodiment, said fusion polypeptide comprises an immunogenic polypeptide unit with at least 80%-identity with SEQ ID NO:8, an immunogenic polypeptide unit with at least 80%-identity with SEQ ID NO:10 and an immunogenic polypeptide unit with at least 80%-identity with SEQ ID NO:12, preferably comprising an immunogenic polypeptide unit with 100%-identity with SEQ ID NO:8, an immunogenic polypeptide unit with 100%-identity with SEQ ID NO:10 and an immunogenic polypeptide unit with 100%-identity with SEQ ID NO:12. To clarify, in the context of the fusion polypeptide, the term unit refers to a immunogenic polypeptide fragment. In other words, the fusion polypeptide may comprises an immunogenic polypeptide fragment with at least 80%-identity with SEQ ID NO:8, an immunogenic polypeptide fragment with at least 80%-identity with SEQ ID NO:10 and an immunogenic polypeptide fragment with at least 80%-identity with SEQ ID NO:12, preferably comprising an immunogenic polypeptide fragment with 100%-identity with SEQ ID NO:8, an immunogenic polypeptide fragment with 100%-identity with SEQ ID NO:10 and an immunogenic polypeptide fragment with 100%-identity with SEQ ID NO:12.

For example, said fusion polypeptide may comprise SEQ ID NO:8, SEQ ID NO:10 and a polypeptide which exhibits at least 80% identity to SEQ ID NO:12; or said fusion polypeptide may comprise SEQ ID NO:8, a polypeptide which exhibits at least 80% identity to SEQ ID NO:10 and a polypeptide which exhibits at least 80% identity to SEQ ID NO:12; or said fusion polypeptide may comprise polypeptide which exhibits at least 80 identity to SEQ ID NO:8, a polypeptide which exhibits at least 80% identity to SEQ ID NO:10 and a polypeptide which exhibits at least 80% identity to SEQ ID NO:12. Thus, encompassed herein are fusion polypeptides wherein one, two or three polypeptide units exhibit at least 80% identity to SEQ ID NO:8, 10 and/or 12. In particular embodiment, said fusion polypeptide comprises SEQ ID NO:35 and SEQ ID NO:8. In one embodiment, the SEQ ID NO:8 is located N-terminally in respect of SEQ ID NO:35. In another embodiment, the SEQ ID NO:8 is located C-terminally in respect of SEQ ID NO:35. In one embodiment, said fusion comprises SEQ ID NO:107 or SEQ ID NO:108 or a polypeptide which exhibits at least 80%-identity thereto. In one embodiment, said fusion comprises SEQ ID NO:109 or SEQ ID NO:110 or a polypeptide which exhibits at least 80%-identity thereto.

In one embodiment, said fusion polypeptide comprises SEQ ID NO:109 or SEQ ID NO:110. In one embodiment, there is provided a fusion polypeptide selected from the group consisting of SEQ ID NO:107, 108, 109, 110 and amino acid sequences which exhibit at least 80%-identity to any one of SEQ ID NO:107, 108, 109 and 110. In one embodiment, the fusion polypeptide is selected from the group consisting of SEQ ID NO:107, 109 and amino acid sequences which exhibit at least 80%-identity to any one of SEQ ID NO:107 and 109. In one embodiment, the fusion polypeptide is selected from the group consisting of SEQ ID NO:108, 110 and amino acid sequences which exhibit at least 80%-identity to any one of SEQ ID NO:108 and 110.

The skilled person will appreciate that the above statements regarding sequence identity and %-identity are equally applicable in the present context and are not repeated for the sake of brevity.

As the skilled person understands, the construction of a fusion polypeptide often involves the use of linkers between functional moieties to be fused. The skilled person is aware of different kinds of linkers with different properties, such as flexible amino acid linkers, rigid amino acid linkers and cleavable amino acid linkers. Linkers have been used to for example increase stability or improve folding of fusion polypeptides, to increase expression, improve biological activity, enable targeting and alter pharmacokinetics of fusion polypeptides.

Thus, in one embodiment of the first aspect, there is provided a fusion polypeptide as defined herein, wherein said linker is selected from the group consisting of flexible amino acid linkers, rigid amino acid linkers and cleavable amino acid linkers. In one embodiment of a fusion polypeptide as defined herein, said linker is arranged between the first immunogenic polypeptide fragment and the second immunogenic polypeptide fragment. The skilled person will appreciate that the presence of a linker arranged between the first immunogenic polypeptide fragment and the immunogenic polypeptide fragment unit does not exclude the presence of additional linkers.

Flexible linkers are often used in the art when the joined domains require a certain degree of movement or interaction, and may be particularly useful in some embodiments of the fusion polypeptide as described herein. Such linkers are generally composed of small, non-polar (for example G) or polar (for example S or T) amino acids. Some flexible linkers primarily consist of stretches of G and S residues, for example $(GGGGS)_p$ and $(SSSSG)_p$. Adjusting the copy number "p" allows for optimization of the linker in order to achieve appropriate separation between the functional moieties or to maintain necessary inter-moiety interaction. Apart from G and S linkers, other flexible linkers are known in the art, such as G and S linkers containing additional amino acid residues, such as T, A, K and E, to maintain flexibility, as well as polar amino acid residues to improve solubility.

Additional non-limiting examples of linkers include GGGGSLVPRGSGGGGS (SEQ ID NO:113), $(GS)_3$ (SEQ ID NO:14), $(GS)_4$ (SEQ ID NO:115), $(GS)_8$ (SEQ ID NO:116), GGSGGHMGSGG (SEQ ID NO:117), GGSGGSGGSGG (SEQ ID NO:118), GGSGG (SEQ ID NO:119), GGSGGGGG (SEQ ID NO:120), GGGSEGGGSEGGGSEGGG (SEQ ID NO:121), AAGAATAA (SEQ ID NO:122), GGGGG (SEQ ID NO:123), GGSSG (SEQ ID NO:124), GSGGGTGGGSG (SEQ ID NO:125), GSGGGTGGGSG (SEQ ID NO:126), GT, GSGSGSGSGGSG (SEQ ID NO:127), GSGGSGGSGGSGGS (SEQ ID NO:128) and GSGGSGSGGSGGSG (SEQ ID NO:129). The skilled person is aware of other suitable linkers.

In one embodiment, said linker is a flexible linker comprising glycine (G), serine (S) and/or threonine (T) residues. In one embodiment, said linker has a general formula selected from $(G_nS_m)_p$ and $(S_mG_n)_p$, wherein, independently, n=1-7, m=0-7, n+m 8 and p=1-7. In one embodiment, n=1-5. In one embodiment, m=0-5. In one embodiment, p=1-5. In a more specific embodiment, n=4, m=1 and p=1-4. In one embodiment, said linker is selected from the group consisting of $5_4G$, $(5_4G)_3$ and $(5_4G)_4$. In one embodiment, said linker is selected from the group consisting of $G_4S$ and $(G_4S)_3$. In one particular embodiment, said linker is $G_4S$ and in another embodiment said linker is $(G_4S)_3$. In one embodiment, said linker has the general formula $(G_eT_f)_q$, wherein, independently, e=1-3, f=1-3, and q=1-4. In one embodiment, q=1-3. In a more specific embodiment, e=1, f=1 and q=1-3. In one embodiment, said linker is selected from the group consisting of GT, $(GT)_2$ and $(GT)_3$. In one embodiment, said linker is GT. In one embodiment, the linker is EF.

It will be appreciated that the immunogenic polypeptide fragment as described herein and the fusion polypeptide as described herein, may further comprise additional amino acid residues at the N- and/or C-terminus and that the description of possible additional amino acid residues in the context of the first aspect of the present disclosure is equally relevant for the second, third and fourth aspects. For the sake of brevity these will not be repeated here or will only be briefly mentioned.

Thus, in one embodiment there is provided an immunogenic polypeptide fragment or a fusion polypeptide as described herein, wherein said fragment or fusion polypeptide further comprises additional amino acid residues at the N- and/or C-terminus. In one embodiment, said immunogenic polypeptide fragment or fusion polypeptide, comprises a methionine residue at the N-terminus. In one embodiment, said immunogenic polypeptide fragment or fusion polypeptide, comprises the amino acids residues MT, MTG or MTGS at the N-terminus. In one embodiment, said additional amino acid residue(s) comprise a tag, such as a tag selected from the group consisting of a His-tag, a "myc" (c-myc) tag, a SL-tag (SEQ ID NO:32), a LSL-tag (SEQ ID NO:33) and a "FLAG" tag. In another embodiment, said immunogenic polypeptide fragment or fusion polypeptide, comprises an amino acid sequence capable of binding to silica. In one embodiment, said immunogenic polypeptide fragment or fusion polypeptide, comprises an amino acid sequence selected from SEQ ID NO:32, SEQ ID NO:33 and amino acids sequences with at least 80%-identity to SEQ ID NO:32 or 33, such as wherein said amino acid sequence is SEQ ID NO:32 or 33. In one embodiment, said amino acid sequence capable of binding to silica SEQ ID NO:32. In another embodiment, said amino acid sequence capable of binding to silica SEQ ID NO:33.

The skilled person will appreciate that the immunogenic polypeptide fragment or fusion polypeptide described herein may be useful as a medicament, for example as a medicament for use prophylactic treatment of a *S. suis* infection, such as in vaccination. Thus in one embodiment, there is provided an immunogenic polypeptide fragment or fusion polypeptide as defined herein, for use as a medicament. In another embodiment, there is said immunogenic polypeptide fragment or said fusion polypeptide may be used in the prophylactic treatment of a *S. suis* infection. In one embodiment, said prophylactic treatment is of an *S. suis* infection selected from the group of infections caused by any one of the 35 identified serotypes of *S. suis*. In another embodiment, said infection is selected from the group of infections caused by any one of serotypes 1, 2, 7, 9 and 1/2, such as the group of infections caused by any one of serotypes 1, 2 and 7, such as the group of infections caused by serotype 2 and 7. In one embodiment, said infection is cause by *S. suis* serotype 2 and in another embodiment said infection is cause by *S. suis* serotype 7. In one embodiment, there is provided an immunogenic polypeptide fragment or fusion polypeptide as described herein, for use in the prophylactic treatment of a *S. suis* infection, which immunogenic polypeptide fragment or fusion polypeptide is effective in the prophylactic treatment of infection caused by any one of at least 2, such as at least 3, such as at least 5, such as at least 7, such as at least 10 of the 35 identified serotypes.

In a fifth aspect of the present disclosure, there is provided a polynucleotide encoding an immunogenic polypeptide for use as defined herein, an immunogenic polypeptide fragment as described herein or a fusion polypeptide as described herein. Also encompassed by this disclosure is an expression vector comprising the polynucleotide and a host cell comprising the expression vector. Encompassed is also a method of producing an immunogenic polypeptide, an immunogenic polypeptide fragment or a fusion polypeptide, comprising culturing said host cell under conditions permissive of expression of said polypeptide from its expression vector, and isolating the polypeptide. Alternatively, the immunogenic polypeptide, immunogenic polypeptide fragment or fusion polypeptide of the present disclosure may alternatively be produced by non-biological peptide synthesis using amino acids and/or amino acid derivatives having protected reactive side-chains, the non-biological peptide synthesis comprising step-wise coupling of the amino acids and/or the amino acid derivatives to form a polypeptide according to the first, second or third aspect having protected reactive side-chains, removal of the protecting groups from the reactive side-chains of the polypeptide, and folding of the polypeptide in aqueous solution.

The skilled person will appreciate that any one of the above mentioned immunogenic polypeptides, immunogenic polypeptide fragments and fusion polypeptides may be useful in an immunogenic composition. For the sake of clarity, the term "immunogenic composition" herein refers to compositions other than bacteria, such as native bacteria or attenuated bacteria. Thus, in a sixth aspect of the present disclosure, there is provided an immunogenic composition comprising at least one immunogenic polypeptide selected from the group consisting of in immunogenic polypeptide as according to the first aspect disclosed herein, an immunogenic polypeptide fragment according to the second or third aspect as disclosed herein or an fusion polypeptide according to the fourth aspect as disclosed herein.

In one embodiment, there is provided an immunogenic composition as disclosed herein, comprising one, two, three or four of said immunogenic polypeptides or immunogenic polypeptide fragments, such as two, three or four of said immunogenic polypeptides or immunogenic polypeptide fragments, such as three or four of said immunogenic polypeptides or immunogenic polypeptide fragments, such as four of said immunogenic polypeptides or immunogenic polypeptide fragments. In one embodiment, said at least one immunogenic polypeptide fragment is provided in fusion with a different at least one different immunogenic polypeptide fragment to form a fusion polypeptide as described herein.

The skilled person will appreciate that it may be beneficial for the immunogenic composition to comprise several distinct immunogenic fragments, which are capable of eliciting an immune response. Said distinct immunogenic fragment may be present on one polypeptide chain or on several polypeptide chains. Thus is one embodiment, there is provided an immunogenic composition, comprising at least one of the immunogenic polypeptides as defined herein, at least one immunogenic polypeptide fragment as defined herein or at least one fusion polypeptide as defined herein. In one embodiment, said immunogenic composition comprises two, three or four immunogenic polypeptides as defined herein. In one particular embodiment, there is provided an the immunogenic composition wherein said at least one fragment as defined herein is provided in fusion with a different at least one different immunogenic polypeptide fragment as defined herein to form a fusion polypeptide as defined herein. The provision of two or more immunogenic fragments in the form of a fusion polypeptide may be beneficial for technical production purposes as well as for cost saving purposes.

In one embodiment, there is provided an immunogenic composition as described herein, wherein said composition comprises a fusion polypeptide as defined herein and optionally one or two immunogenic polypeptide fragments as defined herein not in the form of a fusion polypeptide. In one embodiment, said composition comprises a fusion polypeptide comprising two immunogenic polypeptide fragments as defined herein and optionally one immunogenic polypeptide fragment as defined herein not in the form of a fusion polypeptide.

In one embodiment, there is provided an immunogenic composition, wherein said composition comprises a fusion polypeptide comprising three or four immunogenic polypeptide fragments as defined herein. In one embodiment, said composition comprises a fusion polypeptide comprising three immunogenic polypeptide fragments as defined herein and optionally one immunogenic polypeptide fragments as defined herein not in the form of a fusion polypeptide. In one embodiment, there is provided an immunogenic composition comprising one or two fusion polypeptides. Thus, said immunogenic composition may for example comprise one fusion polypeptide; one fusion polypeptide and one individual polypeptides; one fusion polypeptide and two individual polypeptides; one fusion polypeptide and three or more individual polypeptides; two fusion polypeptides or more fusion polypeptides.

In one particular embodiment, there is provided an immunogenic composition selected from the group consisting of immunogenic compositions comprising a fusion polypeptide comprising SEQ ID NO:9 and SEQ ID NO:7 and at least one polypeptide comprising an amino acid sequence selected from SEQ ID NO: 5, 6, 11 and 12 not in the form of a fusion polypeptide;

a fusion polypeptide comprising SEQ ID NO:10 and SEQ ID NO:7 and at least one polypeptide comprising an amino acid sequence selected from SEQ ID NO: 5, 6, 11 and 12 not in the form of a fusion polypeptide;

a fusion polypeptide comprising SEQ ID NO:11 and SEQ ID NO:7 and at least one polypeptide comprising an amino acid sequence selected from SEQ ID NO: 5, 6, 9 and 10 not in the form of a fusion polypeptide;

a fusion polypeptide comprising SEQ ID NO:12 and SEQ ID NO:7 and at least one polypeptide comprising an amino acid sequence selected from SEQ ID NO: 5, 6, 9 and 10 not in the form of a fusion polypeptide;

a fusion polypeptide comprising SEQ ID NO:5 and SEQ ID NO:7 and at least one polypeptide comprising an amino acid sequence selected from SEQ ID NO: 9, 10, 11 and 12 not in the form of a fusion polypeptide;

a fusion polypeptide comprising SEQ ID NO:6 and SEQ ID NO:7 and at least one polypeptide comprising an amino acid sequence selected from SEQ ID NO: 9, 10, 11 and 12 not in the form of a fusion polypeptide;

a fusion polypeptide comprising SEQ ID NO:9 and SEQ ID NO:8 and at least one polypeptide comprising an amino acid sequence selected from SEQ ID NO: 5, 6, 11 and 12 not in the form of a fusion polypeptide;

a fusion polypeptide comprising SEQ ID NO:10 and SEQ ID NO:8 and at least one polypeptide comprising an amino acid sequence selected from SEQ ID NO: 5, 6, 11 and 12 not in the form of a fusion polypeptide;

a fusion polypeptide comprising SEQ ID NO:11 and SEQ ID NO:8 and at least one polypeptide comprising an amino acid sequence selected from SEQ ID NO: 5, 6, 9 and 10 not in the form of a fusion polypeptide;

a fusion polypeptide comprising SEQ ID NO:12 and SEQ ID NO:8 and at least one polypeptide comprising an amino acid sequence selected from SEQ ID NO: 5, 6, 9 and 10 not in the form of a fusion polypeptide;

a fusion polypeptide comprising SEQ ID NO:5 and SEQ ID NO:8 and at least one polypeptide comprising an amino acid sequence selected from SEQ ID NO: 9, 10, 11 and 12 not in the form of a fusion polypeptide;

a fusion polypeptide comprising SEQ ID NO:6 and SEQ ID NO:8 and at least one polypeptide comprising an amino acid sequence selected from SEQ ID NO: 9, 10, 11 and 12 not in the form of a fusion polypeptide;

a fusion polypeptide comprising SEQ ID NO:11 and SEQ ID NO:9 and at least one polypeptide comprising an amino acid sequence selected from SEQ ID NO: 5, 6, 7 and 8 not in the form of a fusion polypeptide;

a fusion polypeptide comprising SEQ ID NO:12 and SEQ ID NO:9 and at least one polypeptide comprising an amino acid sequence selected from SEQ ID NO: 5, 6, 7 and 8 not in the form of a fusion polypeptide;

a fusion polypeptide comprising SEQ ID NO:5 and SEQ ID NO:9 and at least one polypeptide comprising an amino acid sequence selected from SEQ ID NO: 7, 8, 11 and 12 not in the form of a fusion polypeptide;

a fusion polypeptide comprising SEQ ID NO:6 and SEQ ID NO:9 and at least one polypeptide comprising an amino acid sequence selected from SEQ ID NO: 7, 8, 11 and 12 not in the form of a fusion polypeptide;

a fusion polypeptide comprising SEQ ID NO:11 and SEQ ID NO:10 and at least one polypeptide comprising an amino acid sequence selected from SEQ ID NO: 5, 6, 7 and 8 not in the form of a fusion polypeptide;

a fusion polypeptide comprising SEQ ID NO:12 and SEQ ID NO:10 and at least one polypeptide comprising an amino acid sequence selected from SEQ ID NO: 5, 6, 7 and 8 not in the form of a fusion polypeptide;

a fusion polypeptide comprising SEQ ID NO:5 and SEQ ID NO:10 and at least one polypeptide comprising an amino acid sequence selected from SEQ ID NO: 7, 8, 11 and 12 not in the form of a fusion polypeptide;

a fusion polypeptide comprising SEQ ID NO:6 and SEQ ID NO:10 and at least one polypeptide comprising an amino acid sequence selected from SEQ ID NO: 7, 8, 11 and 12 not in the form of a fusion polypeptide;

a fusion polypeptide comprising SEQ ID NO:5 and SEQ ID NO:11 and at least one polypeptide comprising an amino acid sequence selected from SEQ ID NO: 7, 8, 9 and 10 not in the form of a fusion polypeptide;

a fusion polypeptide comprising SEQ ID NO:6 and SEQ ID NO:11 and at least one polypeptide comprising an amino acid sequence selected from SEQ ID NO: 7, 8, 9 and 10 not in the form of a fusion polypeptide;

a fusion polypeptide comprising SEQ ID NO:5 and SEQ ID NO:12 and at least one polypeptide comprising an amino acid sequence selected from SEQ ID NO: 7, 8, 9 and 10 not in the form of a fusion polypeptide; and a fusion polypeptide comprising SEQ ID NO:6 and SEQ ID NO:12 and at least one polypeptide comprising an amino acid sequence selected from SEQ ID NO: 7, 8, 9 and 10 not in the form of a fusion polypeptide; such as the group consisting of immunogenic compositions comprising a fusion polypeptide comprising SEQ ID NO:10 and SEQ ID NO:8 and at least one polypeptide comprising an e amino acid sequence selected from SEQ ID NO: 5, 6, 11 and 12 not in the form of a fusion polypeptide;

a fusion polypeptide comprising SEQ ID NO:5 and SEQ ID NO:12 and at least one polypeptide comprising an amino acid sequence selected from SEQ ID NO: 7, 8, 9 and 10 not in the form of a fusion polypeptide;

a fusion polypeptide comprising SEQ ID NO:5 and SEQ ID NO:10 and at least one polypeptide comprising an e amino acid sequence selected from SEQ ID NO: 7, 8, 11 and 12 not in the form of a fusion polypeptide;

a fusion polypeptide comprising SEQ ID NO:8 and SEQ ID NO:12 and at least one polypeptide comprising an amino acid sequence selected from SEQ ID NO: 5, 6, 9 and 10 not in the form of a fusion polypeptide;

a fusion polypeptide comprising SEQ ID NO:8 and SEQ ID NO:5 and at least one polypeptide comprising an amino acid sequence selected from SEQ ID NO: 9, 10, 11 and 12 not in the form of a fusion polypeptide; and a fusion polypeptide comprising SEQ ID NO:12 and SEQ ID NO:10 and at least one polypeptide comprising an amino acid sequence selected from SEQ ID NO: 5, 6, 8 and 9 not in the form of a fusion polypeptide; such as the group consisting of immunogenic compositions comprising a fusion polypeptide comprising SEQ ID NO:10 and SEQ ID NO:8 and at least one polypeptide comprising an amino acid sequence selected from SEQ ID NO: 5, 6, 11 and 12 not in the form of a fusion polypeptide;

a fusion polypeptide comprising SEQ ID NO:8 and SEQ ID NO:5 and at least one polypeptide comprising an amino acid sequence selected from SEQ ID NO: 9, 10, 11 and 12 not in the form of a fusion polypeptide; and a fusion polypeptide comprising SEQ ID NO:12 and SEQ ID NO:10 and at least one polypeptide comprising an amino acid sequence selected from SEQ ID NO: 5, 6, 7 and 8 not in the form of a fusion polypeptide; such as the group consisting of immunogenic compositions comprising a fusion polypeptide comprising SEQ ID NO:8 and SEQ ID NO:5 and at least one polypeptide comprising an amino acid sequence selected from SEQ ID NO: 9, 10, 11 and 12 not in the form of a fusion polypeptide; or a fusion polypeptide comprising SEQ ID NO:12 and SEQ ID NO:10 and at least one polypeptide comprising an amino acid sequence selected from SEQ ID NO: 5, 6, 8 and 9 not in the form of a fusion polypeptide.

In particular embodiments, the immunogenic composition as disclosed herein is selected from the one of the groups above, provided that the immunogenic composition does not comprise SEQ ID NO:6 not in the form of a fusion polypeptide. For the sake of brevity, said embodiments will not be repeated here. For example, the immunogenic composition may comprise a fusion polypeptide comprising SEQ ID NO:10 and SEQ ID NO:8 and at least one polypeptide comprising an amino acid sequence selected from SEQ ID NO:5, 11 and 12 not in the form of a fusion polypeptide;
a fusion polypeptide comprising SEQ ID NO:8 and SEQ ID NO:5 and at least one polypeptide comprising an amino acid sequence selected from SEQ ID NO:9, 10, 11 and 12 not in the form of a fusion polypeptide; or
a fusion polypeptide comprising SEQ ID NO:12 and SEQ ID NO:10 and at least one polypeptide comprising an amino acid sequence selected from SEQ ID NO:5, 7 and 8 not in the form of a fusion polypeptide.

In another particular embodiment, there is provided an immunogenic composition selected from the group of immunogenic compositions consisting of immunogenic compositions comprising a fusion polypeptide comprising SEQ ID NO:9 and SEQ ID NO:7 and at least one polypeptide comprising an amino acid sequence selected from SEQ ID NO:11 and 12 not in the form of a fusion polypeptide;

a fusion polypeptide comprising SEQ ID NO:10 and SEQ ID NO:7 and at least one polypeptide comprising an amino acid sequence selected from SEQ ID NO:11 and 12 not in the form of a fusion polypeptide;

a fusion polypeptide comprising SEQ ID NO:11 and SEQ ID NO:7 and at least one polypeptide comprising an amino acid sequence selected from SEQ ID NO:9 and 10 not in the form of a fusion polypeptide;

a fusion polypeptide comprising SEQ ID NO:12 and SEQ ID NO:7 and at least one polypeptide comprising an amino acid sequence selected from SEQ ID NO:9 and 10 not in the form of a fusion polypeptide;

a fusion polypeptide comprising SEQ ID NO:5 and SEQ ID NO:7 and at least one polypeptide comprising an amino acid sequence selected from SEQ ID NO:9, 10, 11 and 12 not in the form of a fusion polypeptide;

a fusion polypeptide comprising SEQ ID NO:6 and SEQ ID NO:7 and at least one polypeptide comprising an amino acid sequence selected from SEQ ID NO:9, 10, 11 and 12 not in the form of a fusion polypeptide;

a fusion polypeptide comprising SEQ ID NO:9 and SEQ ID NO:8 and at least one polypeptide comprising an amino acid sequence selected from SEQ ID NO:11 and 12 not in the form of a fusion polypeptide;

a fusion polypeptide comprising SEQ ID NO:10 and SEQ ID NO:8 and at least one polypeptide comprising an amino acid sequence selected from SEQ ID NO:11 and 12 not in the form of a fusion polypeptide;

a fusion polypeptide comprising SEQ ID NO:11 and SEQ ID NO:8 and at least one polypeptide comprising an amino acid sequence selected from SEQ ID NO:9 and 10 not in the form of a fusion polypeptide;

a fusion polypeptide comprising SEQ ID NO:12 and SEQ ID NO:8 and at least one polypeptide comprising an amino acid sequence selected from SEQ ID NO:9 and 10 not in the form of a fusion polypeptide;

a fusion polypeptide comprising SEQ ID NO:5 and SEQ ID NO:8 and at least one polypeptide comprising an amino acid sequence selected from SEQ ID NO:9, 10, 11 and 12 not in the form of a fusion polypeptide;

a fusion polypeptide comprising SEQ ID NO:6 and SEQ ID NO:8 and at least one polypeptide comprising an amino acid sequence selected from SEQ ID NO:9, 10, 11 and 12 not in the form of a fusion polypeptide;

a fusion polypeptide comprising SEQ ID NO:11 and SEQ ID NO:9 and at least one polypeptide comprising an amino acid sequence selected from SEQ ID NO:7 and 8 not in the form of a fusion polypeptide;

a fusion polypeptide comprising SEQ ID NO:12 and SEQ ID NO:9 and at least one polypeptide comprising an amino acid sequence selected from SEQ ID NO:7 and 8 not in the form of a fusion polypeptide;

a fusion polypeptide comprising SEQ ID NO:5 and SEQ ID NO:9 and at least one polypeptide comprising an amino acid sequence selected from SEQ ID NO:7, 8, 11 and 12 not in the form of a fusion polypeptide;

a fusion polypeptide comprising SEQ ID NO:6 and SEQ ID NO:9 and at least one polypeptide comprising an amino acid sequence selected from SEQ ID NO:7, 8, 11 and 12 not in the form of a fusion polypeptide;

a fusion polypeptide comprising SEQ ID NO:11 and SEQ ID NO:10 and at least one polypeptide comprising an amino acid sequence selected from SEQ ID NO:7 and 8 not in the form of a fusion polypeptide;

a fusion polypeptide comprising SEQ ID NO:12 and SEQ ID NO:10 and at least one polypeptide comprising an amino acid sequence selected from SEQ ID NO:7 and 8 not in the form of a fusion polypeptide;

a fusion polypeptide comprising SEQ ID NO:5 and SEQ ID NO:10 and at least one polypeptide comprising an amino acid sequence selected from SEQ ID NO:7, 8, 11 and 12 not in the form of a fusion polypeptide;

a fusion polypeptide comprising SEQ ID NO:6 and SEQ ID NO:10 and at least one polypeptide comprising an amino acid sequence selected from SEQ ID NO:7, 8, 11 and 12 not in the form of a fusion polypeptide;

a fusion polypeptide comprising SEQ ID NO:5 and SEQ ID NO:11 and at least one polypeptide comprising an amino acid sequence selected from SEQ ID NO:7, 8, 9 and 10 not in the form of a fusion polypeptide;

a fusion polypeptide comprising SEQ ID NO:6 and SEQ ID NO:11 and at least one polypeptide comprising an amino acid sequence selected from SEQ ID NO:7, 8, 9 and 10 not in the form of a fusion polypeptide;

a fusion polypeptide comprising SEQ ID NO:5 and SEQ ID NO:12 and at least one polypeptide comprising an amino acid sequence selected from SEQ ID NO:7, 8, 9 and 10 not in the form of a fusion polypeptide; and a fusion polypeptide comprising SEQ ID NO:6 and SEQ ID NO:12 and at least one polypeptide comprising an amino acid sequence selected from SEQ ID NO:7, 8, 9 and 10 not in the form of a fusion polypeptide; such as the group consisting of immunogenic compositions comprising a fusion polypeptide comprising SEQ ID NO:10 and SEQ ID NO:8 and at least one polypeptide comprising an amino acid sequence selected from SEQ ID NO:11 and 12 not in the form of a fusion polypeptide;

a fusion polypeptide comprising SEQ ID NO:5 and SEQ ID NO:12 and at least one polypeptide comprising an amino acid sequence selected from SEQ ID NO:7, 8, 9 and 10 not in the form of a fusion polypeptide;

a fusion polypeptide comprising SEQ ID NO:5 and SEQ ID NO:10 and at least one polypeptide comprising an amino acid sequence selected from SEQ ID NO:7, 8, 11 and 12 not in the form of a fusion polypeptide;

a fusion polypeptide comprising SEQ ID NO:8 and SEQ ID NO:12 and at least one polypeptide comprising an amino acid sequence selected from SEQ ID NO:9 and 10 not in the form of a fusion polypeptide;

a fusion polypeptide comprising SEQ ID NO:8 and SEQ ID NO:5 and at least one polypeptide comprising an amino acid sequence selected from SEQ ID NO:9, 10, 11 and 12 not in the form of a fusion polypeptide; and a fusion polypeptide comprising SEQ ID NO:12 and SEQ ID NO:10 and at least one polypeptide comprising an amino acid sequence selected from SEQ ID NO:8 and 9 not in the form of a fusion polypeptide; such as the group consisting of immunogenic compositions comprising a fusion polypeptide comprising SEQ ID NO:10 and SEQ ID NO:8 and at least one polypeptide comprising an amino acid sequence selected from SEQ ID NO:11 and 12 not in the form of a fusion polypeptide;

a fusion polypeptide comprising SEQ ID NO:8 and SEQ ID NO:5 and at least one polypeptide comprising an amino acid sequence selected from SEQ ID NO:9, 10, 11 and 12 not in the form of a fusion polypeptide; and a fusion polypeptide comprising SEQ ID NO:12 and SEQ ID NO:10 and at least one polypeptide comprising an amino acid sequence selected from SEQ ID NO:7 and 8 not in the form of a fusion polypeptide; such as the group consisting of immunogenic compositions comprising a fusion polypeptide comprising SEQ ID NO:8 and SEQ ID NO:5 and at least one polypeptide comprising an amino acid sequence selected from SEQ ID NO:9, 10, 11 and 12 not in the form of a fusion polypeptide; and a fusion polypeptide comprising SEQ ID NO:12 and SEQ ID NO:10 and at least one polypeptide comprising an amino acid sequence selected from SEQ ID NO:8 and 9 not in the form of a fusion polypeptide.

In one particular embodiment, said immunogenic composition is selected from the group consisting of immunogenic compositions comprising a fusion polypeptide comprising SEQ ID NO:10 and SEQ ID NO:8 and at least one polypeptide comprising an amino acid sequence selected from SEQ ID NO:5 and 12 not in the form of a fusion polypeptide;

a fusion polypeptide comprising SEQ ID NO:5 and SEQ ID NO:12 and at least one polypeptide comprising an amino acid sequence selected from SEQ ID NO:8 and 10 not in the form of a fusion polypeptide;

a fusion polypeptide comprising SEQ ID NO:5 and SEQ ID NO:10 and at least one polypeptide comprising an amino acid sequence selected from SEQ ID NO:8 and 12 not in the form of a fusion polypeptide;

a fusion polypeptide comprising SEQ ID NO:8 and SEQ ID NO:12 and at least one polypeptide comprising an amino acid sequence selected from SEQ ID NO:5 and 10 not in the form of a fusion polypeptide;

a fusion polypeptide comprising SEQ ID NO:8 and SEQ ID NO:5 and at least one polypeptide comprising an amino acid sequence selected from SEQ ID NO:10 and 12 not in the form of a fusion polypeptide; and a fusion polypeptide comprising SEQ ID NO:12 and SEQ ID NO:10 and at least one polypeptide comprising an amino acid sequence selected from SEQ ID NO:5 and 8 not in the form of a fusion polypeptide; such as the group consisting of immunogenic compositions comprising a fusion polypeptide comprising SEQ ID NO:10 and SEQ ID NO:8 and at least one polypeptide comprising an amino acid sequence selected from SEQ ID NO:5 and 12 not in the form of a fusion polypeptide;

a fusion polypeptide comprising SEQ ID NO:8 and SEQ ID NO:5 and at least one polypeptide comprising an amino acid sequence selected from SEQ ID NO:10 and 12 not in the form of a fusion polypeptide; and a fusion polypeptide comprising SEQ ID NO:12 and SEQ ID NO:10 and at least one polypeptide comprising an amino acid sequence selected from SEQ ID NO:5 and 8 not in the form of a fusion polypeptide; such as the group consisting of immunogenic compositions comprising a fusion polypeptide comprising SEQ ID NO:8 and SEQ ID NO:5 and at least one polypeptide comprising an amino acid sequence selected from SEQ ID NO:10 and 12 not in the form of a fusion polypeptide; and a fusion polypeptide comprising SEQ ID NO:12 and SEQ ID NO:10 and at least one polypeptide comprising an amino acid sequence selected from SEQ ID NO:5 and 8 not in the form of a fusion polypeptide.

In one particular embodiment, said immunogenic composition is selected from the group consisting of immunogenic compositions comprising a fusion polypeptide comprising SEQ ID NO:10 and SEQ ID NO:8 and a polypeptide comprising the amino acid sequence SEQ ID NO:12 not in the form of a fusion polypeptide;

a fusion polypeptide comprising SEQ ID NO:5 and SEQ ID NO:12 and at least one polypeptide comprising an amino acid sequence selected from SEQ ID NO:8 and 10 not in the form of a fusion polypeptide;

a fusion polypeptide comprising SEQ ID NO:5 and SEQ ID NO:10 and at least one polypeptide comprising an amino acid sequence selected from SEQ ID NO:8 and 12 not in the form of a fusion polypeptide;

a fusion polypeptide comprising SEQ ID NO:8 and SEQ ID NO:12 and a polypeptide comprising the amino acid sequence SEQ ID NO:10 not in the form of a fusion polypeptide;

a fusion polypeptide comprising SEQ ID NO:8 and SEQ ID NO:5 and at least one polypeptide comprising an amino acid sequence selected from SEQ ID NO:10 and 12 not in the form of a fusion polypeptide; and a fusion polypeptide comprising SEQ ID NO:12 and SEQ ID NO:10 and a polypeptide comprising the amino acid sequence SEQ ID NO:8 not in the form of a fusion polypeptide; such as the group consisting of immunogenic compositions comprising a fusion polypeptide comprising SEQ ID NO:10 and SEQ ID NO:8 and a polypeptide comprising the amino acid sequence SEQ ID NO:12 not in the form of a fusion polypeptide;

a fusion polypeptide comprising SEQ ID NO:8 and SEQ ID NO:5 and at least one polypeptide comprising an amino acid sequence selected from SEQ ID NO:10 and 12 not in the form of a fusion polypeptide; and a fusion polypeptide comprising SEQ ID NO:12 and SEQ ID NO:10 and a polypeptide comprising the amino acid sequence SEQ ID NO:8 not in the form of a fusion polypeptide; such as the group consisting of immunogenic compositions comprising a fusion polypeptide comprising SEQ ID NO:8 and SEQ ID NO:5 and at least one polypeptide comprising an amino acid sequence selected from SEQ ID NO:10 and 12 not in the form of a fusion polypeptide; and a fusion polypeptide comprising SEQ ID NO:12 and SEQ ID NO:10 and a polypeptide comprising the amino acid sequence SEQ ID NO:8 not in the form of a fusion polypeptide.

In one particular embodiment, said immunogenic composition is selected from the group consisting of immunogenic compositions comprising a fusion polypeptide comprising SEQ ID NO:10 and SEQ ID NO:8 and a polypeptide comprising the amino acid sequence SEQ ID NO:12 not in the form of a fusion polypeptide;

a fusion polypeptide comprising SEQ ID NO:10 and SEQ ID NO:12 and a polypeptide comprising the amino acid sequence SEQ ID NO:8 not in the form of a fusion polypeptide; and a fusion polypeptide comprising SEQ ID NO:8 and SEQ ID NO:12 and a polypeptide comprising the amino acid sequence SEQ ID NO:10 not in the form of a fusion polypeptide.

In one embodiment as defined herein, the immunogenic composition a comprises two amino acid sequences not in the form of a fusion polypeptide, provided that said two amino acid sequences are from different native proteins.

In one particular embodiment of the immunogenic composition as defined herein, said fusion polypeptide is selected from the group consisting of fusion polypeptides comprising SEQ ID NO:92, fusion polypeptides comprising SEQ ID NO:93, fusion polypeptides comprising SEQ ID NO:94, fusion polypeptides comprising SEQ ID NO:95, fusion polypeptides comprising SEQ ID NO:96, fusion polypeptides comprising SEQ ID NO:34, fusion polypeptides comprising SEQ ID NO:35, and any of fusion polypeptides wherein one or both units exhibit at least 80%-identity to any one of SEQ ID NO:8, SEQ ID NO:10, SEQ ID NO:12 or SEQ ID NO:5, such as the group consisting of fusion polypeptides comprising SEQ ID NO:92, fusion polypeptides comprising SEQ ID NO:34 and fusion polypeptides comprising SEQ ID NO:35 and any of fusion polypeptides wherein one or both units exhibit at least 80%-identity to any one of SEQ ID NO:8, SEQ ID NO:10, SEQ ID NO:12 or SEQ ID NO:5, such as the group consisting of fusion polypeptides comprising SEQ ID NO:34 and fusion polypeptides comprising SEQ ID NO:35, and any of said fusion polypeptides wherein one or both units exhibit at least 80%-identity to any one of SEQ ID NO:8, SEQ ID NO:10, SEQ ID NO:12 or SEQ ID NO:5.

In one embodiment of the immunogenic composition defined herein, there is provided an immunogenic composition selected from the group of consisting of immunogenic compositions comprising a fusion polypeptide comprising SEQ ID NO:92 and at least one polypeptide comprising an amino acid sequence selected from SEQ ID NO:5 and 12 not in the form of a fusion polypeptide, a fusion polypeptide comprising SEQ ID NO:93 and at least one polypeptide comprising an amino acid sequence selected from SEQ ID NO:8 and 10 not in the form of a fusion polypeptide, a fusion polypeptide comprising SEQ ID NO:94 and at least one polypeptide comprising an amino acid sequence selected from SEQ ID NO:8 and 10 not in the form of a fusion polypeptide, a fusion polypeptide comprising SEQ ID NO:95 and at least one polypeptide comprising an amino acid sequence selected from SEQ ID NO:8 and 12 not in the form of a fusion polypeptide, a fusion polypeptide comprising SEQ ID NO:96 and at least one polypeptide comprising an amino acid sequence selected from SEQ ID NO:5 and 10 not in the form of a fusion polypeptide, a fusion polypeptide comprising SEQ ID NO:34 and at least one polypeptide comprising an amino acid sequence selected from SEQ ID NO:10 and 12 not in the form of a fusion polypeptide, and a fusion polypeptide comprising SEQ ID NO:35 and at least one polypeptide comprising an amino acid sequence selected from SEQ ID NO:5 and 8 not in the form of a fusion polypeptide; and any of fusion polypeptides wherein one or both units exhibit at least 80%-identity to any one of SEQ ID NO:8, SEQ ID NO:10, SEQ ID NO:12 or SEQ ID NO:5, such as the group consisting of immunogenic compositions comprising a fusion polypeptide comprising SEQ ID NO:92 and at least one polypeptide comprising an amino acid sequence selected from SEQ ID NO:5 and 12 not in the form of a fusion polypeptide;

a fusion polypeptide comprising SEQ ID NO:34 and at least one polypeptide comprising an amino acid sequence selected from SEQ ID NO:10 and 12 not in the form of a fusion polypeptide;

a fusion polypeptide comprising SEQ ID NO:35 and at least one polypeptide comprising an amino acid sequence selected from SEQ ID NO:5 and 8 not in the form of a fusion polypeptide; and any of fusion polypeptides wherein one or both units exhibit at least 80%-identity to any one of SEQ ID NO:8, SEQ ID NO:10, SEQ ID NO:12 or SEQ ID NO:5:

such as the group consisting of immunogenic compositions comprising a fusion polypeptide comprising SEQ ID NO:34 and at least one polypeptide comprising an amino acid sequence selected from SEQ ID NO:10 and 12 not in the form of a fusion polypeptide; and a fusion polypeptide comprising SEQ ID NO:35 and at least one polypeptide comprising an amino acid sequence selected from SEQ ID NO:5 and 8 not in the form of a fusion polypeptide; and any of said fusion polypeptides wherein one or both units exhibit at least 80%-identity to any one of SEQ ID NO:8, SEQ ID NO:10, SEQ ID NO:12 or SEQ ID NO:5.

In one embodiment, said immunogenic compositions comprises two fusion polypeptides selected from the group of fusion polypeptides consisting of fusion polypeptides comprising SEQ ID NO:92, fusion polypeptides comprising SEQ ID NO:93, fusion polypeptides comprising SEQ ID NO:94, fusion polypeptides comprising SEQ ID NO:95, fusion polypeptides comprising SEQ ID NO:96, fusion polypeptides comprising SEQ ID NO:34, fusion polypeptides comprising SEQ ID NO:35, and any of fusion polypeptides wherein one or both units exhibit at least 80%-identity to any one of SEQ ID NO:8, SEQ ID NO:10, SEQ ID NO:12 or SEQ ID NO:5, such as the group of fusion polypeptides consisting of fusion polypeptides comprising SEQ ID NO:92, fusion polypeptides comprising SEQ ID NO:34, fusion polypeptides comprising SEQ ID NO:35 and any of fusion polypeptides wherein one or both units exhibit at least 80%-identity to any one of SEQ ID NO:8, SEQ ID NO:10, SEQ ID NO:12 or SEQ ID NO:5, such as the group of fusion polypeptides consisting of fusion polypeptides comprising SEQ ID NO:34 and fusion polypeptides comprising SEQ ID NO:35, and any of said fusion polypeptides wherein one or both units exhibit at least %-identity 80 to any one of SEQ ID NO:8, SEQ ID NO:10, SEQ ID NO:12 or SEQ ID NO:5. In one embodiment, said immunogenic composition comprises fusion polypeptide SEQ ID NO:34 and fusion polypeptide SEQ ID NO:35.

In one particular embodiment the immunogenic composition as disclosed herein comprises a fusion polypeptide selected from the group consisting of fusion polypeptides comprising SEQ ID NO:5, SEQ ID NO:8 and SEQ ID NO:12;

SEQ ID NO:38, SEQ ID NO:8 and SEQ ID NO:12;

SEQ ID NO:5, SEQ ID NO:10 and SEQ ID NO:12;

SEQ ID NO:38, SEQ ID NO:10 and SEQ ID NO:12;

SEQ ID NO:8, SEQ ID NO:10 and SEQ ID NO:12; and fusion polypeptides wherein at least one of the first, second or third polypeptide units exhibits at least 80%-identity to any one of SEQ ID NO:5; SEQ ID NO:8, SEQ ID NO:38, SEQ ID NO:10 and SEQ ID NO:12. In one embodiment, said fusion polypeptide comprises SEQ ID NO:8, SEQ ID NO:10 and SEQ ID NO:12 or a fusion polypeptide wherein at least one of the first, second or third polypeptide units exhibits at least 80%-identity to any one of SEQ ID NO:8, SEQ ID NO:10 and SEQ ID NO:12. In one embodiment, said fusion polypeptide comprises SEQ ID NO:8, SEQ ID NO:10 and SEQ ID NO:12.

In particular embodiment, the immunogenic composition as disclosed herein comprises a fusion polypeptide comprising SEQ ID NO:35 and SEQ ID NO:8. In one embodiment, the SEQ ID NO:8 is located N-terminally in respect of SEQ ID NO:35. In another embodiment, the SEQ ID NO:8 is located C-terminally in respect of SEQ ID NO:35. In one embodiment, said fusion polypeptide comprises SEQ ID NO:107 or SEQ ID NO:108 or a sequence which exhibits at least 80% identity to SEQ ID NO:107 or SEQ ID NO:108. In one embodiment, said fusion polypeptide comprises SEQ ID NO:107 or SEQ ID NO:108. Optionally, said fusion polypeptide may comprise a tag, as described herein. Said fusion polypeptide may thus be SEQ ID NO:109 or SEQ ID NO:110 or a sequence which exhibits at least 80% identity to SEQ ID NO:109 or SEQ ID NO:110. In one embodiment, said fusion polypeptide comprises SEQ ID NO:109 or SEQ ID NO:110. In one embodiment, there is provided an immunogenic composition comprising a fusion polypeptide selected from the group consisting of SEQ ID NO:107, 108, 109, 110 and amino acid sequences which exhibit at least 80%-identity to any one of SEQ ID NO:107, 108, 109 and 110. In one embodiment, the immunogenic composition comprises a fusion polypeptide selected from the group consisting of SEQ ID NO:107, 109 and amino acid sequences which exhibit at least 80%-identity to any one of SEQ ID NO:107 and 109. In one embodiment, the immunogenic composition comprises a fusion polypeptide selected from the group consisting of SEQ ID NO:108, 110 and amino acid sequences which exhibit at least 80%-identity to any one of SEQ ID NO:108 and 110.

It will be appreciated that the immunogenic polypeptide as described herein, immunogenic polypeptide fragment as described herein and the fusion polypeptide as described herein, may further comprise additional amino acid residues at the N- and/or C-terminus and that the description of possible additional amino acid residues in the context of the first aspect of the present disclosure is equally relevant for immunogenic polypeptides, immunogenic polypeptide fragments and fusion polypeptides making up the immunogenic composition of the fifth aspect. For the sake of brevity these will not be repeated here.

It will be appreciated that the polypeptide components of the immunogenic composition as described herein may be isolated or purified from *S. suis*. Alternatively, they may be produced according to recombinant techniques. Thus, in one embodiment, there is provided an immunogenic composition, comprising one or several polypeptide and/or fusion polypeptide which are recombinantly produced. The skilled person will appreciate that for the purpose of recombinant production, it may be beneficial in terms of cost to produce shorter polypeptides, such as fragments of full length proteins or fragments derived from full length proteins, as compared to polypeptides which correspond to said full length proteins. Additionally, it will be appreciated that it may also be beneficial to produce one polypeptide chain instead of two or more polypeptide chains, in order to reduce production costs. For example, it may be beneficial to produce one polypeptide chain comprising a fusion of a two immunogenic polypeptide fragments instead of producing said two immunogenic polypeptide fragments separately.

It will be appreciated that the choice of suitable immunogenic polypeptides and immunogenic polypeptide fragments is far from trivial. Immunogenic polypeptides and immunogenic polypeptide fragments, both individual fragments and fragments comprised in fusion polypeptides, have to be selected taking into account the identity of the polypeptides, identity of the fragments thereof, the individual functionality of said polypeptides and fragments thereof (for example protease activity), their potential interaction (for example in terms degradation), their individual stability in vivo and in vitro, their stability in vivo and in vitro in the form of a fusion polypeptide, their individual solubility in vivo and in vitro, their solubility in vivo and in vitro in the form of a fusion polypeptide, their immunogenic properties, their ability to elicit antibody response of desired kind and their protective properties, just to mention a few.

The skilled person is aware of the fact that in order to elicit an immune response in a subject, an agent with adjuvant properties may be provided to said subject together with one or more immunogenic polypeptides, fragments or fusion polypeptides. Thus, in one embodiment, said immunogenic composition as described herein further comprises an agent with adjuvant effect.

Also within scope of the present disclosure is a vaccine composition for protecting mammalian subjects against infection of *S. suis*, which comprises an immunogenic composition as described above as immunizing component, and a pharmaceutically acceptable carrier.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, in Alfonso R Gennaro, Remington: The Science and Practice of Pharmacy. 20th edition, ISBN: 0683306472). Examples of pharmaceutically acceptable carriers include, but are not limited to sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate.

A pharmaceutically acceptable carrier may be selected from the group consisting of a cream, oil, emulsion (such as a fat emulsion or a lipid emulsion), carbohydrate, cellulose, gel, liposome, nanoparticle, ointment and glycerol, such as the group consisting of a cream, emulsion (such as a fat emulsion or a lipid emulsion), gel, liposome, nanoparticle, ointment and glycerol. A pharmaceutically acceptable carrier may be selected from the group consisting of a cream, emulsion, gel, liposome, nanoparticle and ointment.

Thus, in another aspect of the present disclosure, there is provided a vaccine composition comprising an immunogenic composition as defined herein and a pharmaceutically acceptable carrier or excipient. In one embodiment, said vaccine composition further comprises an agent with adjuvant effect. In one embodiment, said vaccine composition further comprises an immune-effective amount of an agent with adjuvant effect.

As used herein, the term "immune-effective" refers a sufficient amount of an adjuvant to increase the vaccine's immunogenicity to a level high enough to effectively vaccinate a typical patient.

As discussed above, an immunogenic composition and a vaccine composition may comprise an agent with adjuvant effect in an amount that is immuno-effective. Suitably, said adjuvant stimulates systemic or mucosal immunity. The skilled person is aware of suitable adjuvant. Non-limiting examples of suitable adjuvant in the context of the present disclosure include polymers of acrylic or methacrylic acid, maleic anhydride and alkenyl derivative polymers, immunostimulating sequences (ISS), an oil in water emulsion, cation lipids containing a quaternary ammonium salt, cytokines, aluminum hydroxide or aluminum phosphate, saponin or nanoparticles or any combinations or mixtures thereof. Further examples of suitable adjuvants may also be found in literature cited in WO 2007/115059.

A suitable adjuvant for use according to the present invention is the adjuvant Abisco/Matrix M, Matrix C or Matrix Q from Novavax, Sweden.

Another suitable adjuvant is *Ginseng*. *Ginseng* is a dry extract prepared from the root of the plant *Panax ginseng*, C. A. Meyer. *Ginseng* contains a number of active substances named ginsenosides that are a kind of saponins, chemically tri-terpenoid glycosides of the dammaren series. The ginsenosides have adjuvant properties and one of the most active adjuvants is the fraction named Rb1. It has been proved that the fraction Rb1 elicits a balanced Th1 and Th2 immune response as determined by measuring the levels of the cytokines IFN-γ, IL-2, IL-4, IL-10 secreted post vaccination with a Rb1 adjuvanted vaccine. In addition *ginseng* and the fraction Rb1 stimulate a strong antigen specific antibody response.

In one embodiment, said agent with adjuvant effect is selected from the group consisting of polymers of acrylic or methacrylic acid, maleic anhydride and alkenyl derivative polymers, immunostimulating sequences (ISS), an oil in water emulsion, cation lipids containing a quaternary ammonium salt, cytokines, aluminum hydroxide, aluminum phosphate, saponin, nanoparticles, silica, Abisco/Matrix M, Matrix C, Matrix Q and silica.

In one particular embodiment, said agent with adjuvant effect is selected from the group consisting of polymers of acrylic or methacrylic acid, maleic anhydride and alkenyl derivative polymers, immunostimulating sequences (ISS), an oil in water emulsion, cation lipids containing a quaternary ammonium salt, cytokines, aluminum hydroxide, aluminum phosphate, saponin, nanoparticles and silica. In one embodiment, said agent in selected from the group consisting of Abisco/Matrix M, Matrix C and Matrix Q. In one particular embodiment, said agent with adjuvant effect is silica.

The vaccine composition of the present disclosure is formulated in form suitable for physiological administration. Thus in one embodiment, there is provided a vaccine composition as described herein formulated for intramuscular, subcutaneous, intradermal or intranasal administration, such as for intramuscular administration.

In one embodiment, the vaccine composition as described herein, is, upon administration, capable of eliciting serum and/or mucosal antibody responses in a mammalian subject, such as a porcine or human subject, such as a porcine subject. In one embodiment, said antibody response is in the form of IgG, IgA and/or IgM antibodies in the serum and/or mucosa.

In one embodiment of the present aspect, there is provided a vaccine composition as described above, for use in the prophylactic treatment of a mammalian subject susceptible to *S. suis* infection, such as a human subject or porcine subject, such as a porcine subject. According to one embodiment, the vaccine composition is a vaccine that protects susceptible mammalian subjects, such human or porcine subjects, against an infection caused by *S. suis*.

Suitably, the vaccine composition of the present invention stimulates serum, mucosal and/or bronchial antibody responses directed to *S. suis* antigens in mammalian subjects susceptible to these bacteria, such as in human or porcine subjects, such as porcine subjects.

As mentioned above, the present disclosure provides a vaccine composition comprising one or several immunogenic polypeptides, immunogenic polypeptide fragments or fusion polypeptides for use as a medicament, which have been prepared according to the present method using *E. coli* as host cells, however other host cells may be used. The source of the immunogenic polypeptides might also be the native bacteria, if methods are developed for expression and purification thereof. Alternatively, the fusion strategies where various parts of the respective antigen are recombined may be employed resulting in a fusion polypeptides comprised of parts from different immunogenic polypeptides as described herein. This fusion strategy may also be suitable for introducing an immune reactive part(s), e.g. T-cell epitopes or attenuated toxins (or parts thereof), thereby introducing other features suitable for optimizing the antigen presentation or localization.

The present disclosure also relates to a method for the production of an antiserum, said method comprising administering an immunogenic composition as described herein to mammalian host to produce antibodies in said host and recovering antiserum containing the antibodies produced in said animal host. Within the scope of the present disclosure is also an antiserum obtainable by said method.

In a related aspect of the present disclosure, there is provided a method for prophylactic treatment of a *S. suis* infection in a mammalian subject, comprising administering to said mammalian subject in need thereof an immunologically effective amount of an immunogenic composition as described above, vaccine composition as described above or an antiserum as obtainable by the method described above. In one embodiment, said mammalian subject is a porcine or human subject, such as a porcine subject.

The skilled person will appreciate that many vaccines require administration of more than one dose in order to elicit a protective immune response. The first dose administered to a naïve subject, often referred to as a priming dose, directs the immune system to recognize the foreign antigen. In some cases, the priming dose alone may elicit sufficient protective levels of immunity. However, in other cases the priming dose may not elicit protective levels of immunity. Therefore, priming doses may be followed by one or several subsequently administrations of the identical vaccine in order to increase the magnitude of the antigen specific immune responses. These subsequently administered doses are referred to as boosting doses. Suitably, the elicited immune response is in the form of IgG, IgA and/or IgM antibodies in the mucus and/or serum of piglets or sows/gilts, and/or colostrums of sows.

Thus, in some embodiments, said method for prophylactic treatment comprises administering of an immunologically effective amount of said immunogenic composition, said vaccine composition or said antiserum at one single occasion.

In other embodiments, said method for prophylactic treatment comprises administering of an immunologically effective amount of said immunogenic composition, said vaccine composition or said antiserum at multiple separate occasions, such as two, three, four or more separate occasions. In one embodiment the method for prophylactic treatment comprises administering of an immunologically effective amount of said immunogenic composition, said vaccine composition or said antiserum at two separate occasions. In one embodiment, said administration is of said immunogenic composition or said vaccine composition, such as of said vaccine composition. In one embodiment said multiple separate occasions are at least 2 weeks apart, such as 3-6 weeks apart, such as 3-5 weeks apart, such as 3-4 weeks apart, such as 3 or 4 weeks apart.

In one embodiment, said administration is in an amount of immunogenic polypeptide, immunogenic polypeptide fragment or fusion polypeptide which elicits an immune response resulting in protection. In a particular embodiment, said administration is at a dose in the range of approximately 4-300 μg per immunogenic polypeptide, immunogenic polypeptide fragment or fusion polypeptide. For example, said administration may be in the range of approximately 10-300 μg, such as in the range of approximately 10-250 μg, such as in the range of approximately 10-200 μg, such as in the range of approximately 10-100 μg, such as in the range of approximately 10-80 μg, such as in the range of approximately 10-60 μg, such as in the range of approximately 10-50 μg per immunogenic polypeptide, immunogenic polypeptide fragment or fusion polypeptide. In one embodiment, said dose is in the range of approximately 20-50 μg, such as in the range of approximately 30-50 μg, such as approximately 40 μg per immunogenic polypeptide, immunogenic polypeptide fragment or fusion polypeptide. In another embodiment, said dose is in the range of approximately 10-30 μg, such as in the range of approximately 10-20 μg, such as approximately 16 μg per immunogenic polypeptide, immunogenic polypeptide fragment or fusion polypeptide.

In one embodiment of the method disclosed herein, said administration is to piglets, gilts or sows.

In the case wherein priming dose alone elicits sufficient protective levels of immunity, the administration to piglets may be between postnatal day 1-28. For example said administration may be during the first postnatal week, for example at postnatal day 4. Alternatively, said administration may also be during postnatal week 2, 3 or 4. Thus, in one embodiment, said administration to piglets at one single occasion is during any one of postnatal weeks 1-4, such as any one of postnatal weeks 2-4, such as any one of postnatal weeks 3-4, such as during postnatal week 3 or 4. In one embodiment, said administration is during postnatal week 1.

In embodiments wherein a priming dose and a boosting dose are administered, the first administration to piglets may be during postnatal week 2-4, such as during postnatal week 3-4. In such embodiments, the second administration to piglets is at least 2 weeks after the first administration as described above. For example, the second administration to piglets may be during postnatal week 6-8.

It may be beneficial to make use of the vaccine composition as described herein in a method wherein said vaccine is administrated to a sow or gilt, to protect a piglet through the intake of colostrum from the said sow or gilt, against an infection caused *S. suis*. Thus in another embodiment of the method disclosed herein, said administration is to pregnant sows or gilts at one or two occasions at a time such as to obtain an immune response in colostrum at time of partum. For example such administration may be on two occasions. In one embodiment, the first administration is to pregnant sows or gilts 6-8 weeks prior to partum and the second administration is 2-4 weeks prior to partum.

Encompassed by the scope of the present disclosure are also antibody preparations comprising at least one, and suitably at least two, antibodies specific for a component of the immunogenic composition as described herein, which antibody/antibodies is/are polyclonal or monoclonal; or which preparation comprises a fragment of said antibodies. It is contemplated that said preparation could be used prophylactically against *S. suis* and provide passive immunization when administered to a mammalian subject susceptible to *S. suis* infection.

Thus, in one embodiment of eighth aspect of the present disclosure, there is provided an antibody or fragment thereof, which is specific for an immunogenic polypeptide, immunogenic polypeptide fragment or a fusion polypeptide as described herein, which antibody or fragment thereof is polyclonal or monoclonal. In another embodiment, there is provided an antibody preparation comprising one of several of said antibody/antibodies. Related hereto is a method for prophylactic treatment of a *S. suis* infection in a mammalian subject, comprising passive immunization by administering to said mammalian subject in need thereof said antibody preparation.

In another aspect of the present disclosure, there is provided the use of an immunogenic peptide, an immunogenic peptide fragment or a fusion polypeptide as described herein, for the manufacture of a medicament for use in the prophylactic treatment of a mammalian subject susceptible to *S. suis* infection.

As discussed above, an immunogenic composition or a vaccine composition usually requires the presence of an agent with an adjuvant effect for said composition to elicit the desired immune response upon administration to a subject, such as a mammalian subject. The immunogenic composition or a vaccine composition may require the presence of an immune-effective amount of agent with an adjuvant effect for said composition to elicit the desired immune response upon administration to a subject, such as a mammalian subject. Therefore, most immunogenic or vaccine compositions require the additional of an external agent with adjuvant effect. Examples of such agents are listed above. In the context of the present disclosure there is contemplated the use of silica bound via SEQ ID NO:32 (SL2-tag), SEQ ID NO:33 (LSL-tag) or an amino acid sequence with at least 80%-identity to SEQ ID NO:32 or SEQ ID NO:33 to am immunogenic polypeptide, immunogenic polypeptide fragment or fusion polypeptide as disclosed herein as an adjuvant component. The skilled person will appreciated that the said silica-based adjuvant system is not limited to the immunogenic polypeptide, immunogenic polypeptide fragment or fusion polypeptide disclosed herein or to proteins derived from *S. suis* in general, but may be used with any other immunogenic protein.

The term "silica tag" herein refers to SEQ ID NO:32 (SL2-tag), SEQ ID NO:33 (LSL-tag) or an amino acid sequence with at least 80%-identity to SEQ ID NO:32 or SEQ ID NO:33 and this term is used herein for clarity. Again, the skilled person will appreciate that the above statements regarding sequence identity and %-identity are equally applicable in this context and are not repeated for the sake of brevity.

Thus, in the context of the present disclosure there is contemplated a method for production of an immunogenic mixture with adjuvant properties, comprising

- providing an immunogenic polypeptide construct comprising an immunogenic polypeptide in fusion with a silica tag as disclosed herein, which silica tag is capable of binding to silica, and
- bringing said construct in contact with silica, thereby obtaining an immunogenic mixture with adjuvant properties. Herein the immunogenic polypeptide construct is under physiological conditions, is associated to silica via said tag, which silica is capable of providing adjuvant properties.

In one embodiment, there is provided a method for production of an immunogenic mixture with adjuvant properties, wherein said step of providing an immunogenic polypeptide construct comprises

- providing an expression vector comprising a polynucleotide encoding said immunogenic polypeptide in fusion with said silica tag in a suitable host cell,
- culturing said host cell under conditions permissive of expression of said immunogenic polypeptide in fusion with said silica tag, and
- isolating said immunogenic polypeptide in fusion with said silica tag.

In one embodiment of said method, said immunogenic polypeptide construct is provided in a bacterial lysate.

In one embodiment, said method further comprising purifying said immunogenic polypeptide construct.

In one embodiment of said method, said step of bringing said immunogenic polypeptide construct in contact with silica comprises mixing said lysate with silica.

In one embodiment, said method comprises allowing said immunogenic polypeptide construct to bind to silica at a pH-value in the range of pH 5-10, such as in the range of pH 6-9. In one embodiment, said method comprises allowing said immunogenic polypeptide construct to bind to silica at low salt conditions, such as at a salt concentration in the range of 5-50 mM, such as in the range of 10-20 mM. In one embodiment said method further comprises purifying said immunogenic polypeptide construct based on the affinity of said tag for silica. In one embodiment, said purification comprises a step of gravity based separation (for example by centrifuging the mixture of said immunogenic polypeptide construct and silica), whereby separating said immunogenic polypeptide construct bound to silica from unbound polypeptides.

In one embodiment, said method further comprises the sonication of said immunogenic polypeptide construct bound to silica.

In one embodiment of said method, said silica has an average diameter in the range of approximately 5 nm-0.5 μm, such as a diameter in the range of approximately 0.2-0.3 μm or a diameter of approximately 7 nm. Also encompassed by the present disclosure are immunogenic mixtures with adjuvant properties, obtainable by the method described herein; immunogenic polypeptides in fusion with said silica tag; immunogenic polypeptides in fusion with said silica tag, which are bound to silica; immunogenic polypeptide in fusion with said silica tag for use in prophylactic therapy; polynucleotide encoding said polypeptides; expression vectors comprising said polynucleotides; host cells comprising said expression vectors.

Also encompassed by the present disclosure is said silica tag per se, which tag corresponds to SEQ ID NO:32, SEQ ID NO:33 or an amino acid sequences with at least 80%-identity to SEQ ID NO:32 or 33. For the sake of clarity, silica tags as disclosed herein are equally suitable as N-terminal and C-terminal tags. Kits comprising an immunogenic polypeptide in fusion with said silica tag and silica are also contemplated.

While the invention has been described with reference to various exemplary aspects and embodiments, it will be understood by those skilled in the art that various changes may be made and equivalents may be substituted for elements thereof without departing from the scope of the invention. In addition, many modifications may be made to adapt a particular situation or molecule to the teachings of the invention without departing from the essential scope thereof. Therefore, it is intended that the invention not be limited to any particular embodiment contemplated, but that the invention will include all embodiments falling within the scope of the appended claims.

BRIEF DESCRIPTION OF FIGURES

FIG. 9B shows the two fusions when mixed and incubated at 37° C. compared to frozen samples.

FIG. 13 shows the amino acid sequences of the polypeptides disclosed herein. In particular in SEQ ID NO:13-31, note that amino acids in bold originate from vector and cloning site and italicized amino acids indicate either a His-tag, SL2-tag or LSL-tag sequence. In SEQ ID NO:34-37 and 107-110, note that the amino acids in bold originate from the construction work of the fusion polypeptide and that these amino acids could be changed or even absent if another fusion strategy is used.

FIGS. 17A and B are bar graphs showing the IgG-antibodies against SP274C—S in piglets vaccinated with SP274C—S and control piglets measured on day 1 and day 31 of the study. SP274C—S is abbreviated SP274 in the figure.

EXAMPLES

Figure 1:
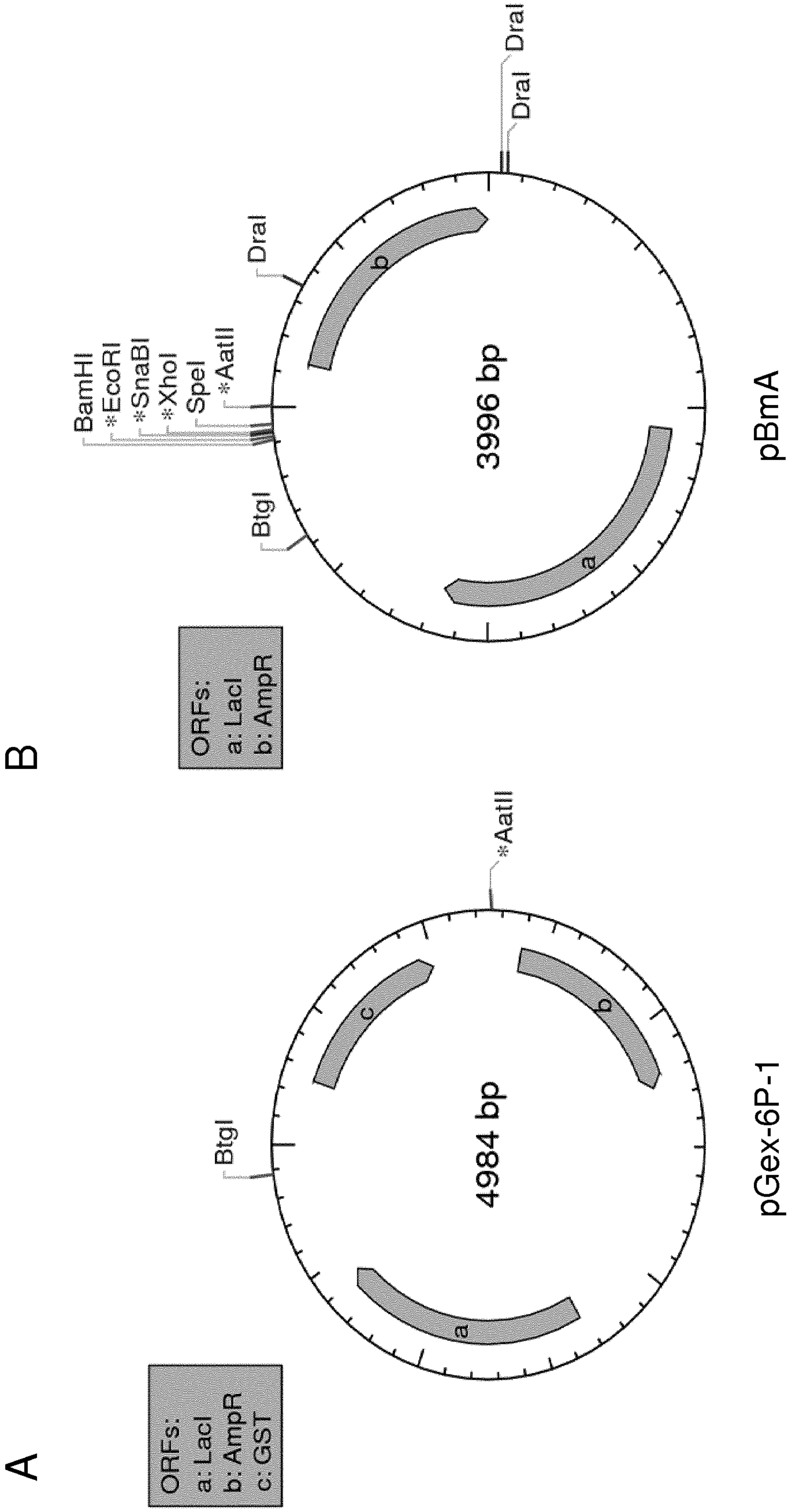
FIG. 1A-E shows schematic drawings of expression vectors used in this disclosure; (A) pPGex-6P-1, (B) pBmA, (C) pBmK, (D) pBmKny, (E) pBmKSL2 and (F) pBmKLSL.
Figure 1:
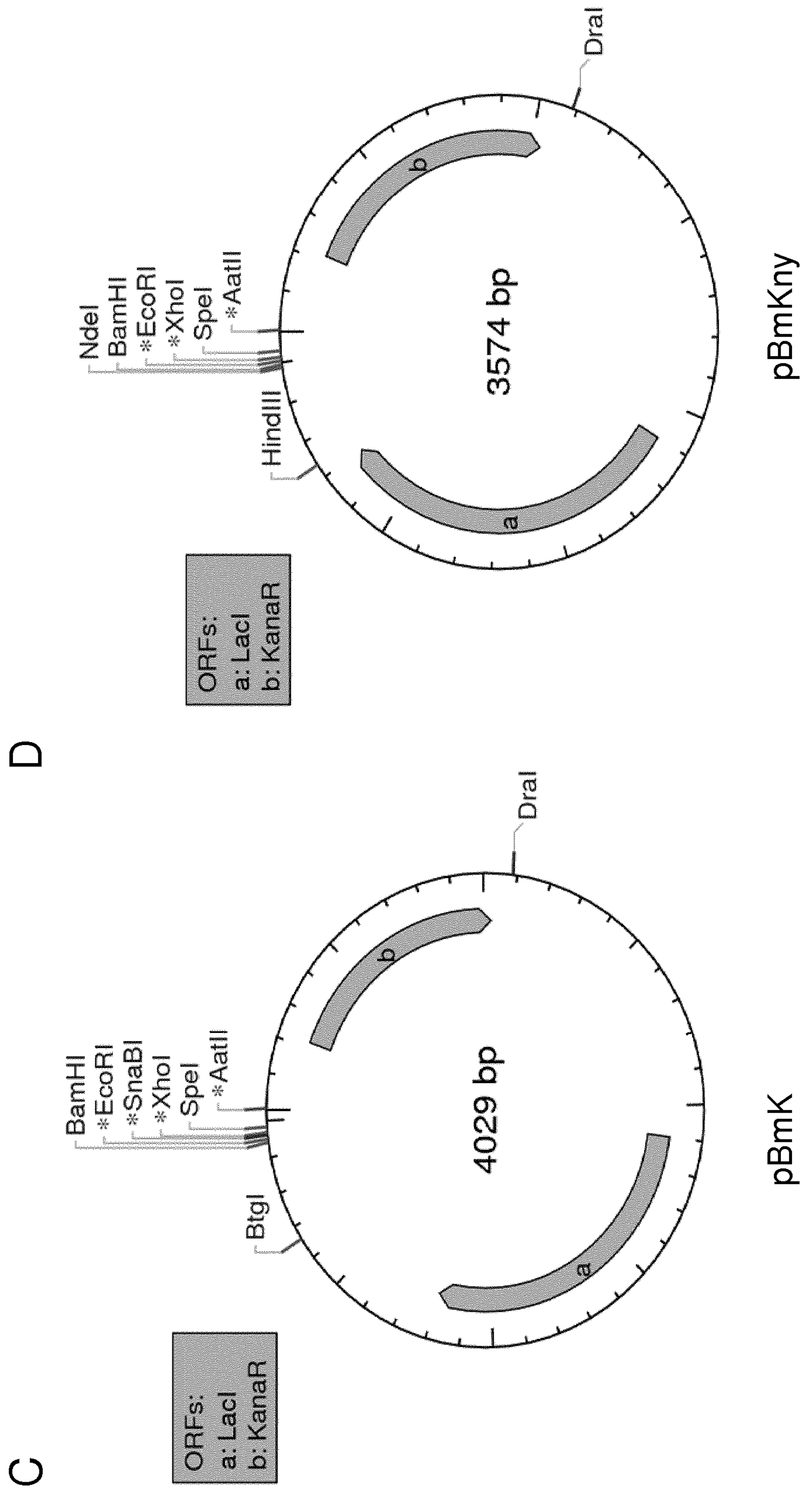
Figure 1:
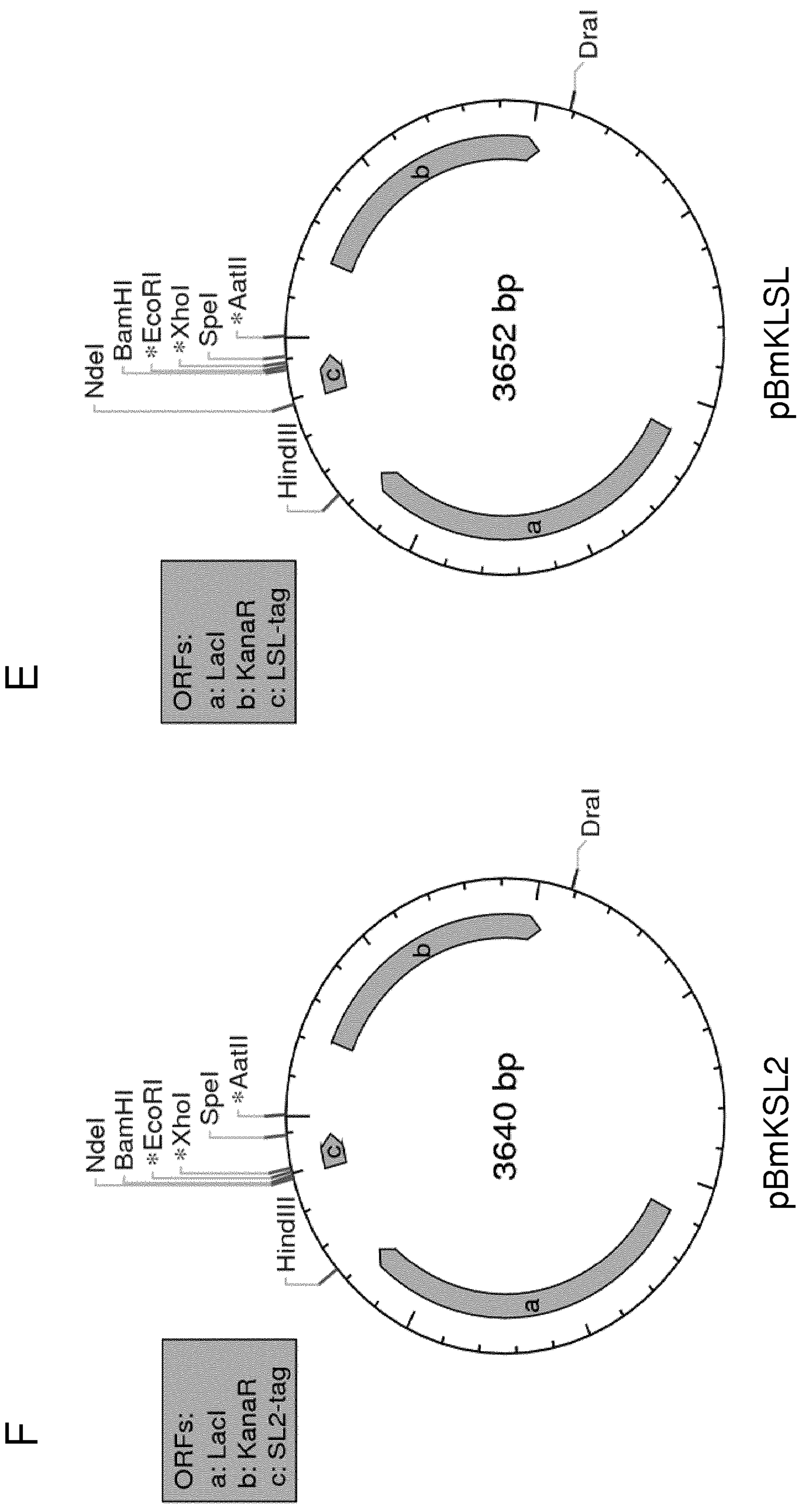

In the following examples the identification, cloning and purifications of antigen fragments for use in a vaccine against *S. suis* infection is disclosed. Also disclosed is data from immunization of mice with said fragments and immunization and vaccine studies in porcine subjects using said fragments, combinations of said fragments and fusion polypeptides comprising said fragments.

Materials and Methods

The molecular work has been done according to the information in "Molecular Cloning: A Laboratory Manual" by J. Sambrook, E. F. Fritsch, T. Maniatis. The different methods used are described in short below.

Electroporation of *E. coli*: In all instances the strain *E. coli* BL21 have been used as recipient of plasmids. 1 μl of plasmid was added to 50 μl of electrocompetent cells (on ice) and the mixture was transferred to cold cuvettes (1 mm gap). The conditions for the electroporation were; 200-400 ohm, 25 microfarad and 2.5 kV. After the electroporation the cells were resuspended in 1 ml LB-medium and incubated for one hour at 37° C. (phenotypic expression) after which the cells are spread on LB-plates with the appropriated antibiotics.

Ligations: The ligations were performed using T4 DNA ligase (New England Biolabs) in a DNA concentration of approximately 20-50 μg/ml for at least one hour. Thereafter the DNA was EtOH precipitated, washed with 70 EtOH and dried. The pellet was dissolved in $H_2O$ and used for electroporation.

Purification of DNA: For plasmid purification, an overnight growth culture of *E. coli* BL-21 was harvested of which 2-4 ml was used for plasmid preparation. The plasmid was purified using QIAprep Spin Miniprep kit (Qiagen) according to the supplier's instructions. Purification of DNA after CIP treatment of PCR products was done by using QIAquick PCR purification kit (QIAGEN).

Cleavage with restriction enzymes: The appropriated buffer was added to the DNA and DTT (Dithiothreitol; Amersham Biosciences) was added to a final concentration of 1 mM. Thereafter the restriction enzyme(s) (New England Biolabs) was added to a concentration of 2-10 units/μg and the mixture was incubated for 2-3 hours.

CIP treatment of vectors: All vectors used for cloning were treated with Calf Intestinal Alkaline Phosphatase (CIP) (New England Biolabs) for one hour in the same buffer used for restriction enzyme cleavage. Thereafter the vector was purified using QIAquick PCR purification kit (QIAGEN).

PCR conditions: Fidelity Taq PCR Master Mix (USB, Affymetrix) was been used according to the instructions. If not stated otherwise, the annealing temperature has been 5-10° C. under the melting point for the primers, the number of cycles has been 30 and the extension time has been approximately 1 minute per 1 kbp of DNA.

DNA sequencing:

All DNA sequencing was performed by the Uppsala Genome Center Sequencing Service (Uppsala, Sweden).

SDS-Page Analysis:

SDS-PAGE analyses were performed using the PhastSystem (GE-Healthcare). Samples were analyzed under reducing conditions using precasted 8-25% gradient gels.

Expression of recombinant proteins: In general, similar conditions have been used for all proteins expressed in this application. A single colony was inoculated into 20-30 ml LB medium supplemented with kanamycin (25-50 μg/ml) and the culture was incubated while shaking over night at 25° C. From the overnight culture 10-20 ml was inoculated into 11 LB supplemented with kanamycin (25-50 μg/ml) and the culture was incubated with shaking at 25° C. for a few hours (5-7 hours). The expression of recombinant protein was induced by addition of 11 LB supplemented with kanamycin (25-50 μg/ml) and 0.2 mM isopropyl β-D-1-thiogalactopyranoside (IPTG) and the culture was incubated while shaking over night at 25° C.

Protein Lysate:

After the induction phase, the culture was harvested by centrifugation and the cells are resuspended in lysis buffer (100 mM NaCl, 20 mM Tris (pH 7-7.5) and 0.05% Tween 20) and 10-100 μg/ml lysozyme was added after which the cells were lysed using freeze/thaw cycles. The lysate was then sonicated (40-60% amplitude) on ice-water for 2×10 minutes with 1 second pulses. The lysate was centrifuged for 20-30 minutes at 10K RPM. The supernatant was collected and sterile filtered (using a 0.45 μm filter) after which the lysate was frozen in aliquots.

Silica:

Silica fumed 0.2-0.3 μm (article number S5505) and Silica fumed 0.007 μm (article number S5130) was purchased from Sigma (St. Louis, USA). Silica fumed 0.2-0.3 μm was used for all protein purifications and also used as adjuvant for mouse immunization. Silica fumed 0.007 μm was used as adjuvant for mouse immunization. Before use, stock solutions were made from the silica powders by adding silica powder to a volume corresponding to 40 ml. The powder was prepared into a slurry in 40 ml $H_2O$.

In weight, 40 ml silica fumed 0.2-0.3 μm corresponds to approximately 1 gram and 40 ml silica fumed 0.007 μm corresponds to approximately 2 gram. The protein purification using silica was performed using approximately 1/10 volume of silica slurry and 1/10 volume of protein lysate and 1/50 volume Tris (1 M, pH 9) and 8/10 volume $H_2O$ supplemented with 0.02% Tween 20 was added. The protein binding to silica was performed for a few hours or overnight with slow shaking, after which the silica was collected by centrifugation and washed.

The silica slurry used in immunization experiments was pretreated by sonication and autoclaving before mixing with the purified proteins.

Construction of Plasmid Vectors

Construction of Plasmid Vector pBmA:

The plasmid pGex6p-1 (GE-Healthcare) was used as a scaffold for the construction of the expression plasmids (FIG. 1A). The first step in construction of the expression plasmid was to exchange the domain encoding the GST-polypeptide for a synthetic DNA fragment using the restriction sites BtgI and AatII. The synthetic DNA fragment BmT (SEQ ID NO:87) was synthesized by GenScript (Piscataway, USA) and contains the tac-promoter with 5'-flanking sequences, a translation enhancer element (AT-rich DNA) just upstream of the ribosomal binding site, cloning sites (BamHI, EcoRI, SnaBI and XhoI), translational stop codons and a transcriptional termination sequence (from His-operon in *E. coli*). The BmT fragment is flanked by the restriction enzyme site BtgI and AatII and after cleavage with these enzymes the fragment was ligated into pGex-6P-1 (cleavage with BtgI and AatII). The vector obtained is called pBmA (SEQ ID NO:59) (FIG. 1B).

Construction of the pBmK Plasmid:

The pBmK vector (SEQ ID NO:60) was made from the pBmA vector with the main difference that the β-lactamase gene is exchanged with a gene encoding kanamycin resistance.

The pBmA vector was digested with AatII and DraI and a PCR fragment containing the kanamycin gene was ligated into the cleaved vector. As a template to obtain the kanamycin gene, the plasmid pJexpress 401 (obtained from DNA2.0 (Menlo Park, Calif., USA)) was used. The primers used to amplify the kanamycin resistance gene are called "kana1" and "TR2 mod" (Table 1). TR2 mod also contains a transcriptional terminator sequence. The new vector was called pBmK and a schematic drawing of the plasmid is shown in FIG. 1C.

Construction of the pBmKny Vector:

The main reason for constructing the new vector, called pBmKny (SEQ ID NO:61) (FIG. 1D), was a repetitive DNA sequence present two times in pBmK. This sequence "GTGTGGAATTGTGAGCGGATAACAATTTCACA" is located just after the LacI gene and in the Tac-promoter. The copy located after the LacI gene was removed and also the distance between the LacI gene and the cloning cassette is shortened and a transcriptional termination sequence (from phage T7Te) is added just downstream the LacI gene. The BmKny vector was made by joining two DNA fragments using the restriction sites AatII and HindIII. One DNA fragment was a PCR-product of pBmK from the AatII including the LacI gene with the 3"-primer containing the restriction enzyme site HindIII (primers BmaatII and LacIRev (Table 1)). The other fragment was a synthetic DNA Kny (SEQ ID NO:88) (obtained from Genescript) containing a transcriptional termination sequence (T7Te), Tac-promoter, translation enhance element (AT-rich DNA) upstream of the ribosomal binding site, cloning-sites and a transcriptional termination sequence. This fragment was flanked by the restriction sites HindIII and AatII. The DNA fragment is very similar to the one in pBmK with the following differences; one extra nucleotide is added between the ribosomal binding site and the translation start codon, one nucleotide is changed in proximity of the start-codon which results in a NdeI-site, and the cloning site SnaBI is removed.

Construction of the BmKSL2 Vector:

The vector BmKSL2 (SEQ ID NO:62) was made by insertion of synthetic DNA called SL2 (SEQ ID NO:90) (obtained from GenScript) into pBmKny, using the restriction sites XhoI and SpeI (FIG. 1D). The SL2 fragment encodes a 22 amino acid tag that binds to silica (SEQ ID NO:32). The silica binding tag SL2 corresponds to the C-terminal part of ribosomal protein L2 from *S. suis*. The ribosomal protein L2 from *E. coli* has earlier been shown to bind silica (Taniguchi et al (2007) Biotechnol Bioeng; April 15; 96(6):1023-9) and the main binding domain in L2 is located in the C-terminal part (Li et al (2013), Appl Microbiol Biotechnol, March; 97(6):2541-9 and Li et al (2013), J Chromatogr B Analyt Technol Biomed Life Sci, February 15; 917-918:30-5). The C-terminal 22 amino acids part of L2 from *E. coli* and *S. suis* exhibit 55% sequence identity and contain a high number of positively charged amino acids. Positively charge stretches of amino acids such as poly-arginine have earlier been shown to bind to silica (Fuchs and Raines (2005), Protein Sci. June; 14(6):1538-44).

Construction of the BmKCHis Vector:

The BmKCHis vector (SEQ ID NO:63) encodes seven histidines immediately downstream of the XhoI site. The vector was constructed by annealing the two oligonucleotides C1his and C2his together followed by ligation into the vector BmKny cleaved with the restriction enzymes XhoI and SpeI.

Construction of the BmKLSL Vector:

The BmKLSL (SEQ ID NO:64) vector contains a variant of the SL2-tag, denoted LSL-tag (SEQ ID NO:33), which variant is 4 amino acid longer and is located directly upstream of the cloning site BamHI (FIG. 1E). The vector was made by insertion of a PCR fragment into the NdeI and BamHI sites in the BmKny vector. The fragment was obtained by PCR using BmKSL2 as template and the primers used was LSLs and LSLr.

TABLE 2

List of primers/oligonucleotides used herein.

| SEQ ID NO: | Name | Sequence 5'-3' |
|---|---|---|
| 65 | kana1 | ATAT**GACGTC**AGGTGGGACCACCGCGCTAC |
| 66 | TR2mod | GCGT**TTTAAAA**AAAAACGCGGTCGATTACCCG ACCGCGAAAGGTTTTGCGCCATTCG |
| 67 | BmaatII | ATAT**GACGTC**AGGTGGGACCAC |
| 68 | LacIRev | ATAT**AAGCTT**GGTGCCTAATGAGTGAGCTAAC |
| 69 | C1his | TCGAGCATCACCATCACCATCACCATTAAA |
| 70 | C2his | CTAGTTTAATGGTGATGGTGATGGTGATGC |
| 71 | LSLs | ATAT**CATATG**ACAAAACCTGCACTGGGACTGA AGACCCGC |
| 72 | LSLr | TATA**GGATCC**CTTCTGATTGCGACGGCG |
| 73 | M2p1 | ATAT**GGATCC**GATACGGTAGTAACGGGTG |
| 74 | M2p3 | TATA**CTCGAG**ATTGAAATACTCTTCCCACAG |
| 75 | sp2CBam | ATATGGATCCGACGAAATCAAAGCAAAATACG |
| 76 | Sp2CXhoVal | TATA**CTCGAG**ACCTGCTTTGGTCGTTTTTGC |
| 77 | Tac5 | GCCGACATCATAACGGTTCTGG |
| 78 | SP2CKpnI | TATA**GGTACC**ACCTGCTTTGGTCGTTTTTGC |
| 79 | NMAKpn | ATAT**GGTACC**GATACGGTAGTAACGGGTG |
| 80 | NP7Kpn | TATAGGTACCGGTTTGGTTGCCACTTGC |
| 81 | SP4CKpnI | ATAT**GGTACC**GGCGAAACGACGGC |
| 82 | BmR2 | GGTGGTCCCACCTGACGTC |
| 83 | M2p4 | ATAT**GGATCC**AGCGAGCAGCCGGACAG |
| 84 | M2p5 | TATA**CTCGAG**GCTGCTCACCGCGGTC |
| 85 | sp2NXho-H | TATA**CTCGAG**GTCGACCAGTGCGGCG |
| 86 | Sp4NXho | TATA**CTCGAG**CGTGGTTTCACCGACTTGC |

Primers used in the experiments described in the following examples are shown in Table 2 above.

Example 1

General Description of Antigens Chosen

Four surface proteins encoded by *S. suis* were chosen as candidates for vaccine trials. The genes encoding these proteins are SSU0496 (SEQ ID NO:1), SSU0860 (SEQ ID NO:2), SSU1879 (SEQ ID NO:3) and SSU1355 (SEQ ID NO:4) and the encoded proteins are expressed by many different strains and serotypes of *S. suis* (Gómez-Gascóna et al, supra) and are conserved in the publically available databases (NCBI and Welcome Trust Sanger Institute). In the context of the present disclosure said *S. suis* proteins are denoted according to the following: SSU0496 is denoted M2 (SEQ ID NO:1), SSU0860 is denoted SP2 (SEQ ID NO:2), SSU1879 is denoted SP4 (SEQ ID NO:3) and SSU1355 is denoted SP7 (SEQ ID NO:4). The version of the genes used in herein corresponds to the sequence of *S. suis* strain P1/7 (Welcome Trust Sanger Institute).

Figure 2:
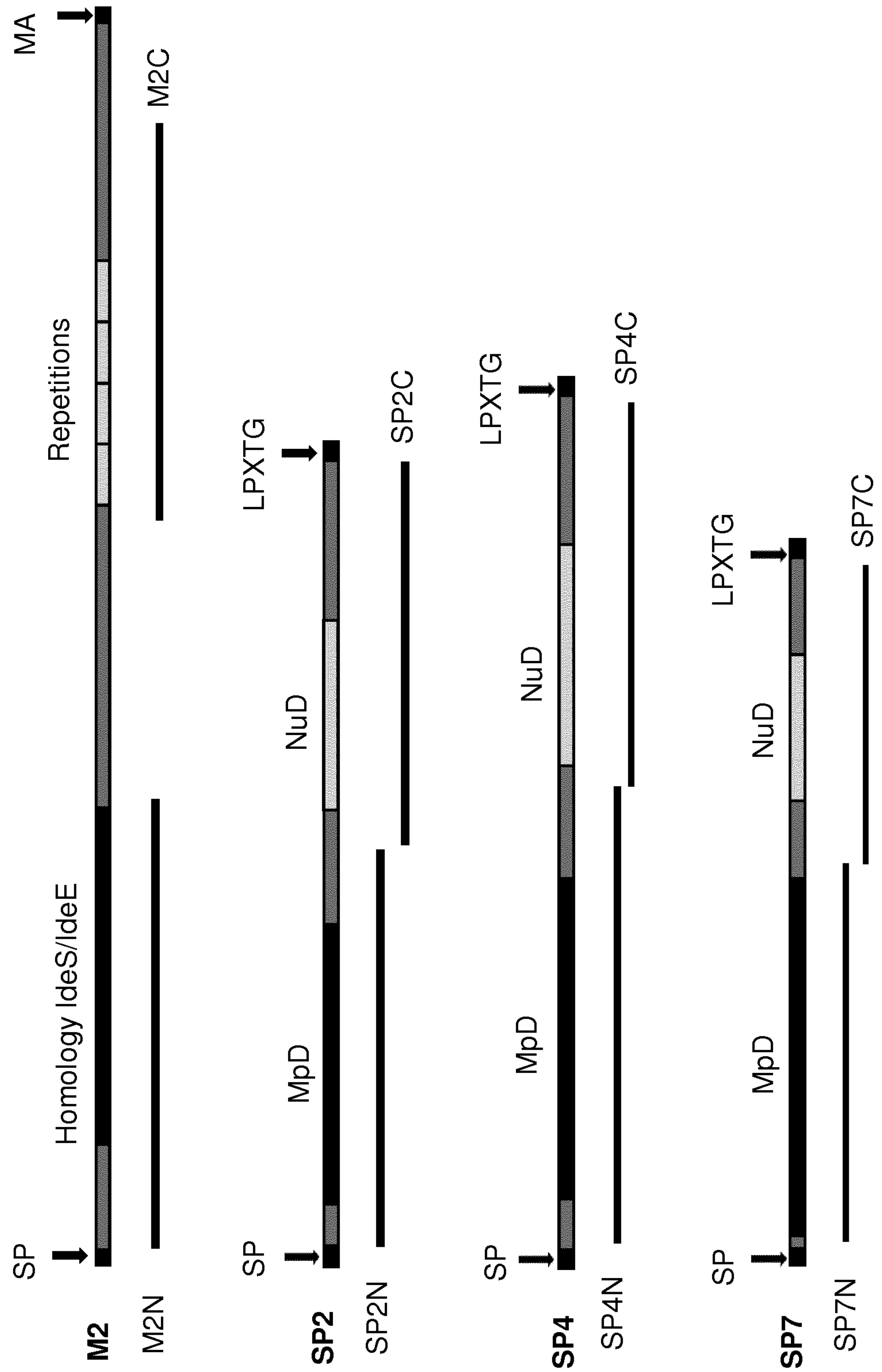
FIG. 2 is a schematic drawing of the four proteins chosen as vaccine candidates. Characteristic features of the proteins are indicated and the boarder for each domain is based on NCBI blast search and NCBI conserved domains. The bars below each gene indicate separate protein fragment that have been expressed and purified. Abbreviations: SP=signal peptide, MA=membrane anchor, LPXTG=cell wall anchor motif, MpD=metallophosphatase domain, NuD=nucleotidase domain.

A schematically drawing of M2, SP2, SP4 and SP7 is shown in FIG. 2. Characteristic features of the proteins are indicated and the boarder for each domain is based on NCBI blast search and NCBI conserved domains. The bars below each gene indicate separate protein fragments that have been expressed and purified.

Example 2

Expression and Purification of Fragments of M2, SP2, SP4 and SP7 from *S. suis*

This Example describes the cloning, expression and purification of two fragments of each of the antigens M2, SP2, SP4 and SP7 in fusion with a His-tag. The size of said fragments was confirmed by SDS-PAGE analysis.

Material and Method:

The fours antigens M2 (SEQ ID NO:1), SP2 (SEQ ID NO:2), SP4 (SEQ ID NO:3), and SP7 (SEQ ID NO:4) were expressed as an N-terminal and a C-terminal fragment and denoted as follows M2N, M2C, SP2N, SP2C, SP4N, SP4C, SP7N and SP7C, corresponding to SEQ ID NO:5, 6, 7, 8, 9, 10, 11 and 12, respectively. The gene fragments were obtained from external providers as indicated below and cloned into the BmKny vector in fusion with 6 histidines (indicated herein by the letter H) according to the following:

pM2N—H:

M2 was ordered codon optimized from DNA 2.0. The N-terminal part of the gene was amplified by PCR and cloned into the vector BmKCHis (SEQ ID NO:63) using the restriction enzyme sites BamHI and XhoI. The PCR conditions were 52° C. annealing temperature, 2 minutes extension and 30 cycles, using the codon optimized DNA as a template and the primers M2p1 and M2p3. The obtained His-tagged polypeptide is denoted M2N—H (SEQ ID NO:13).

pM2C—H:

M2 was ordered codon optimized from DNA 2.0. The gene was used as a template with the primers M2p4 and M2p5 in a PCR reaction. The product was cleaved with the restriction enzymes BamHI and XhoI and cloned into the vector BmKCHis cleaved with the corresponding enzymes. The obtained His-tagged polypeptide is denoted M2C—H (SEQ ID NO:14).

pSP2N—H:

The SP2N gene fragment was ordered codon optimized from GenScript. The DNA fragment contains the restriction enzymes site BamHI and XhoI and a DNA sequence encoding six histidines before the XhoI site. This fragment was cleaved with BamHI and XhoI and ligated into the vector BmKny in the corresponding sites. The obtained His-tagged polypeptide is denoted SP2N—H (SEQ ID NO:15).

pSP2C—H:

The gene fragment SP2C was ordered codon optimized from GenScript and was flanked by the restriction enzymes sites BamHI and XhoI. In addition, the fragment encodes six histidines after the BamHI site. The fragment was cloned into the vector BmKny using the sites BamHI and XhoI. The obtained His-tagged polypeptide is denoted SP2C—H (SEQ ID NO:16).

pSP4N—H:

The SP4N gene fragment was ordered codon optimized from GenScript. The DNA fragment contains the restriction enzymes site BamHI and XhoI and a DNA sequence encoding six histidines just before the XhoI site. This fragment was cleaved with BamHI and XhoI and ligated into the vector BmKny in the corresponding sites. The obtained His-tagged polypeptide is denoted SP4N—H (SEQ ID NO:17).

pSP4C—H:

The SP4C gene fragment was ordered codon optimized from GenScript and was flanked in the N-terminal by the restriction enzymes site NdeI followed by a DNA sequence encoding six histidines after which a BamHI site follows and the C-terminal ends with the restriction site XhoI. The fragment was cleaved with NdeI and XhoI and cloned into the vector BmKny in the corresponding sites. The obtained His-tagged polypeptide is denoted SP4C—H (SEQ ID NO:18).

pSP7N—H:

The SP7N gene fragment was ordered codon optimized from GenScript and was flanked by the restriction enzymes site BamHI and XhoI. The fragment was cleaved with BamHI and XhoI and ligated into the vector BmKCHis in the corresponding sites. The obtained His-tagged polypeptide is denoted SP7N—H (SEQ ID NO:19).

pSP7C—H:

The SP7C gene fragment was ordered codon optimized from GenScript and was flanked N-terminally by the restriction enzymes site NdeI followed by a DNA sequence encoding six histidines after which a BamHI site follows and the C-terminal ends with the restriction site XhoI. The fragment was cleaved with NdeI and XhoI and cloned into the vector BmKny in the corresponding sites. The obtained His-tagged polypeptide is denoted SP7C—H (SEQ ID NO:20).

The *E. coli* clones were grown and the protein expression induced after which protein lysates was made and purified on Talon columns and analyzed by SDS-Page as described above.

Figure 3:
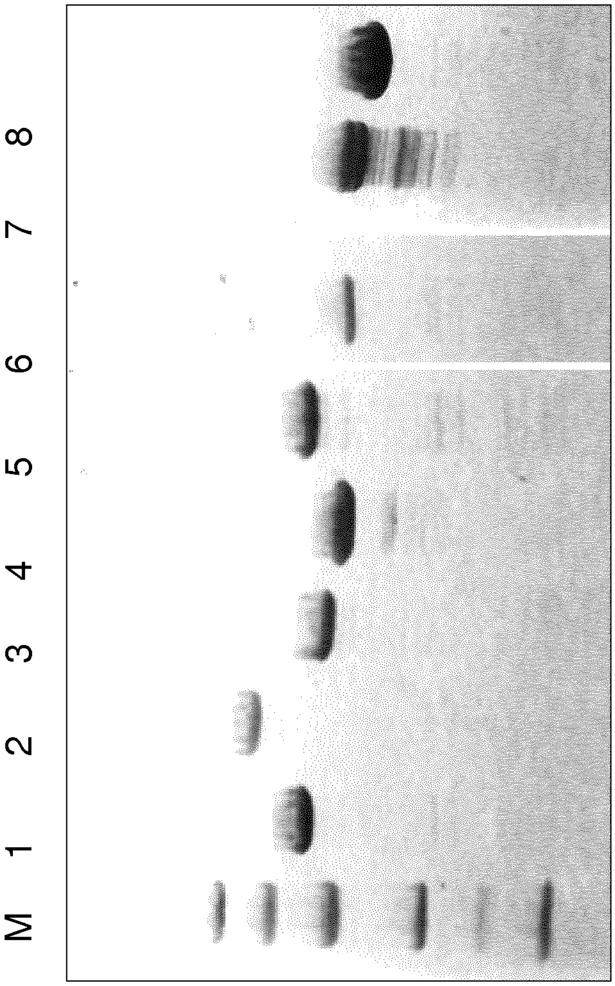
FIG. 3 shows the results of an SDS-PAGE analysis of eight His-tagged recombinant *S. suis* protein fragments: M2N—H, M2C—H, SP2N—H, SP2C—H, SP4N—H, SP4C—H, SP7N—H and SP7C—H. Molecular weight markers (kDa): 97, 66, 45, 30, 20.1 and 14.4.

Results:

A SDS-PAGE gel with the eight purified His-tagged protein fragments is shown in FIG. 3. The sizes of most proteins correspond well to the predicted size. It was observed that M2C—H migrates slower than expected which may be due to that it forms a dimer. Several fragments of different sizes of SP7N—H were observed and most likely represent breakdown products. The protein fragment SP4C—H was difficult to purify due to its high tendency to precipitate.

In conclusion, we were able to successfully express and purify the fragments M2N, M2C, SP2N, SP2C, SP4N, SP4C, SP7N and SP7C in fusion with the His-tag.

Example 3

Expression of Fragments of M2, SP2, SP4 and SP7 Fused to an SL2-Tag

This Example describes the cloning, expression and purification of two fragments of each of the antigens M2, SP2, SP4 and SP7 in fusion with the SL2-tag (SEQ ID NO:32). The size of said fragments was confirmed by SDS-PAGE analysis.

Material and Method:

The eight gene fragments encoding the protein fragments M2N, M2C, SP2N, SP2C, SP4N, SP4C, SP7N and SP7C were cloned into the Bm Kny vector in fusion with the SL2-tag (GLKTRNKKAKSDKLIVRRRNQK (SEQ ID NO:32)), indicated herein by the letter S and located in the C-terminus according to the following:

pM2N—S:

For cloning of MN2-S the same PCR product was used as for M2N—H. It was ligated into the vector BmKSL2 using the sites BamHI and XhoI. The obtained SL2-tagged polypeptide is denoted M2N—S(SEQ ID NO:21).

pM2C—S:

A codon optimized version of the gene M2 was made by DNA2.0. The gene was used as a template with the primers M2p4 and M2p5 in a PCR. The product was cleaved with the restriction enzymes BamHI and XhoI and cloned into the vector BmKSL2 cleaved with the said enzymes. The obtained SL2-tagged polypeptide is denoted M2C—S(SEQ ID NO:22).

pSP2N—S:

The SP2N gene fragment, lacking the region encoding six histidines, was cloned into the vector BmKSL2 using the sites BamHI and XhoI. The DNA fragment cloned was obtained by PCR using the SP2N—H clone as template with the primers Tac5 and sp2NXho-H. The obtained SL2-tagged polypeptide is denoted SP2N—S(SEQ ID NO:23).

pSP2C—S:

To clone the SP2C gene fragment into the BmKSL2 vector the fragment was amplified by PCR using the primers sp2CBam and sp2CXho-Val and as template the DNA from the SP2C—H clone was used. The PCR conditions were 52° C. annealing temperature, 2 minutes extension and 30 cycles. The PCR product was cleaved with enzymes BamHI and XhoI and ligated into the corresponding sites in the BmKSL2 vector. The obtained SL2-tagged polypeptide is denoted SP2C—S(SEQ ID NO:24).

pSP4N—S:

The SP4N gene fragment, lacking the region encoding six histidines, was cloned into the vector BmKSL2 using the sites BamHI and XhoI. The DNA fragment cloned was obtained by PCR using the SP4N—H clone as template with the primers tac5 and sp4NXho. The obtained SL2-tagged polypeptide is denoted SP4N—S(SEQ ID NO:25).

pSP4C—S:

The same SP4C gene fragment as described in connection with SP4C—H was used for cloning. It was cleaved with the restriction enzymes BamHI and XhoI and ligated into the vector BmkSL2 in the corresponding sites. The obtained SL2-tagged polypeptide is denoted SP4C—S (SEQ ID NO:26).

pSP7N—S:

The same SP7N gene fragment as described in connection with SP7N—H was used for cloning. It was cleaved with BamHI and XhoI and ligated into the vector BmKSL2 in the corresponding sites. The obtained SL2-tagged polypeptide is denoted SP7N—S(SEQ ID NO:27).

pSP7C—S:

The same SP7C codon optimized gene fragment as described in connection with SP7C—H was used for cloning. It was cleaved with the restriction enzymes BamHI and XhoI and ligated into the vector BmkSL2 in the corresponding sites. The obtained SL2-tagged polypeptide is denoted SP7C—S(SEQ ID NO:28).

The *E. coli* clones were grown and the protein expression induced after which protein lysates were made and analyzed using SDS-PAGE as described above.

Figure 4:
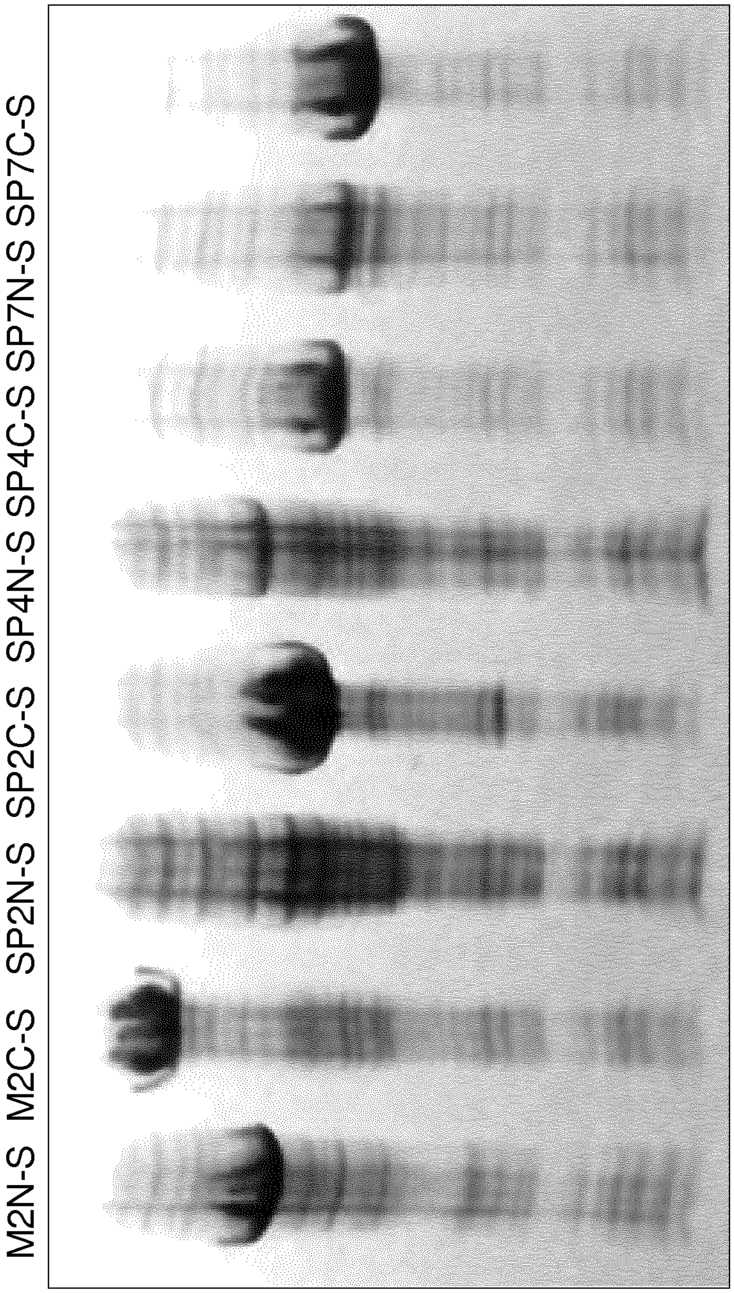
FIG. 4 shows the results of an SDS-PAGE analysis of *E. coli* lysates from eight clones expressing C-terminal SL2-tagged recombinant *S. suis* protein fragments M2N—S, M2C—S, SP2N—S, SP2C—S, SP4N—S, SP4C—S, SP7N—S, SP7C—S.

Results:

A SDS-PAGE gel of eight lysates of *E. coli* expressing the SL2-tagged protein fragments is shown in FIG. 4. The sizes of the most prominent band (corresponding to the expressed SL2-tagged protein fragments) correspond well to the predicted size. The M2C—S protein migrates approximately like a dimer as it did in fusion with the His-tag. The expression of some of the protein is very high. In general, the expression levels of the C-terminal part of the three nucleotidases is higher than the N-terminal parts. In conclusion, we were able to successfully express—the fragments M2N, M2C, SP2N, SP2C, SP4N, SP4C, SP7N and SP7C in fusion with the SL2-tag.

Example 4

Purification of Protein Fragments with SL2-Tag on Silica

In this Example the purification of a subset of SL2-tagged proteins fragments is described.

Material and Method:

Lysates of clones M2N—S, SP2C—S, SP4C—S and SP7C—S (corresponding to SEQ ID NO:21, 24, 26 and 28, respectively) were used. Silica was prepared as described above. The binding to silica were performed under low salt concentration to minimize the binding of other proteins to the silica particles. The binding to silica was performed using 0.1 ml protein lysate, 20 μl Tris (1 M, pH 9), 0.15 ml silica solution (0.2-0.3 μm) and 0.8 ml $H_2O$ supplemented with 0.02% Tween 20. The mixture was shaken slowly over night at room temperature. After binding, silica was collected by centrifugation for a few seconds and washed two times in 1 ml buffer (20 mM Tris, pH 7.3 and 20 mM NaCl) supplemented with 0.02 Tween 20. The volumes of the silica pellet were dissolved in total up to 0.1 ml and an aliquot was mixed with SDS gel loading buffer and analyzed by SDS-PAGE.

Figure 5:
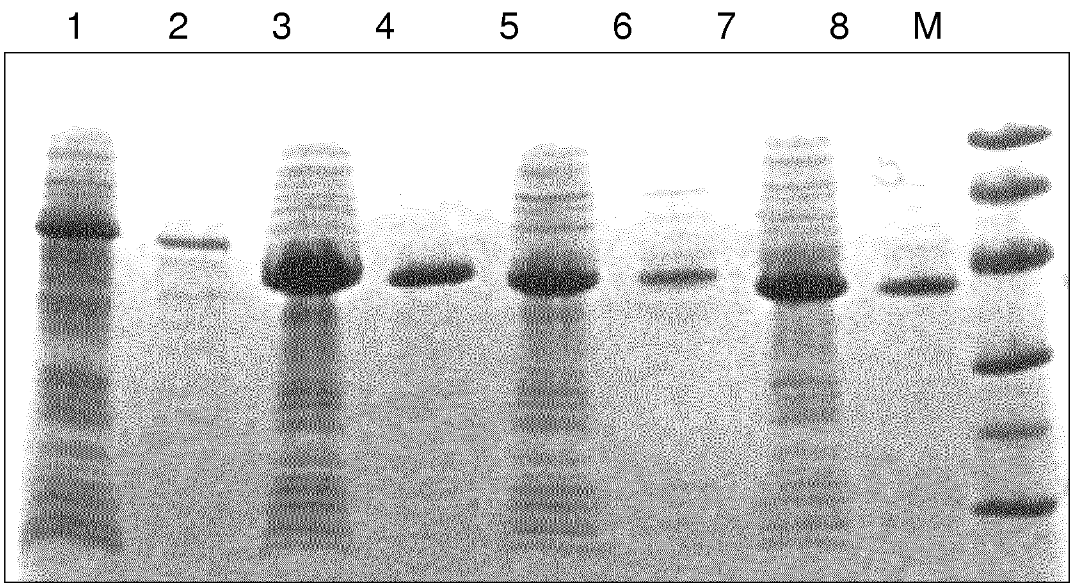
FIG. 5 shows the results of an SDS-PAGE analysis of recombinant *S. suis* protein fragments M2N—S, SP2C—S, SP4C—S and SP7C—S bound to silica particles. As a comparison *E. coli* lysates from respective clone are also shown.
Figure 6:
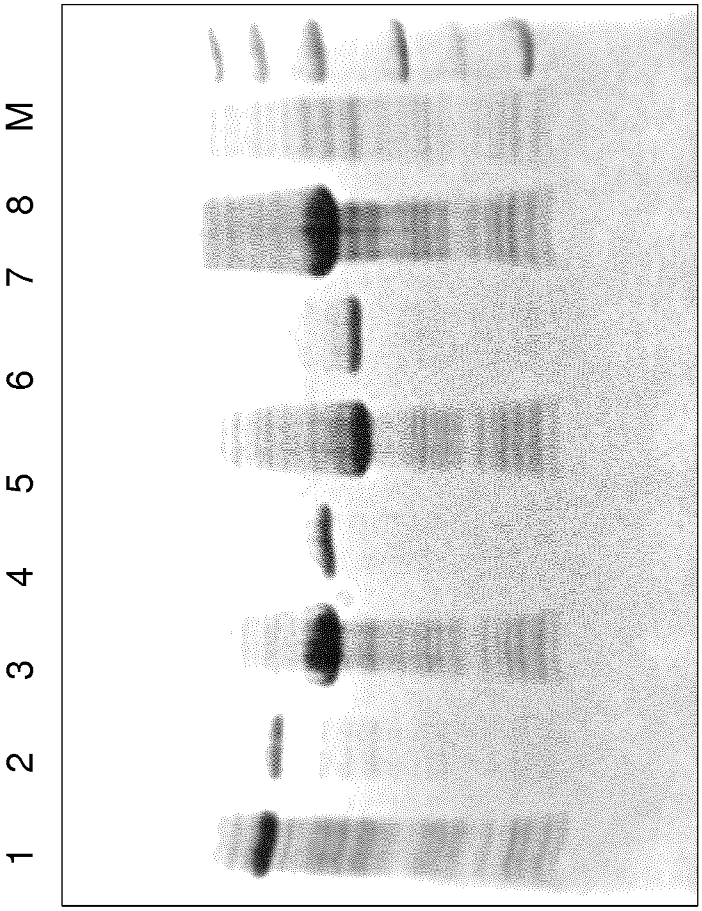
FIG. 6 shows the results of an SDS-PAGE analysis of recombinant *S. suis* protein fragments using a modified silica tag (LSL). This figure also shows that proteins which are not derived from *S. suis* can be purified using a silica tag. In addition SP2C—H (no silica tag) does not bind to silica showing the importance of the affinity tag in binding to silica.

Results:

This example shows that different proteins fused to the SL2-tag may be purified on silica (FIG. 5).

Example 5

Purification of Protein Fragments with LSL-Tag or SL2-Tag on Silica

In this example, an N-terminal version of the SL2-tag is used for purification of two protein fragments (M2N, SP2C) and the SL2-tag is used for the purification of IdeE (*S. equi*), a protein from a different bacterial species.

Material and Method:

The modified tag version, called LSL (KPALGLKTRNKKAKSDKLIVRRRNQK) (SEQ ID NO:33), is four amino acids longer than the SL2-tag, and was engineered so that it is located at the N-terminal end of the fusion polypeptide. M2N and SP2C were cloned into the BmKLSL vector in fusion with the LSL-tag located in the N-terminal while a codon optimized version of IdeE (*S. equi*) (Lannergård and Guss (2006) FEMS Microbiol Lett. September; 262(2): 230-5 (Accession number: ABF57910.1)) was cloned into BmKSL2 vector in fusion with the SL2-tag located in the C-terminal according to the following:

pM2N-LSL:

To make the M2N-LSL construct, the same PCR product was used as for the cloning of M2N—H. The cleaved PCR product was ligated into the vector BmKLSL cleaved with BamHI and XhoI. The obtained LSL-tagged polypeptide is denoted M2N-LSL (SEQ ID NO:29).

pSP2C-LSL:

To make the SP2C-LSL construct, the same PCR product was used as for the cloning of SP2C—H. The cleaved PCR product was ligated into the vector BmKLSL cleaved with BamHI and XhoI. The obtained LSL-tagged polypeptide is denoted SP2C-LSL (SEQ ID NO:30).

pldeE-S:

A codon optimized version of IdeE (*S. equi*) (Accession number: ABF57910.1) obtained from DNA2.0 was used. The IdeE (*S. equi*) gene was flanked by the sites BamHI and XhoI and was cloned into the vector BmKSL2 using the restriction sites BamHI and XhoI. The obtained SL2-tagged polypeptide is denoted IdeE-S(SEQ ID NO:31).

Recombinant proteins were expressed in *E. coli* and protein lysates were obtained as described above.

The binding to silica was performed by using 0.1 ml protein lysate, 20 μl Tris (1 M, pH 9), 0.1 ml silica slurry (0.2-0.3 μm) and 0.8 ml $H_2O$ supplemented with 0.02% Tween 20. The binding was performed with slow shaking for five hours. Next, the silica were collected by centrifugation for a few seconds and washed two times in 1 ml buffer (20 mM Tris, pH 7.3 and 20 mM NaCl) supplemented with 0.02% Tween 20. The volumes of the silica pellets were dissolved in total up to 0.1 ml and an aliquot was analyzed using SDS-PAGE.

Results:

Both M2N-LSL (SEQ ID NO:29) and SP2C-LSL (SEQ ID NO:30) can be purified on silica. The example also shows the purification of protein IdeE-S(SEQ ID NO:31). IdeE is a protein derived from *S. equi* and is included herein to show that proteins that are not *S. suis* proteins can be purified on silica using the SL2-tag. Importantly, SP2C comprising a His-tag (SP2C—H (SEQ ID NO:16) does not bind to silica, demonstrating that the SL- or LSL-tag is required for binding to silica. This data shows that silica tags, such as SL or LSL are useful for the purification of various proteins irrespective of origin. Additionally, a silica tag used for purification may be N-terminally or C-terminally located in the proteins to be purified.

Example 6

Cloning of Fusion Polypeptides and Purification Thereof Using the SL2-Tag

In this Example, the cloning of fusion polypeptides comprising SP2C and M2N, referred to herein as SP2M2 (SEQ ID NO:34), as well SP4C and SP7C, referred to herein as SP74C (SEQ ID NO:35) is described. Also described is the silica based purification of said fusion polypeptide with an SL2-tag. Additionally, fusion proteins comprising three immunogenic fragments (such as SP274C (SEQ ID NO:107) SP742C (SEQ ID NO:108)) are in fusion with SL2-tag (SEQ ID NO:109 and SEQ ID NO:110) are disclosed herein.

Cloning of Fusion Polypeptide SP2M2:

The SP2M2 construct (SEQ ID NO:34) is a fusion of the gene fragments SP2C and M2N. The SP2C fragment was PCR amplified using the template Sp2C—S(SEQ ID NO:24) and the primers Tac5 and SP2CKpnl. The M2Nlong fragment (SEQ ID NO:38) was PCR amplified using the codon optimized version template M2 (SEQ ID NO:1) and primers NMAKpn and CLMAXho. The PCR condition for the two reactions was 50° C. annealing temperature, 2 minutes extension and 30 cycles. The SP2C PCR product was digested with BamHI and KpnI and the M2N PCR product was digested with KpnI and XhoI. The digested fragments were ligated into the vector BmKSL2 digested with BamHI and XhoI.

The M2Nlong fragment (SEQ ID NO:38) in this fusion is 6 amino acids longer (PLAKAK) than in the M2N fragment (SEQ ID NO:2) in the M2N—S construct (SEQ ID NO:21). The two lysines in close connection to the SL2-tag were thought to improve the binding to silica.

Cloning of Fusion Polypeptide SP74C:

The SP74C construct (SEQ ID NO:35) is a fusion of the gene fragments SP7C and SP4C. The SP7C fragment was PCR amplified using the template SP7C—S(SEQ ID NO:28) and primers Tac5 and NP7Kpn. The SP4C fragment was PCR amplified using the template SP4C—S(SEQ ID NO:26) and primers SP4CKpnl and BmR2. The PCR condition for the two reactions was 50° C. annealing temperature, 2 minutes extension and 30 cycles. The SP7C PCR product was digested with BamHI and KpnI and the SP4C PCR product was digested with KpnI and XhoI. The cleaved fragments were ligated into the vector BmKSL2 digested with BamHI and XhoI.

Lysis:

Recombinant proteins were expressed in *E. coli* as described above. The procedure of making a bacterial lysate includes a step with sonication for several minutes. This step results in fragmentation of chromosomal DNA and plasmid DNA, which makes any DNA binding to silica difficult to analyze. To overcome this problem, a second lysate was made from cells containing the BmKSL2 vector. These cells were lysed, but only sonicated for 25 seconds, which was long enough to decrease the viscosity but short enough to still have DNA that is visible on a standard agarose gel. After sonication, the lysate was processed according to standard procedures described above and used in the assay "DNA lysate" described herein.

Silica Based Purification:

Binding to silica (0.5 ml) was performed by mixing 0.5 ml lysate (either SP74C or SP2M2) with 0.25 ml DNA lysate and 50 μl Tris (1 M, pH 9) and 9 ml $H_2O$ was added. As a control, the binding to silica of the DNA lysate was investigated. The binding was performed with slow shaking for two hours. For each specific lysate, the binding was performed in three identical samples, while varying number of washing in 1 ml buffer (20 mM Tris, pH 7.3 and 20 mM NaCl) supplemented with 0.02% Tween 20. Each sample was analyzed by agarose gel electrophoresis (FIG. 7A) and by SDS-PAGE gel electrophoresis (FIG. 7B).

Figure 7:
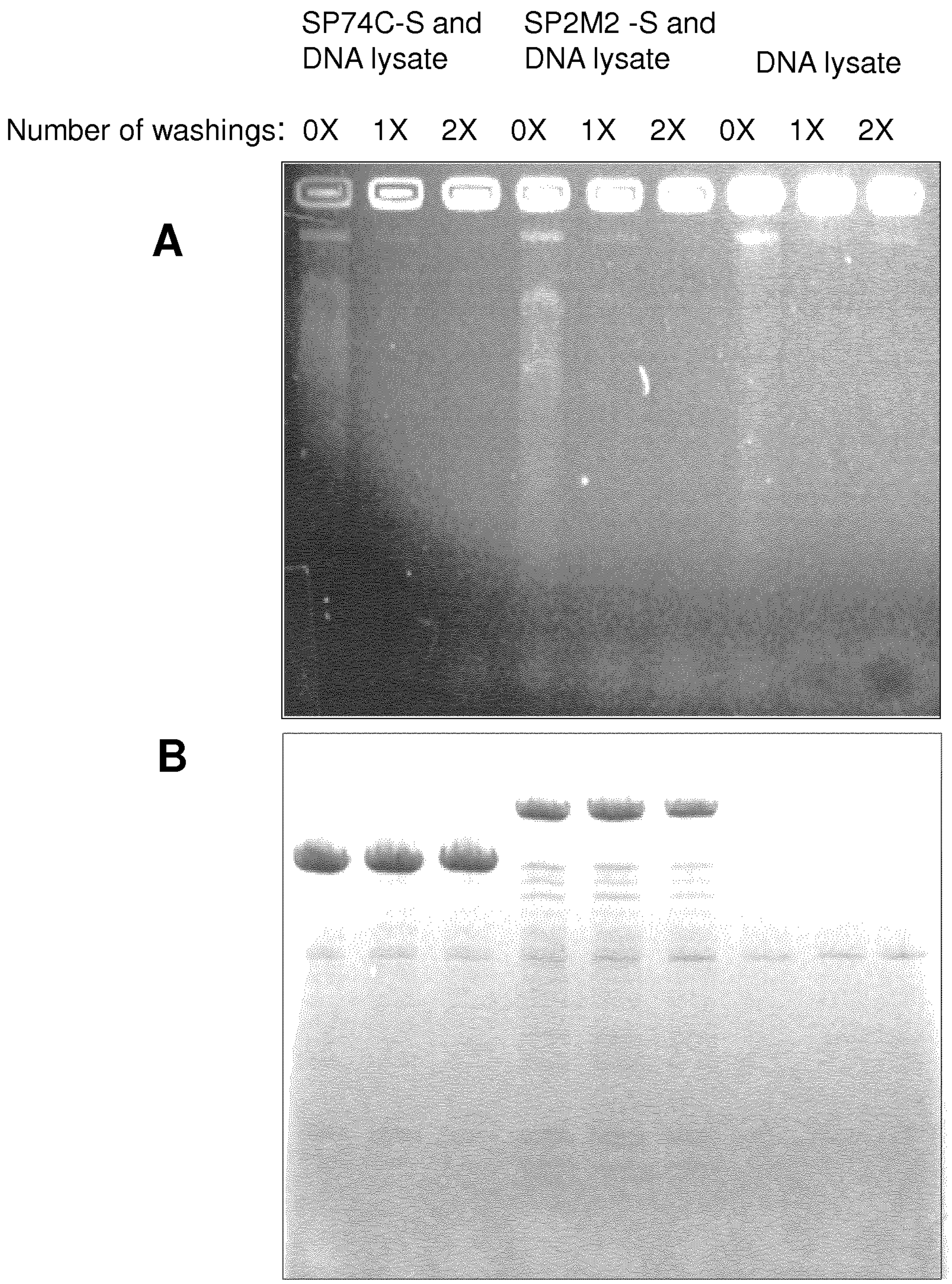
FIG. 7 shows the results of purification of the SL2-tagged fusion polypeptides SP74C—S and SP2M2-S using silica. (A) Gel electrophoresis analysis of DNA bound to silica particles using various number of washing. Analysis was performed by electrophoresis using a 1% agarose gel. (B) SDS-PAGE analysis of silica bound fusion polypeptides using the same washing procedure as in A.

Results:

As observed in FIGS. 7A and B, the amount of DNA associated to silica is decreased after each washing but the amount of bound protein is stable. This example shows that the fusion polypeptides SP74C and SP2M2 with a SL2-tag can be purified on silica and that DNA binding is very low under the low salt conditions employed.

Summary of Results from Examples 3-6

As shown in Examples 3-6 several different proteins can be purified using silica with the use of the SL2-tag and the LSL-tag. In all these examples the concentration of salt has been kept low (10-20 mM). The reason for this is that with higher salt concentrations the background binding of other proteins increases. The problem with background binding of other proteins to silica cannot be solved by increasing the number of washings. Most likely, the binding to silica occurs as a two-step reaction in which the initial binding is enhanced by the silica tag but once a protein associates with the silica particle, it deforms and starts to bind to the silica particle via other parts of the protein molecule (Mathé et al (2013) PLoS ONE 8(11): e81346). The secondary binding to silica of the proteins disclosed cannot easily be reversed. For example, the number of washings has little effect on the amount of protein bound by the silica particle. Neither the target protein nor background binding proteins from the *E. coli* lysate was significantly affected by the number of washings. Importantly, it is still possible to directly use the silica with bound proteins for immunization.

Example 7

Purification of Fragments and Fusion Polypeptides on Q-Sepharose Columns

In order to obtain soluble proteins that can be associated with silica or used with other adjuvants, the antigens with SL2-tag were purified by ion exchange chromatography using Q-sepharose. Additionally, His-tagged antigens purified on Talon columns were used as controls. Purifications were performed according to the following:

Protein Purification on Talon:

Premade columns with 1 ml Talon (GE Healthcare) were used. All proteins were purified according to the description below (step 1-11). The columns were reused but only the same protein was purified on each column.

1. The column was washed with 10 ml TN0.4 buffer (10 mM Tris Ph 7.1, 0.4 M NaCl).
2. 10-15 ml lysate was applied two times on the column.
3. The column was washed with 2×5-10 ml TN0.4 buffer.
4. Sometimes an extra washing step with 5 ml 5 mM Imidazole i TN 0.4 buffer was applied.
5. The recombinant protein was eluted with 0.1 M Imidazole i TN 0.4 buffer.
6. The column was wash with 5 ml 8 M UREA.
7. The column was regenerated with 10 ml MES (20 mM)+NaCl (0.4 M).
8. The column was washed with 20 ml $H_2O$ and saved for the next purification of the same protein.
9. The eluted protein samples were dialyzed against PBS (2×5 l).
10. The samples were sterile filtered (0.2 μm).
11. The absorbance was measured and the samples were frozen.

Protein Purification on Q-Sepharose:

M2N—S, SP2C—S, SP4C—S, SP7C—S, SP74C—S and SP2M2-S were purified according to the description below:

Step 1-2 were the same for all purifications:

1. The column was packed with med 4 ml Q-sepharose (GE Healthcare).
2. The column was washed with 10 ml $H_2O$.

Protein Purification of M2N—S:

3. The column was washed with 2×10 ml TN0.05 (Tris 20 mM pH 7.1 and NaCl 0.05 M).
4. 10 ml M2N—S lysate was mixed with 10 ml $H_2O$ and applied to the column two times.
5. The column was washed with 2×10 ml TN0.05.

6. The column was washed with 5-10 ml TN0.1 (Tris 20 mM pH 7.1 and NaCl 0.1 M).
7. The column was washed with 5-10 ml TN0.15 (Tris 20 mM pH 7.1 and NaCl 0.15 M).
8. The recombinant protein was eluted with 2×5 ml TN0.2 (Tris 20 mM pH 7.1 and NaCl 0.2 M).
9. The eluate was diluted to 30 ml with $H_2O$.
10. The diluted eluate was added to a new column which was washed and the recombinant protein eluted as described above.
11. The eluted sample was diluted with $H_2O$ to 0.15 M NaCl and sterile filtered (0.2 μM).
12. The absorbance was measured and the samples were frozen.
Purification of SP2C—S:
3. The column was washed with 2×10 ml TN0.1 (Tris 20 mM pH 7.1 and NaCl 0.1 M).
4. 10 ml SP2C—S lysate was mixed with 10 ml $H_2O$ and 0.4 ml NaCl (5 M).
5. The sample was applied on the column two times.
6. The column was washed with 15 ml TN0.2.
7. The column was washed with 5 ml TN0.25.
8. The recombinant protein was eluted with 2×5 ml TN0.3.
9. The eluate (10 ml) was diluted with $H_2O$ to 25 ml and applied on the column two times.
10. The column was washed and the recombinant protein eluted as described above.
11. The eluate was diluted to 20 ml with $H_2O$ and sterile filtered (0.2 μm).
12. The absorbance was measured and the samples were frozen.
Purification of SP4C—S:
3. The column was washed with 2×10 ml TN0.05 (Tris 20 mM pH 7.1 and NaCl 0.05 M).
4. 20 ml SP4C—S lysate was mixed with 20 ml $H_2O$ and applied on the column two times.
5. The column was washed with 2×10 ml TN 0.05.
6. The recombinant protein was eluted with 5 ml TN 0.1.
7. The recombinant protein was eluted with 2×4 ml TN 0.15.
8. The eluates were pooled and 30 ml $H_2O$ was added.
9. The eluate was applied to a new column two times.
10. The column was washed with 2×10 ml TN0.05.
11. The column was washed with 5 ml TN0.1.
12. The recombinant protein was eluted with 3×4 ml TN0.15.
13. The eluate was sterile filtered (0.2 μm).
14. The absorbance was measured and the samples were frozen.
Purification of SP7C—S:
3. The column was washed with 2×10 ml TN0.05 (Tris 20 mM pH 7.1 and NaCl 0.05 M).
4. 20 ml SP7C—S lysate was mixed with 20 ml $H_2O$ and applied on the column two times.
5. The column was washed with 2×10 ml TN 0.05.
6. The recombinant protein was eluted with 5 ml TN 0.1.
7. The recombinant protein was eluted with 3×4 ml TN0.2.
8. The eluates was pooled and 30 ml $H_2O$ was added.
9. The eluate was applied to a new column two times.
10. The column was washed and the recombinant protein eluted as described above.
11. The eluate was pooled and sterile filtered (0.2 μm).
12. The absorbance was measured and the samples were frozen.
Purification of SP74C—S:
3. The column was washed with 2×10 ml TN0.05 (Tris 20 mM pH 7.1 and NaCl 0.05 M).
4. 10 ml SP74C—S lysate was mixed with 10 ml $H_2O$ and applied on the column two times.
5. The column was washed with 10 ml TN0.05.
6. The column was washed with 2×10 ml TN0.1.
7. The recombinant protein was eluted with 2×5 ml TN0.2.
8. The eluate was diluted to 40 ml using $H_2O$.
9. The eluate was applied to a new column two times.
10. The column was washed and the recombinant protein eluted as described above.
11. The eluate was pooled and sterile filtered (0.2 μm).
12. The absorbance was measured and the samples were frozen.
Purification of SP2M2-S:
3. The column was washed with 2×10 ml TN0.05 (Tris 20 mM pH 7.1 and NaCl 0.05 M).
4. 10 ml SP2M2-S lysate was mixed with 10 ml $H_2O$ and applied on the column two times.
5. The column was washed with 3×10 ml TN0.2 (pH 8).
6. The column was washed with 10 ml TN0.25 (pH 8).
7 The column was washed with 10 ml TN0.3 (pH 8).
8. The recombinant protein was eluted with 10 ml TN0.35 (pH 8).
9. The eluate was diluted to 20 ml with $H_2O$ and applied on the column two times.
10. The column was washed and the recombinant protein eluted as described above.
11. The eluate was pooled and sterile filtered (0.2 μm).
12. The absorbance was measured and the samples were frozen.

Figure 8:
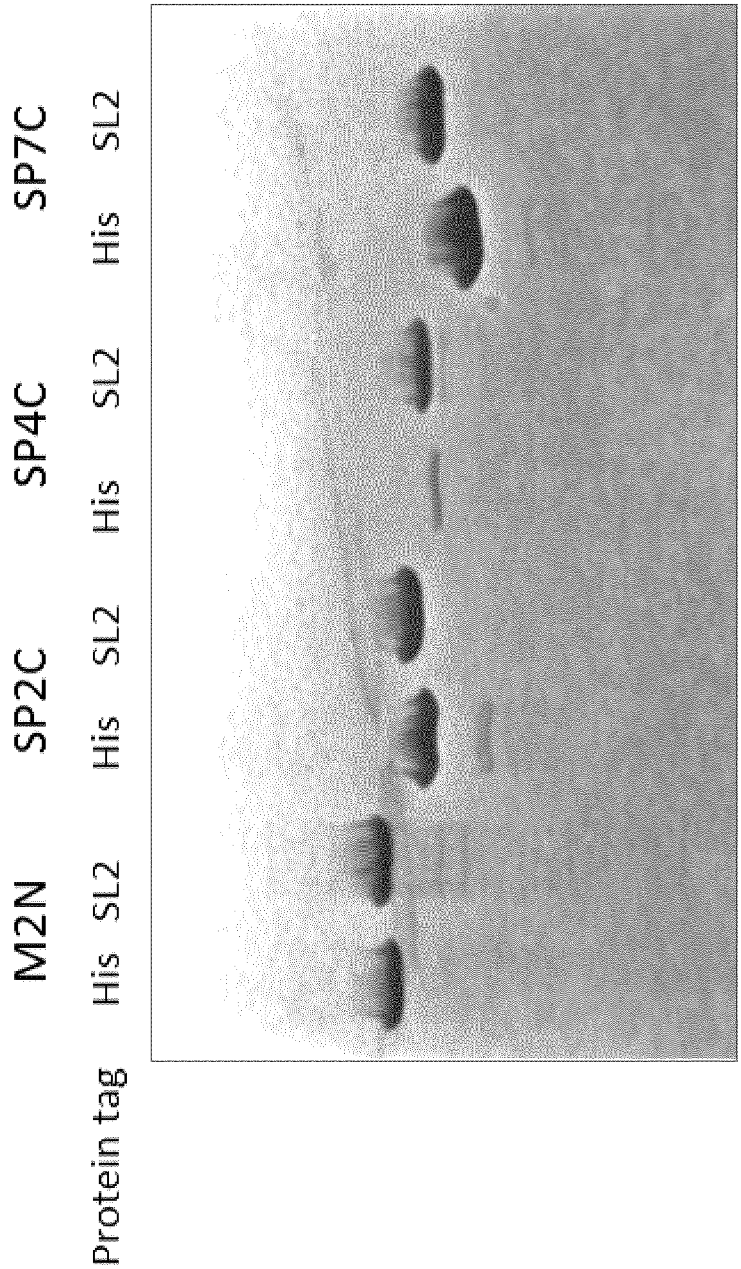
FIG. 8 shows the results of a comparison of Talon purified His-tagged recombinant *S. suis* protein fragments M2N—H, SP2C—H, SP4C—H and SP7C—H and Q-Sepharose ion exchange chromatography purified SL2-tagged recombinant *S. suis* protein fragments M2N—S, SP2C—S, SP4C—S and SP7C—S using SDS-PAGE.

As can be seen in FIG. 8, the purity of the SL2-tagged Q-sepharose purified proteins as estimated using SDS-PAGE gel is similar to the purity of His-tagged proteins purified on Talon. The SL2-tag is 22 amino acids long, thus these proteins are slightly larger than the corresponding protein with His-tag.

Example 8

Stability of Purified Antigens

Figure 9:
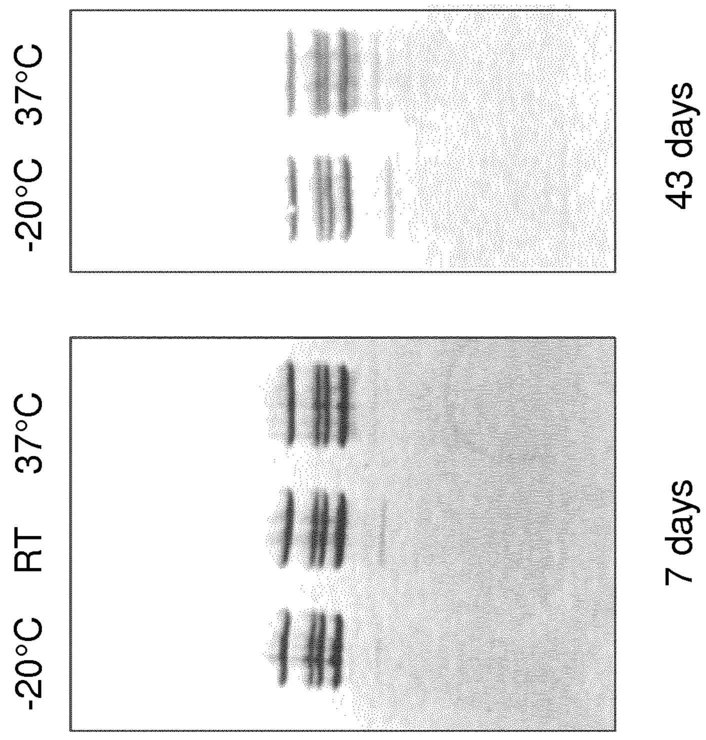
FIG. 9 shows the results of an analysis of the stability of Q-Sepharose purified antigens M2N—S, SP2C—S, SP4C—S and SP7C—S using SDS-PAGE.

The stability of Q-sepharose purified antigens obtained in Example 7 was tested. The antigens M2N—S, SP2C—S, SP4C—S and SP7C—S were mixed and aliquots were incubated at 37° C., room temperature (RT) and frozen (−20° C.) as a control. After 43 days at 37° C. the antigens exhibited a high level of stability (FIG. 9).

Example 9

Stability of Fusion Antigens

Several different combination of fusion polypeptides have been made using M2N, SP2C, SP4C and SP7C, for example corresponding to SEQ ID NO:34-35 and SEQ ID NO; 92-95. Additionally, fusion proteins comprising three immunogenic fragments are contemplated, such as SP274C (SEQ ID NO:107) SP742C (SEQ ID NO:108).

Figure 10:
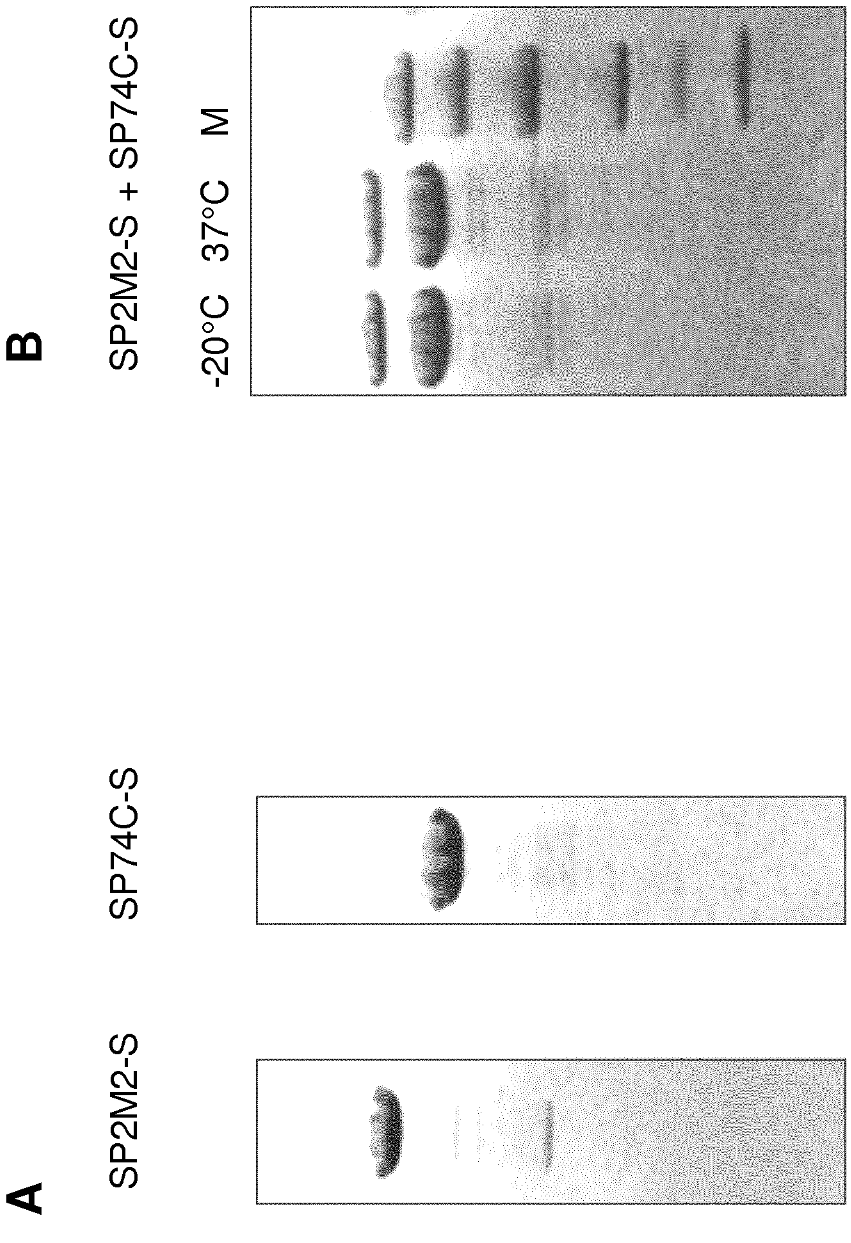
FIG. 10 shows the results of an analysis of the Q-Sepharose purified fusion polypeptides SP2M2-S and SP74C—S using SDS-PAGE. The purified fusion polypeptides are shown in FIG. 9A.
Figure 11A:
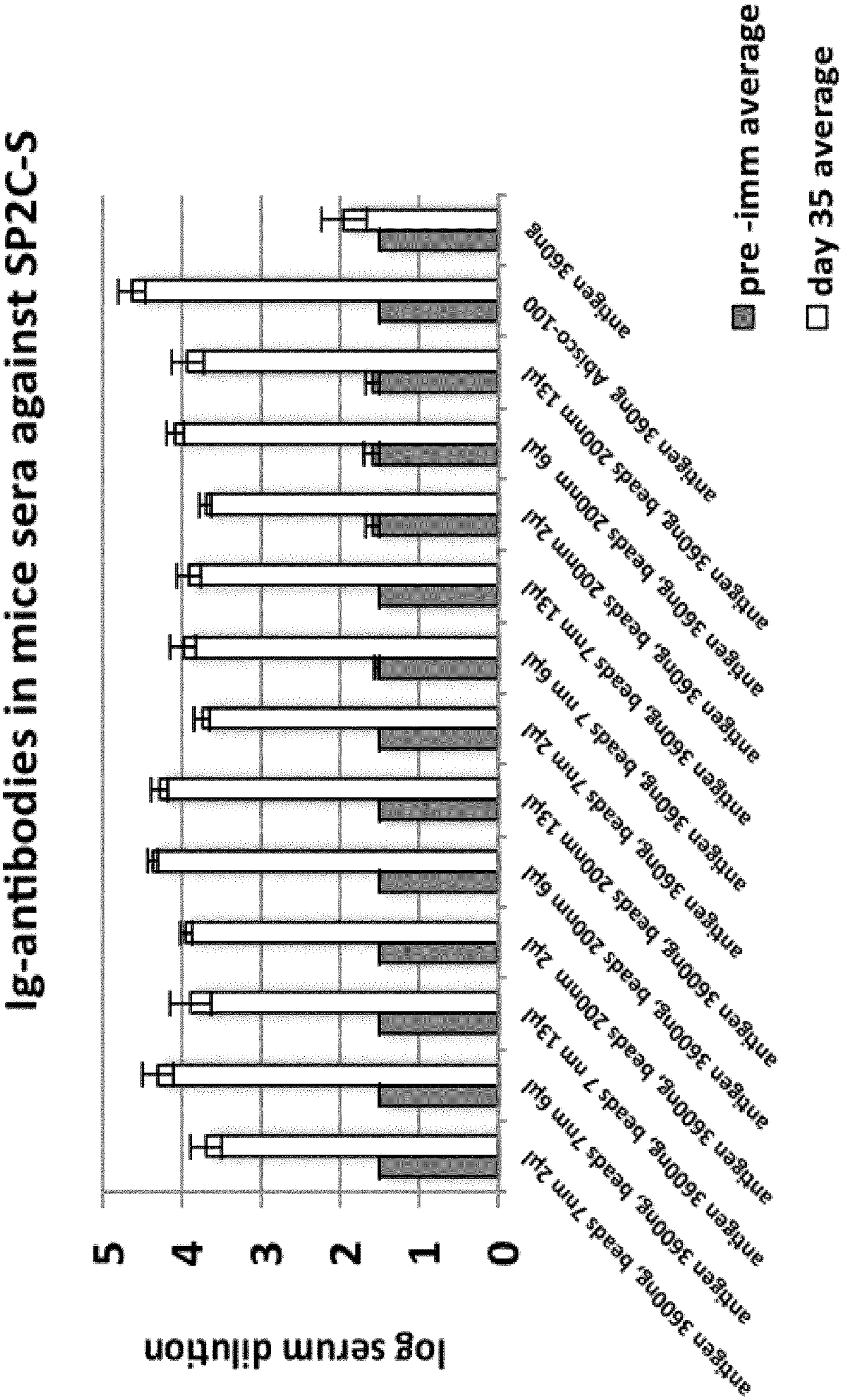
FIGS. 11A, B, C and D are bar graphs showing the results of the ELISA analysis on days 0 (pre-imm average) and 35 (day 35 average) of the mouse immunizations with SP2C—S, SP4C—S, SP7C—S and M2N—S, respectively, described in Example 9. Mean values (n=3) and standard errors are shown.
Figure 11B:
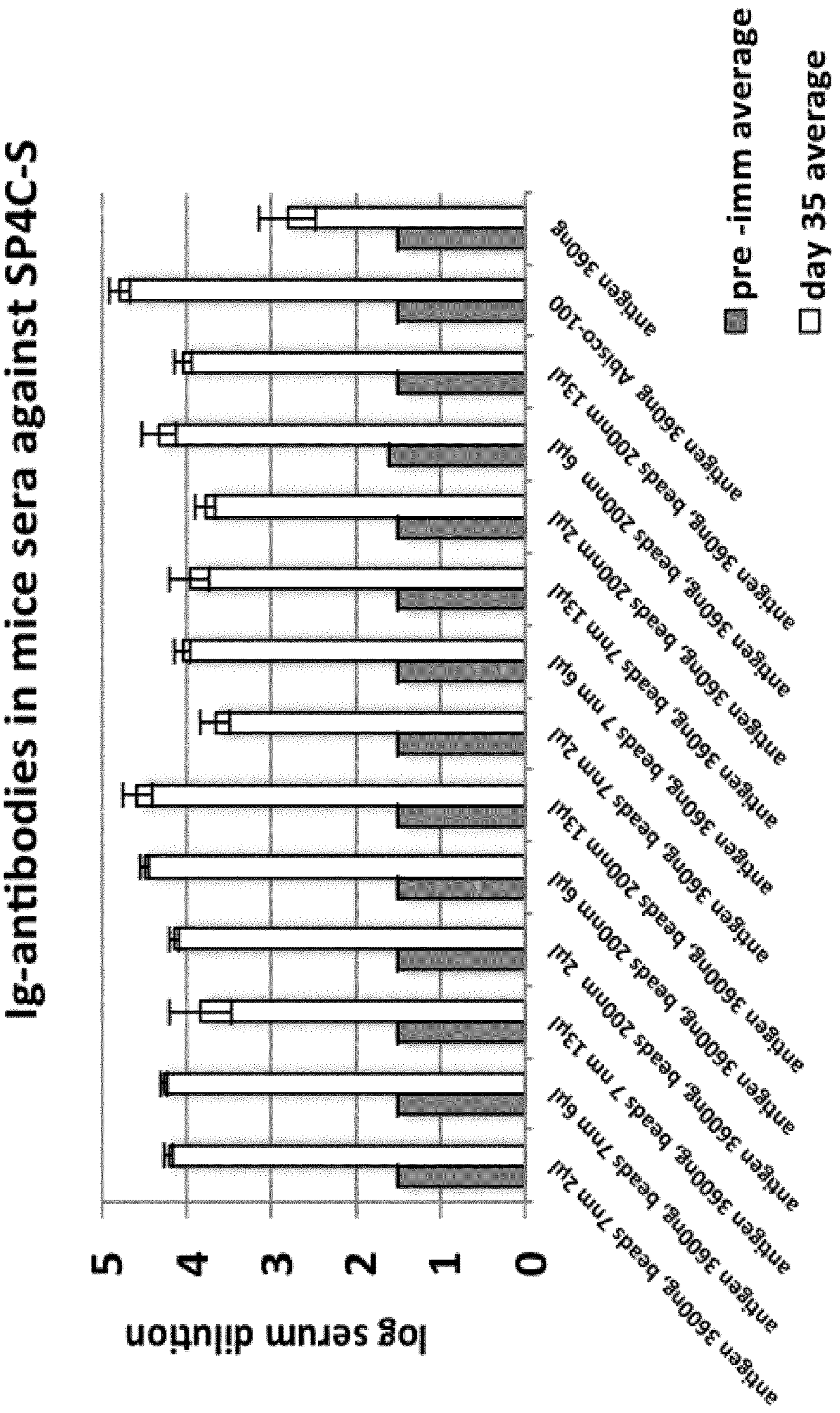
Figure 11C:
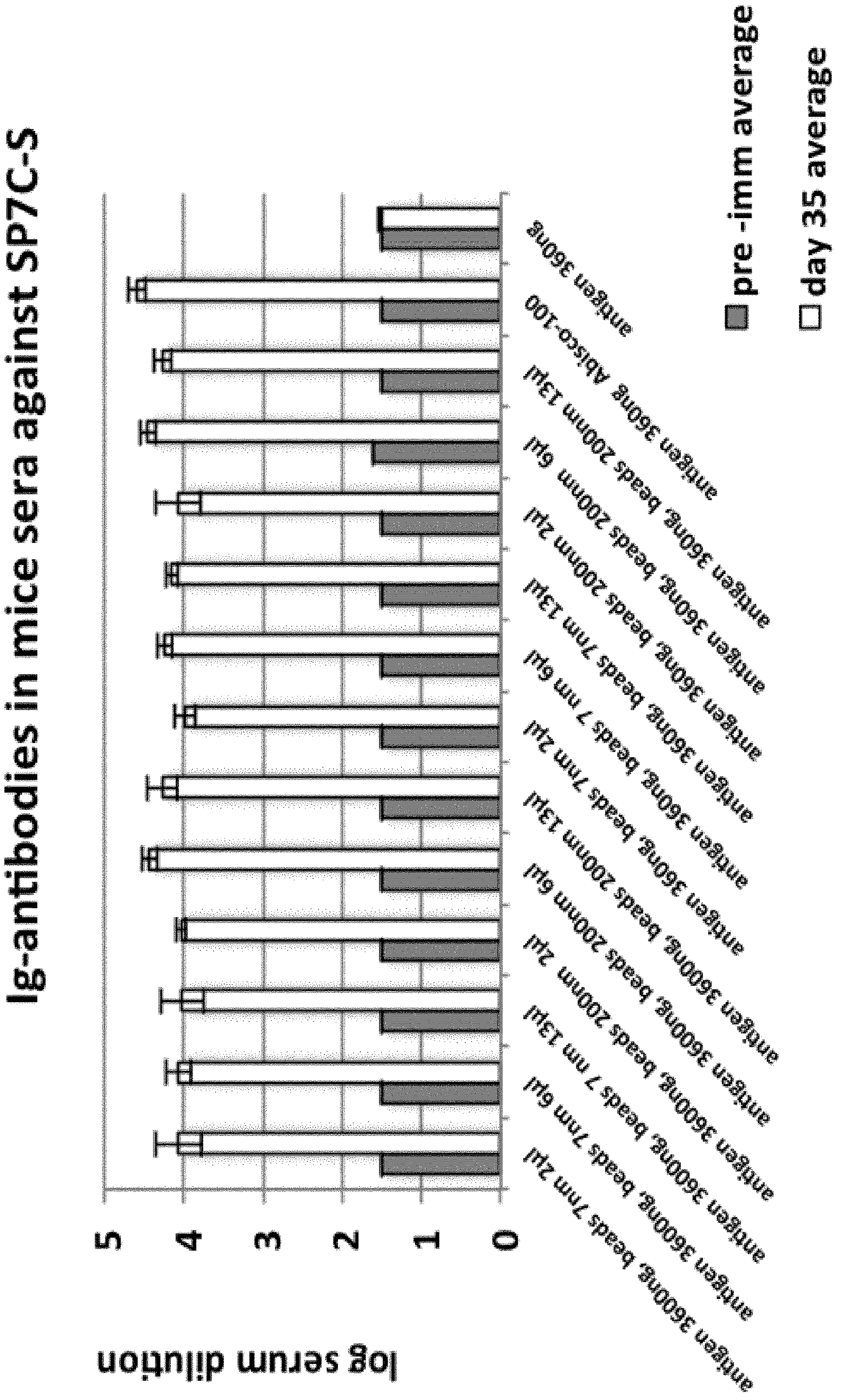
Figure 11D:
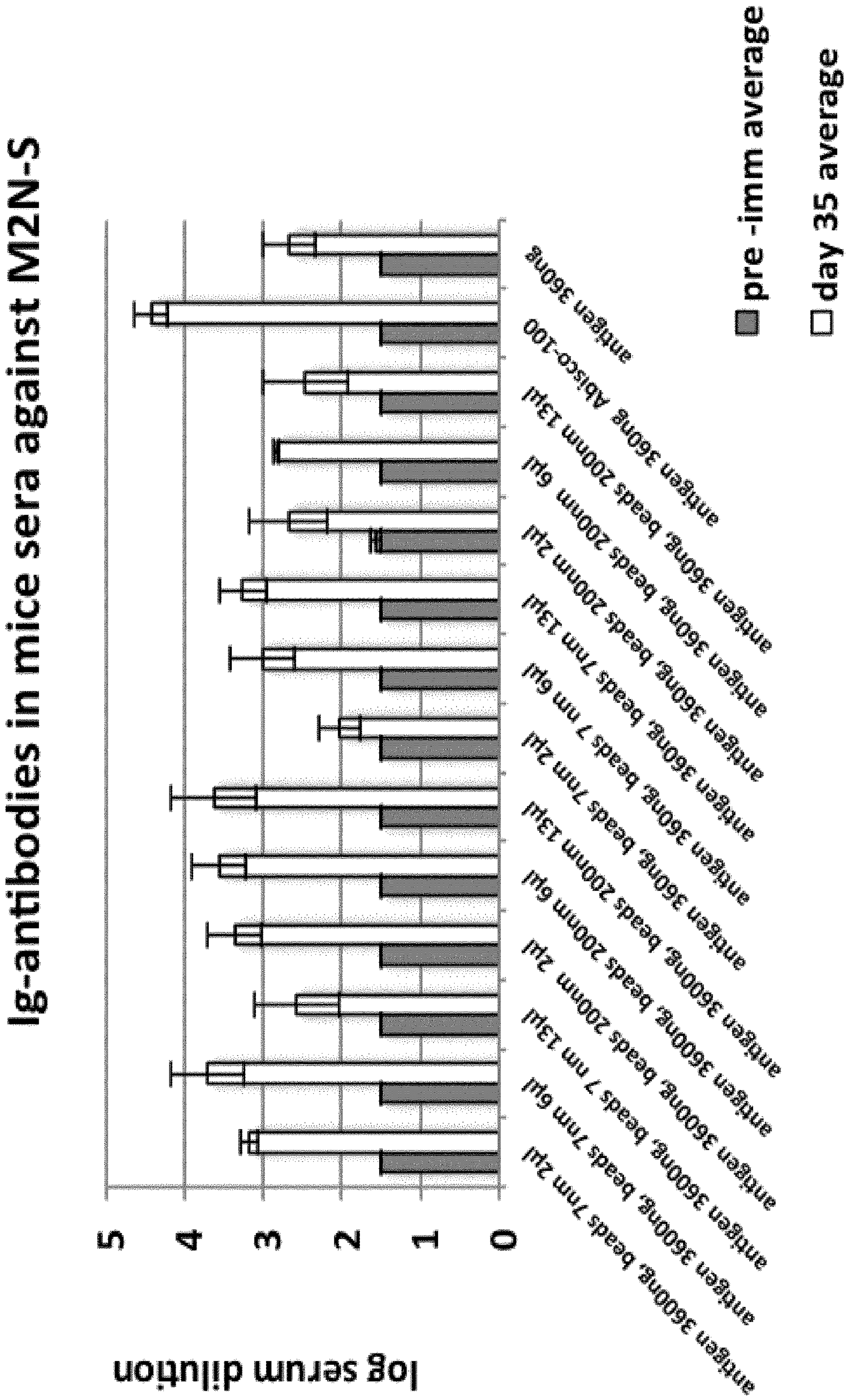

SP2M2 (SEQ ID NO:34) and SP74C (SEQ ID NO:35) described in Example 6 were selected for further study. Both fusion polypeptide were cloned in the BmKSL2 vector and thus contains the SL2-tag resulting in SP2M2-S(SEQ ID NO:36) and SP74C—S(SEQ ID NO:37). These fusion polypeptides were purified on silica and analyzed by SDS-PAGE gel electrophoresis (FIG. 10). The fusion polypeptides were also purified on Q-sepharose as described in Example 8 and analyzed by SDS-PAGE gel electrophoresis (FIG. 10A). The stability of the fusion polypeptides after purification on Q-sepharose was also tested. The two fusion polypeptides were mixed and one aliquot of the mix was frozen and the other was incubated at 37° C. FIG. 10B shows an SDS-PAGE analysis of the mixed fusion polypeptides after 5 days at −20° C. compared to 5 days at 37° C. Both fusion polypeptides exhibited good stability.

Example 10

Immunological Response in Mice Against SP2C—S, SP4C—S, SP7C—S, and M2N—S

In this Example the four antigens SP2C—S, SP4C—S, SP7C-2, and M2N—S were injected into mice and the antibody responses thereto were investigated.

Material and Method:

Immunization:

Forty two mice (BalbC, weight 18-22 g) were divided into 14 groups with three animals in each group. Procedures were performed on the days as indicated in the Table below; on days 0, 14, 21 and 28 the mice were immunized with a mixture of antigens by injection of 25 μl intra muscularly. Blood samples were collected from the tail vein on days 0, 14, 21, 28 and 35, prior to immunizations. Sera was prepared by allowing the blood to clot and the sera after centrifugation was transferred to a new tube stored at −20° C.

TABLE 3

Overview of immunization procedure.

| Day | Procedure |
|---|---|
| 0 | collection of serum samples, immunization |
| 14 | collection of serum samples, immunization |
| 28 | collection of serum samples, immunization |
| 35 | collection of serum samples |

The 42 animals were immunized with a mixture containing the four antigens (SP2C—S, SP4C—S, SP7C-2, and M2N—S, corresponding to SEQ ID NO:24, 26, 28 and 21, respectively) with either 3.6 μg of each antigen or 0.36 μg of each antigen. Different amounts of silica beads were used; 2, 6 or 13 μl per dose containing 25 μl and two different sizes of silica beads were used, 7 nm or 0.2-0.3 μm. In group 13, silica beads were replaced by 4 μg per dose of MatrixM/Abisco 100 (Isconova AB, Sweden), and in group 14 no adjuvant was used.

TABLE 4

Summary of the content of vaccines in the different test groups.

| Group number | Antigen amount (ng per dose in 25 μl) | Adjuvant (silica particle size; amount per dose in 25 μl) |
|---|---|---|
| 1 | 3600 | 7 nm; 2 μl |
| 2 | 3600 | 7 nm; 6 μl |
| 3 | 3600 | 7 nm; 13 μl |
| 4 | 3600 | 200 nm; 2 μl |
| 5 | 3600 | 200 nm; 6 μl |
| 6 | 3600 | 200 nm; 13 μl |
| 7 | 360 | 7 nm; 2 μl |
| 8 | 360 | 7 nm; 6 μl |
| 9 | 360 | 7 nm; 13 μl |
| 10 | 360 | 200 nm; 2 μl |
| 11 | 360 | 200 nm; 6 μl |
| 12 | 360 | 200 nm; 13 μl |
| 13 | 360 | Matrix M/Abisco 100 |
| 14 | 360 | nil |

Analysis of Serum Samples:

Serum samples were analyzed for immune response against the different antigens using a conventional ELISA procedure as described below.

1. Coating: Microtiter plates (Nunc), were coated separately with one of SP2C—S, SP4C—S, SP7C-2 and M2N—S dissolved in PBS (Phosphate buffered Saline) pH 7 at 4 μg/ml. 100 μl was added to each well in 96-well plate. Coating was performed overnight at room temperature, 20° C.-25° C.
2. Blocking: 100 μl bovine serum albumin (BSA) (Sigma) at a concentration of 2% in PBS was added to each well and left at 37° C. for 1 hour. Next, wells were washed 4-5 times in PBST (PBS supplemented with 0.05% Tween20). The plates were not allowed to dry.
3. Next serum samples obtained from immunized mice were added to the wells. 200 μl PBST was added to the first well and 100 μl to the rest of the wells. 5 μl of sample was to the first well resulting in a 40-fold dilution and 100 μl were transferred from first well to the next and mixed, resulting in a 2-fold dilution. 2-fold dilutions were continued in the same manner to the second last well and the last 100 μl were discarded. The last wells were left without antibodies and used as negative controls. The samples were incubated for 2 hours 37° C. and then wash 4-5 times with PBST.
4. In order to detect antibody binding anti-mouse-IgG antibodies (raised in rabbit) conjugated with HRP (Dako) diluted 3000× were added. The samples were incubated for 1 hour at 37° C. and thereafter washed 4-5 times with PBST.
5. Detection of anti-mouse antibodies was performed as follows: 100 μl OPD substrate, prepared according to manufacturer's recommendation (Dako), was added per well and incubated for 14 minutes. The reaction was terminated by adding 100 μl 0.5 mol/L $H_2SO_4$ and the plates were read in an ELISA spectrophotometer at 495 nm.
6. Data was transferred to an Excel worksheet and the absorbance at 495 nm (A495) was plotted as a function of serum dilution. A horizontal line was draws through A495=1.5 and the log value of the dilution for each serum sample where the titration curve cuts the A495=1.5 line was determined. Mean values and standard errors for each group of mice sera were calculated.

Results:

ELISA values on days 0 and 35 were plotted for the four separate antigens and shown in FIGS. 11A-D. Average (n=3) and standard errors are shown. All four antigens elicited an antibody response in mice at both concentrations used (360 or 3600 ng per dose). The use of silica beads resulted in a better immune response as compared with antigen being used without adjuvant. This is particularly noticeable for the three antigens SP2C, SP4S and SP7S. It can further be noted that the size of the silica beads (7 or 200 nm) does not seem to be of importance for the elicited antibody response. Within the range used, 2-13 μl per dose, no dose effect was observed. This implies that the use of the lowest amount (2 μl) of silica beads in a dose of 25 μl is sufficient to result in adjuvanticity.

Example 11

Immunological Response in Piglets Against SP2M2-S and SP74C—S

In this Example we assess the IgG serum levels in piglets following an initial immunization with *Streptococcus suis* fusion antigens SP2M2-S(SEQ ID NO:36) and SP74C—S (SEQ ID NO:37) and the response following a booster immunization, compared with a placebo. The test material, study setup, analysis and results are described.

Material and Methods

Test Animals:

Details on the animals used in this study are given in Table 5 below and the inclusion criteria, exclusion criteria and post inclusion withdrawal criteria applied were the same as in Example 12.

TABLE 5

Detail on animals used in the study.

| Animal details | Sows | Piglets |
|---|---|---|
| Species | Porcine | Porcine |
| Breed | Yorkshire - Landrace | Yorkshire - Landrace |
| Sex | Female | Female/Male |
| Other | Stage of gestation: 106 days gestation on arrival | Age: Approximately 4 days of age on Day 0 (±1 day) |
| Body weight | — | ≥1.0 kg on Day 0 |
| Number | 3 | 26 piglets |
| Source | Commercial pig farm - (Millerhill, UK) | Commercial pig farm - (Millerhill, UK) |
| Fate of animals | All study animals will be euthanized and incinerated. | All study animals will be euthanized and incinerated. |

Allocation/randomization was performed according to the following. On day 0, suitable piglets in each litter were blocked into groups of three (based on descending body weight) and allocated to one of three groups such that within each block of three, one piglet was allocated to each group. For subsequent litters allocation started from where the previous litter's allocation finished. A minimum of eight piglets were required per group. Using a random number generator, each group was then allocated to a study treatment group. No blinding was performed due to the investigative nature of the study.

Test and Control Material:

The test material—was prepared according to Table 6 and the control group received a control dose of placebo, which is selected in order to mimic the test material dose regime. For SP74C—S lot #141118 was used and for SP2M2-S lot #141118 was used.

TABLE 6

Information on test and control material. The formulation comprising SP74C-S (SEQ ID NO: 37) and SP2M2-S (SEQ ID NO: 36) is herein also referred to as "Piggy vaccine".

| Test material | Study 1 | Control |
|---|---|---|
| Name/Code Number | SP74C-S (SEQ ID NO: 37) and SP2M2-S (SEQ ID NO: 36) | Placebo |
| Formulation | Protein solution in 50 mM Tris pH 7.3 | Adjuvant solution in 50 mM Tris pH 7.3 |
| Concentration | 40 μg per antigen in 500 μl injection volume | 100 μg/ml of adjuvant |
| Storage Conditions Required | +2 to +8° C. | +2 to +8° C. |
| Method of Administration | Intramuscular injection | Intramuscular injection |
| Dose Regime | Day 0 and 14 | Day 0 and 14 |

Study Design and Procedure:

A summary of the study design is given in Table 7. A total of three pregnant pigs (approximately 1 week before farrowing) were sourced from a commercial pig farm with no history of *Streptococcus suis* clinical disease. Animals were kept and monitored as described in Example 11.

TABLE 7

Summary of the study design.

| | | Treatment | | | |
|---|---|---|---|---|---|
| Group | No. of animals | Day 0 test material | Day 14 test material | Route/ volume | End of study day |
| 1 | 4 | Antigen 16 μg | Antigen 16 μg | Intramuscular/ 0.5 ml | 28 |
| | 4 | Antigen 16 μg | Placebo | | |

The study was performed as summarized in Table 8. The procedures on day −1, 0, 14 were as described in Example 12. Blood samples were collected from all animals and the body weight of all piglets was recorded on day 0, 7, 14, 21 and 28.

TABLE 8

Summary of the study design.

| Study day | Procedure(s) |
|---|---|
| −3 | Farrowing, ear tagging |
| −1 | Blood sample |
| 0 | Physical examination, body weight, allocation, test material administration |
| 0 (+1 h and +4 h) | Clinical observation |
| 7 | Blood sample, body weight |
| 14 | Blood sample, body weight, test material administration |
| 14 (+1 h and +4 h) | Clinical observation |
| 21 | Blood sample, body weight |
| 28 | Blood sample, body weight |

Test Material Preparation and Administration

Test Material Preparation:

Test and control material were supplied as ready to use, but were allowed to reach room temperature before administration. The test material was shaken before use.

Test Material Administration:

On day 0 and on day 14, each animal was administered a 0.5 ml volume of the antigen concentration and adjuvant concentration or adjuvant, respectively, according to Tables 6 and 7 by the intramuscular route. All injections were administered to the neck muscle on the right side.

Clinical Observations:

Clinical observation/Injection site reactions post treatment as well as general heath observations were performed as described in Example 12.

Serological Testing:

All samples collected from sows during screening the piglets during the study were analyzed on completion of the study.

Sample Collection and Processing

Blood samples of maximum 2 ml were collected from all piglets on day −1, then again on day 0, 7, 14, 21 and 28. The sample were processed as described in Example 12.

Analysis of Serum Samples:

Serum samples were analyzed for immune response against the SP2M2 and SP74C antigens using the ELISA procedure as described in Example 10, with the following exceptions in steps 1, 3 and 4: Step 1: microtiter plates (Nunc), were coated separately with SP2M2C—S(SEQ ID NO:36), lot #141118), or SP74C—S(SEQ ID NO:37) lot #141118), dissolved in PBS pH 7.3 at 4 μg/ml. 100 μl was added to each well in 96-well plate. Coating was performed overnight at room temperature, 20° C.-25° C. followed by blocking with 100 μl 2% BSA for 1 hour at room temperature; Step 3: after washing of the microtiter wells, serum samples obtained from immunized piglets were added to the wells in serial dilutions and the samples were incubated for 2 hours 37° C. followed by washing 5 times with PBST; and Step 4: in order to detect antibody binding anti-pig-IgG antibodies (Sigma A5670t) conjugated with HRP (Dako) and diluted 10,000× was added. The samples were incubated for 1 hour at 37° C. and then washed 5 times with PBST. Detection of anti-pig antibodies and data analysis were performed as described in step 5 and 6 in Example 9.

Results:

All three sows were negative against the two antigens SP74C—S (SEQ ID NO:37) and SP2M2-S(SEQ ID NO:36) included in the Piggy vaccine when screening samples were applied to a serological test.

The body weight of all piglets increased throughout the observation period as shown in Table 9.

TABLE 9

Body weight of piglets (mean and st. dev. shown).

| Group | Study day | | | | | Mean weight gain |
|---|---|---|---|---|---|---|
| 1 | 0 | 7 | 14 | 21 | 28 | (kg) |
| Mean | 2.30 | 4.51 | 6.47 | 8.44 | 11.20 | 8.90 |
| StDev | 0.42 | 1.38 | 1.93 | 2.56 | 3.42 | 2.73 |

All animals were successfully administered the test material on days 0 and 14 with no occurrence of mis-dosing and no injection site reactions were observed.

On day 0, one hour post treatment, with the exception of one animal in Group 1 (animal 6164), no abnormal clinical signs were observed in any animal. Animal 6164 was observed to have a lame left hind leg. No pyrexia was observed in any animal, with temperatures ranging between 38.0° C. to 39.9° C. On assessment four hours post treatment, animal 6164 was observed to be lame and depressed with a rectal temperature of 40.2° C. and was diagnosed with suspected abscess upon veterinary examination. No treatment was administered to said animal. No pyrexia was observed in any other study animal, with temperatures ranging between 38.0° C. to 39.7° C.

No abnormal clinical signs were observed in any animal on day 14 post vaccination. No pyrexia was observed in any animal, with temperatures ranging between 38.7° C. to 39.9° C.

Figure 12:
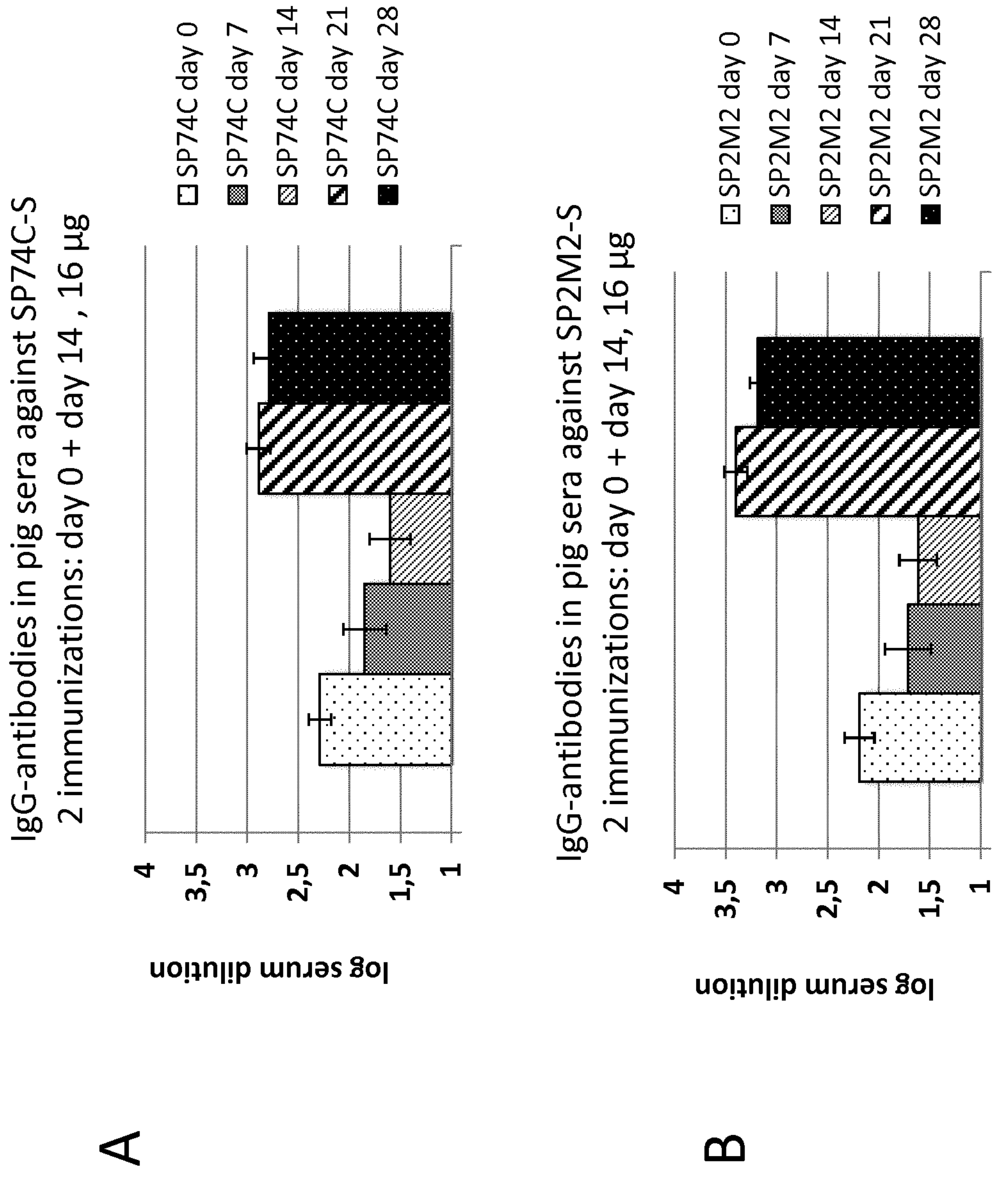
FIGS. 12A and B shows bar graphs showing the results of the ELISA analysis of serum samples obtained at day 0, 7, 14, 21 and 28 from piglets immunized two times with SP2M2-S and SP74C—S as described in Example 11. Mean values and standard errors are shown. The indication "—S" has been omitted in the graph.

FIG. 12 shows that piglets responded against both SP74C—S and SP2M2-S after immunization with "The piggy vaccine". Initially, a decline of antibody levels is noted from day 0 to day 14, presumably as a result of maternal antibodies obtained via colostrum. A significant enhancement of antibody levels is observed after the second immunization on day 14 (p $p<0.001$ for SP74C—S and $p<0.001$ for SP2M2-S)

Thus, this data shows that both SP74C and SP2M2 are able to elicit antigen specific antibody responses after immunisation.

Example 12

Efficacy of a Vaccine Against a *Streptococcus suis* Challenge in Piglets

In this Example we describe the determination of whether an experimental *S. suis* vaccine as disclosed herein is effective in the prevention of an artificially induced *Streptococcus suis* infection in piglets of weaning age. The test material, study setup and analysis of results are described.

Material and Methods

Test Animals:

Details of the animals used in this study are given in Table 10 below.

TABLE 10

Details on animals used in the study.

| Animal details | Sows | Piglets |
|---|---|---|
| Species | Porcine | Porcine |
| Breed | Large white/Landrace | Large white/Landrace |
| Sex | Female | Female/Male |
| Other | Stage of gestation: Approximately 103 days gestation on arrival | Age: Between 9 and 10 days of age on Day 0. |
| Body weight | — | ≥1.0 kg on day 0 |
| Number | 3 | 18 piglets |
| Source | Commercial high health status pig farm | Commercial high health status pig farm |

Inclusion Criteria:

Piglets included in the study were confirmed to be in good general health and weigh more than 1.0 kg on day 0.

Exclusion Criteria:

Any piglets not in good general health or weighing less than 1.0 kg were excluded from the study.

Post Inclusion Withdrawal:

Animals were withdrawn from the study if they were injured or showed clinical signs of illness or disease which either could not be treated or constituted a welfare issue. Any animal that showed unacceptable abnormal health following vaccination was euthanized.

Allocation/Randomization:

On day 0, randomization of the group order in each block was carried out using a random number generator.

TABLE 11

| Information on test and control material. | | |
|---|---|---|
| Test material | Vaccine | Control |
| Name/Code number | Group 1: SP274C-S (SEQ ID NO: 109) | Placebo |
| Formulation | Protein + adjuvant solution in 50 mM Tris pH 7.3 | Adjuvant solution in 50 mM Tris pH 7.3 |
| Concentration | 40 μg antigen + 50 μg adjuvant in 500 μl injection volume | 100 μg/ml of adjuvant |
| Storage conditions required | +2 to +8° C. | +2 to +8° C. |
| Method of administration | Intramuscular injection | Intramuscular injection |
| Dose regime | Day 0 and Day 10 | Day 0 and Day 10 |

Challenge Material:

Detailed information of the challenge material is given in Table 12 below.

TABLE 12

| Challenge information. | |
|---|---|
| Name | *Streptococcus suis*, serotype 2 |
| Year of isolation | 2011 |
| County of isolation | England, UK |
| Clinical history | 3 month old pig with nervous system symptoms |
| Method of administration | Intranasal |
| Anticipated titer | Approximately $1.0 \times 10^9$ colony forming units (cfu) total in 5 ml |
| Dosage regime | 5 ml on single occasion (Day 27/31) |

Study Design and Procedure:

A summary of the study design is given in Table 13. A total of three pregnant sows (approximately 3 weeks before farrowing) were sourced from a commercial pig farm with no history of *S. suis* clinical disease, and transported to the Contract Research Organization (CRO).

TABLE 13

Summary of the study design.

| Group number | Group | No. of animals | Test material | Route/ volume | Challenge | End of study day |
|---|---|---|---|---|---|---|
| 1 | Vaccine | 9 | SP274C-S, 40 μg | Intra-mus-cular/ 0.5 ml | *S. suis* isolate by intranasal route at $1 \times 10^9$ cfu total in 5 ml. | Day 34/38 |
| 2 | Control | 9 | Adjuvant only | | | |

Approximately one week before the expected farrowing date, the sows were placed into farrowing crates within temperature controlled accommodation.

The animals were be routinely monitored around the expected farrowing dates to provide assistance where necessary with farrowing. Following farrowing, the number of piglets produced by each sow was recorded along with the sex of each animal and each animal was ear tagged in duplicate. The navels of all animals were also be sprayed with iodine to prevent infection.

The animals were under veterinary care from the start of the study and animal husbandry will follow standard procedures unless otherwise indicated. The study procedure is outlined below and summarized in Table 14.

TABLE 14

A summary of the study design employed.

| Study day | Procedure(s) |
|---|---|
| −10 | Farrowing, ear tagging |
| −1 | Blood sample |
| 0 | Physical examination, body weight, allocation, test material administration, |
| 0 (+1 hr and +4 hr) | Clinical observation |
| 7 | Blood sample, body weight |
| 14 | Blood sample, body weight, test material administration |
| 14 (+1 hr and +4 hr) | Clinical observation |
| 21 | Blood sample, body weight |
| 27/31 | Clinical observation, blood sample, body weight, challenge primer, challenge |
| Day 27/31 (+1 hour) | challenge |
| Day 27/31 (4 hours post challenge) | Clinical observation |
| Day 28/32-33/37 | Clinical observations 2 times a day (minimum) |
| Day 34/38 | Clinical observation, body weight, blood sample, necropsy |

At parturition, the number and sex of piglets born and whether they were alive, healthy or weak, dead (stillborn) or mummified fetuses were recorded for each animal.

On day −1 (9 days post farrowing) blood samples were collected from all piglets.

On day 0, the animals were examined by a veterinarian to confirm that they were in good health and suitable for inclusion on the study. The animals were then weighed. Piglets were allocated to two groups and each piglet was then vaccinated with the appropriate material by intramuscular injection. Piglets from each sow were allocated to different groups. A clinical observation was carried out on all animals approximately 1 hour and 4 hours post vaccination to ensure that no adverse reactions are present. Due to the prolonged period between farrowing dates, it was deemed necessary to vaccinate the litters at two separate time points to ensure all piglets were approximately 10 days of age on vaccination.

On day 14, the animals were vaccinated a second time by the intramuscular route with the appropriate material and a clinical observation was carried out on all animals approximately 1 hour and 4 hours post vaccination.

On day 27/31, the animals were weighed then challenged by the intranasal route with *S. suis*. All litters were challenged on the same day to ensure that all study animals received the same concentration of challenge material, hence the two respective study days for challenge (Day 27 or Day 31 depending on time of birth).

A clinical observation was carried out prior to challenge and then approximately 4 hours post challenge.

Further clinical observations were performed twice daily from Day 28/32 to end of study. Additional welfare observations were carried out as and when required depending on the condition of the animals and the progress of the disease.

On day 34/38, a final clinical observation was carried out, the animals were weighed, then euthanized and samples collected for bacteriology and histopathology.

Blood samples were collected from all animals on Day −1, 7, 14, 21, 27/31 and 34/38.

Test Material Preparation and Administration

Test Material Preparation—

Test and control material were supplied as ready to use and shaken before use.

Test Material Administration—

On day 0 and 14 each animal was administered a 0.5 ml volume by the intramuscular route.

Challenge Preparation and Administration

Challenge Preparation:

On day 26/30, a Microbank™ seed stock cryovial containing the challenge isolate was removed from −70° C. storage and placed in a pre-chilled (−70° C.±10° C.) cryoblock which was transported directly to a class 2 microbiological safety cabinet. Two beads were removed from the vial and streaked onto separate 5% sheep blood agar plates. The plates were incubated aerobically overnight for 21 hours 40 minutes at +37° C. (±2° C.). Following incubation, plates were examined and confirmed as having growth consistent with that expected for the isolate. Colonies were removed from each plate and added to 3×3 ml of pre-warmed vegetable peptone broth supplemented with 3% (v/v) horse serum (supplemented VPB) in bijou bottles to a turbidity of 1.5 McFarland turbidity units (McF) (density measured using a Densitometer, BioMerieux). Each 3 ml volume was then added to 97 ml of pre-warmed VPB to give 3×100 ml challenge cultures which were incubated for 4 hours 5 minutes at +37° C. (±2° C.) on an orbital shaker set at 150 rpm. After incubation the turbidity of each culture was recorded (target was between 2.5 and 3.5 McF—actual turbidity was 3.8 McF).

The cultures were be pooled, then 140 ml of the culture was removed and added to 210 ml of VPB to produce challenge material with a target concentration of $2\times10^8$ cfu/ml ($1\times10^9$ cfu total in 5 ml). The challenge material was transported immediately to the animal accommodation for challenge administration. A sample of the challenge material was retained for titration.

Challenge Administration:

On day 27/31, all animals were administered 5 ml of 1% acetic acid by intranasal application (using a syringe), to the left nostril as a challenge primer and 1 hr later administered 5 ml of the *S. suis* challenge material, at a concentration of approximately $1\times10^9$ cfu total in 5 ml by intranasal application (using a syringe and an aerosol adapter) to the left nostril.

Clinical Observations

Clinical Observation/Injection Site Reactions Post Treatment:

A clinical observation was performed on all animals one hour and four hours post test material administration on Days 0 and 14. The observation consisted of an assessment of the demeanor of the animal as well as an assessment of any local injection site reactions. The rectal temperature of the animals will also be measured on each occasion using a calibrated digital thermometer.

The injection site observations consisted of an assessment of the presence of any swelling at the injection site, and if present, an assessment of the type of reaction (hot, painful, firm or soft). Where possible an estimate of the size of the swelling was recorded.

Clinical Observation Post Challenge:

Clinical observations consisted of assessments of demeanor, behavioral/central nervous system changes, lameness and rectal temperature (° C.) according to a scoring system (see Table 15).

TABLE 15

Clinical observations

| | Score | | | |
|---|---|---|---|---|
| Parameter | 0 | 1 | 2 | 3 |
| Rectal temp | 38.0° C.-39.5° C. | >39.5° C.-40.0° C. | >40.0° C.-40.9° C. | ≥41.0° C. or <38° C. |
| Demeanor | Normal | Mild depression | Moderate depression | Severe depression |
| Description | Normal demeanor | Slightly dull but active and mobile | Unwilling but able to rise, staying apart from others | Unable to rise |
| Behavioral/CNS | Normal | Minor changes | Moderate changes | Severe changes |
| Description | Normal demeanor | Tremors | Uncoordinated | Fitting, involuntary muscle movement |
| Mobility | None | Mild | Moderate | Severe |
| Description | Normal locomotion | Lameness in one limb | Unsteady when walking or walking on front knees, lameness in more than one limb | Paralysis |

The individual scores for each clinical symptom were summed during tabulation of data to give the total clinical score for each animal on each observation to assess temporal progression of disease.

Pigs which were recumbent/moribund and/or showing signs of severe distress, were euthanized immediately on humane grounds by a. intravenous/intraperitoneal/intracardiac administration of a lethal dose of Pentobarbitone Sodium BP.

Necropsy:

On Day 34/38 (or as required following early euthanasia on welfare grounds), animals were euthanized by lethal injection. A gross pathological examination of each carcass will be conducted and samples will be collected.

General Health Observations:

The general health of the animals was assessed twice daily by a suitably qualified person from arrival until the end of the study.

Sample Collection and Processing

Pre-Study Blood Sample Collection:

Blood samples were collected from all sows before farrowing. A maximum of 2 ml of blood was collected into a clotted blood tube on each occasion.

Blood samples were collected from all piglets on day −1, then again on day 7, 14, 21, 27/31 and 34/38 and at necropsy. A maximum of 2 ml of blood will be collected into a clotted blood tube on each occasion.

Blood Sample Processing:

The clotted blood samples were allowed to clot by incubating at +37° C. (±2° C.) for between 30 and 45 minutes. Blood samples were centrifuged at 1,400×g (3000 rpm) for 20 minutes and the sera were transferred into duplicate sterile bijous labeled with reference number, sample type, animal number, study day, collection date, aliquot number. Samples will be stored at −20° C. (±10° C.).

Tissue Samples:

At necropsy, the whole brain was removed from each animal using sterile forceps and scalpels and three brain samples were removed from the brain tissue.

One sample was placed in a sterile container for bacteriological assessment. One sample was stored at −70° C. (±10° C.) as an archive sample. The remaining brain tissue was placed in a container along with 10% formal saline for histopathological analysis.

Analysis

Serological Testing:

All samples collected from sows during screening and from the piglets during the study were analyzed on completion of the study.

Measurement of Challenge Concentration:

A 0.1 ml aliquot of the challenge material (pre- and post-challenge administration) was diluted by tenfold serial dilutions in 0.9 ml volumes of peptone water ($10^{-1}$ to $10^{-7}$). Duplicate 10 μl aliquots of all dilutions were spotted onto the surface of a 5% sheep blood agar plate and incubated aerobically at +37° C. (±2° C.) for 20 to 24 hours. The number of cfu per ml of culture was calculated by multiplying the number of colonies by the relevant dilution factor.

*S. suis* Culture from Tissue Samples:

The brain samples from each animal were placed in a separate stomacher bag together with 9.0 ml of peptone water to provide a nominal dilution of $10^{-1}$ and homogenized for 30 seconds in a Seward "Stomacher 80" set at high speed. The homogenate will be poured into a sterile universal container. A 20 μl aliquot of homogenate was diluted in 180 μl of peptone water in a sterile U-well microtitration plate to give a $10^{-2}$ dilution. This dilution process was repeated until the homogenate was diluted to $10^{-7}$. Duplicate 10 μl aliquots of each homogenate dilution from $10^{-1}$ to $10^{-7}$ were placed on the surface of a well dried 5% sheep blood agar plate. After samples are dry the plate were incubated overnight (20 to 24 hours) at 37° C. (±2° C.). Plates were inspected for typical colonies of *S. suis*. If present, colonies will be counted.

Histopathological Analysis:

Formalin fixed brain samples were processed and examined following standard procedures by a histopathologist.

Statistical Analysis:

Statistical analysis was carried out on the raw data obtained from the study and data is presented with means and standard deviations as appropriate.

Results

Animal Details:

Animal details One piglet was withdrawn from the study on Day 17 due to death from extensive external bruising as a result of being crushed by the dam. Diagnosis was not considered attributable to the Test Material and no further testing was performed.

Observations Associated with Test Material Administration:

Observations were performed as described above and all animals were deemed to be normal for demeanor following both administration timepoints and no injection reaction were observed.

*S. suis* Challenge Concentration:

*S. suis* challenge was successfully administered to all animals on Day 27/31 with no incidence of mis-dosing recorded. The concentrations of the pre- and post-challenge material were $2.8\times10^{8}$ cfu/ml and $2.35\times10^{8}$ cfu/ml respectively, giving a mean challenge concentration of $2.58\times10^{8}$ cfu/ml. This equates to a challenge dose of $1.29\times10^{9}$ cfu total per pig (in 5 ml) which was higher than the target dose of $1.00\times10^{9}$ cfu total but well within the ±0.5 log acceptable range.

Clinical Observations Post-Challenge:

The body weight of all piglets increased throughout the observation period. There was a slight variation in total weight gain between groups, with animals in the control group (Group 2) having the lowest overall weight gain, but differences were marginal. The rectal temperature results were similar in both groups prior to challenge.

Figure 14:
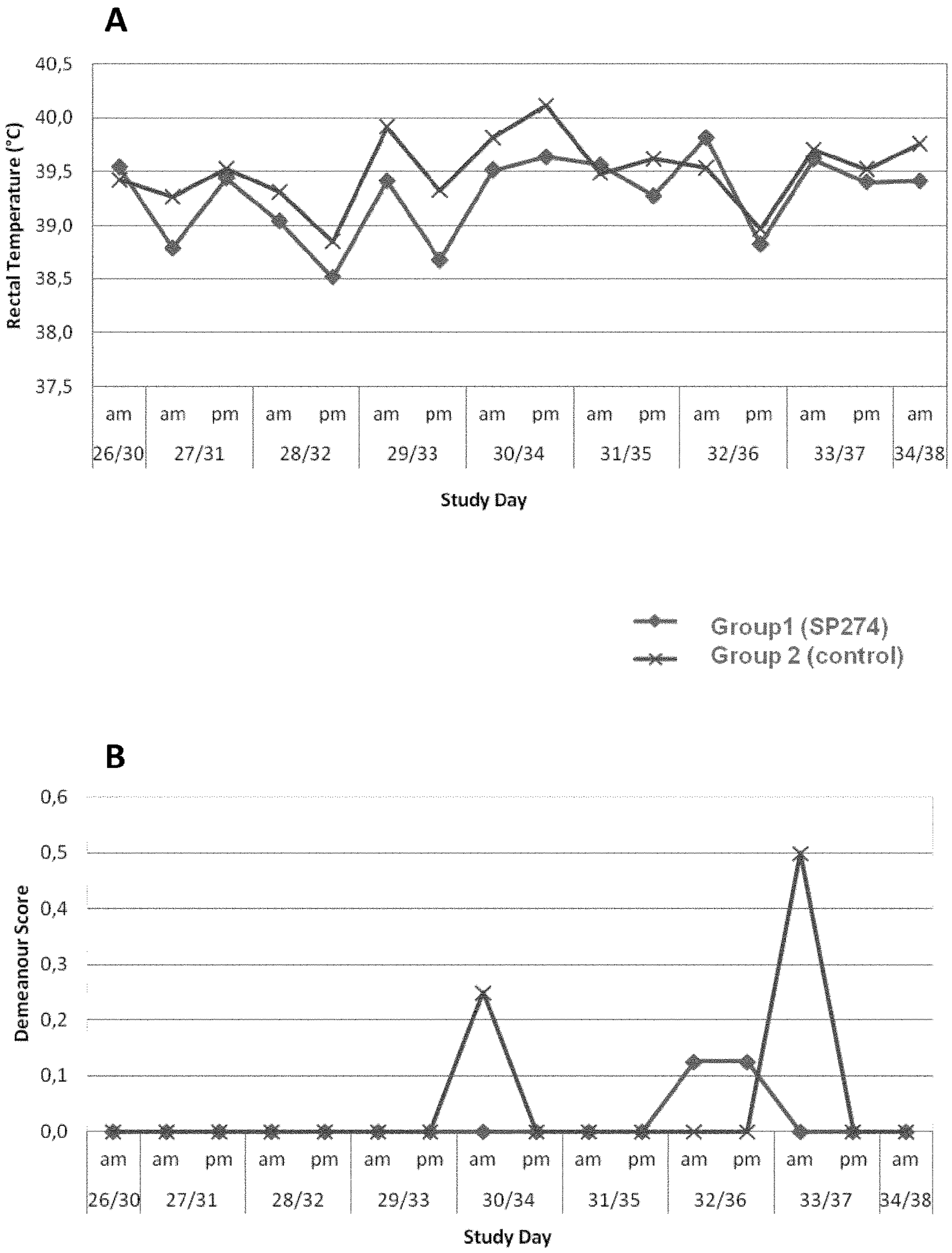
FIGS. 14A and B is a graph showing the rectal temperatures and demeanor score of animals vaccinated with SP274C—S and control animal (adjuvant only) as measured at study days 26/30 to 34/38. SP274C—S is abbreviated SP274 in the figure.

Post-challenge, the mean rectal temperatures in both groups increased markedly on Day 29/33 am and remained elevated for the rest of the monitoring period (FIG. 14A). Instances of high rectal temperatures generally were associated with or preceded the onset of clinical signs of *S. suis* infection and subsequent euthanasia. The frequency of abnormal rectal temperature scores (>39.5° C.) at all scheduled post-challenge observations is summarised in Table 16. Post-challenge the occurrence of abnormal scores was highest in control group (Group 2) at 46.2% and lowest in vaccine group (Group 1) at 28.6%.

TABLE 16

Summary of rectal temperature scores post-challenge.

| Group number | Group | Number of Observations | Number of Abnormal Scores | Number of Normal Scores | % Abnormal Scores |
|---|---|---|---|---|---|
| 1 | Vaccine | 105 | 30 | 75 | 28.6% |
| 2 | Control | 106 | 49 | 57 | 46.2% |

Figure 15:
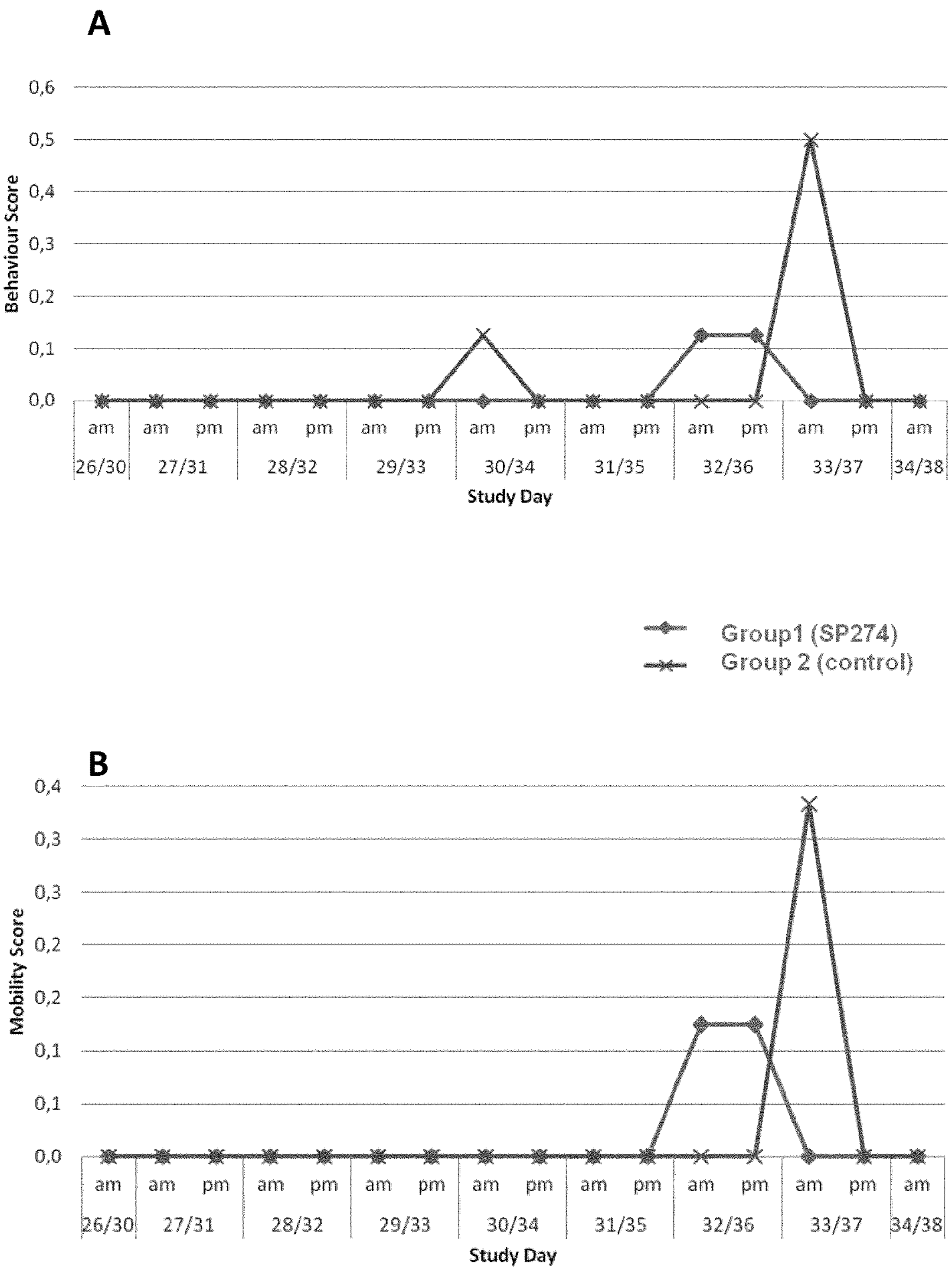
FIGS. 15A and B is a graph showing the behavior score and mobility score scores of animals vaccinated with SP274C—S and control animal (adjuvant only) as measured at study days 26/30 to 34/38. SP274C—S is abbreviated SP274 in the figure.

Prior to challenge, the demeanour scores, behavioural/CNS scores and mobility scores for all animals were normal (score=0). Post-challenge, the mean scores began to rise in Group 2 by Day 30/34 (see FIGS. 14B, 15A and 15B. High demeanour scores were generally associated with euthanasia of animals on welfare grounds.

Figure 16:
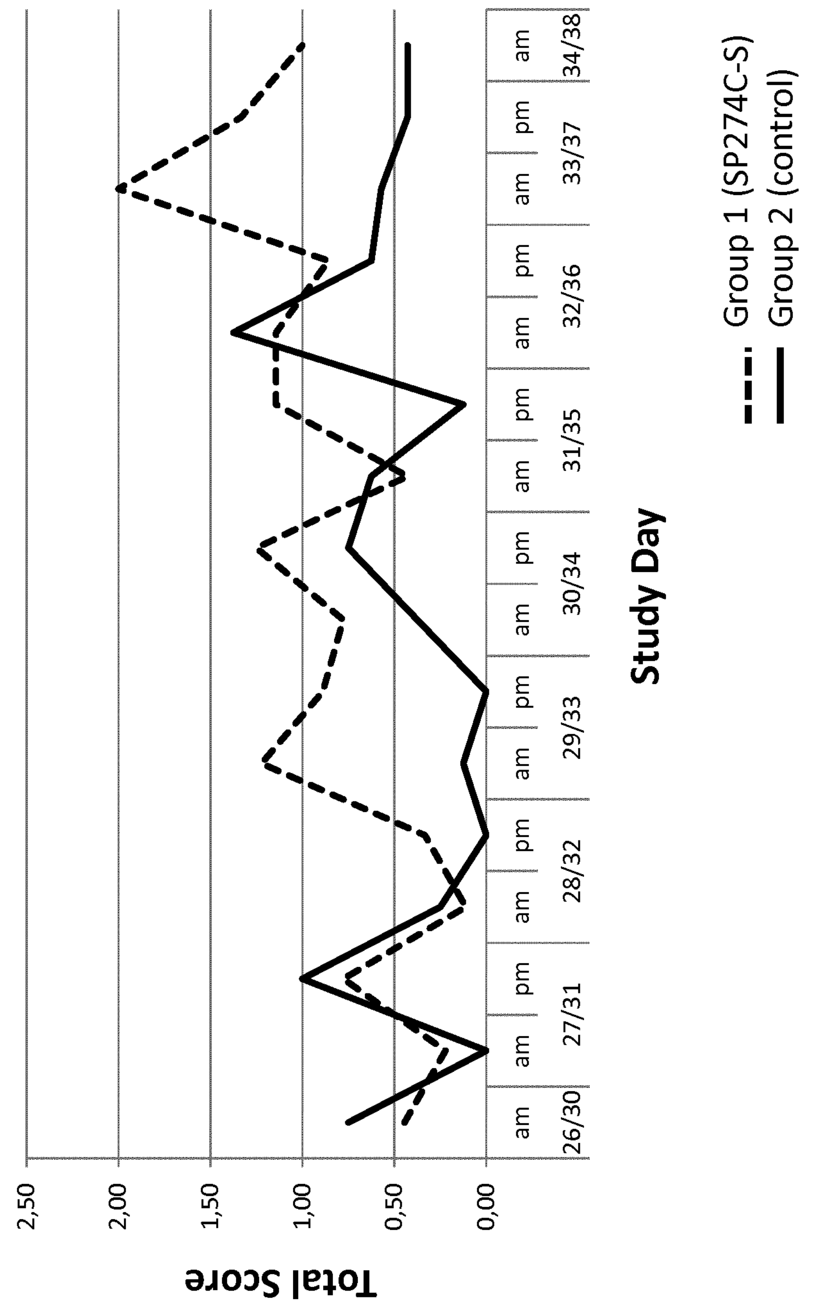
FIG. 16 is a graph showing the total score of animals vaccinated with SP274C—S and control animal (adjuvant only) as measured at study days 26/30 to 34/38.
Figure 18:
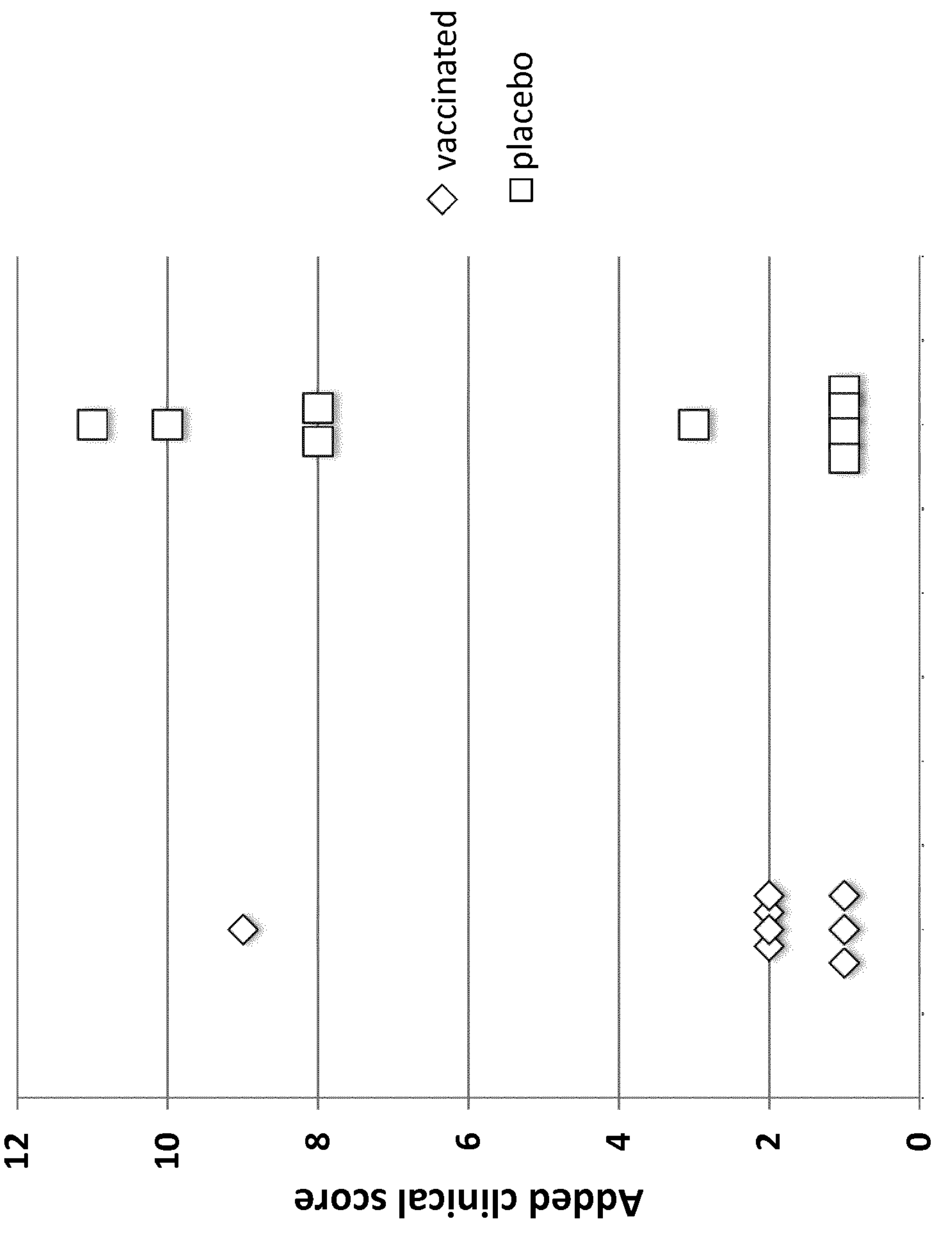
FIG. 18 shows the added clinical score for piglets vaccinated with SP274C—S and control piglets administered placebo.

Total clinical scores comprised rectal temperature, demeanour, mobility and behavioural/CNS scores. Full details of total clinical scores are listed in Table 17. Group mean total clinical scores for scheduled observations are summarised in FIG. 16. Prior to challenge, total clinical scores for most animals were normal (score=0) with the exception of sporadic high rectal temperatures in a small number of animals, likely to be stress related. Post-challenge, the mean scores began to rise initially in all groups on Day 29/33. High total clinical scores were generally associated with euthanasia of animals on welfare grounds. Overall, the vaccine group (Group 1) had lower mean scores throughout the monitoring period when compared to the control group (Group 2) (FIG. 16).

TABLE 17 A

Total clinical score for vaccine group (Antigen SP274C-S, 40 μg) monitored at morning clinical observation (am) and at afternoon clinical observation (pm). Underscore"_" marks animal euthanized on welfare grounds.

| Animal | Study Day | | | | | | | | |
|---|---|---|---|---|---|---|---|---|---|
| | 26/30 | 27/31 | | 28/32 | | 29/33 | | 30/34 | |
| number | am | am | pm | am | pm | am | pm | am | pm |
| 6475 | 0 | 0 | 2 | 1 | 0 | 0 | 0 | 0 | 0 |
| 6774 | 0 | 0 | 1 | 0 | 0 | 0 | 0 | 0 | 0 |
| 6776 | 1 | 0 | 2 | 1 | 0 | 0 | 0 | 2 | 1 |
| 6781 | 1 | 0 | 2 | 0 | 0 | 0 | 0 | 0 | 0 |
| 6782 | 1 | 0 | 1 | 0 | 0 | 0 | 0 | 0 | 2 |
| 6787 | 1 | 0 | 0 | 0 | 0 | 0 | 0 | 0 | 0 |
| 6793 | 1 | 0 | 0 | 0 | 0 | 1 | 0 | 1 | 2 |
| 6794 | 1 | 0 | 0 | 0 | 0 | 0 | 0 | 0 | 1 |
| Group Mean | 0.75 | 0.00 | 1.00 | 0.25 | 0.00 | 0.13 | 0.00 | 0.38 | 0.75 |
| St Dev | 0.46 | 0.00 | 0.93 | 0.46 | 0.00 | 0.35 | 0.00 | 0.74 | 0.89 |

| Animal | Study Day | | | | | | |
|---|---|---|---|---|---|---|---|
| | 31/35 | | 32/36 | | 33/37 | | 34/38 |
| number | am | pm | am | pm | am | pm | am |
| 6475 | 0 | 0 | 1 | 0 | 1 | 1 | 0 |
| 6774 | 0 | 0 | 1 | 0 | 1 | 0 | 0 |
| 6776 | 1 | 0 | 6 | 5 | | | |
| 6781 | 1 | 0 | 0 | 0 | 1 | 1 | 1 |
| 6782 | 2 | 1 | 0 | 0 | 0 | 1 | 0 |
| 6787 | 0 | 0 | 0 | 0 | 1 | 0 | 0 |
| 6793 | 1 | 0 | 2 | 0 | 0 | 0 | 1 |
| 6794 | 0 | 0 | 1 | 0 | 0 | 0 | 1 |
| Group Mean | 0.63 | 0.13 | 1.38 | 0.63 | 0.57 | 0.43 | 0.43 |
| St Dev | 0.74 | 0.35 | 2.00 | 1.77 | 0.53 | 0.53 | 0.53 |

TABLE 17 B

Total clinical score for controls monitored at morning clinical observation (am) and at afternoon clinical observation (pm). Underscore"_" marks animal euthanized on welfare grounds.

| Animal | Study Day | | | | | | | | |
|---|---|---|---|---|---|---|---|---|---|
| | 26/30 | 27/31 | | 28/32 | | 29/33 | | 30/34 | |
| number | am | am | pm | am | pm | am | pm | am | pm |
| 6477 | 0 | 0 | 2 | 0 | 1 | 2 | 2 | 0 | 1 |
| 6482 | 1 | 1 | 2 | 1 | 2 | 3 | 2 | 4 | |
| 6773 | 1 | 0 | 2 | 0 | 0 | 1 | 0 | 0 | 0 |
| 6779 | 1 | 0 | 0 | 0 | 0 | 1 | 0 | 2 | 3 |
| 6783 | 0 | 0 | 0 | 0 | 0 | 2 | 3 | 1 | 3 |
| 6786 | 0 | 0 | 1 | 0 | 0 | 1 | 0 | 0 | 1 |
| 6788 | 1 | 1 | 0 | 0 | 0 | 0 | 1 | 0 | 1 |
| 6789 | 0 | 0 | 0 | 0 | 0 | 1 | 0 | 0 | 0 |
| 6792 | 0 | 0 | 0 | 0 | 0 | 0 | 0 | 0 | 1 |
| Group Mean | 0.44 | 0.22 | 0.78 | 0.11 | 0.33 | 1.22 | 0.89 | 0.78 | 1.25 |

| Animal | Study Day | | | | | | |
|---|---|---|---|---|---|---|---|
| | 31/35 | | 32/36 | | 33/37 | | 34/38 |
| number | am | pm | am | pm | am | pm | am |
| 6477 | 1 | 4 | 5 | 4 | 3 | 5 | 2 |
| 6482 | | | | | | | |
| 6773 | 0 | 2 | 1 | 2 | 10 | | |
| 6779 | | | | | | | |

TABLE 17 B-continued

Total clinical score for controls monitored at morning clinical observation (am) and at afternoon clinical observation (pm). Underscore"_" marks animal euthanized on welfare grounds.

| | | | | | | | |
|---|---|---|---|---|---|---|---|
| 6783 | 1 | 0 | 1 | 0 | 0 | 2 | 1 |
| 6786 | 0 | 1 | 1 | 0 | 0 | 1 | 1 |
| 6788 | 0 | 1 | 0 | 0 | 0 | 0 | 1 |
| 6789 | 1 | 0 | 0 | 0 | 1 | 0 | 1 |
| 6792 | 0 | 0 | 0 | 0 | 0 | 0 | 0 |
| Group Mean | 0.43 | 1.14 | 1.14 | 0.86 | 2.00 | 1.33 | 1.00 |

A total of 4 animals were euthanized or died prior to scheduled necropsy.

Animals were generally euthanized at early to moderate stages of disease development for welfare reasons.

The first mortality occurred three days post-challenge administration (Study Day 20/34) and animals were withdrawn from study until 6 day post-challenge (Study Day 33/37). Mortalities occurred with 33.3% (3/9) mortality rate in the control group (Group 2) and 12.5% in vaccine group (Group 1). All post-challenge mortalities were consistent with *S. suis* disease (based on clinical signs and/or bacteriology/histopathology).

Recovery of *S. suis* from Brain Tissue:

Colonies consistent with *S. suis* were recovered from brain tissue in all animals that were euthanized or died prior to scheduled necropsy (Table 18). No colonies consistent with *S. suis* were recovered from brain tissue of any animal which survived to scheduled necropsy

TABLE 18

Summary of bacteriology results

| Group number | Group | Number of animals | Number of *S. suis* positive animals | Mean cfu/g |
|---|---|---|---|---|
| 1 | Vaccine | 8 | 1 | 1.13E+02 |
| 2 | control | 9 | 3 | 1.71E+04 |

Sample Analysis:

Serum samples were analysed for immune response against SP274C—S with standard ELISA method as described in Example 11, wherein plates were coated with the corresponding antigen. Briefly, antigens were used to coat microtiter wells at 4 μg/ml and serum samples at various dilutions were applied. Binding was detected with HRP conjugated anti-swine antibodies. Serum titer is expressed as the log value of the dilution required to result in an A490 value of 1.5. As an example, a titer expressed as 3.3 means that a dilution of 2000 times gives A490=1.5.

Serum titers in sows and average serum titres in piglets are shown in Tables 19 and 20, respectively. Prior to vaccination (Day −1) animals in vaccine group were observed to have mean antibody titre of 2.16 against the SP274C—S antigen (range between 1.45 and 2.65). Following vaccination, seven of the eight animals, had an antibody response to vaccination with the SP274C—S antigen, with a mean antibody titre of 3.14 (see FIG. 17A). In the control group (adjuvant only), animals had antibodies against the antigen, due to maternally derived antibodies. There was a decline in the antibody response of animals in the control group following vaccination (see FIG. 17B.

TABLE 19

Antibody titres in sows included in the study.

| Animal ID. | SP274C-S |
|---|---|
| 66 | 3.15 |
| 376 | 2.45 |
| 966 | 2.7 |

TABLE 20

Group mean antibody titres in piglets.

| | | SP274C-S | |
|---|---|---|---|
| Group number | Group | Day −1 | Day 27/31 |
| 1 | vaccine | 2.16 | 3.14 |
| 2 | control | 1.98 | 1.86 |

In summary, the animals vaccinated with SP274C—S exhibited a lower added clinical score as compared to the control animals as well as a lower mortality rate (FIG. 19 and Table 17).

Itemized List of Embodiments

1. An immunogenic polypeptide for use as a medicament, wherein said polypeptide comprises an amino acid sequence selected from the group consisting of SEQ ID NO:4 and fragments thereof; SEQ ID NO:3 and fragments thereof; SEQ ID NO:2 and fragments thereof; a fragment comprising SEQ ID NO:5, provided the fragment comprising SEQ ID NO:5 is less than 500 amino acids long; a fragment comprising SEQ ID NO:6, provided the fragment comprising SEQ ID NO:6 is less than 500 amino acids long; and amino acid sequences with at least 80%-identity to any one of said amino acid sequences, such as an amino acid sequence selected from the group consisting of SEQ ID NO:2 and fragments thereof; SEQ ID NO:3 and fragments thereof; SEQ ID NO:4 and fragments thereof; SEQ ID NO:5; SEQ ID NO:38, SEQ ID NO:6; and amino acid sequences with at least 80%-identity to any one of said amino acid sequences.
2. An immunogenic polypeptide for use in the prophylactic treatment of a *Streptococcus suis* infection, wherein said immunogenic polypeptide comprises an amino acid sequence selected from the group consisting of SEQ ID NO:4 and fragments thereof; SEQ ID NO:3 and fragments thereof; SEQ ID NO:2 and fragments thereof; a fragment comprising SEQ ID NO:5, provided the fragment comprising SEQ ID NO:5 is less than 500 amino acids long; a fragment comprising SEQ ID NO:6, provided the fragment comprising SEQ ID NO:6 is less than 500 amino acids long; and amino acid sequences with at least 80%-identity to any one of said amino acid sequence, such as an amino acid sequence selected from the group consisting of SEQ ID NO:4 and fragments thereof; SEQ ID NO:3 and fragments thereof; SEQ ID NO:2 and fragments thereof; SEQ ID NO:5; SEQ ID NO:38, SEQ ID NO:6; and amino acid sequences with at least 80%-identity to any one of said amino acid sequences.

3. Immunogenic polypeptide for use according to item 1 or 2, wherein said immunogenic polypeptide comprises an amino acid sequence selected from the group consisting of SEQ ID NO:4 and fragments thereof; SEQ ID NO:3 and fragments thereof; SEQ ID NO:2 and fragments thereof; a fragment comprising SEQ ID NO:5, provided the fragment comprising SEQ ID NO:5 is less than 500 amino acids long; and amino acid sequences with at least 80%-identity to any one of said amino acid sequences, such as an amino acid sequence selected from the group consisting of SEQ ID NO:4 and fragments thereof; SEQ ID NO:3 and fragments thereof; SEQ ID NO:2 and fragments thereof; SEQ ID NO:5; SEQ ID NO:38 and amino acid sequences with at least 80%-identity to any one of said amino acid sequences, such as an amino acid sequence selected from the group consisting of SEQ ID NO:4 and fragments thereof; SEQ ID NO:3 and fragments thereof; SEQ ID NO:2 and fragments thereof; and amino acid sequences with at least 80%-identity to any one of said amino acid sequences.

4. Immunogenic polypeptide for use according to any one of items 1-3, wherein said amino acid sequence is selected from the group consisting of fragments of SEQ ID NO:4, fragments of SEQ ID NO:3, fragments of SEQ ID NO:2, a fragment comprising SEQ ID NO:5, provided the fragment comprising SEQ ID NO:5 is less than 500 amino acids long and amino acid sequences with at least 80%-identity to any one of said fragments, such as an amino acid sequence selected from the group consisting of fragments of SEQ ID NO:4, fragments of SEQ ID NO:3, fragments of SEQ ID NO:2, SEQ ID NO:5, SEQ ID NO:38 and amino acid sequences with at least 80%-identity to any one of said fragments.

5. Immunogenic polypeptide for use according to any one of items 1-4, wherein said fragment is approximately 100-500 amino acids long, such as approximately 200-500 amino acids long, such as approximately 250-450 amino acids long.

6. Immunogenic polypeptide for use according to any one of items 1-5, wherein said fragment is an N-terminal or a C-terminal fragment.

7. Immunogenic polypeptide for use according to any one of items 1-6, wherein said fragment is selected from the group consisting of fragments comprising SEQ ID NO:7 or SEQ ID NO:8; fragments comprising SEQ ID NO:9 or SEQ ID NO:10; fragments comprising SEQ ID NO:11 or SEQ ID NO:12; a fragment comprising SEQ ID NO:5, provided the fragment comprising SEQ ID NO:5 is less than 500 amino acids long; a fragment comprising SEQ ID NO:6, provided the fragment comprising SEQ ID NO:6 is less than 500 amino acids long; and amino acid sequences with at least 80%-identity to any one of said fragments, such as a fragment selected from the group consisting of fragments comprising SEQ ID NO:7 or SEQ ID NO:8; fragments comprising SEQ ID NO:9 or SEQ ID NO:10; fragments comprising SEQ ID NO:11 or SEQ ID NO:12; SEQ ID NO:5 or SEQ ID NO:38 (M2long); and amino acid sequences with at least 80%-identity to any one of said fragments, such as a fragment selected from the group consisting of fragments comprising SEQ ID NO:7 or SEQ ID NO:8; fragments comprising SEQ ID NO:10; fragments comprising SEQ ID NO:12; SEQ ID NO:5; and amino acid sequences with at least 80%-identity to any one of said fragments.

8. Immunogenic polypeptide for use according to any one of items 1-7, wherein said fragment is selected from the group consisting of fragments comprising SEQ ID NO:8; fragments comprising SEQ ID NO:10; fragments comprising SEQ ID NO:12; SEQ ID NO:5; and amino acid sequences with at least 80%-identity to any one of said fragments.

9. Immunogenic polypeptide for use according to any one of items 1-8, wherein said fragment further comprises additional amino acid residues at the N- and/or C-terminus.

10. Immunogenic polypeptide for use according to item 9, wherein said fragment comprises a methionine residue at the N-terminus.

11. Immunogenic polypeptide for use according to any one of the preceding items, further comprising an amino acid sequence capable of binding to silica.

12. Immunogenic polypeptide for the use according to item 11, wherein said amino acid sequence capable of binding to silica is selected from SEQ ID NO:32 and SEQ ID NO:33 and amino acids sequences with at least 80%-identity to SEQ ID NO:32 or SEQ ID NO:33, such as wherein said amino acid sequence capable of binding to silica is SEQ ID NO:32 or SEQ ID NO:33.

13. Immunogenic polypeptide fragment, comprising an amino acid sequence selected from
   i) an amino acid sequence selected the group consisting of SEQ ID NO: 7, SEQ ID NO:8, SEQ ID NO:9, SEQ ID NO:10, SEQ ID NO:11 and SEQ ID NO:12, and
   ii) an amino acid sequence with at least 80%-identity to an amino acid sequence defined in i).

14. Immunogenic polypeptide fragment, comprising an amino acid sequence selected from
   iii) an amino acid sequence selected the group consisting of SEQ ID NO:5; SEQ ID NO:38, SEQ ID NO:6, SEQ ID NO:7, SEQ ID NO:8, SEQ ID NO:9, SEQ ID NO:10, SEQ ID NO:11 and SEQ ID NO:12, and
   iv) an amino acid sequence with at least 80%-identity to an amino acid sequence defined in iii), for use in the prophylactic treatment of a *Streptococcus suis* infection.

15. Immunogenic polypeptide fragment according to item 14, wherein the sequence iii) is selected from the group consisting of SEQ ID NO:5, SEQ ID NO:38, SEQ ID NO:8, SEQ ID NO:10 and SEQ ID NO:12, such as the group consisting of SEQ ID NO:5, SEQ ID NO:8, SEQ ID NO:10 and SEQ ID NO:12.

16. Immunogenic polypeptide fragment according to item 13 or 15, wherein the sequence i) or iii) is selected from the group consisting of SEQ ID NO:8, SEQ ID NO:10 and SEQ ID NO:12, such as the group consisting of SEQ ID NO:10 and SEQ ID NO:12, such as the group consisting of SEQ ID NO:8 and SEQ ID NO:12, such as the group consisting of SEQ ID NO:8 and SEQ ID NO:10.

17. Fusion polypeptide comprising
  a) a first immunogenic polypeptide unit, and
  b) a second immunogenic polypeptide unit,
  wherein at least one of said first and second immunogenic polypeptide units is an immunogenic polypeptide fragment selected from the group consisting of fragments of SEQ ID NO:4; fragments of SEQ ID NO:3; fragments comprising SEQ ID NO:2; a fragment comprising SEQ ID NO:5, provided the fragment comprising SEQ ID NO:5 is less than 500 amino acids long; a fragment comprising SEQ ID NO:6, provided the fragment comprising SEQ ID NO:6 is less than 500 amino acids long; and amino acid sequences with at least 80%-identity to any one of said fragments,
  such as the group consisting of fragments of SEQ ID NO:4; fragments of SEQ ID NO:3; fragments of SEQ ID NO:2; SEQ ID NO:5; SEQ ID NO:38; SEQ ID NO:6, and amino acid sequences with at least 80%-identity to any one of said fragments, provided that said first and said second immunogenic polypeptide units are from different native proteins.
18. Fusion polypeptide according to item 17,
  wherein said first and second immunogenic polypeptide units are immunogenic polypeptide fragments selected from the group consisting of fragments of SEQ ID NO:4; fragments of SEQ ID NO:3; fragments comprising SEQ ID NO:2; a fragment comprising SEQ ID NO:5, provided the fragment comprising SEQ ID NO:5 is less than 500 amino acids long; a fragment comprising SEQ ID NO:6, provided the fragment comprising SEQ ID NO:6 is less than 500 amino acids long; and amino acid sequences with at least 80%-identity to any one of said fragments,
  such as the group consisting of fragments of SEQ ID NO:4; fragments of SEQ ID NO:3; fragments of SEQ ID NO:2; SEQ ID NO:5; SEQ ID NO:38; SEQ ID NO:6, and amino acid sequences with at least 80%-identity to any one of said fragments,
  provided that said first and said second immunogenic polypeptide units are from different native proteins.
19. Fusion polypeptide according to item 18, wherein said first and second immunogenic polypeptide units are immunogenic polypeptide fragments selected from the group consisting of fragments of SEQ ID NO:4; fragments of SEQ ID NO:3; fragments of SEQ ID NO:2; SEQ ID NO:5; and SEQ ID NO:38, and amino acid sequences with at least 80%-identity to any one of said fragments.
20. Fusion polypeptide according to any one of items 17-19, wherein each of the first and second immunogenic polypeptide unit independently is approximately 100-500 amino acids long, such as approximately 200-500 amino acids long, such as approximately 250-450 amino acids long.
21. Fusion polypeptide according to any one of items 17-20, wherein said first and second immunogenic polypeptide units are selected from the group consisting of fragments comprising SEQ ID NO:7 or SEQ ID NO:8; fragments comprising SEQ ID NO:9 or SEQ ID NO:10; fragments comprising SEQ ID NO:11 or SEQ ID NO:12; a fragment comprising SEQ ID NO:5, provided the fragment comprising SEQ ID NO:5 is less than 500 amino acids long and), a fragment comprising SEQ ID NO:6, provided the fragment comprising SEQ ID NO:6 is less than 500 amino acids long; and amino acid sequences with at least 80%-identity to any one of said fragments; such as the group consisting of fragments comprising SEQ ID NO:8; fragments comprising SEQ ID NO:10; fragments comprising SEQ ID NO:12; a fragment comprising SEQ ID NO:5, provided the fragment comprising SEQ ID NO:5 is less than 500 amino acids long; and amino acid sequences with at least 80%-identity to any one of said fragments.
22. Fusion polypeptide according to any one of items 17-21, wherein first and second immunogenic polypeptide units are selected from the group consisting of fragments SEQ ID NO:5, SEQ ID NO:38, SEQ ID NO:6, SEQ ID NO:7, SEQ ID NO:8, SEQ ID NO:9, SEQ ID NO:10, SEQ ID NO:11 and SEQ ID NO:12, and amino acid sequences with at least 80%-identity to any one of said fragments; such as the group consisting of fragments SEQ ID NO:5, SEQ ID NO:38, SEQ ID NO:8, SEQ ID NO:10, and SEQ ID NO:12, and amino acid sequences with at least 80%-identity to any one of said fragments, such as the group consisting of fragments SEQ ID NO:8, SEQ ID NO:10, and SEQ ID NO:12, and amino acid sequences with at least 80%-identity to any one of said fragments.
23. Fusion polypeptide according to any one of items 17-22, wherein said fusion polypeptide is selected from the group consisting of fusion polypeptides comprising SEQ ID NO:10 and SEQ ID NO:8; fusion polypeptides comprising SEQ ID NO:5 and SEQ ID NO:12; fusion polypeptides comprising SEQ ID NO:5 or SEQ ID NO:38 and SEQ ID NO:10; fusion polypeptides comprising SEQ ID NO:8 and SEQ ID NO:12; fusion polypeptides comprising SEQ ID NO:8 and SEQ ID NO:5 or SEQ ID NO:38; and fusion polypeptides comprising SEQ ID NO:12 and SEQ ID NO:10,
  such as the group consisting of fusion polypeptides comprising SEQ ID NO:10 and SEQ ID NO:8; fusion polypeptides comprising SEQ ID NO:8 and SEQ ID NO:5 or SEQ ID NO:38; and fusion polypeptides comprising SEQ ID NO:12 and SEQ ID NO:10,
  such as the group consisting of fusion polypeptides comprising SEQ ID NO:8 and SEQ ID NO:5; and fusion polypeptides comprising SEQ ID NO:12 and SEQ ID NO:10.
24. Fusion polypeptide according to any one of items 17-23, wherein said fusion polypeptide comprises an amino acid sequence selected from the group consisting of SEQ ID NO:92, SEQ ID NO:93, SEQ ID NO:94, SEQ ID NO:95, SEQ ID NO:96, SEQ ID NO:34, SEQ ID NO:35 and any of said fusion polypeptides wherein at least one of said units exhibits at least 80%-identity to any one of SEQ ID NO:8, SEQ ID NO:10, SEQ ID NO:12 or SEQ ID NO:5.
25. Fusion polypeptide according to any one of items 17-24, wherein said fusion polypeptide comprises an amino acid sequence selected from the group consisting of SEQ ID NO:34; SEQ ID NO:35; SEQ ID NO:92 and any fusion polypeptide wherein at least one of said units exhibits at least 80%-identity to any one of SEQ ID NO:8, SEQ ID NO:10, SEQ ID NO:12 and SEQ ID NO:5, such as the group consisting SEQ ID NO:34; SEQ ID NO:35, and any fusion polypeptide wherein at least one of said units exhibits at least 80%-identity to any one of SEQ ID NO:8, SEQ ID NO:10, SEQ ID NO:12 and SEQ ID NO:5.
26. Fusion polypeptide according to any one of items 17-25, wherein said fusion polypeptide is SEQ ID NO:34 or SEQ ID NO:35, or a fusion polypeptide wherein at least one of said units exhibits at least 80%-identity to any one of SEQ ID NO:8, SEQ ID NO:10, SEQ ID NO:12 and SEQ ID NO:5.

27. Fusion polypeptide according to any one of items 17-26 comprising three or four of the immunogenic polypeptide fragments as defined in any one of items 13-16.

28. Fusion polypeptide according to item 27, comprising an amino acid sequence selected from the group consisting SEQ ID NO:8, SEQ ID NO:10, SEQ ID NO:12 and amino acid sequences which exhibit at least 80%-identity to any one of SEQ ID NO:8, SEQ ID NO:10 and SEQ ID NO:12.

29. Fusion polypeptide according to item 28, comprising an immunogenic polypeptide fragment with at least 80%-identity with SEQ ID NO:8, an immunogenic polypeptide fragment with at least 80%-identity with SEQ ID NO:10 and an immunogenic polypeptide fragment with at least 80%-identity with SEQ ID NO:12, preferably comprising an immunogenic polypeptide fragment with 100%-identity with SEQ ID NO:8, an immunogenic polypeptide fragment with 100%-identity with SEQ ID NO:10 and an immunogenic polypeptide fragment with 100%-identity with SEQ ID NO:12.

30. Fusion polypeptide according to item 28 or 29, comprising SEQ ID NO:8, SEQ ID NO:10 and SEQ ID NO:12.

31. Fusion polypeptide according to item 29, comprising SEQ ID NO:107 or SEQ ID NO:108 or a amino acid sequence which exhibits at least 80%-identity to SEQ ID NO:107 or SEQ ID NO:108.

32. Fusion polypeptide according to item 30 or 31, selected from the group consisting of SEQ ID NO:107, 108, 109 and 110.

33. Fusion polypeptide according to any one of items 17-32, further comprising a linker.

34. Immunogenic polypeptide fragment according to any one of items 13-16 or fusion polypeptide according to any one of items 17-33, wherein said fragment or fusion polypeptide further comprises additional amino acid residues at the N- and/or C-terminus.

35. Immunogenic polypeptide fragment or fusion polypeptide according to item 34 further comprising a methionine residue at the N-terminus.

36. Immunogenic polypeptide fragment according to any one of items 13-16 and 34-35 or fusion polypeptide according to any one of items 17-35, further comprising an additional amino acid sequence capable of binding to silica.

37. Immunogenic polypeptide fragment or fusion polypeptide according to item 36, wherein said amino acid sequence capable of binding to silica is selected from SEQ ID NO:32, SEQ ID NO:33 and amino acids sequences with at least 80%-identity to SEQ ID NO:32 or SEQ ID NO:33, such as wherein said amino acid sequence capable of binding to silica is SEQ ID NO:32 or SEQ ID NO:33.

38. Immunogenic polypeptide fragment or fusion polypeptide according to any one of items 13, 15-37 for use as a medicament.

39. Immunogenic polypeptide fragment or fusion polypeptide according to item 38 for use in the prophylactic treatment of a *Streptococcus suis* infection.

40. Polynucleotide encoding an immunogenic polypeptide, an immunogenic polypeptide fragment or a fusion protein as defined in any one of items 1-39.

41. Expression vector comprising a polynucleotide according to item 40.

42. Host cell comprising an expression vector according to item 41.

43. Method of producing an immunogenic polypeptide, an immunogenic polypeptide fragment or a fusion protein according to any one of items 1-39, comprising culturing a host cell according to item 42 under conditions permissive of expression of said polypeptide from said expression vector, and
isolating said polypeptide.

44. Immunogenic composition comprising at least one immunogenic polypeptide as defined in any one of items 1-12, at least one immunogenic polypeptide fragment as defined in any one of items 13-16 and 34-39 or at least one fusion polypeptide as defined in any one of items 17-39.

45. Immunogenic composition according to item 44, comprising one, two, three or four of said immunogenic polypeptides or immunogenic polypeptide fragments, such as two, three or four of said immunogenic polypeptides or immunogenic polypeptide fragments, such as three or four of said immunogenic polypeptides or immunogenic polypeptide fragments, such as four of said immunogenic polypeptides or immunogenic polypeptide fragments.

46. Immunogenic composition according to any one of items 44-45, wherein said at least one immunogenic polypeptide fragment is provided in fusion with a different at least one different immunogenic polypeptide fragment to form a fusion polypeptide as defined in any one of items 17-39.

47. Immunogenic composition according to items 46, wherein said composition comprises a fusion polypeptide as defined in any one of items 17-39 and optionally one or two immunogenic polypeptide fragments as defined in any one of items 13-16 and 34-39 not in the form of a fusion polypeptide.

48. Immunogenic composition according to item any one of items 46-47, wherein said composition comprises at a fusion polypeptide comprising three immunogenic polypeptide fragments as defined in any one of items 13-16 and 34-39 and optionally one immunogenic polypeptide fragments as defined in any one of items 13-16 and 34-39 not in the form of a fusion polypeptide.

49. Immunogenic composition according to any one of items 44-48, selected from the group consisting of immunogenic compositions comprising the group consisting of
a fusion polypeptide comprising SEQ ID NO:10 and SEQ ID NO:8 and at least one polypeptide comprising an amino acid sequence selected from SEQ ID NO:5, 6, 11 and 12 not in the form of a fusion polypeptide; a fusion polypeptide comprising SEQ ID NO:8 and SEQ ID NO:5 and at least one polypeptide comprising an amino acid sequence selected from SEQ ID NO:9, 10, 11 and 12 not in the form of a fusion polypeptide; and
a fusion polypeptide comprising SEQ ID NO:12 and SEQ ID NO:10 and at least one polypeptide comprising an amino acid sequence selected from SEQ ID NO:5, 6, 7 and 8 not in the form of a fusion polypeptide; such as the group consisting of a fusion polypeptide comprising SEQ ID NO:8 and SEQ ID NO:5 and at least one polypeptide comprising an amino acid sequence selected from SEQ ID NO: 9, 10, 11 and 12 not in the form of a fusion polypeptide; and a fusion polypeptide comprising SEQ ID NO:12 and SEQ ID NO:10 and at least one polypeptide comprising an amino acid sequence selected from SEQ ID NO:5, 6, 8 and 9 not in the form of a fusion polypeptide.

50. Immunogenic composition according to item 49, selected from the group consisting of immunogenic compositions comprising
   a fusion polypeptide comprising SEQ ID NO:10 and SEQ ID NO:8 and at least one polypeptide comprising an amino acid sequence selected from SEQ ID NO:5 and 12 not in the form of a fusion polypeptide;
   a fusion polypeptide comprising SEQ ID NO:8 and SEQ ID NO:5 and at least one polypeptide comprising an amino acid sequence selected from SEQ ID NO:10 and 12 not in the form of a fusion polypeptide; and a fusion polypeptide comprising SEQ ID NO:12 and SEQ ID NO:10 and at least one polypeptide comprising an amino acid sequence selected from SEQ ID NO:5 and 8 not in the form of a fusion polypeptide; such as the group consisting of consisting of immunogenic compositions comprising
   a fusion polypeptide comprising SEQ ID NO:8 and SEQ ID NO:5 and at least one polypeptide comprising an amino acid sequence selected from SEQ ID NO:10 and 12 not in the form of a fusion polypeptide; and a fusion polypeptide comprising SEQ ID NO:12 and SEQ ID NO:10 and at least one polypeptide comprising an amino acid sequence selected from SEQ ID NO:5 and 8 not in the form of a fusion polypeptide.
51. Immunogenic composition according to item 49 or 50, comprising two amino acid sequences not in the form of a fusion polypeptide, provided that said two amino acid sequences are from different native proteins.
52. Immunogenic composition according to any one of items 44-51, wherein said fusion polypeptide is selected from the group of fusion polypeptides consisting of fusion polypeptides comprising SEQ ID NO:92, fusion polypeptides comprising SEQ ID NO:93, fusion polypeptides comprising SEQ ID NO:94, fusion polypeptides comprising SEQ ID NO:95, fusion polypeptides comprising SEQ ID NO:96, fusion polypeptides comprising SEQ ID NO:34, fusion polypeptides comprising SEQ ID NO:35, and any of said fusion polypeptides wherein one or both units exhibit at least 80%-identity to any one of SEQ ID NO:8, SEQ ID NO:10, SEQ ID NO:12 or SEQ ID NO:5, such as the group of fusion polypeptides consisting of fusion polypeptides comprising SEQ ID NO:92, fusion polypeptides comprising SEQ ID NO:34 and fusion polypeptides comprising SEQ ID NO:35 and any of said fusion polypeptides wherein one or both units exhibit at least 80%-identity to any one of SEQ ID NO:8, SEQ ID NO:10, SEQ ID NO:12 or SEQ ID NO:5, such as the group of fusion polypeptides consisting of fusion polypeptides comprising SEQ ID NO:34 and fusion polypeptides comprising SEQ ID NO:35, and any of said fusion polypeptides wherein one or both units exhibit at least 80%-identity to any one of SEQ ID NO:8, SEQ ID NO:10, SEQ ID NO:12 or SEQ ID NO:5.
53. Immunogenic composition according to any one of items 44-52, wherein said immunogenic composition is selected from the group consisting of immunogenic compositions comprising
   a fusion polypeptide comprising SEQ ID NO:34 and at least one polypeptide comprising an amino acid sequence selected from SEQ ID NO:10 and 12 not in the form of a fusion polypeptide; and
   a fusion polypeptide comprising SEQ ID NO:35 and at least one polypeptide comprising an amino acid sequence selected from SEQ ID NO:5 and 8 not in the form of a fusion polypeptide;
   and any of said fusion polypeptides wherein one or both units exhibit at least 80%-identity to any one of SEQ ID NO:8, SEQ ID NO:10, SEQ ID NO:12 or SEQ ID NO:5.
54. Immunogenic composition according any one of items 44-53, comprising one or two fusion polypeptides, such as a fusion polypeptide comprising SEQ ID NO:34 and a fusion polypeptide comprising SEQ ID NO:35.
55. Immunogenic composition according to item 54, wherein said composition comprises a fusion polypeptide comprising three or four immunogenic polypeptide fragments as defined in any one of items 13-16 and 34-39.
56. Immunogenic composition according to item 55, wherein said composition comprises a fusion polypeptide comprising an amino acid sequence selected from the group consisting of SEQ ID NO:8, SEQ ID NO:10, SEQ ID NO:12 and amino acid sequences which exhibit at least 80%-identity to any one of SEQ ID NO:8, SEQ ID NO:10 and SEQ ID NO:12.
57. Immunogenic composition according to item 56, wherein said composition comprises a fusion polypeptide comprising an immunogenic polypeptide fragment with at least 80%-identity with SEQ ID NO:8, an immunogenic polypeptide fragment with at least 80%-identity with SEQ ID NO:10 and an immunogenic polypeptide fragment with at least 80%-identity with SEQ ID NO:12, preferably comprising an immunogenic polypeptide fragment with 100%-identity with SEQ ID NO:8, an immunogenic polypeptide fragment with 100%-identity with SEQ ID NO:10 and an immunogenic polypeptide fragment with 100%-identity with SEQ ID NO:12.
58. Immunogenic composition according to item 57, wherein said composition comprises a fusion polypeptide comprising SEQ ID NO:8, SEQ ID NO:10 and SEQ ID NO:12.
59. Immunogenic composition according to item 57, wherein said composition comprises a fusion polypeptide comprising SEQ ID NO:107 or SEQ ID NO:108 or an amino acid sequence which exhibits at least 80%-identity to SEQ ID NO:107 or SEQ ID NO:108.
60. Immunogenic composition according to item 58 or 59, wherein said composition comprises a fusion polypeptide selected from the group consisting of SEQ ID NO:107, 108, 109 and 110.
61. Immunogenic composition according to any one of items 44-60, wherein said polypeptide are isolated or purified.
62. Immunogenic composition according to any one of items 44-61, wherein said immunogenic polypeptide or fusion polypeptide is recombinantly produced.
63. Immunogenic composition according to any one of items 44-62, further comprising an agent with adjuvant effect.

64. Immunogenic composition according to item 63, further comprising an agent with adjuvant effect in an immuno-effective amount.
65. Vaccine composition comprising an immunogenic composition according to any one of items 44-64 and a pharmaceutically acceptable carrier or excipient, such as a pharmaceutically acceptable carrier or excipient selected from the group consisting of a cream, emulsion, gel, liposome, nanoparticle, or ointment.
66. Vaccine composition according to item 65, further comprising an agent with adjuvant effect, such as an agent with adjuvant effect in an immune-effective amount.
67. Vaccine composition according to any one of items 65-66 or immunogenic composition according to item 63 or 64, wherein said agent with adjuvant effect is selected from the group consisting of Abisco/Matrix M, Matrix C and Matrix Q and silica.
68. Vaccine composition or immunogenic composition according to item 67, wherein said agent with adjuvant effect is silica.
69. Vaccine composition according to any one of items 65-68, which composition is formulated for intramuscular, intradermal, subcutaneous or intranasal administration, such as for intramuscular administration.
70. Vaccine composition according to any one of items 65-69, which composition is capable of eliciting serum and/or mucosal antibody responses in a mammalian subject, such as a porcine or human subject, such as a porcine subject.
71. Vaccine composition according to item 70, wherein said antibody response is in the form of IgG, IgA and/or IgM antibodies in the serum and/or mucosa.
72. Vaccine composition according to any one of items 65-71, for use in the prophylactic treatment of a mammalian subject susceptible to *Streptococcus suis* infection, such as a human subject or porcine subject, such as a porcine subject.
73. Method for the production of an antiserum comprising the step of administering an immunogenic composition according to any one of items 44-64, to a mammalian host to produce antibodies in said host and recovering antiserum containing the antibodies produced in the host.
74. Antiserum obtainable by the method defined item 73.
75. Method for prophylactic treatment of a *Streptococcus suis* infection in a mammalian subject, comprising administering to said mammalian subject in need thereof an immunologically effective amount of an immunogenic composition as defined in any one of items 44-64, of a vaccine composition as defined in any one of items 65-72, or of an antiserum as defined in item 74.
76. Method for prophylactic treatment of a *Streptococcus suis* infection in a mammalian subject, comprising administering to said mammalian subject in need thereof an immunologically effective amount of an immunogenic polypeptide as defined in any one of items 1-12, a immunogenic polypeptide fragment as defined in any one of items 13-16 or 34-39, or as fusion polypeptide as defined in any one of items 17-39.
77. Method for prophylactic treatment according to item 75 or 76, wherein said mammalian subject is a porcine or human subject, such as a porcine subject.
78. Method for prophylactic treatment according to any one of items 75-77, comprising administering on one single occasion or on multiple separate occasions.
79. Method for prophylactic treatment according to any one of items 75-78, wherein said administration is to piglets, gilts or sows.
80. Method for prophylactic treatment according to any one of times 75-79, wherein said administration is intramuscular, intradermal, subcutaneous or intranasal administration, such as intramuscular administration.
81. Method for prophylactic treatment according to any one of times 75-80, wherein, upon administration, serum and/or mucosal antibody response is elicited in said mammalian subject.
82. Method for prophylactic treatment according to item 81 wherein said antibody response is in the form of IgG, IgA and/or IgM antibodies in the serum and/or mucosa.
83. Antibody or fragment thereof, which is specific for an immunogenic polypeptide as defined in any one of items 1-12, an immunogenic polypeptide fragment as defined in any one of items 13-16 and 24-39 or a fusion polypeptide as defined in any one of items 17-39, which antibody or fragment thereof is polyclonal or monoclonal.
84. An antibody preparation comprising one antibody or several antibodies or fragments thereof according to item 83.
85. Method for prophylactic treatment of a *Streptococcus suis* infection in a mammalian subject, comprising passive immunization by administering to said mammalian subject in need thereof an antibody preparation according to item 84.
86. Immunogenic composition according to any one of items 44-64 for the use in the prophylactic treatment of a mammalian subject susceptible to *Streptococcus suis* infection, such as a human subject or porcine subject, such as a porcine subject.
87. Use of an immunogenic peptide as defined in any one of items 1-12, a immunogenic peptide fragment as defined in to any one of items 13-16 or 34-39 or a fusion polypeptide as defined in any one of items 34-39, for the manufacture of a medicament for use in the prophylactic treatment of a mammalian subject susceptible to *Streptococcus suis* infection.

The invention claimed is:

1. A fusion polypeptide comprising
a) a first immunogenic polypeptide unit, and
b) a second immunogenic polypeptide unit, wherein said first and second immunogenic polypeptide units are immunogenic polypeptide fragments selected from the group consisting of amino acid sequences of at least 100 amino acids in length with at least 80% identity to fragments of SEQ ID NO:4, amino acid sequences of at least 100 amino acids in length with at least 80% identity to fragments of SEQ ID NO:3, amino acid sequences of at least 100 amino acids in length with at least 80% identity to fragments of SEQ ID NO:2, an amino acid sequence with at least 80% identity to a fragment comprising SEQ ID NO:5, provided the fragment comprising the amino acid sequences with at least 80% identity to SEQ ID NO:5 is 100-500 amino acids long; and an amino acid sequence with at least 80% identity to a fragment comprising SEQ ID NO:6, provided the fragment comprising the amino acid sequences with at least 80% identity to SEQ ID NO:6 is 100-500 amino acids long.

2. The fusion polypeptide according to claim 1, wherein the first and second immunogenic polypeptide units comprise an amino acid sequence that is at least 80% identical to the contiguous amino acid sequence of SEQ ID NOS: 38, 7, 8, 9, 10, 11 or 12.

3. The fusion polypeptide according to claim 1, wherein the first and second immunogenic polypeptide units comprise an amino acid sequence that is at least 80% identical to the contiguous amino acid sequence of SEQ ID NOS: 7, 8, 9, 10, 11 or 12.

4. The fusion polypeptide according to claim 1, wherein said fragments are 100-500 amino acids long.

5. The fusion polypeptide according to claim 2, wherein said fusion polypeptide comprises an amino acid sequence selected from the group consisting of SEQ ID NO:92, SEQ ID NO:93, SEQ ID NO:94, SEQ ID NO:95, SEQ ID NO:96, SEQ ID NO:34, and SEQ ID NO:35.

6. The fusion polypeptide according to claim 1, further comprising a third immunogenic polypeptide unit, wherein said third immunogenic polypeptide unit is from a different native protein than said first and second immunogenic polypeptide units.

7. The fusion polypeptide according to claim 6, comprising an immunogenic polypeptide unit with at least 80% identity with SEQ ID NO:8, an immunogenic polypeptide unit with at least 80% identity with SEQ ID NO:10 and an immunogenic polypeptide unit with at least 80% identity with SEQ ID NO:12.

8. The fusion polypeptide according to claim 7, comprising SEQ ID NO:107 or SEQ ID NO:108 or an amino acid sequence which exhibits at least 80% identity to SEQ ID NO:107 or an amino acid sequence which exhibits at least 80% identity to SEQ ID NO:108.

9. The fusion polypeptide according to claim 6, wherein said fusion polypeptide comprises an amino acid sequence selected from the group consisting of amino acid sequences which exhibit at least 80% identity to SEQ ID NO:107, amino acid sequences which exhibit at least 80% identity to SEQ ID NO:108, amino acid sequences which exhibit at least 80% identity to SEQ ID NO:109, and amino acid sequences which exhibit at least 80% identity to SEQ ID NO:110.

10. The fusion polypeptide according to claim 1, wherein said first and second immunogenic polypeptide units are immunogenic polypeptide fragments selected from the group consisting of amino acid sequences of at least 100 amino acids in length with at least 95% identity to fragments of SEQ ID NO:4, amino acid sequences of at least 100 amino acids in length with at least 95% identity to fragments of SEQ ID NO:3, amino acid sequences of at least 100 amino acids in length with at least 95% identity to fragments of SEQ ID NO:2, a fragment comprising an amino acid sequence with at least 95% identity to SEQ ID NO:5, provided the fragment comprising the amino acid sequences with at least 95% identity to SEQ ID NO:5 is 100-500 amino acids long; and a fragment comprising an amino acid sequences with at least 95% identity to SEQ ID NO:6, provided the fragment comprising the amino acid sequences with at least 95% identity to SEQ ID NO:6 is 100-500 amino acids long.

11. An immunogenic polypeptide, comprising an amino acid sequence selected from
i) an amino acid sequence selected from the group consisting of SEQ ID NO: 7, SEQ ID NO:8, SEQ ID NO:9, SEQ ID NO:10; and
ii) an amino acid sequence with at least 80% identity to an amino acid sequence defined in i),
wherein the amino acid sequence selected from (i) and (ii) is 100-500 amino acids long, and wherein said immunogenic polypeptide further comprises terminal,
a tag selected from the group consisting of a His-tag, a myc tag, a SL-tag according to SEQ ID NO:32, a LSL-tag according to SEQ ID NO:33, an amino acid sequence with a least 80% identity to SEQ ID NO:32, and a FLAG tag,
and/or methionine-threonine at the N-terminus.

12. An immunogenic polypeptide, comprising an amino acid sequence selected from
i) an amino acid sequence of at least 100 amino acids length selected from the group consisting of, SEQ ID NO:7, SEQ ID NO:8, SEQ ID NO:9, SEQ ID NO:10; and
ii) an amino acid sequence of at least 100 amino acids length with at least 85% identity to an amino acid sequence defined in i),
wherein said immunogenic polypeptide further comprises,
a tag selected from the group consisting of a His-tag, a myc tag, a SL-tag according to SEQ ID NO:32, a LSL-tag according to SEQ ID NO:33, an amino acid sequence with a least 80% identity to SEQ ID NO:32, and a FLAG tag,
and/or methionine-threonine at the N-terminus.

13. An isolated immunogenic composition comprising at least one immunogenic polypeptide according to claim 11.

14. A vaccine composition comprising an immunogenic composition according to claim 13 and a pharmaceutically acceptable carrier or excipient.

15. An isolated immunogenic composition according to claim 13, further comprising an agent with adjuvant effect, which composition is capable of eliciting serum and/or mucosal antibody responses in a mammalian subject.

16. An isolated immunogenic composition according to claim 15, which composition is formulated for intramuscular, intradermal, subcutaneous or intranasal administration.

17. A method comprising administering a vaccine composition according to claim 14 to a mammalian subject susceptible to *Streptococcus suis* infection.

18. The fusion polypeptide according to claim 1, wherein said first and second immunogenic polypeptide units are immunogenic polypeptide fragments selected from the group consisting of fragments of SEQ ID NO:4 of at least 100 amino acids in length, fragments of SEQ ID NO:3 of at least 100 amino acids in length, fragments of SEQ ID NO:2 of at least 100 amino acids in length, a fragment comprising SEQ ID NO:5, provided the fragment is 100-500 amino acids long; and a fragment comprising SEQ ID NO:6, provided the fragment is 100-500 amino acids long.

19. The fusion polypeptide according to claim 1, wherein said immunogenic polypeptide fragments are selected from the group consisting of SEQ ID NO:5; SEQ ID NO:38, SEQ ID NO:6, SEQ ID NO:7, SEQ ID NO:8, SEQ ID NO:9, SEQ ID NO:10, SEQ ID NO:11 and SEQ ID NO:12.

20. The fusion polypeptide according to claim 1, wherein said immunogenic polypeptide fragments are selected from the group consisting of fragments SEQ ID NO: 7, SEQ ID NO:8, SEQ ID NO:9, SEQ ID NO:10, SEQ ID NO:11 and SEQ ID NO:12.

21. An immunogenic composition comprising at least one fusion polypeptide according to claim 1.

22. A vaccine composition comprising a fusion polypeptide according to claim 1 and a pharmaceutically acceptable carrier or excipient.

23. An isolated immunogenic composition according to claim 21, further comprising an agent with adjuvant effect, which composition is capable of eliciting serum and/or mucosal antibody responses in a mammalian subject.

24. An immunogenic composition according to claim 21, which composition is formulated for intramuscular, intradermal, subcutaneous or intranasal administration.

25. A method comprising administering a vaccine composition according to claim 23, to a mammalian subject susceptible to *Streptococcus suis* infection.

* * * * *